US008815505B2

(12) United States Patent
Couillard-Despres et al.

(10) Patent No.: US 8,815,505 B2
(45) Date of Patent: Aug. 26, 2014

(54) USE OF REGULATORY SEQUENCES FOR SPECIFIC, TRANSIENT EXPRESSION IN NEURONAL DETERMINED CELLS

(75) Inventors: Sébastien Couillard-Despres, Regensburg (DE); Claudia Karl, Regensburg (DE); Hans-Georg Kuhn, Billdal (SE); Ludwig Aigner, Regensburg (DE)

(73) Assignee: F. Hoffmann-La Roche Inc., Nutley, NJ (US)

( * ) Notice: Subject to any disclaimer, the term of this patent is extended or adjusted under 35 U.S.C. 154(b) by 1000 days.

(21) Appl. No.: 12/894,884

(22) Filed: Sep. 30, 2010

(65) Prior Publication Data

US 2011/0020790 A1    Jan. 27, 2011

Related U.S. Application Data

(62) Division of application No. 12/209,974, filed on Sep. 12, 2008, now Pat. No. 7,947,448, which is a division of application No. 10/543,713, filed as application No. PCT/EP2004/000760 on Jan. 28, 2004, now abandoned.

(30) Foreign Application Priority Data

Jan. 28, 2003   (EP) .................................... 03002027

(51) Int. Cl.
*C12Q 1/70*  (2006.01)
*C12Q 1/68*  (2006.01)

(52) U.S. Cl.
USPC ............................................... 435/6.1; 435/5

(58) Field of Classification Search
CPC ....................... C12N 2830/008; C12N 2830/85
See application file for complete search history.

(56) References Cited

FOREIGN PATENT DOCUMENTS

| EP | 0918091 | 5/1999 |
|---|---|---|
| WO | WO 93/07280 | 4/1993 |
| WO | WO 95/25792 | 9/1995 |
| WO | WO 98/32879 | 7/1998 |
| WO | WO 00/23571 | 4/2000 |
| WO | WO 01/53503 | 7/2001 |

OTHER PUBLICATIONS

Arvidsson et al., "Neuronal replacement from endogenous precursors in the adult brain after stroke," *Nat. Med.*, 8:963-970, 2002.
Bernier et al., "Newly generated neurons in the amygdala and adjoining cortex of adult primates," *Proc. Natl. Acad. Sci. USA*, 99:11464-11469, 2002.
Bonfanti and Theodosis, "Expression of polysialylated neural cell adhesion molecule by proliferating cells in the subependymal layer of the adult rat, in its rostral extension and in the olfactory bulb," *Neuroscience*, 62:291-305, 1994.
Brown et al., "Transient expression of doublecortin during adult neurogenesis," *J. Comparative Neurology*, 467:1-10, 2003.
Cooper-Kuhn and Kuhn, "Is it all DNA repair? Methodological considerations for detecting neurogenesis in the adult brain," *Dev. Brain Res.*, 134:13-21, 2002.
Couillard-Despres et al., "Molecular mechanisms of neuronal migration disorders, quo vadis?" *Current Molecular Medicine*, 1:677-688, 2001.
Couillard-Despres et al., "Targeted transgene expression in neuronal precursors: watching young neurons in the old brain," *European Journal of Neuroscience*, 24:1535-45, 2006.
des Portes et al., "A novel CNS gene required for neuronal migration and involved in X-linked subcortical laminar heterotopia and lissencephaly syndrome," *Cell*, 92:51-61, 1998.
Englund et al., "Transplantation of human neural progenitor cells into the neonatal rat brain: extensive migration and differentiation with long-distance axonal projections," *Exp. Neurol*, 173:1-21, 2002.
Francis et al., "Doublecortin is a developmentally regulated, microtubule-associated protein expressed in migrating and differentiating neurons," *Neuron*, 23:247-256, 1999.
Freed et al., "Transplantation of Embryonic Dopamine Neurons for Severe Parkinson's Disease," *New Eng. J. Med.*, 344:710-719, 2001.
Gambhir et al., "Imaging Transgene Expression with Radionuclide Imaging Technologies," *Neoplasia*, 2(1-2):118-38, 2000.
Genbank Accession No. AL450490, Jul. 10, 2007.
Genbank Accession No. U55762, Aug. 22, 2003.
Gleeson et al., "Doublecortin, a brain-specific gene mutated in human X-linked lissencephaly and double cortex syndrome, encodes a putative signaling protein," *Cell*, 92:63-72, 1998.
Gould et al., "Hippocampal neurogenesis in adult Old World primates," *Proc. Natl. Acad. Sci. USA*, 96:5263-5267, 1999.

(Continued)

*Primary Examiner* — Scott Long
(74) *Attorney, Agent, or Firm* — Park Highlander PLLC

(57) ABSTRACT

The present invention relates to the use of regulatory sequences for mediating specific, early transient expression in proliferative neuronal determined cells. Furthermore, the uses of recombinant nucleic acid molecules comprising said defined regulatory sequences for mediating specific, early transient expression in proliferative neuronal determined cells as well as for the generation of non-human transgenic organisms and/or host cells are disclosed. In addition, the invention provides for transgenic non-human animals and/or host cells comprising said regulatory sequences and/or recombinant nucleic acid molecules. The invention also describes methods for the preparation of such vectors, host cells and transgenic non-human animals as well as methods for the detection and/or isolation of neuronal determined cells. Additionally, methods for screening of compounds capable of regulating neuronal determined cell activity, neurogenesis, stimulating proliferation of neuronally committed precursor cells and/or neuronal differentiation are provided and the invention also relates to methods for the detection and analysis of neuronal differentiation, neuronal migration and/or neuronal determination processes. Finally, the invention relates to diagnostic and pharmaceutical compositions comprising the regulatory sequences, recombinant nucleic acid molecules, host-cells or isolated neuronal determined cells described herein.

24 Claims, 56 Drawing Sheets

(56) References Cited

OTHER PUBLICATIONS

Figure 1:
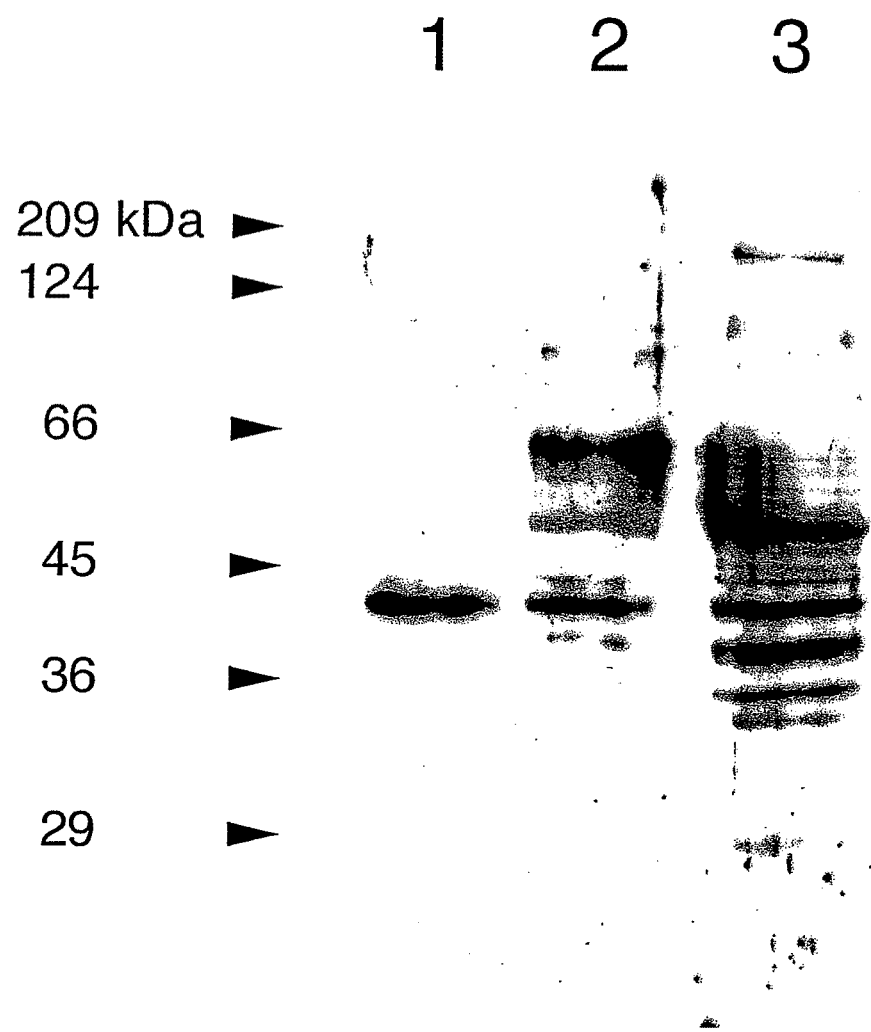

Gress et al., "Hybridization fingerprinting of high-density cDNA-library arrays with cDNA pools derived from whole tissues," *Mammalian Genome*, 3:609-19, 1992.

Jin et al., "Vascular endothelial growth factor (VEGF) stimulates neurogenesis in vitro and in vivo," *Proc. Natl. Acad. Sci. USA*, 99:11946-11950, 2002.

Kawaguchi et al., "Nestin-EGFP transgenic mice: visualization of the self-renewal and multipotency of CNS stem cells," *Mol. Cell Neurosci.*, 17:259-273, 2001.

Kempermann et al., "Early determination and long-term persistence of adult-generated new neurons in the hippocampus of mice," *Development*, 130:391-399, 2003.

Kempermann, "Why new neurons? Possible functions for adult hippocampal neurogenesis," *J. Neuroscience*, 22:635-638, 2002.

Kuhn et al., "Epidermal growth factor and fibroblast growth factor-2 have different effects on neural progenitors in the adult rat brain," *J. Neurosci*, 17:5820-5829, 1997.

Kuhn et al., "Neurogenesis in the dentate gyrus of the adult rat: age-related decrease of neuronal progenitor proliferation," *J. Neurosci*, 16:2027-2033, 1996.

Lei and Warrior, "The *Drosophila lissencephalyl* (DLis1) gene is required for nuclear migration," *Dev. Biol.*, 226:57-72, 2000.

Leventer et al., "LIS1: from cortical malformation to essential protein of cellular dynamics," *Trends Neurosci*, 24:489-492, 2001.

Liu et al., "*Drosophila* Lis1 is required for neuroblast proliferation, dendritic elaboration and axonal transport," *Nat. Cell Biol.*, 2:776-783, 2000.

Magavi et al., "Induction of neurogenesis in the neocortex of adult mice," *Naute*, 405:951-955, 2000.

Nacher et al., "Doublecortin expression in the adult rat telencephalon," *Eur. J. Neurosci*, 14:629-644, 2001.

Office Action, issued in U.S. Appl. No. 10/543,713, dated Dec. 11, 2007.

Office Action, issued in U.S. Appl. No. 10/543,713, dated May 12, 2008.

Office Action, issued in U.S. Appl. No. 12/209,974, dated Mar. 8, 2010.

Office Action, issued in U.S. Appl. No. 12/209,974, dated May 19, 2010.

Office Action, issued in U.S. Appl. No. 12/209,974, dated Nov. 2, 2010.

Pencea et al., "Neurogenesis in the subventricular zone and rostral migratory stream of the neonatal and adult primate forebrain," *Exp. Neurol.*, 172:1-16, 2001.

Roy et al., "Promoter-targeted selection and isolation of neural progenitor cells from the adult human ventricular zone," *J. Neurosci. Res.*, 59:321-331, 2000.

Roy et al., "Identification, isolation, and promoter-defined separation of mitotic oligodendrocyte progenitor cells from the adult human subcortical white matter," *J. Neurosci.*, 19:9986-9995, 1999.

Sawamoto et al., "Direct isolation of committed neuronal progenitor cells from transgenic mice coexpressing spectrally distinct fluorescent proteins regulated by stage-specific neural promoters," *J. Neurosci. Res.*, 65:220-227, 2001.

Swan et al., "*Drosophila lissencephaly*-1 functions with Bic-D and dynein in oocyte determination and nuclear positioning," *Nat. Cell Biol*, 1:444-449, 1999.

Wang et al., "Promoter-based isolation and fluorescence-activated sorting of mitotic neuronal progenitor cells from the adult mammalian ependymal/subependymal zone," *Dev. Neurosci.*, 22:167-176, 2000.

Wolcott, "Advances in nucleic acid-based detection methods," *Clinical Microbiology Reviews*, 5:370-86, 1992.

Wu, "Noninvasive optical imaging of firefly luciferase reporter gene expression in skeletal muscles of living mice," *Mol. Ther.*, 4(4):297-306, 2001.

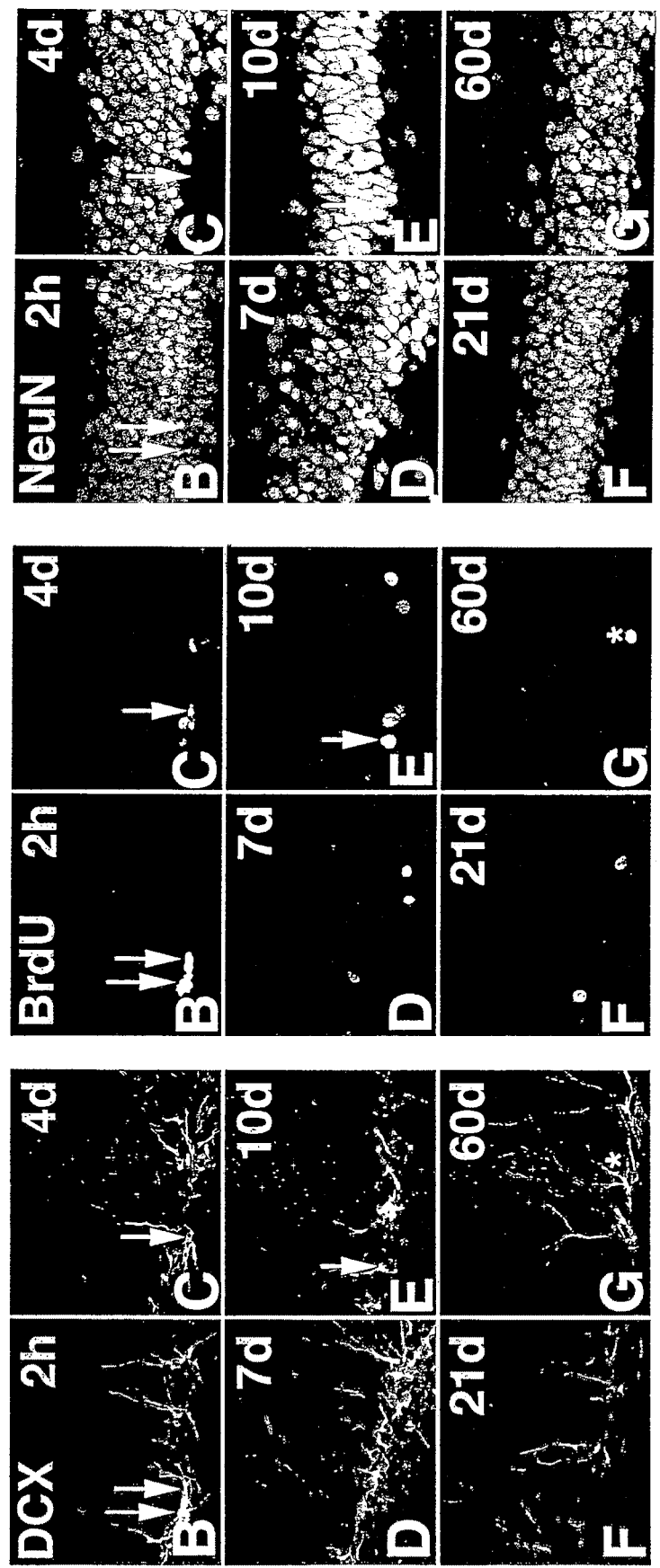
FIG. 2B-F

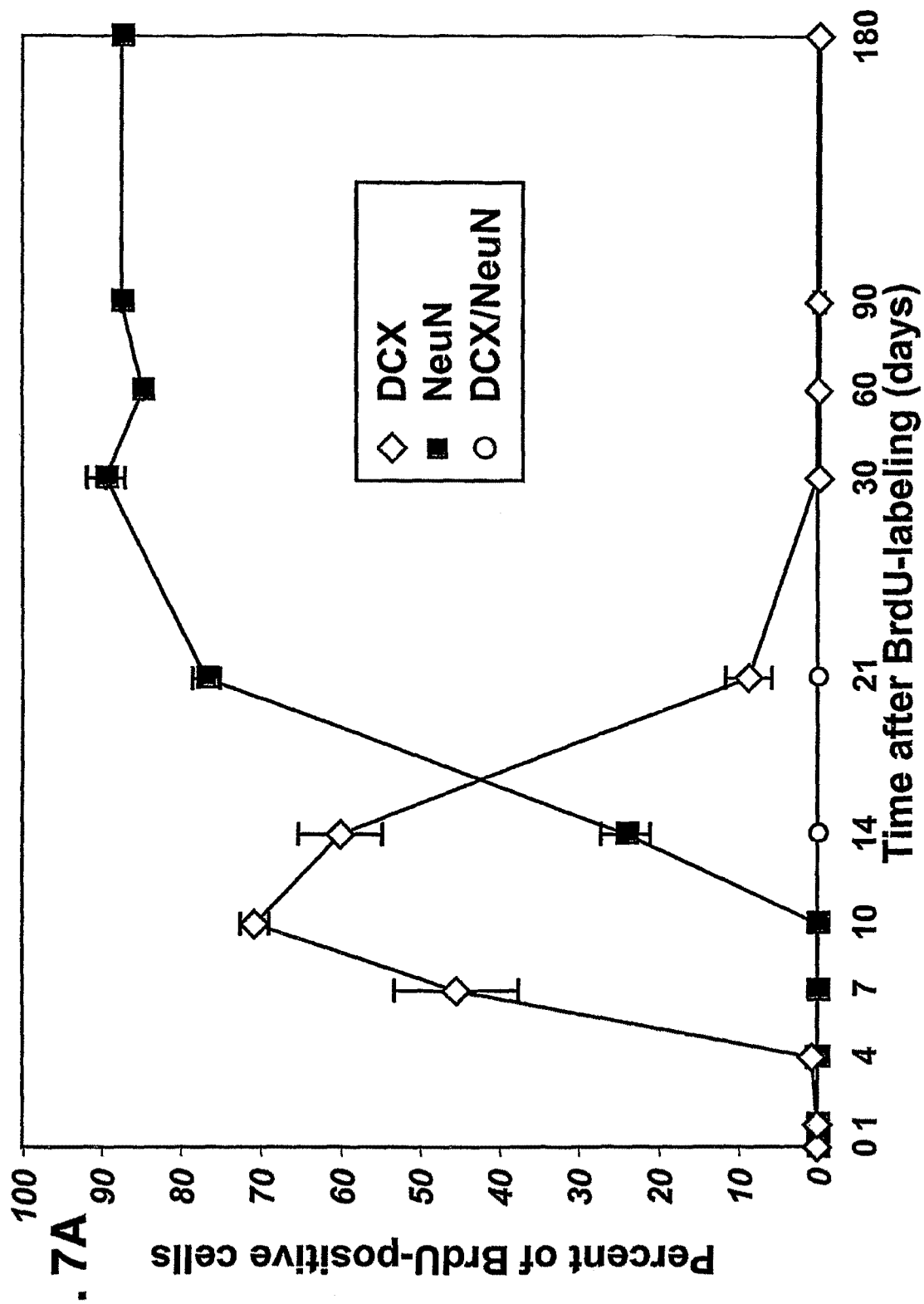

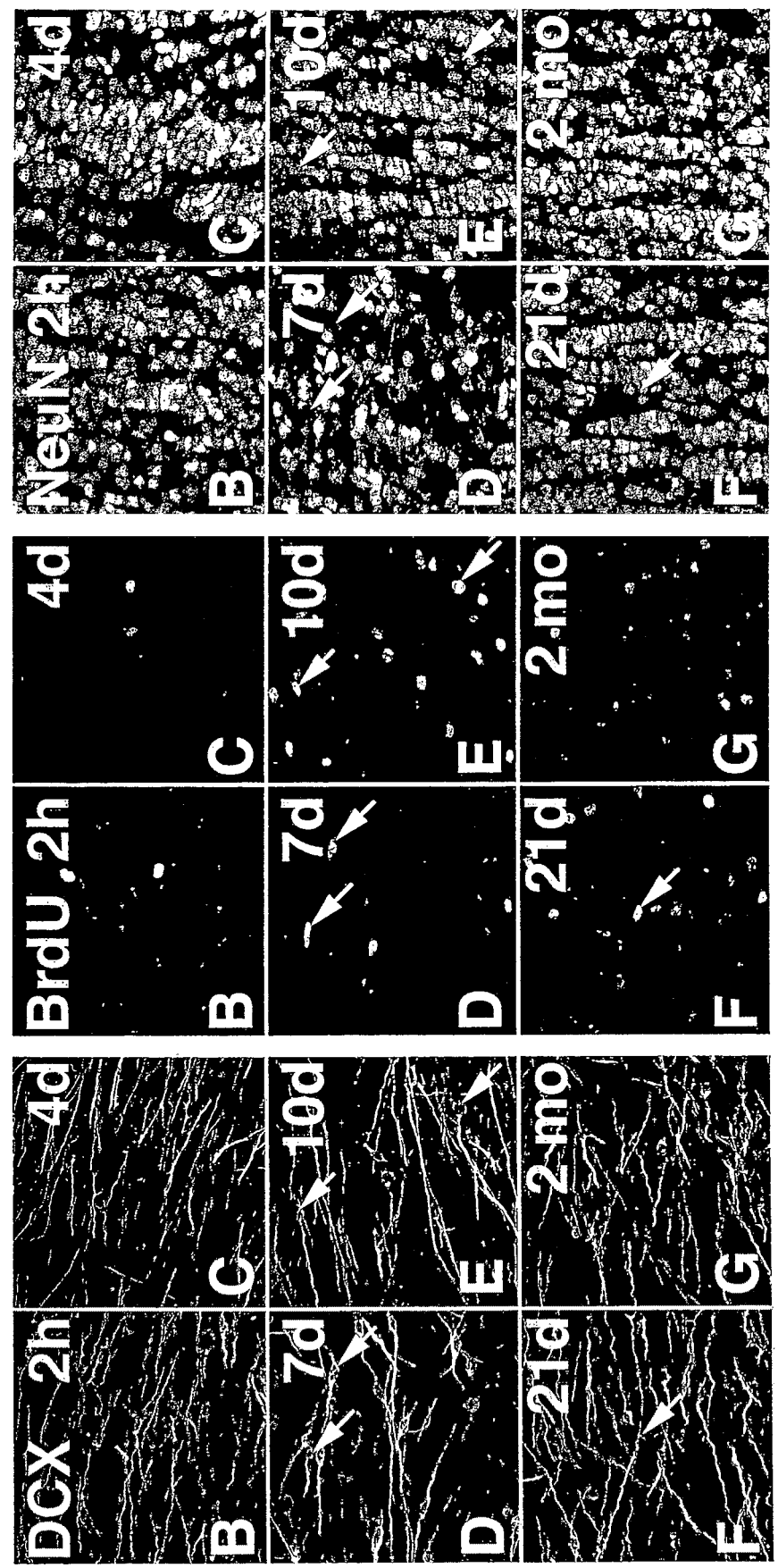
FIG. 7B-G

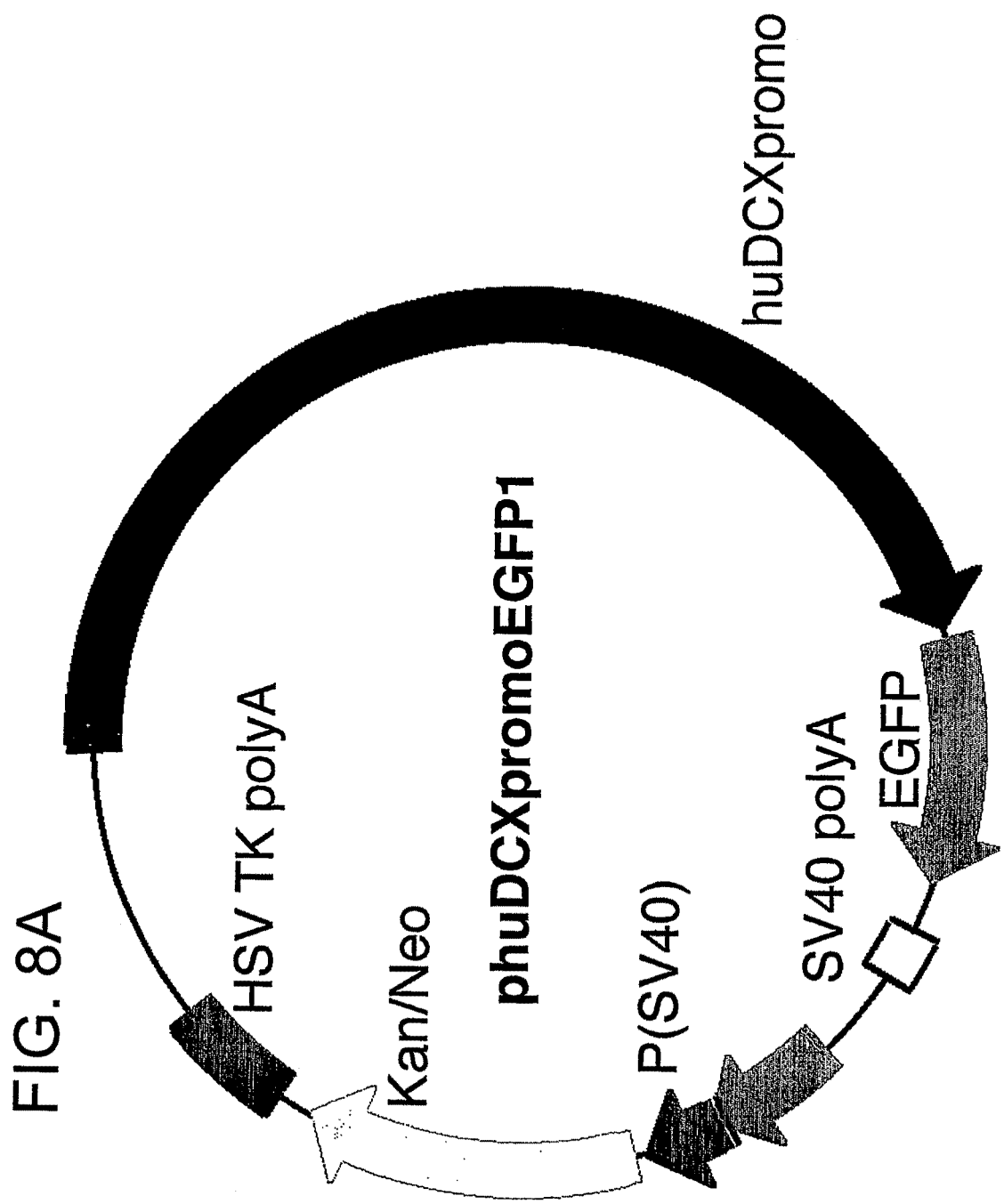

FIG. 9 (cont.)

Sequence_ID_1 3509 nt vs.
Sequence_ID_2 2881 nt 64.6% identity;    Global alignment score: 5093

```
AACACCTATT AATGCCCACA TATCTCAAAC AAGGAAATAT TGATCCTGCC
---------- ---TCCCATA TG----AAAG AAAGAAA-AT AAATCCT---

TATCCCTCTG CTCTCTATTA TATATAAAGC AAACAAAGTC ATTTATCCTA
--TTGTCT-- CTCTC----- ---------- -----AGCC TCGGATACT-

GGCTGTCTCA TAAAAACATT TTGTAGCTTC CACAGTAGCA -TTGCAAAGC
---TCACTCA GTATATCATT TTC--GGTTC CACACAATTT CTTGCAAATC

CTATATTATG AGGAATTTTC CTCTGAAATA CATTCCAAAT GGTTCGTGTT
TCATAATTTC AC--ATTTTA CTG------- -------AT GG----GTGAT
```

FIG. 9 (cont. 1)

```
TAAGTTTTAT TATCCCATCC ATTGTTGTAT CTTCACCAGA AATAAAATGA
TAAAAT---- ----CATGC A----TATAT CTTGC----- -------A

TTTTTAGTTC TGATGCAAAA TTAATTGCTA CATATTTACT GAATGCTTAT
TTTTCATTAC CCATTCATC- ---------- --TGTTAAC- ----------

GATGTGCAAG AAAGAAGTTT TAAGACATTA GCTTGTTGG AATTTCCATA
---------- ---------- --AGACAT-- -CTGGGCTG- --TTTC--TA

TTTTCCTGCC CTTATTCCTT GATTTTTCTT TGCCTCTAGC CTGAATAATG
TTTTC----- ---------- ---------- TGGCTTTTG- -TGAATA---

TTGATTTTTC ATGAGGTTGC CACAAGGTAA GGCAACAACA CATGGAAGAA
---------- ---------- ---------- ---------- ----------

AACAGGGCAG ACACATGCAT TCCCCTGAGG TACTTGTATA GTAACCAAGA
---GAGCAG --GAGCAG CCATA----- ---------- ---------- --AACACAGA
```

FIG. 9 (cont. 2)

```
AATCAGCAGC AAGGTGTTGG GGGACTTAA  CTA-GGTAGG TTGCACATTT
TAT----GC  AAG-TGT--- ------CT-- CTATGGTAGG TT--------

GAGGCTATCC ACTCAACTAA CAGACAGTTC CAGGCTTTGC TGAGTCAACA
CCTTTGGG-- ---------- --ATAGT--- ---------- -------CT

CCTTTCACAG AAGAAAGACC ATCATATATT TTATCCCACT TGGTGGCAGC
CCTTTGGG-- ---------- --TATATG-- ----CCCAGG AGTGGGAAGG

TTACAATAAA ACACATGCAG AGAAAATGCT TAAATATAAA AGTTCAACAG
TGA----A   ACA------- -------T   TAACCA----A TGTTTACAT

CACTATATAA AAGGAAGGGT TAATTATACT AGGAATCAGA TATAAAATAA
CAGTCTA-AA ATGTTTTGG- -AGTCATGCT GGGCCT-AGA GACC---TAA

TTACTGAGCA TGCTCTTAGC TCTGAGCTTC CTGGAAGCCA AGCAAAAATA
GTGCTG-GCA AATT-TTAGT ---------- ----AGCCA  AG---AAGCA
```

FIG. 9 (cont. 3)

```
GAACCATGAT AGTTCAAGGC TGCTACATAT TGATGCATGT AGCTTCAATT
GAAC------ AG-----AGGC TGA-----AAAT T--------- ----TTCA--

GTGAAGATGG TAGCATCCCC CTACCCCATT TAACCTCTCA CCTTTCTCTT
--GCAAATG- ---------- ---------- ---------- ----------

TTGTTTTATA GTTCGGCCTG ATCTAATTAG TTCAATTTGG ATGCTTCCTT
-----AGA   GGTCAGCCTG GGCTACACAG C--------- ----------

GAGTTTTTTT TGTAACATAT TTTATATAAA GAAGTCAGTT AGTGACAAAT
GAGTTC---- ---------- ---------- ----CAGA-- -----ACAACT

AAGCAGTTTG AGGAGAAATC TGTTAATATT TATTTTGTAG CCATCAGATT
A--------- ---------- ---------- ---------- ----------

TACTTCACAT AGAAAGGTCT TTGGGTTGGG TTTGAACTTC CAAACTCTCA
---TCAC-T  ATAAAGCT-- ---------- ----GGAC--C CTGACTC---
```

FIG. 9 (cont. 4)

```
AAGGTAAATG  CCACATTAAC  CTTTCATTAA  CCAAATTCTT  ACACCAAGCT
--GATAAA--  --ACA-----  ----ACTGA-  ---ACAAAACTT  GGA-------

GATAGATTTG  GGATGTCCTT  TTTACTTCTA  TCTTCCATAA  TATTCTAAAA
---GAAGTG-  CCA---CTT   TTCAATTCCA  GCCTTCATGA  T-TCCTGCAA

TTATTTTCCC  TTGTTTTGTT  CCTATCCTAC  TTCCTCTTAG  TCTACTTTGT
CTATTTTCCC  GTGTACTGTC  AATTTACTA-  TTCCT-----  -----GC

TGACTTCATT  AAAAAAACAAA  AAACCAGTTG  TTGGATACTT  GAGCTAAACT
TGACTTCGTT  TAAAAA---A  CAACCAGT-G  TTGGATGCAT  GAGCCGAAAT

GCCTTAAAGA  ATCTGCAGAT  TTTATTTTAT  TTTTTTCTC   TCAAGAGGGT
G---TTAAAAA  ATTTACATAT  TTT-------  TTATTTCTT   TGAAGAAGAT

AAAAGGAAGA  GAGCTACAAT  TTCTAAGAAG  CCTGGCTTGG  CTGTCTGAGT
AAAAGAGGA   GATCTGTAAT  TTCTAAGAAA  CTTGATTTGG  CCTGCTGAGT
```

FIG. 9 (cont. 5)

```
CTGGCCCCA   GGCAGATTAG   GCCAAGGTTT   TGCCAAGTG    AAATTGCCAA
CCAGCCACTA  GGCAGA----   ----AGGTTT   TAGCCAAGTA   AAATTGCCAA

TTTCTAAAA   GAAAGGGCTA   GCACATTGCT   CATTAGAGCA   TTCTGATTTT
TTTCTAAGA   GAAAGGGCTA   GCACATTGCT   CATTAGAGCA   TTCTGAGCTT

GTCTGCGCAA  TCTTTTTG--   -CTACCCCGC   AATTCCTGT    TGGTTATAAA
GCCTGTGCAA  TCTTTTTTT    CCTACCCTGC   AATTCCTGT    GCGTTATAAA

TGAAACCTTT  CTAGCTGTTA   ATGCAGCCTG   TGAATTTTTT   TAAAA---GC
CGAAACCTTT  CTAGCTGTTA   ATGCAGGCTG   TGAATTGAAG   AAAAAAAAGC

ATGTAATTAA  TCATAGGAGG   TTGGGGGGAT   TCACTAAGCC   TGAGTTACAT
ATGTAATTAA  TCATAGGAGG   TTGGGGGTGT   TCGCTAAGCT   TCAGTTACAG

GGGAGAAGCT  GGACAAGGCA   CTAGGACCTA   GAAGGCATCT   ATCCACCCTG
GGGAGAAGCT  GGACAAGGCA   CTAGGACCTA   GAAGGCAACT   ATCCACCCTG
```

FIG. 9 (cont. 6)

```
GCAGGAATTT CTTGCTTGGA GCTCAGACAA CAAAGGCATA GAGAGATTGG
GCAGGAATTT CTTGCTTGGA GCTCAGACAA CAAAGGCATA GAGAGATTGG

TTTCTTTCT CTCAGCATCT CCACCCAACC AGCAGAAAAC CGGTGAGTGG
TTTCTTTCT CTCAGCATCT CCACCCAACC AGCAGAAAAC CGGTGAGTGG

GGCTTTTAAG TGATTTTCAA GAAGAATGTA ACAGATGTCA AACGGGAAAA
GGCTTTCGAG TGATTTTCAA GCAGAATGTA ACAGATGTCA ACCGGGAAA-

GCACAAGGCA AA--GCCTGC TCTCTCTGTC TCTCTGTCTC CT-CTTCTCC
GCACAAGGCA CACGGCTTTC TTTCTCTGTG TTTCTCTGTC TTTCTTTCT

TTT-TTTGCC TTATTCTATC CGATTTTT-T CC-CTAAGCT TCTACCTGGG
TTTATTTGCC TTATTCTATA GGATTTTTGT CCTCTAAGAT TCTACCTGGG

ATTTCCTTT GGAAAAGTGA GTTTGATGTT CCTTGTTTT CACTGTGATG
ATTTCCTTT GGAAAAGTGA GTTTGTTGTT CCTTGTTTT CACTATGATG
```

FIG. 9 (cont. 7)

```
TTAATTTAGA ATAATACTAC CTCTGATCCT AAAGCAAAGC AAAGCCTTAC
CTAATTTAGA ATAATAGCAC TTCTGATTCT AAAGC----- -TAGCTTTAT

TGGCA----- TGCCTGGGGA AA-TGTTTGC TGCTTGCCTT GAGGAGGTGG
TTGCACAGCC TGCCTGGGGA AAATGCTTGC TACTCATCTT GAGGAGGTGG

GGTCTCTTAC CACTGCAGGT TGTCTGACAG AGACAATGCT GAGCTCAGCA
G--CTCTTAC TACTGCAGGT TGTCTGACAG AGACAATGCT GAGCTCAGCA

TAGGTCATGG TGACATTGGA AAAAA-GGCG GAATTGAGCC TGGCAGACCC
TAGGTCATGG TGACACTGGA AAAAAAGGGG GTACTGAGCC TGGCAAATAT

ATTAGGCACC AGTCTTTCTT -ATCCCTGT  CCTCCTGGTC CCTTGCAAAT
ACCAACTACC AGTCCCCTT  TATCTCCTTT CTCCCTGGTT TCTTGCAAAT

ATATTGATGT GGCAGTGTGT A----GCAGC TGAGCCCTGC TTGCTTTGTG
CT--CGATGT GGCAGTATAT ATATAGCAGC TGAGCCCT-C TTGCTTTGTG
```

FIG. 9 (cont. 8)

```
AGTCCTTTTA  TCCCCATCTG  TGAGATGCAT  GTTAATAGTT  TGGCTCGTAG
AGTCTTTTTC  CCCCCATTTG  TGAGATGAAT  GTTAATAGTT  TGGTTTCTTG

GATGTCAC--  TACATTTGCT  AGCATTTGTG  GCTTCAGTTG  TATT---GGG
GATGTCACAT  TACCTTTGTA  AGGGGTTAGG  GCTTTGGTTG  TATTATTGGG

TTTCATGTTT  TGATTGTTTG  GG--GTTCTT  ----GGTG    GGGGAGGGGG
TTGCATGTTT  TCATTGTTTT  GGACGTTTTT  TTTCTGGTG   GGGGACGGGT

TTCAACAGAA  GGGAGAAAAG  CAAAGCCTGA  CAAATGACCA  TCTTTT---C
T----CAGGG  GGGTTGAAAT  CCAAGCTTGA  CAGATGACTT  TTTTTTTCCC

TCAGCTAATG  CACCTGGGCA  ATATACAAGT  TTGGGGTGAA  TTGCCTGCTG
TCCATCAATA  CACCTAAGCA  ATAGACAAGT  TTGAAGTGAA  TTGCCTGCTT

TGAGGGTAAA  -TGTCACTTC  AATTAAGGTA  GAAACCCAGA  ACAATGAAAG
CGAGGGCAAA  ATATTCCTTC  AGTCAGGGGA  GAAACCCAGA  ACAATGAAAG
```

FIG. 9 (cont. 9)

```
GTGTGCTTCC  TTCTAAAGGT  CCCGTATGCT  GTTCGGAGAG  TCATTTGTGA
GTGTACCTAC  TTGGAAAGGT  CCCATGTGCT  ATTCAGGGAC  CCATTTGGGA

ATCTTTCAAC  AATTAAATTA  TTCCATTAAG  AGGTGTTGCT  GCAT-CAGTG
ATCTTTCCAC  AA----TTA   TTCCATTAAG  AGGTGTTGCT  GCATTCATTG

G---GGAGG   GGGTGGAGCA  CCTGGGGGGG  AAAAAAAAGG  ATTTGTGAA
GTCGGGGAGG  GGATGAAACA  CCTGAAAGG-  -AGAAAAAGG  ATTCTGTGAT

CAAATGGAAC  CGG--GGGAA  GACAGAGCTA  GTAACTTGTT  AAATAACTTA
CAAATGGAAA  TGAAAGGGAA  G-CAGAGCTA  ATAGCTTGCT  AAATAACTGG

TTTTTCT---  -AATCC----  ---TTTTTCC  CCCCAGCTTA  TTTCTTATGA
GTTTTTTCGA  CAATCCCTCC  CCCTTTAGA   CCCCAGCTTA  TTTCTTATGG

ATGTCGGATA  GCTGCACCAG  CTTGGTGGGG  AAAGGGTTTG  ATGAATAGCA
ATGCCGGTATA GCGGCACCAG  CTTGATGGGG  AGAGGGTTTG  ATGAATAGCA
```

FIG. 9 (cont. 10)

```
CAAAGACACT GGCTGTTCCC TGGAGGCTGT CCCTTTAAAG GAGAATCTTA
CAAAGGCACT GGGTATTCCC TGGAGGCTGT CCCTTTAAAA GAGAATCCTA

GTTTATTCTG GGGGGAGGGG ATGCACACAT TAGAGTAGG- -AAAGAGGGC
GTTTATTCTG GGGG-AGGGG ATACACATAT TAGAGCAGGC AAAAAGGAC

TTGGAATAAA ATGAAAACAC TCCCCCTTCA TAGTCATTGT ACTGAAATGC
AAGGAATAAA AGTAATTCA- -CCCCCTTCC TAGCCATTGT ATTGAGATGC

AAAGACTGCT TCCTAAGCTG GAGA-TGCTA ACCTTGGGTA GCTCCTTCTG
AAAGGCTGCT TCCTA--CAG GAGGGTGCTA ACCTTGGCTA GCTCCCTCTG

TT-CTCTTCA AGGGGAATTT TGTCAGGCTA TGGATTCATT TACAACTGTT
TTTCTCTTTG AGGG-AATTT AGTCAGGCTA TGGATTCATT TACAACTGTT

AGTCATGTGG GCATGTGTGA GGAAACAGAT GCCAGTTTTA ATGTATTTAG
AGTCATGTGG CCATGTGTGA AGGAGCAGAT GCCAGTTTTA ATGTATTTTG
```

FIG. 9 (cont. 11)

```
CCCGAAGTTC  CAATTTGATA  GGAGCCACTG  TCAGTAAGTC  TCAGGATTTT
CCCGAAGTTA  CAATTTGATA  GGAGCCACTG  TCAGGAAGCT  CCAGGTTTTT

CAGCTATTTC  AAAATCTCCC  CTTCTCCTCT  GTCTGGAACA  GTGCCAAGAG
AAGCTATTTC  AACA---CGC  C--CTCCCCA  AATTGGAACA  GTGCCAAAAG

TGCCTCCCTC  TCTATCTCTT  ACTCCCAACC  CCCACA--AC  CAC-CAG---
TGCCACCCTT  TCTATCTCTT  CCTCCTATCC  CCCTCCCCAC  CATTCAGTCC

-CACCC--CC  GCCCAGCCCC  -TCCTTCTTC  TCTATTAAGA  TCAATATTCC
TCAGCCTACT  GCCCAGCCCC  CTCCTTCTTC  TCTATTAAGA  TCAATATTCC

TGCAGGTCAG  GGGCAAGCAG  CAGATGGGTC  ACAGGCTTTT  TTCAACCAGT
TGCAGGTCAG  GGACAAGCAG  CAGATGGGTC  ACAGGCTTTT  TTCAACCAGT

TCTTTTCACA  AGCAGCAGAT  TGCAGATCTG  GATCTGGCTA  ATATTTAAAA
TCTTTTCACA  GGCAGCAGAT  TGCAGCTCTG  GATCTGGCTA  ATATTTAAT
```

FIG. 9 (cont. 12)

```
TCCCTTCTTT TTTCCTTCTC CTTGTCCCTT TTTGTTTTTG CCTCTCTTCA
TCTCCCCCCT C--CCTTATC CAT---CCTT ATTCTT---TG CCTCTCCTTA

CCCCCATCCC TTTCTCCCAC GCTCAGGTCT CTGA------ ----------
TCTCCACCCT TTTCTCTAAC AATCAGGTTG CTGTGGTTCC ACCAAAAT
```

Figure 10B:
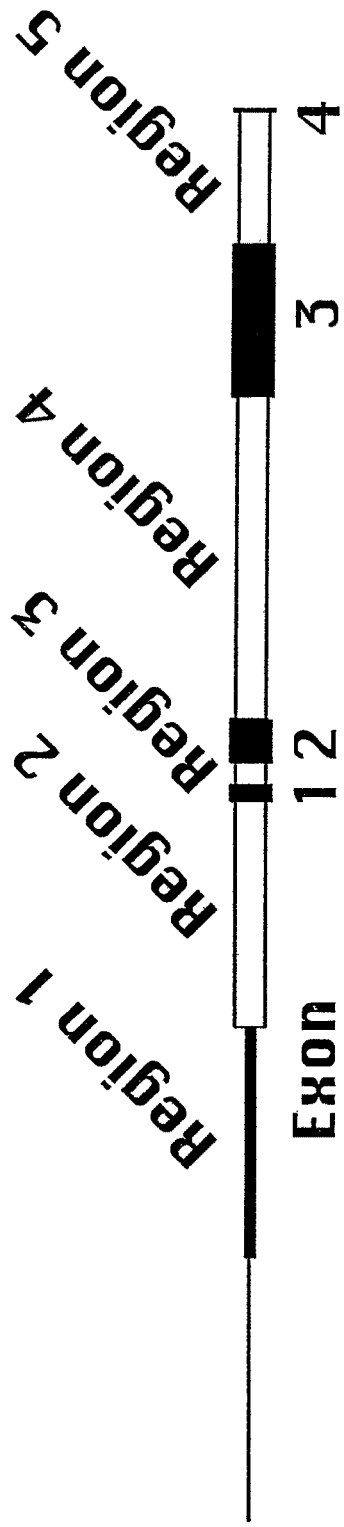

FIG. 10A
Human DCX regulatory sequence
(bp 1 - 3509)
Mouse DCX regulatory sequence
(bp 1 - 2881)

| Sequences | Human | Mouse | % Identity |
|---|---|---|---|
| Exon 1 | 1747-1784 | 1080-1117 | 100,0 |
| Exon 2 | 1844-1952 | 1176-1290 | 82,6 |
| Exon 3 | 2776-3168 | 2138-2524 | 86,4 |
| Region 1 | 638-1165 | 1-528 | 46,0 |
| Region 2 | 1166-1746 | 529-1079 | 79,6 |
| Region 3 | 1785-1843 | 1118-1175 | 91,5 |
| Region 4 | 1953-2775 | 1291-2137 | 76,4 |
| Region 5 | 3169-3501 | 2525-2859 | 78,7 |

FIG. 11 (cont.)

Sequence_ID_3 2344 nt vs.
Sequence_ID_4 2353 nt 79.9% identity;   Global alignment score: 7067

```
CTTTTACTT  CTATCTTCCA  TAATATTCTA  AAATTATTTT  CCCTGTTTT
CTTTCAATT  CCAGCCTTCA  TGAT-TCCTG  CAACTATTTT  CCCGTGTACT

GTTCCTATCC  TACTTCCCTCT  TAGTCTACTT  TGTTGACTTC  ATTAAAAAAC
GTCAATTTAC  TA-TTCCT--  ---------  -GCTGACTTC  GTTTAAAA--

AAAAAACCAG  TTGTTGGATA  CTTGAGCTAA  ACTGCCTTAA  AGAATCTGCA
-AACAACCAG  T-GTTGGATG  CATGAGCCGA  AATG--TTAA  AAAATTTACA

GATTTTATTT  TATTTTTTT  CTCTCAAGAG  GGTAAAAGGA  AGAGAGCTAC
TATTTT----  ---TTATTT  CTTTGAAGAA  GATAAAAAGA  GGAGATCTGT
```

FIG. 11 (cont. 1)

```
AATTTCTAAG AAGCCTGGCT TGGCTGTCTG AGTCTGGCCC CCAGGCAGAT
AATTTCTAAG AAACTTGATT TGGCCTGCTG AGTCCAGCCA CTAGGCAG--

TAGGCCAAGG TTTTGGCCAA GTGAAAATTGC CAATTTTCTA AAAGAAAGGG
-----AAGG TTTTAGCCAA GTAAAATTGC CAATTTTCTA AGAGAAAGGG

CTAGCACATT GCTCATTAGA GCATTCTGAT TTTGTCTGCG CAATCTTTTT
CTAGCACATT GCTCATTAGA GCATTCTGAG CTTGCCTGTG CAATCTTTTT

G---CTACCC CGCAATTTCC TGTTGGTTAT AAATGAAAACC TTTCTAGCTG
TTTCCTACCC TGCAATTTCC TGTGCGTTAT AAACGAAACC TTTCTAGCTG

TTAATGCAGC CTGTGAATTT TTTTAAAA-- -GCATGTAAT TAATCATAGG
TTAATGCAGG CTGTGAATTG AAGAAAAAAA AGCATGTAAT TAATCATAGG

AGGTTGGGGG GATTCACTAA GCCTGAGTTA CATGGGAGAA GCTGGACAAG
AGGTTGGGGG TGTTCGCTAA GCTTCAGTTA CAGGGGAGAA GCTGGACAAG
```

FIG. 11 (cont. 2)

```
GCACTAGGAC  CTAGAAGGCA  TCTATCCACC  CTGGCAGGAA  TTTCTTGCTT
GCACTAGGAC  CTAGAAGGCA  ACTATCCACC  CTGGCAGGAA  TTTCTTGCTT

GGAGCTCAGA  CAACAAAGGC  ATAGAGAGAT  TGGTTTTCTT  TCTCTCAGCA
GGAGCTCAGA  CAACAAAGGC  ATAGAGAGAT  TGGTTTTCTT  TCTCTCAGCA

TCTCCACCCA  ACCAGCAGAA  AACCGGTGAG  TGGGGCTTTT  AAGTGATTTT
TCTCCACCCA  ACCAGCAGAA  AACCGGTGAG  TGGGGCTTTC  GAGTGATTTT

CAAGAAGAAT  GTAACAGATG  TCAAACGGGA  AAAGCACAAG  GCAAA--GCC
CAAGCAGAAT  GTAACAGATG  TCAACCGGGA  AA-GCACAAG  GCACACGGCT

TGCTCTCTCT  GTCTCTCTGT  CTCCT-CTTC  TCCTTT-TTT  GCCTTATTCT
TTCTTTCTCT  GTGTGTTCGC  CTCTTTCTTC  TCTTTTATTT  GCCTTATTCT

ATCCGATTTT  T-TCC-CTAA  GCTTCTACCT  GGGATTTTCC  TTTGGAAAAG
ATAGGATTTT  TGTCCTCTAA  GATTCTACCT  GGGATTTTCC  TTTGGAAAAG
```

FIG. 11 (cont. 3)

```
TGAGTTTGAT  GTTCCTTTGT  TTTCACTGTG  ATGTTAATTT  AGAATAATAC
TGAGTTTGTT  GTTCCTTTGT  TTTCACTATG  ATGCTAATTT  AGAATAATAG

TACCTCTGAT  CCTAAAGCAA  AGCAAAGCCT  TACTGGCA--  ----TGCCTGG
CACTTCTGAT  TCTAAAGCTA  ----GCTT    TATTTGCACA  GCCTGCCCTGG

GGAAA-TGTT  TGCTGCTTGC  CTTGAGGAGG  TGGGGTCTCT  TACCACTGCA
GGAAAATGCT  TGCTACTCAT  CTTGAGGAGG  TGGG--CTCT  TACTACTGCA

GGTTGTCTGA  CAGAGACAAT  GCTGAGCTCA  GCATAGGTCA  TGGTGACATT
GGTTGTCTGA  CAGAGACAAT  GCTGAGCTCA  GCATAGGTCA  TGGTGACACT

GCGGAATTGA  GCCTGGCAGA  CCCATTAGGC  ACCAGTCTTT
GGGGTACTGA  GCCTGGCAAA  TATACCAACT  ACCAGTCCTC

CTT-ATCTCC  TGTCCCTCCTG  GTCCCTTGCA  AATATATTGA  TGTGGCAGTG
CTTTATCTCC  TTTCCCCTG   GTTCTTGCA   AATCT--CGA  TGTGGCAGTA
```

FIG. 11 (cont. 4)

```
TGTA----GC  AGCTGAGCCC  TGCTTGCTTT  GTGAGTCCTT  TTATCCCCAT
TATATATAGC  AGCTGAGCCC  T-CTTGCTTT  GTGAGTCTTT  TTCCCCCAT

CTGTGAGATG  CATGTTAATA  GTTTGGCTCG  TAGGATGTCA  C--TACATTT
TTGTGAGATG  AATGTTAATA  GTTTGGTTTC  TTGGATGTCA  CATTACCTTT

GCTAGCATTT  GTGGCTTCAG  TTGTATT---  GGGTTTCATG  TTTTGATTGT
GTAAGGGGTT  AGGGCTTTGG  TTGTATTATT  GGGTTGCATG  TTTTCATTGT

TTGGG--GTT  CTT------G  GTGGGGGAGG  GGGTTCAACA  GAAGGGAGAA
TTTGGACGTT  TTTTTTCTG   GTGGGGGACG  GGTT----CA  GGGGGTTGA

AAGCAAAGCC  TGACAAATGA  CCATCTTTT-  --CTCAGCTA  ATGCACCTGG
AATCCAAGCT  TGACAGATGA  CTTTTTTTT   CCCTCCATCA  ATACACCTAA

GCAATATACA  AGTTTGGGGT  GAATTGCCTG  CTGTGAGGGT  AAA-TGTCAC
GCAATAGACA  AGTTTGAAGT  GAATTGCCTG  CTTCGAGGGC  AAAATATTCC
```

FIG. 11 (cont. 5)

| | | | | | |
|---|---|---|---|---|---|
| TTCAATTAAG | GTAGAAACCC | AGAACAATGA | AAGGTGTGCT | TCCTTCTAAA |
| TTCAGTCAGG | GGAGAAACCC | AGAACAATGA | AAGGTGTACC | TACTTGGAAA |
| | | | | |
| GGTCCCGTAT | GCTGTTCGGA | GAGTCATTTG | TGAATCTTTC | AACAATTAAA |
| GGTCCCATGT | GCTATTCAGG | GACCCATTTG | GGAATCTTTC | CACAAT---- |
| | | | | |
| TTATTCCATT | AAGAGGTGTT | GCTGCAT-CA | GTGG----GG | AGGGGGTGGA |
| -TATTCCATT | AAGAGGTGTT | GCTGCATTCA | TTGGTCGGGG | AGGGATGAA |
| | | | | |
| GCACCTGGGG | GGGAAAAAAA | AGGATTTTGT | GAACAAATGG | AACCGG--GG |
| ACACCTGAAA | GG--AGAAAA | AGGATTCTGT | GATCAAATGG | AAATGAAAGG |
| | | | | |
| GAAGACAGAG | CTAGTAACTT | GTTAAATAAC | TTATTTTTCT | ----AATCC- |
| GAAG-CAGAG | CTAATAGCTT | GCTAAATAAC | TGGGTTTTTT | CGACAATCCC |
| | | | | |
| ----TTTT | TCCCCCCAGC | TTATTTCTTA | TGAATGTCGG | ATAGCTGCAC |
| TCCCCCTTTT | AGACCCCAGC | TTATTTCTTA | TGGATGCCGT | ATAGCGGCAC |

FIG. 11 (cont. 6)

```
CAGCTTGGTG  GGGAAAGGGT  TTGATGAATA  GCACAAAGAC  ACTGGCTGTT
CAGCTTGATG  GGGAGAGGGT  TTGATGAATA  GCACAAAGGC  ACTGGGTATT

CCCTGGAGGC  TGTCCCTTTA  AAGGAGAATC  TTAGTTTATT  CTGGGGGAG
CCCTGGAGGC  TGTCCCTTTA  AAAGAGAATC  CTAGTTTATT  CTGGGG-AG

GGGATGCACA  CATTAGAGTA  GG--AAAGAG  GGCTTGGAAT  AAAATGAAAA
GGGATACACA  TATTAGAGCA  GGCAAAAAAG  GACAAGGAAT  AAAAGTAATT

CACTCCCCCT  TCATAGTCAT  TGTACTGAAA  TGCAAAGACT  GCTTCCTAAG
CAC--CCCCT  TCCTAGCCAT  TGTATTGAGA  TGCAAAGGCT  GCTTCCTA--

CTGGAGA-TG  GTAGCTCCTT  CTGTT-CTCT  TCAAGGGAA
CAGGAGGGTG  CTAGCTCCCT  CTGTTTCTCT  TTGAGGG-AA

TTTGTCAGG  CTATGGATTC  ATTACAACT  GTTAGTCATG  TGGGCATGTG
TTTAGTCAGG  CTATGGATTC  ATTACAACT  GTTAGTCATG  TGGCCATGTG
```

FIG. 11 (cont. 7)

```
TGAGGAAACA GATGCCAGTT TTAATGTATT TAGCCCGAAG TTCCAATTTG
TGAAGGAGCA GATGCCAGTT TTAATGTATT TTGCCCGAAG TTACAATTTG

ATAGGAGCCA CTGTCAGTAA GTCTCAGGAT TTTCAGCTAT TTCAAAATCT
ATAGGAGCCA CTGTCAGTAA GCTCCAGGTT TTTAAGCTAT TTCAA---CA

CCCCTTCTCC TCTGTCTGGA ACAGTGCCAA GAGTGCCCTC CTCTCTATCT
CGCC--CTCC CCAAATTGGA ACAGTGCCAA AAGTGCCACC CTTTCTATCT

CTTACTCCCA ACCCCCACA- -ACCAC-CAG ----CACCC- -CCGCCCAGC
CTTCCTCCTA TCCCCCTCCC CACCATTCAG TCCTCAGCCT ACTGCCCAGC

CCC-TCCTTC TTCTCTATTA AGATCAAATAT TCCTGCAGGT CAGGGGCAAG
CCCCTCCTTC TTCTCTATTA AGATCAAATAT TCCTGCAGGT CAGGGACAAG

CAGCAGATGG GTCACAGGCT TTTTTCAACC AGTTCTTTTC ACAAGCAGCA
CAGCAGATGG GTCACAGGCT TTTTTCAACC AGTTCTTTTC ACAGGCAGCA
```

FIG. 11 (cont. 8)

GATTGCAGAT CTGGATCTGG CTAATATTTA AAATCCCTTC TTTTTCCTT
GATTGCAGCT CTGGATCTGG CTAATATTTT AATTCTCCCC CCT--CCCTT

CTCCTTGTCC CTTTTGTTT TTGCCTCTCT TCACCCCCAT CCCTTCTCC
ATCCAT---C CTTATTCTTT --GCCCTCTCC TTATCTCCAC CCTTTCTCT

CACGCTCAGG TCTCTGA--- ---------- ---------- -
AACAATCAGG TTGCTGTGGT TCCACCAAAA T

FIG. 12
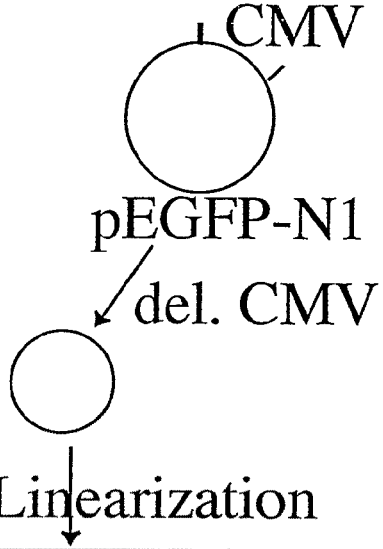
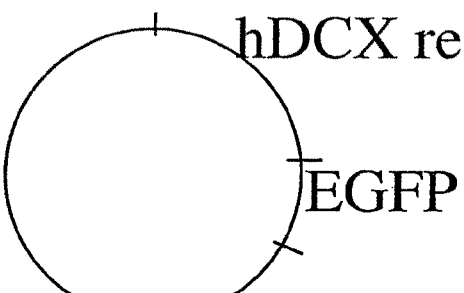
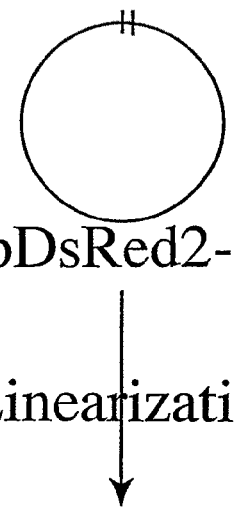
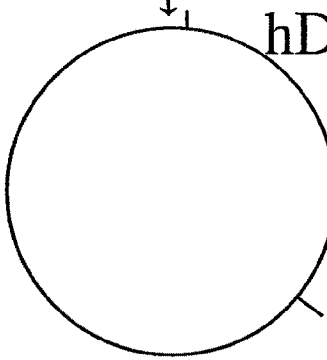

FIG. 13
A
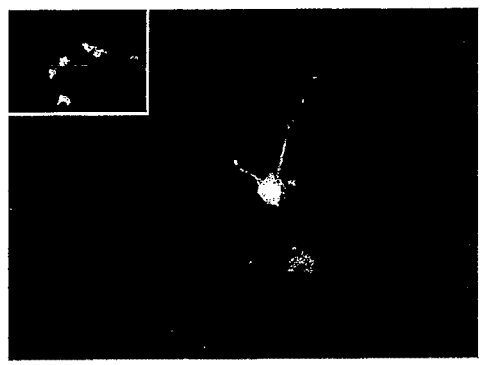
EGFP
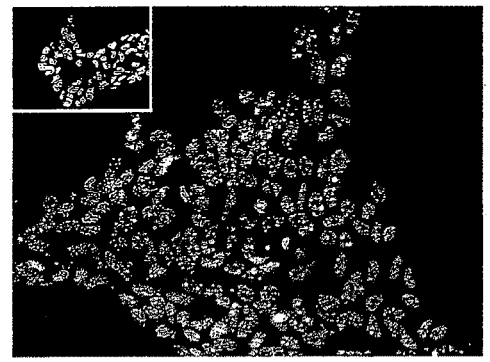
DAPI
B
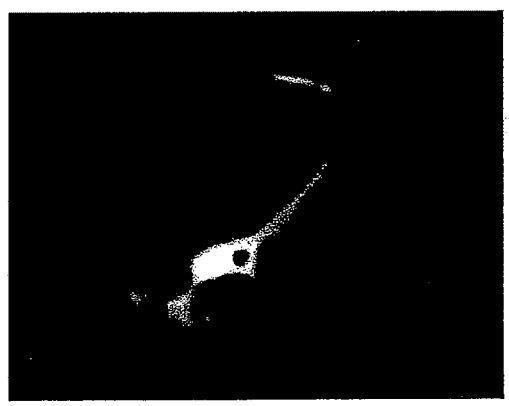
EGFP
C
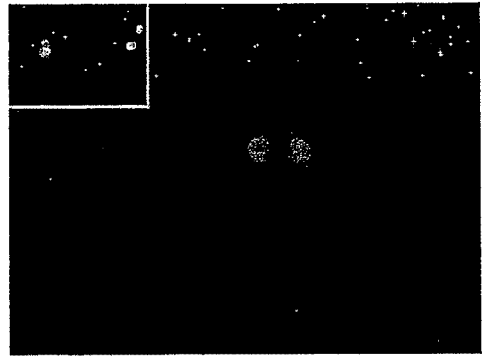
EGFP
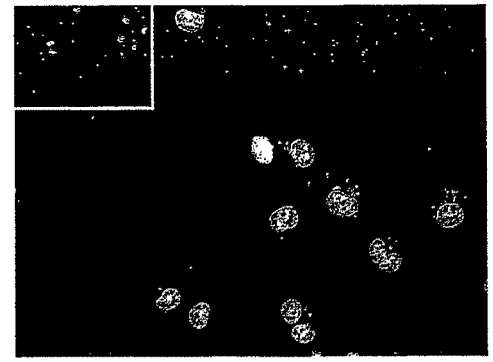
DAPI

FIG. 15
Mouse 33 line 299
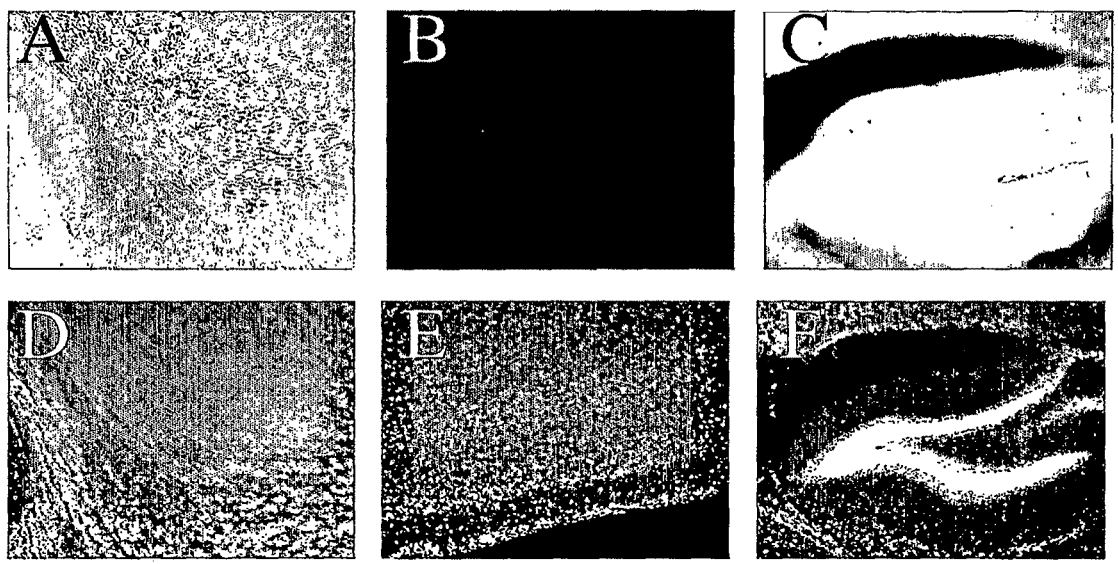
Mouse 71 line 303
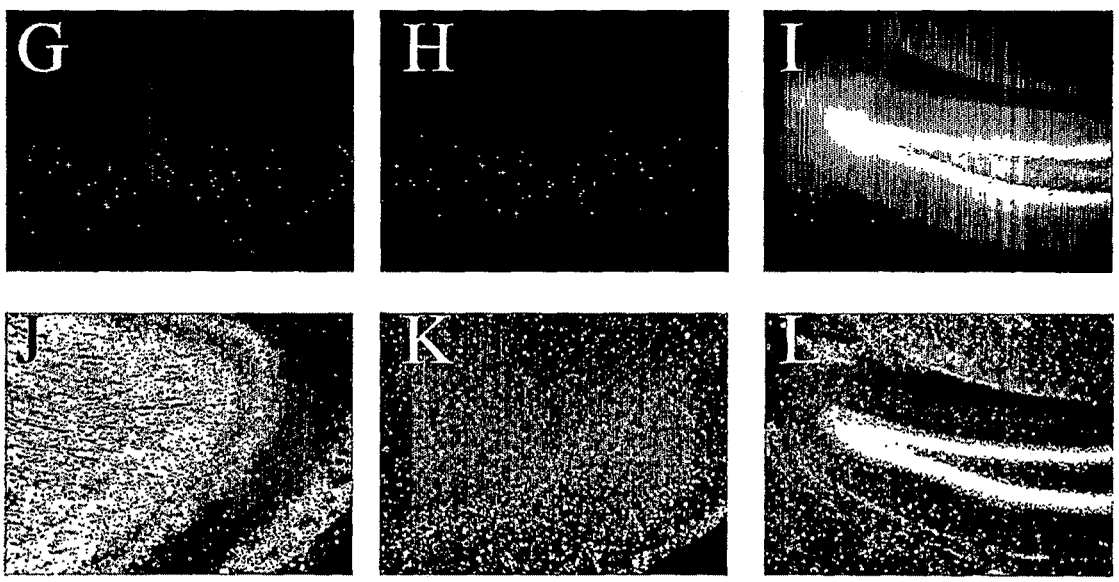

Figure 20B:
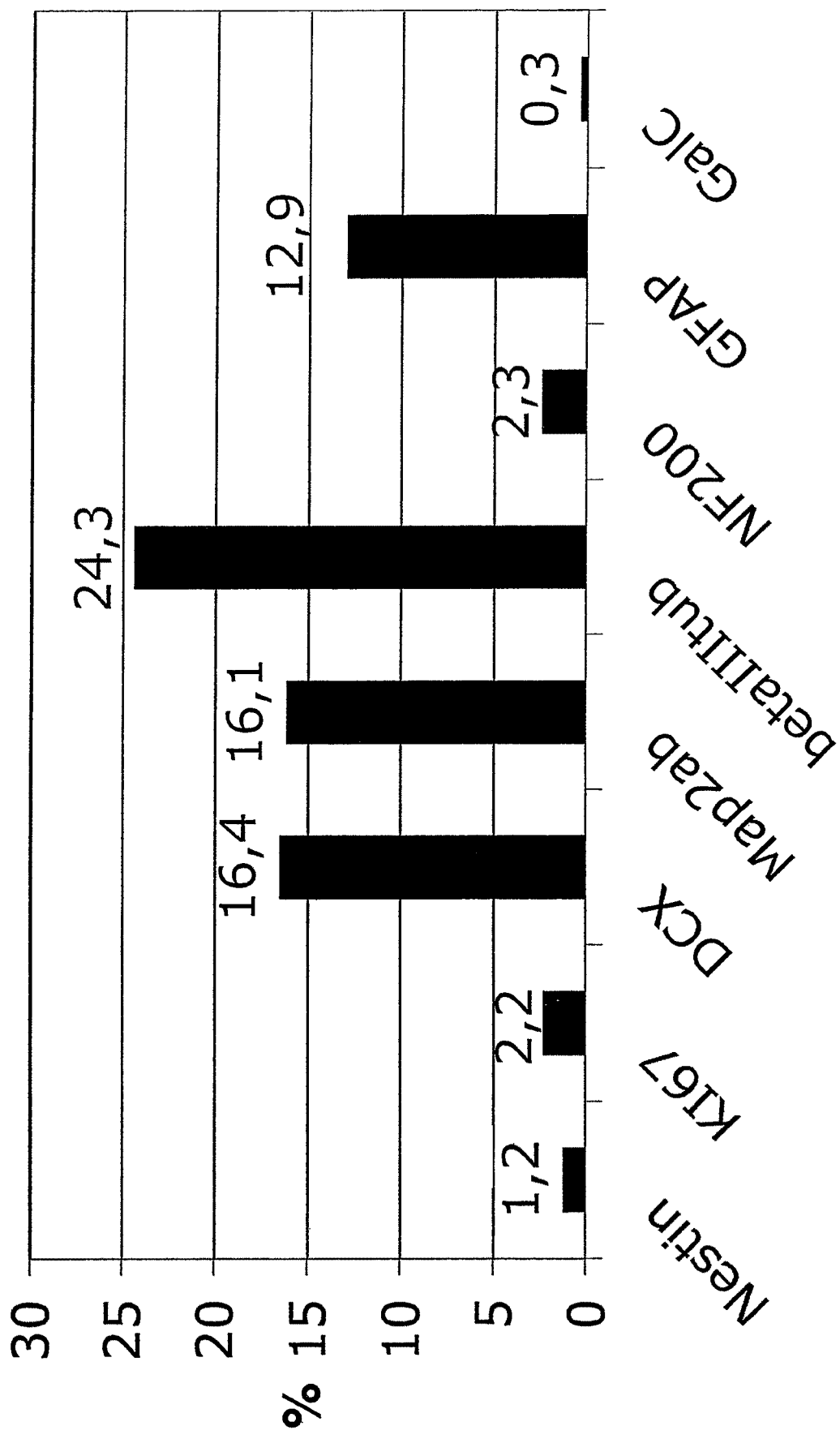

FIG. 20A
DCX     KI67     Nestin
DCX     NF200     betaIIItub
DCX     GFAP     Map2a/b
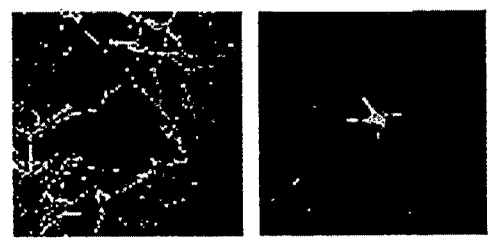
DCX     GalC

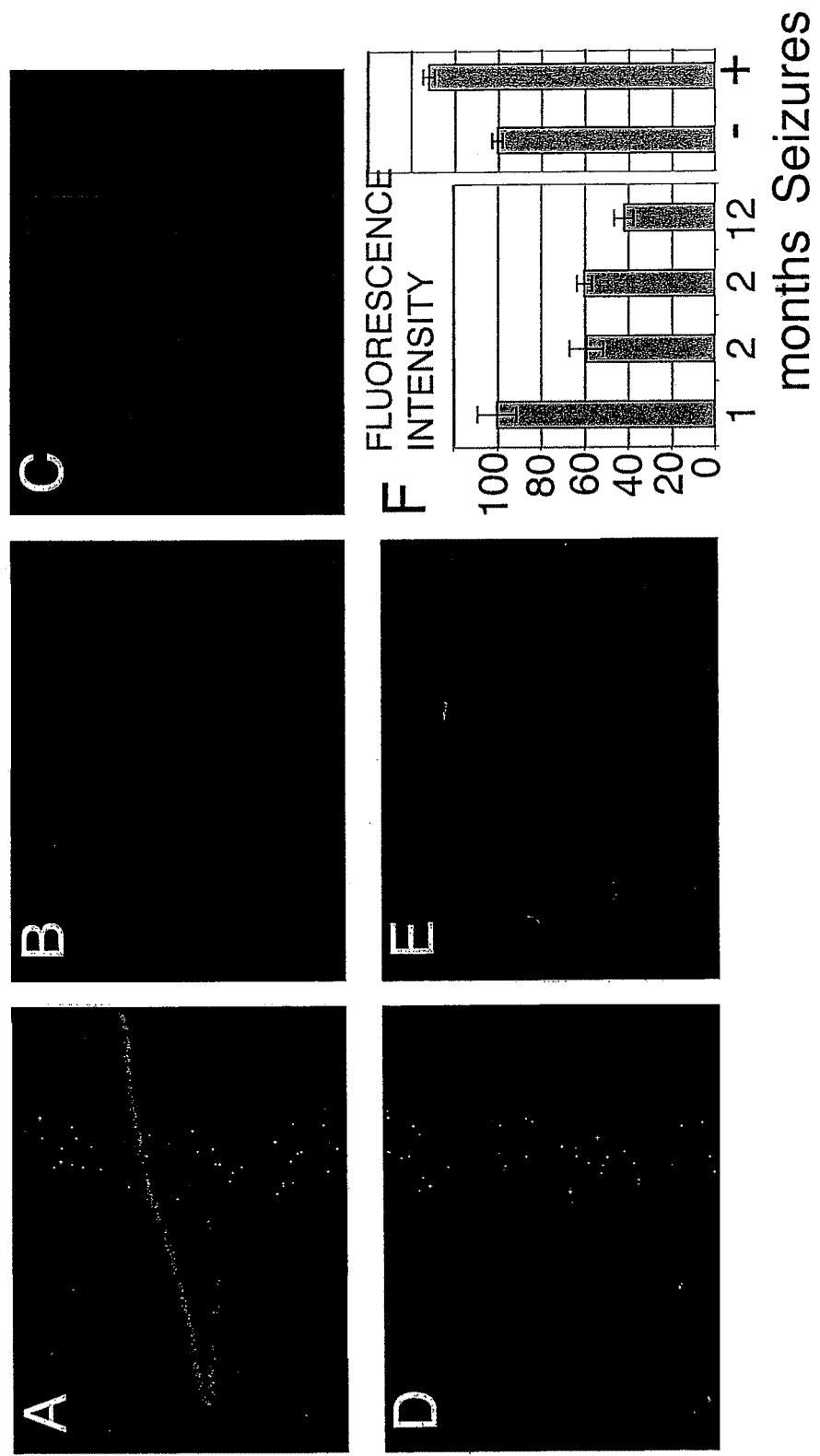

USE OF REGULATORY SEQUENCES FOR SPECIFIC, TRANSIENT EXPRESSION IN NEURONAL DETERMINED CELLS

This application is a divisional of application Ser. No. 12/209,974 filed Sep. 12, 2008, now U.S. Pat. No. 7,947,448, which is a divisional of application Ser. No. 10/543,713 filed Oct. 19, 2006, now abandoned, which is a national phase application under 35 U.S.C. §371 of International Application No. PCT/EP2004/000760, filed on Jan. 28, 2004, which claims priority to European Application No. 03002027.5 filed Jan. 28, 2003 which is hereby incorporated by reference in its entirety.

The present invention relates to the use of regulatory sequences for mediating specific, early transient expression in proliferative neuronal determined cells. Furthermore, the uses of recombinant nucleic acid molecules comprising said defined regulatory sequences for mediating specific, early transient expression in proliferative neuronal determined cells as well as for the generation of non-human transgenic organisms and/or host cells are disclosed. In addition, the invention provides for transgenic non-human animals and/or host cells comprising said regulatory sequences and/or recombinant nucleic acid molecules. The invention also describes methods for the preparation of such vectors, host cells and transgenic non-human animals as well as methods for the detection and/or isolation of neuronal determined cells. Additionally, methods for screening of compounds capable of regulating neuronal determined cell activity, neurogenesis, stimulating proliferation of neuronally committed precursor cells and/or neuronal differentiation are provided and the invention also relates to methods for the detection and analysis of neuronal differentiation, neuronal migration and/or neuronal determination processes. Finally, the invention relates to diagnostic and pharmaceutical compositions comprising the regulatory sequences, recombinant nucleic acid molecules, host-cells or isolated neuronal determined cells described herein.

Multipotent neural stem cells (NSCs) from the developing and adult brain proliferate, self renew and give rise to neurons, astrocytes and oligodendroglia, the three major cell types of the central nervous system (CNS). Neurogenesis, the neuronal differentiation of multipotent NSCs, requires cell fate commitment, neuronal lineage restriction and subsequent differentiation and maturation. Subsequent changes in cell identity from NSCs to neuroblasts, neuronal restricted/determined precursor cells and mature neurons are regulated by intrinsic changes in gene expression. Multipotent NSCs are characterized by expression of "markers", like nestin, Notch1 and Musashi (see Lendahl, Cell 60 (1990), 585-595). However, these markers are not restricted to NSCs, and therefore insufficient for the identification of NSCs. For example, Musashi is found in hepatic cells, testis sertoli cells and cord blood cells, as shown in Shu, Biochem. Biophys. Res. Commun. 293 (2002), 150-154; Saunders, Biol. Reprod. 66 (2002), 500-507 and Sanchez-Ramos, Exp. Neurol. 171 (2001), 109-115. Neuronal restricted/determined precursor cells are characterized by expression of PSA-NCAM (Doetsch, J. Neurosci. 17 (1997), 5046-5061). However, PSA-NCAM expression is not restricted to neuronal determined precursor cells, but it is also found on oligodendrocyte precursors; see Grinspan, J. Neurosci. Res. 41 (1995), 540-551. The βIII isotype of tubulin is used as an early neuronal marker (inter alia, Palmer, Nature 411 (2001), 42-43). Its expression, however, is not restricted to neuronal determined precursor cells, but can still be detected in some mature neurons and also in non-neuronal cells from the pigment epithelium as shown by Moskowitz, J. Neurosci. Res. 34 (1993), 129-134 and Vinores, Exp. Eye Res. 60 (1995), 385-400.

The adult mammalian CNS, although classically seen as a non-regenerative tissue, retains the potential to generate new neurons. Two areas of adult neurogenesis are well documented: the dentate gyrus of the hippocampal formation and the lateral ventricle wall/olfactory bulb axis, as first described by Altman ((1965) J. Comp. Neurol 124, 319-335 and (1969) J. Comp. Neurol. 137, 433-457). Within the hippocampus, newly generated neurons arise from proliferating cells at the border between the hilus and the granule cell layer, see (Cameron, Neuroscience 56 (1993), 337-344; Kuhn, J. Neurosci 16 (1996), 2027-2033 or Seri, J. Neurosci 21 (2001), 7153-7160). Neurogenesis of hippocampal granule cells continues throughout life, although a steady decline is observed with aging (Kuhn (1996), loc. cit; Kempermann, J. Neuroscience 18 (1998), 3206-3212). Cells destined for the olfactory bulb (OB), originate from a population of neural stem cells and progenitors dividing in the wall of the lateral ventricle (Doetsch, J. Neurosci 17 (1997), 5046-5061). The newly generated neuronal restricted/determined precursor cells migrate towards the OB along a structure referred to as the rostral migratory stream (RMS). In the OB, the incoming neuronal restricted precursor cells integrate and complete differentiation as granule cells and periglomerular neurons (Betarbet, J. Dev. Neurosci 14 (1996), 921-930; Winner, Eur J Neurosci. 16(9 (2002)), 1681-1689).

Although neurogenesis still takes place in the adult mammalian CNS, the damaged brain is largely incapable of functionally significant structural self-repair. This reflects the incapacity of NSCs and neuronal restricted precursors present in the neurogenic regions to migrate toward the damaged regions in large amount and rebuild circuitries. In order to reach a critical mass of replacement cells in a specific CNS location, cell grafting appears to be a promising approach. Different sources of cells, such as dissociated fetal mesencephalic tissue, in vitro expanded stem cells derived from blastocysts or embryonic forebrains and neural stem cells from the adult brain have been investigated for their potential use in transplantation experiments, see, inter alia, Brundin, Brain 123 (2000), 1380-1390; Freed. N. Engl. J. Med. 344 (2001), 710-719; Bjorklund, Proc. Natl. Acad. Sci. USA 99 (2002), 2344-2349; Brustle, Curr. Opin. Neurobiol. 6 (1996), 688-695; Englund, Exp. Neurol. 173 (2002), 1-21 or Gage, Science 287 (2000), 1433-1438. In humans suffering of Parkinson's disease, implantation of fetal tissue has resulted in some degree of functional recovery (Piccini, Nat. Neurosci. 2 (1999), 1137-1140; Brundin (2000), loc. cit. or Freed (2001), loc. cit.). However, the highly limited access to fetal tissue and the ethical concerns surrounding its use in patients have strengthened the search for alternative neuronal-restricted precursor cell sources, in particular those harvested from adult tissues. Only recently, first attempts for the direct isolation of NSCs by cell surface antigens or by promoter driven reporter gene expression were undertaken. Multipotent NSCs were directly isolated from fetal human brain tissue using positive selection for CD133 and negative selection for CD34 and CD45 (Uchida, Proc. Natl. Acad. Sci. USA 97 (2000), 14720-14725) or selection for the extracellular domain of Notch1 (Johansson (1999), loc. cit). However, both approaches have their limitations, since neither CD133, nor Notch1 expression is specific for neural stem cells, as shown in Yin, Blood 90 (1997), 5002-5012 or Stier, Blood 99 (2002), 2369-2378. Genetic markers such as the neural stem cell specific enhancer element of the nestin gene, the pan-neuronal tubulin α1 (Tα1) promoter or the oligodendroglia precursor 2',3'-cyclic nucleotide 3'-phosphodiesterase (CNP)

promoter were employed for the isolation and enrichment of specific neuronal progenitor populations by expressing green fluorescent protein (GFP) under control of the different cell type promoter/enhancer elements; see Roy, J. Neurosci. Res. 59 (2000), 321-331, Wang, Dev. Neurosci. 22 (2000), 167-176; Roy, J. Neurosci. 19 (1999), 9986-9995; Sawamoto, J. Neurosci. Res. 65 (2001), 220-227; Kawaguchi, Mol. Cell. Neurosci. 17 (2001)m 259-273; WO 00/23571; WO 98/32879 or WO 01/53503. Yet, the genetic elements employed are merely useful for the isolation of certain cell populations: the nestin-promoter element is useful for the isolation of multipotent neural stem cells, the tubulin α1 (Tα1) promoter for differentiated neurons, and the CNP promoter for the isolation of oligodendrocyte precursors. None of the genetic elements described so far is specific for and can be used for the detection and isolation of neuronal restricted/determined precursor cells, in particular cells which are capable of further proliferation. Such a genetic element or such a marker should ideally be induced in the neuronal restricted precursor population, in order to detect the new neurons while being generated, and later downregulated in mature neurons. Progress in the field of neurogenesis, NSC (neural stem cell) biology, cell isolation techniques and future clinical applications for NSCs is currently limited by the lack of cell type specific gene or marker expression, in particular markers for neuroblasts, neuronal determined cells or neuronal precursor cells which uniquely lead to neurons. There is a clear need for the identification and introduction of such markers.

Adult neurogenesis is typically detected by incorporation of bromodeoxyuridine (BrdU) into dividing cells and co-labeling of BrdU-positive cells with markers for mature neurons. BrdU is a birth-dating marker which permanently labels cells born at the moment of BrdU application and allows, in combination with cell type specific markers, distinct cell fate analysis. Yet, such methods, like the BrdU-incorporation has severe limitations in medical and scientific use, due, inter alia, to the technical and physiological hurdles and the toxicological properties of BrdU. Furthermore, retroviral labeling has been used to track dividing cells and their cell fate within the CNS. However, these methods have their limitations in the detection of neurogenesis (Cooper-Kuhn, Brain Res. Dev. Brain. Res. 134 (2002), 13-21). For example, retroviral incorporation requires invasive intracranial injection, which causes parenchymal lesions and possible inflammatory reactions. Moreover, diffusion barriers prevent retroviral labeling of larger progenitor populations. Finally, though the transfection is stable, virally encoded reporter genes may be downregulated with time (Duch, J. Virol 68 (1994), 5596-5601). On the other hand, BrdU, which integrates in the DNA of dividing cells, is diluted within the progeny of a labeled cell after multiple subsequent divisions. The difficulties associated with these methods and incompatibility with human tissue analysis call for new, specific and quantifiable indicators of neurogenesis.

During the development of the central nervous system, the microtubule binding protein doublecortin (DCX) is associated with migration of neuroblasts. Besides this developmental role, expression of DCX remains high within certain areas of the adult mammalian brain. These areas, mainly the dentate gyrus and the lateral ventricle wall in conjunction with the rostral migratory stream and olfactory bulb, retain the capacity to generate new neurons into adulthood.

Doublecortin (DCX) is first detected at mouse embryonic day 10.5, DCX is expressed at high levels in the developing mouse CNS (des Portes, Cell 92 (1998), 51-61; Francis, Neuron 23 (1999), 247-256 and WO 99/27089). DCX expression is retained within the areas of continuous neurogenesis in the adult brain (Nacher, Eur. J. Neurosci 14 (2001), 629-644). The morphology of DCX expressing cells is consistent with that of migrating neurons. Moreover, many of these cells were co-labeled with PSA-NCAM, an antigen also present on migrating neurons (Bonfanti, Neurosci 62 (1994), 291-305). The Dcx gene was originally described in the context of human cortical disorders (Gleeson Cell 92 (1998), 63-72). Mutant alleles of Dcx provoke a migratory impairment of neurons and lead to cortical dysplasia (des Portes (1998), loc. cit.; Gleeson (1998) loc. cit.; and Couillard-Despres, Curr. Mol. Med. 1 (2001), 677-688).

As mentioned herein above, some further neuro-system related markers or expression patterns have been described in the art. For example, WO 93/07280 describes astrocyte-specific transcription of human genes. In particular, WO 93/07280 discloses sequences capable of regulating astrocyte-specific transcription of glial fibrillary acidic protein (GFAP). WO95/25792 describes an endogenous neuron promoter expressed during growth of both developing and mature neurons, namely the Tα1 α-tubulin promoter. According to WO 95/25792 this promoter drives expression in embryonic neurons, neurons of newborns and remains expressed in adult neurons. In WO 98/32879 a plurality of promoters are employed in a method for separating cells, wherein some of the described promoters are either neuronal or neuron-specific promoters comprising the enolase promoter, MAP-1B promoter, decarboxylase promoter, dopamine β-hydroxylase promoter, NCAM promoter, HES-5, HLH protein promoter, the α1 tubulin promoter (also described in the above-mentioned WO 95/25792), α-internexin promoter, peripherin promoter or the GAP-43 promoter. All the promoters mentioned in WO 98/32879 are promoters which are not specific for neuron-specific early progenitor cells. In particular are disclosed: the neuron-specific enolase promoter (Andersen, Eur J. Cell Bio 62 (1993), 324-332; Alouani, Hum. Gene Ther. 3 (1992), 487-499); the MAP-1B promoter (Liu and Fischer, Gene 171 (1996), 307-308); the L1 promoter (Chalepakis, DNA Cell Biol. 13 (1994), 891-900); the aromatic amino acid decarboxylase promoter (Le Van That, Mol. Brain Res. 17 (1993), 227-238); the dopamine β-hydroxylase promoter (Mercer, Neuron 7 (1991), 703-716); the NCAM promoter (Hoist, J. Biol. Chem. 269 (1994), 22245-22252); the HES-5 HLH protein promoter (Takebashi, J. Biol. Chem. 270 (1995), 1342-1349); the α1-tubulin promoter (WO 95/25792, loc. cit.); the α-internexin promoter (Ching, J. Biol. Chem. 266 (1991), 19459-19468); the peripherin promoter (Karpov, Biol. Cell 76 (1992), 43-48); the synapsin promoter (Chin, J. Biol. Chem. 269 (1994), 18507-18513); the GAP-43 promoter (Starr, Brain Res. 638 (1994), 211-220); the cyclic nucleotide phosphorylase I promoter (Scherer, Neuron 12 (1994), 1363-1375); the myelin basic protein promoter (Wrabetz, J. Neurosci. Res. 36 (1993), 455-471); the JC virus minimal core promoter (Krebs, J. Virol. 69 (1995), 2434-2442); the proteolipid protein promoter (Cambi and Kamholz, Neurochem. Res. 19 (1994), 1055-1060); the cyclic nucleotide phosphorylase II promoter (Scherer, Neuron 12 (1994), 1363-1375). In order to provide means of identifying oligodendrocytic precursor cells, WO 00/23571 proposes the use of a promoter which specifically drives expression in said oligodendrocytes or progenitor cells thereof. As specific promoters, the following promoters are disclosed: the CNP-P1 promoter, the CNP-P2 promoter, the CNP-P1+P2 promoter, the NCAM promoter, the myelin basic protein promoter, the JC virus minimal core promoter, the myelin-associated glycoprotein promoter, the proteolipid protein promoter or the P/CNP2 promoter. WO 01/53503 describes a method for enriching hippocampal neural progenitor cells by employing a promoter which specifically drives expression in neural progenitor cell but not in other cells of hippocampal tissue. Yet, WO 01/53503 proposes the use of Tα1 tubulin promoter or nestin enhancer (Lothian, Eur. J. Neurosci. 9 (1997), 452-462). As pointed out herein above Tα1 tubulin promoter is also active in mature neurons and nestin is not only expressed in neuroepithelial cells but also in other cell populations (see Cai, Dev. Biol. 251 (2002), 221-240). Furthermore, the intermediate filament nestin is also expressed after traumatic injury of spinal cord or brain tissue; see, inter alia, Shibuya, Neurosci. 114 (2002), 905-916. In addition, nestin expression persists in astrocytes (Schmid-Kastner, Int. J. Dev. Neurosci. 20 (2002), 29-38) and a large percentage of nestin-expressing cells have been proposed to be committed to astroglial cells (Wei, Brain Res. Dev. Brain Res. 139 (2002), 9-17). The neuron-specific enolase promoter is often expressed in various tumors, and is found routinely in histopathological analysis. Therefore the medical or diagnostic use of this promoter is risky since it may lead to an enrichment of cells which are tumorigenic or an enrichment of poorly differentiated cells of non-neuronal origin; see Lee, Surg. Today 30(7) (2000), 658-662; Nakachi, J. Gastroenterol 35(8) 6 (2000), 31-634; Standop, Pancreas 23(1) (2001), 36-39 or Muroi, Intern. Med. 39(10) (2000), 843-846. MAP-1B promoter is expressed at high level in mature neurons undergoing synaptic rearrangement or sprouting. It is also highly expressed in mature neurons present in the dorsal root ganglia and the motor neurons of the spinal cord, see Illing, Audiology and Neurootology 6 (2001), 319-345 or Soares, Eur. J. Neurosci. 16(4) (2002), 593-606. The L1 promoter leads to protein expression in mature neurons of the brain such as Golgi, granule, basket and stellate cells of the cerebellum and pyramidal, granule, hilar interneurons in the hippocampus and ganglion, amacrine and horizontal cells in the retina; Rünker, J. Neurosci. 23(1) (2003), 277-286. In adult mammals, the aromatic amino acid decarboxylase promoter is active in the dopaminergic and serotonergic neurons, therefore the promoter is merely active in mature, differentiated neurons; Chatelin, Brain Res. Mol. Brain. Res. 97(2) (2001), 149-160. The dopamine beta-hydroxylase promoter is mainly active in dopaminergic, differentiated neurons, Matsushita, J. Neurochem. 82(2) (2002), 295-304. The NCAM promoter is not neuron-specific, since during in vitro myogenesis of muscle cells, an upregulation of some NCAM transcripts can be observed. Furthermore, NCAM can also be expressed on Schwann cells; Roubin, Exp. Cell Res. 200(2) (1992), 500-505 or Dedkov, Acta Neuropathol 103(6) (2002), 565-574. HES-5 helix-loop-helix promoter is a promoter which is known to be active in cells differentiating into astrocytes; Ohtsuka, J. Biol. Chem. 276(32) (2001), 30467-30474. In the adult CNS the alpha-internexin promoter is active mainly in differentiated neurons of the brain, cerebellum and spinal cord. In particular, it is still active in the cerebellar granule cells; Ching, J. Neurosci. 19(8) (1999), 2974-2986 and Lavavasseur, Mol. Brain. Res. 69 (1999), 104-112. Peripherin promoter is still active in many differentiated, mature neurons of the peripheral nervous system. In the central nervous system, it is expressed in neurons with peripheral projection. It can be reinduced in the central nervous system following stab injury and cerebral ischemia; see, inter alia, Beaulieu. Brain Res. 946 (2002), 153-161. Also the synapsin promoter is active in mature, differentiated neurons; see Chin, J. Biol. Chem. 269 (1994), 18507-18513. Similarly, the GAP43 promoter is induced in regenerating mature neurons; see Uvadia, Development 128(7) (2001), 1175-1182. Cyclic nucleotide phosphorylase I promoter, proteolipid protein promoter and myelin basic protein promoter are activated and specific in oligodendrocytes; see Scherer, Neuron 12(6) (1994), 1365-1375; Wrabetz, J. Neurosci. Res. 36(4) (1993), 455-471 and Cambi, Neurochem. Res. 19(8) (1994), 1055-1060. Similarly, cyclic nucleotide phosphorylase I promoter is active in oligodendrocyte precursors; Scherer, Neuron 12(6) (1994), 1365-1375. Also, the previously described JC virus minimal core promoter is in vivo merely active in glial cells; see Krebs, J. Virol. 69(4) (1995), 2432-2442.

In summary, to date there are neither a highly-specific markers nor gene regulation sequences available which provide for either detection means of neuronal restricted/determined cells or which would mediate specific expression in such cells in mammalians, preferably in humans.

The discussion of the prior art herein above highlights the need for means and methods for the detection and/or isolation of specific cells which are restricted to a neuronal fate, i.e. for the detection and isolation of neuronal restricted precursor cells. The difficulties associated with prior art methods discussed herein above and incompatibility with human tissue analysis confirm that novel, specific and quantifiable indicators of neurogenesis are desired. Considering the therapeutic benefit of such cells and the constant need for cell-specific gene expression, the technical problem underlying the present invention is the provision as selective markers and labeling-methods for neuronal determined cells in vivo and in vitro.

According to the invention, this problem is solved by the provision of the embodiments of the claims.

Thus, the present invention relates to the use of a regulatory sequence for specific, early transient expression of a heterologous nucleotide sequence in proliferative neuronal determined cells, whereby said regulatory sequence is selected from the group consisting of (a) regulatory sequences comprising the nucleotide sequence shown in SEQ ID NO: 1, as shown in SEQ ID NO: 2, as shown in SEQ ID NO: 3 or as shown in SEQ ID NO: 4;

(b) regulatory sequences comprising the nucleotide sequence contained in the insertion of clone DSM 15111 and obtainable by amplification using two oligonucleotides having the sequences indicated under SEQ ID NO: 9 and SEQ ID NO: 10;

(c) regulatory sequences comprising at least one nucleotide sequence of SEQ ID NO: 1 from position 1166 to 1746, from position 1166 to 2049, from position 1785 to 1843 or from position 1953 to 2775;

(d) regulatory sequences comprising at least one nucleotide sequence of SEQ ID NO: 2 from position 529 to 1079, from position 529 to 1390, from position 1118 to 1175 or from position 1291 to 2137;

(e) regulatory sequences comprising at least a functional part of a sequence of (a) to (d) and causing specific expression in neuronal determined cells;

(f) regulatory sequences comprising a nucleotide sequence which is at least 75% identical to a sequence as defined in (a) to (d) or which comprises a nucleotide sequence which is at least 78% identical to the nucleotide sequence as shown in SEQ ID NO: 1 from position 1166 to 1746 or from position 1166 to 2049 or to the nucleotide sequence shown in SEQ ID NO: 2 from position 529 to 1079, from position 529 to 1390 which comprises a nucleotide sequence which is at least 82% identical to the nucleotide sequence as shown in SEQ ID NO: 1 from position 1785 to 1843 or to the nucleotide sequence as shown in SEQ ID NO: 2 from position 1118 to 1175 or which comprises a nucleotide sequence which is at least 75% identical to the nucleotide sequence as shown in SEQ ID NO: 1 from position 1953 to 2775 or to the nucleotide sequence as shown in SEQ ID NO: 2 from position 1291 to 2137; and (g) regulating sequences comprising a nucleotide sequence which hybridises with a complementary strand of the regulatory sequence as defined in (a) to (f).

The regulatory sequences described herein are capable of imparting neuronal determined, cell-specific expression to nucleotide sequences which are controlled by them. Furthermore, the herein described regulatory sequence have the advantage that they are active in proliferating neuronal determined cells.

As documented in the appended examples the invention is based on the surprising finding that doublecortin (DCX) is transiently and early expressed in proliferating neuronal progenitor cells, newly generated proliferating neuroblasts, migrating neuronal precursor cells as well as proliferating neuronal determined/restricted cells. All these cells lead to neurons, and the regulatory sequence as defined herein can successfully drive expression of heterologous genes or coding sequences in cells which are neuronal determined/neuronal restricted and mitotically active.

In this invention, it is shown that doublecortin acts as an indicator for adult neurogenesis, and the temporal expression pattern of DCX in neurogenic regions of the adult brain was determined. The invention as documented in the examples also relates to the fact that it can be shown that when newly generated cells begin expressing mature neuronal markers, DCX immunoreactivity is sharply decreased below the level of detection and remains undetectable thereafter. This transient expression pattern of DCX in proliferative neuronally committed progenitor cells/neuroblasts documents that DCX is a suitable marker for adult neurogenesis and provides, inter alia, for an alternative to BrdU labeling. It is also observed and documented that the amount of cells expressing DCX is decreased with age, which coincides with the reduction of neurogenesis in the aging dentate gyrus. The results of the invention could only be obtained since the antibodies employed in this study are highly specific for DCX. Furthermore, the examples convincingly show that the regulatory sequence, relating to DCX expression in vivo and as defined herein, is sufficient and specifically active in neuronal determined/neuronal restricted cells. As documented in the appended examples, in an adult transgenic mouse expressing EGFP under control of the regulatory sequence of the invention, high expression of EGFP is found exclusively in neurogenic regions of the brain. Expression can not be detected in organs other than the CNS, such as skin, muscle, gut, kidney, liver, heart, lung, etc. Within the neurogenic regions (dentate gyrus of the hippocampus, ventricle wall, rostra-migratory stream and olfactory bulb), expression of EGFP largely overlaps with the endogenous expression of DCX. Therefore, EGFP under control of the regulatory sequence as defined herein is expressed in neuronal restricted/determined cells which are mitotically active. Furthermore, the morphology of EGFP expressing cells resembles that of young immature neurons or of migrating neuronal precursors cells. In context of this invention, it can be shown that EGFP expression does not co-localize with glial fibrillary acidic protein (GFAP), a marker for astrocytes, excluding a astroglial cell fate of EGFP positive cells. Similarly, the regulatory sequence of the invention does not drive expression of EGFP in HEK293 cells, a non-neuronal lineage cell type.

Neurogenesis is a process that involves the regulation of cell proliferation, determination and differentiation, in particular of neuronal cells like, but not limited to, dopaminergic/ cholinergic/GABA-ergic or noradrenergic neurons. Neural stem cells are slowly dividing multipotent cells residing in neurogenic regions. They give rise to fast dividing neuronal determined precursor cells that by proliferation increase and potentiate the neurogenic activity of a neural stem cell. After several rounds of division they turn postmitotic and start to neuronally differentiate and to mature. Therefore, dynamic changes of the level of neurogenesis occur mainly at the level of neuronal precursor proliferation. Cells that give rise to cells expressing DCX might have been proliferative or quiescent. In context of this invention, "quiescent" means currently not dividing cells which have the potential to divide in the future. The term "neurogenesis" as used herein describes all events that occur when cells at one point of their life induce and start a neuronal determination/neuronal differentiation program that ultimately leads to the acquisition of a neuronal phenotype. Said cells may be neural stem cells, but may also be other cells/cell types of the organism that have the potential to acquire a neuronal phenotype. Corresponding examples are given below and in the experimental part.

In accordance with this invention, the term "transient and early expression"/"early transient expression" defines a period of time starting after the moment that a cell has restricted to a neuronal fate, but before said cell expresses marker for mature neuronal cells/neurons, such as NeuN. In accordance with this intervention and documented in the examples, the activity of the DCX regulatory sequence described herein is progressively down-regulated concomitantly with neuronal maturation, defined by the appearance of mature neuronal markers, like NeuN.

As demonstrated in the experimental part, it could be shown that DCX is expressed early, already during neuroblast proliferation, and long before (7 days) the onset of expression of NeuN in the rat dentate gyrus. This is in sharp contrast to data from Kempermann, Development 130 (2003), 391-399, which demonstrate that neurons acquire a mature phenotype (NeuN expression) right after cell birth (1 day after BrdU incorporation). Based on these data, Kempermann concludes that the use of DCX is not sufficient as a indicator of neurogenesis. Furthermore, and in contrast to this invention, Cooper-Kuhn (2002), loc. cit. showed that DCX is not present in the proliferative pool of neuronal precursors, but only in postmitotic, non-proliferative cells. However, for the uses, methods, genetically modified cells and non-human organisms provided in this invention it is particularly important that DCX is expressed in proliferating cells. For example for the isolation of neuronally committed progenitor cells, for in vitro propagation, for (drug) screening procedures that search for compounds with the capacity to increase the pool of neuronally committed progenitor cells in vitro as well as for medical interventions in the adult brain as described herein, it is important that proliferative, neuronally committed cells capable of specifically expressing heterologous sequences (nucleic acid molecules, genes, etc.) as described herein are employed. All these uses and methods, accordingly, require that the targeted cell type is proliferatively active.

The term "neuronal determined cell" relates to a cell/cell type that will (upon and during differentiation) exclusively lead, directly or via its progeny, to neurons. It is also envisaged that said term relates to cells/cell types which, under experimental settings or under in vitro conditions selected, acquire a neuronal phenotype. An example of such conditions is given in the appended experimental part relating to retinal pigmented epithelium (RPE) cells, wherein it is illustrated that the regulatory sequences described herein may be active in RPE cells and that these cells have the capacity to acquire a neuronal phenotype. Therefore, the term "neuronal determined cell" also comprises cells which are not necessarily of neuro-ectodermal origin, like inter alia, cells from the hematopoietic system, mesenchymal cells or ectodermal cells. Further definitions and explanations of the term "neuronal determined cell" are given herein below and in the experimental part.

The transient and early expression of the heterologous nucleotide sequence is specifically and/or uniquely observed in the above defined neuronal determined cells. Accordingly, the term "specific, early and transient expression" means that the early and transient expression is due to the activity of the regulatory sequence defined herein and that said activity leads to the expression of a heterologous nucleic acid molecule in neuronal determined cells.

The invention provides for a selection and marker system for neuronal-restricted cells, preferably neuronal-restricted precursor cells and for an indicator system for neurogenesis, preferably for neurogenesis occurring in a mammal postnatally, most preferably for neurogenesis in the mammalian adult brain. The findings as documented in this invention are in clear contrast to results and interpretations in the art. For example Kempermann (2003), loc. cit. is of the opinion that it is not sufficient to use the neuronal marker doublecortin (DCX) as indicator of neurogenesis. In Kempermans work, the relative number of new neurons, as detected by BrdU/NeuN doublelabeling remains stable during the period of investigation (1 day to 11 months after BrdU labeling). Yet, Kempermann and co-workers miss the early time points (between 2 h and 7 days after single BrdU-injection) and, accordingly, the initial wave of BrdU/DCX positive cells that later turn into Brdu/NeuN cells is not observed. Therefore the results presented herein are in clear contrast to data from Kempermann, Development 130 (2003), 391-399, which demonstrate that neurons acquire a mature phenotype (NeuN expression) right after cell birth (1 day after BrdU incorporation). Based on these data, Kempermann concludes that the use of DCX is not sufficient as a indicator of neurogenesis.

Similarly, Nacher, European Journal of Neuroscience 14 (2001). 629-644, teaches that DCX is expressed and found in cells within areas, where "no adult neuronal migration occurs". Nacher concludes that DCX is expressed in differentiated neurons and speculates "that DCX expression in differentiated neurons could be related to its capacity for microtubule reorganization". In contrast to Nacher (2001), the invention and the appended examples document that DCX-downregulation in newly born neuronal determined cells coincides with the maturation into neurons and that in matured neurons, DCX is not detected. Therefore, the prior art was neither able to relate the DCX expressing cell population to the later NeuN positive mature neurons nor to the fact that DCX is merely transiently expressed early in neuronally committed proliferating progenitor cells. The prior art was not able to relate DCX expression to the proliferating pool of neuronally determined precursor cells. At the most, the prior art, like Nacher (2001), loc. cit. and Cooper-Kuhn (2002), loc. cit., has speculated that DCX may be a marker for "immature", "young" and/or "migrating" non-proliferative and post-mitotic neurons or even non-neuronal cells, such as glial cells. In contrast, the present invention shows that DCX-promoter driven expression is a useful transient marker for early neurogenic events such as neuronal commitment and neurogenic proliferation and can be successfully be employed in the uses and methods provided herein.

The prior art considered DCX as a marker specific for postmitotic, non-proliferative young neurons, i.e. postmitotic cells which lost irreversibly their capacity to divide. Yet, in contrast to the prior art it is documented herein and in particular in the appended examples that DCX is expressed already in the proliferating pool of neuronal precursor cells. This surprising finding does not only allow the detection of these neuronal restricted/determined cells and, accordingly, the detection of dynamic changes in neurogenesis but also provides for unique tools for the detection/identification and/or verification of neurogenetic substance; as will be described herein below.

Furthermore, the invention shows that neither DCX immunoreactivity nor EGFP expression under control of the human DCX regulatory sequence described herein does co-localize with glial fibrillary acidic protein (GFAP), a marker for astrocytes, excluding an astroglial cell fate of cells expressing DCX protein or EGFP under the herein defined regulatory sequences. The invention documents in addition that DCX is not expressed in glial cells, such as astrocytes or oligodendrocytes, which is in clear contrast to the notion by (Nacher, Europ. J. Neurosc. 14 (2001), 629-644) that DCX is also expressed in glial cells.

With the provision of the specific uses of the regulatory sequences provided herein, it is now possible to detect and/or select neuronal-determined cells (i.e. newly generated neurons) in vivo and in vitro. Accordingly, the present invention provides for specific uses (detailed herein below) for said regulatory sequences as well as for useful host cells and host organisms, like transgenic non-human animals, which comprise said regulatory sequences and are particularly useful in methods described herein below. In contrast to methods in the prior art employing immunohistological approaches which comprise detrimental fixation and/or permeabilization steps, the invention now provides for means wherein neuronal progenitor/stem cell activity may be determined, measured and analyzed without fixation. Accordingly, the present invention provides for methods for in vitro and in vivo detecting and selecting neuronal-restricted precursor cells, deriving, inter alia, from organs and larger population of mixed cell types from mammals, preferably from mouse or rat, most preferably from human. Therefore, the invention also comprises specific uses of a regulatory nucleic acid sequence defined herein. The inventive regulatory sequences may be used, inter alia, to isolate neuronal-restricted proliferative cells, to alter the biology of neuronal-restricted cells, as well as to identify neuronal-restricted cells within a large population of mixed cell types, both in vitro and in vivo. Preferably said cells are neuronal restricted/determined progenitor cells. The specific neurogenesis marker/indicator provided herein and documented in the appended examples are also useful for the analysis of potential therapeutics and the discovery of drug targets to stimulate endogenous CNS stem cells in order to generate new nerve cells in the CNS. In addition, such a genetic indicator provided herein allows the in vitro and in vivo detection and isolation of any cell in an organ or larger population of mixed cell types that is in the process of acquiring a neuronal phenotype. Therefore, such a marker/indicator system provided herein allows the detection means for processes associated with neuronal transdifferentiation. The corresponding embodiments for these uses and methods are provided herein below.

The term "regulatory sequence" refers to nucleotide sequences which influence the expression level of a nucleic acid molecule, e.g. a gene (or of a nucleic acid sequence coding for an, inter alia, antisense molecule), for instance by rendering expression tissue- or cell specific. In this sense, regulatory sequences are understood to mean elements hereinafter also called regulatory elements, which impart to a promoter, preferably to a minimal promoter, additional expression properties. In the context of the invention, the term "promoter" refers to nucleotide sequences which are necessary to initiate transcription, that is to say to bind RNA polymerase, and for instance contain the TATA box or a TATA-box like motif. Moreover, the term "regulatory sequence" may also comprise sequences outside the 5'-flanking promoter region. Such sequences are functional in both orientations and are less fixed in their position than promoters, they are preferably within the region of the non-translated sequences of the mammalian DCX gene, preferably mouse or human, as they are described within the framework of the present invention (SEQ ID NOs. 1 to 4). Such sequence elements may include enhancers, silencers as well as further modulators which may regulate the expression of a gene up or down or which may render the promoter described herein inducible. Enhancers or silencers are often located in introns or in the 3'-flanking region of a gene. The regulatory sequence may also be a promoter which within the meaning of the invention is characterized by exerting all functions of a promoter, that is to say initiation of RNA polymerization, mediation of a specific expression strength and regulation of expression, preferably depending on the cell type, especially preferably with specificity for neuronal determined/neuronal restricted cells, preferably neuronal determined/restricted progenitor cells. The sequences represented in SEQ ID NOs. 1 to 4 or the above-defined segments of said sequences are regulatory sequences which at the same time correspond to the definition of a promoter.

An example of such a regulatory sequence in accordance with this invention is the insert of deposited clone DSM 15111. DSM 15111 is the plasmid pEGFP-N1 (from Clontech, GenBank U55762; with deleted CMV promoter) comprising an insert corresponding to nucleotide 1 to nucleotide 3509 of SEQ ID NO. 1, and referenced by the depositor as STBL2-phuDCXpromoEGFP1. DSM 15111 was deposited at the Deutsche Sammiung von Microorganismen und Zellkulturen GmbH, Braunschweig, Germany on Jul. 25, 2002. Said deposit was made in by University of Regensburg (Klinikum), Franz-Josef-Strauss Allee 11, 93053 Regensburg, Germany. The insert of deposited clone comprises the human regulatory sequence of DCX as defined herein above may be obtained by methods known in the art, which comprise, e.g. PCR-reactions. For example, with the use of oligonucleotides, for instance sequences as indicated under SEQ ID NOs. 9 and 10, the complete promoter/regulatory sequence of the human DCX gene can be amplified; see also appended Example II. Said two oligonucleotides (oligo no: 1: AAC ACC TAT TAA TGC CCA; SEQ ID NO.: 9 and oligo no: 2: TCA GAG ACC TGA GCG TGG GAG M; SEQ ID NO.: 10) may also be employed to obtain a regulatory sequence of the present invention from the deposited clone DSM 15111. By means of oligonucleotide pairs 5'-deleted or 3'-deleted fragments of the human DCX regulatory sequences which still allow neuronal determined cell-specific expression, can be amplified and obtained. By provision of the sequences disclosed herein, the person skilled is readily in a position to deduce corresponding oligonucleotides. Accordingly, oligonucleotide pairs which enable a skilled person to amplify the corresponding promoter fragments from the deposited clone can be derived from the nucleotide sequences indicated in SEQ ID NOs. 1 to 4. When the regulatory sequences of the invention are provided from the human DCX regulatory sequence by amplification from clone DSM15111, the specificity of the PCR reaction can be increased by a preceeding additional PCR reaction. Moreover, the sequence of the promoter fragments can be detected by direct sequencing with the deposited clone serving as a template. To this end, a skilled person can derive sequencing primers from the nucleotide sequences indicated under SEQ ID NOs. 1 to 4.

The invention is based on the finding that transient, early DCX expression—provides for means for the detection and isolation of neuronal determined and proliferative cells and that an about 3.5 kb promoter fragment of the human DCX gene (FIG. 9 and SEQ ID NO. 1, respectively) cloned upstream of the coding region of a reporter gene (green fluorescent protein, EGFP, or DsRed2) led to the expression of said reporter gene in, inter alia, neuronal precursor cells from dissociated telencephalon (mouse) cultures, in young neuroblasts of human fetal cortical stem cell cultures (see appended examples) or in cultured cells, like day 10 to 14 mouse embryonic forehead cells. In addition, it could be documented that non-human transgenic animals expressing marker genes (e.g. EGFP) under the control of the regulatory sequences disclosed herein, only show marker-gene expression in newly generated, neuronal determined/restricted precursors, in particular in brain regions involved in active neurogenesis. So far, the prior art has not provided sequences or means which bring about the above described specificity of DCX expression. The specificity for neuronal-restricted/neuronal determined cells of the regulatory sequences functional parts thereof can be proven, inter alia, by deletion and transfections studies provided herein. For example, transfection of recombinant molecules, comprising a regulatory sequence (or a functional fragment or part thereof) of the present invention will not lead to a expressed (marker/reporter) sequence in non-neuronal cells, like fibroblasts or HEK293 cells. Yet, a corresponding transfection into cells which are neuronal precursor cells, like transfection into cultured day 10 to day 14.5 embryonic mouse forebrain cells, leads to an activation of the regulatory sequence as disclosed herein and the corresponding marker/reporter sequence is expressed. Therefore, the skilled artisan is in a position to deduce, inter alia, functional parts or fragments of the inventive regulatory sequences.

Isolation of partial sequences from one of the above-described regulatory sequences can be achieved by standard molecular-biological methods known to a skilled person, for instance according to Sambrook (Molecular Cloning: A Laboratory Manual, $2^{nd}$ edition, Cold Spring Harbor Laboratory Press, Cold Spring Harbor N.Y. (1989)). This source can also be drawn on for all other molecular-biological techniques mentioned in the present description. In order to test the isolated fragments for cell-specificity in neuronal restricted cells, the methods described in the examples and herein below can be used. For this purpose, the fragments of sequences as defined above, are, inter alia, cloned into expression vectors comprising an additional marker gene/reporter gene and, in parallel experiments, the expression of a reporter gene in neuronal-restricted cells and in cells not expressing DCX or cells which are not or are not yet neuronal-restricted/determined (for instance, still pluripotent stem cells, glial precursor cells, glioblasts, astrocytes, mature neurons, nonnervous system cells, like fibroblasts or epithelial cells). Subsequently, it is measured in (transient) assays whether the fragment of the regulatory sequence disclosed herein leads to a specific expression of the marker/reporter gene in the neuronal restricted/determined cell. Specific expression in neuronal-restricted cells within the meaning of the invention is, e.g., acknowledged if the level of expression compared to the cells not expressing DCX or the corresponding marker gene is increased at least 5-fold, preferably at least 8-fold, especially preferably at least 10-fold, particularly preferably at least 15-fold and most preferably at least 20-fold.

Functional fragments of the regulator sequences to be employed in accordance with the present invention preferably comprise, but are not limited to, regulatory sequences comprising at least one nucleotide sequence of SEQ ID NO: 1 from position 1166 to 1746 (or from position 1166 to 2049), from position 1785 to 1843 or from position 1953 to 2775 and/or at least one nucleotide sequence of SEQ ID NO: 2 from position 529 to 1079 (or from position 529 to 1390), from position 1118 to 1175 or from position 1291 to 2137. However, in a more preferred embodiment of the present invention, the functional fragment of the regulatory sequence for DCX expression (i.e, the regulatory sequence capable of causing early transient expression of heterologous nucleotide sequences in neuronal determined cells) comprises or is the nucleotide sequence as shown SEQ ID. NO. 1 from nucleotides 1166 to 1746 or from nucleotides 1166 to 2049 and from nucleotides 1953-2775 (corresponding to "regions 2 and 4" as defined in appended FIG. 12). Similarly, said regulatory sequence may comprise or may be the nucleotides as shown SEQ ID. NO. 2 from nucleotides 529-1079 or from nucleotides 529 to 1390 and from nucleotides 1291-2137 (also corresponding to "region 2 and 4" as defined in appended FIG. 12). In a most preferred embodiment of the present invention, the regulatory sequence to be employed is the nucleotide sequence defined as "region 2" herein and in the appended examples, whereby said region may also (and in addition) comprise the following "exon" or "exons". Accordingly, the regulatory sequence to be employed, in one embodiment, is or comprises nucleotides 1166 to 1746 (or 1166 to 2049) of SEQ ID NO. 1 or is or comprises nucleotides 529 to 1079 (or 529 to 1390). In this context, also nucleotide sequences which are at least 78%, more preferably at least 80%, more preferably at least 85%, more preferably at least 90%, more preferably at least 95% and most preferably at least 99% identical to the nucleotide sequence as shown in SEQ ID NO: 1 from position 1166 to 1746 (or 1166 to 2049) or to the nucleotide sequence shown in SEQ ID NO: 2 from position 529 to 1079 (or 529 to 1390) and/or nucleotide sequences which are at least 75% more preferably at least 80%, more preferably at least 85%, more preferably at least 90%, more preferably at least 95% and most preferably at least 99% identical to the nucleotide sequence as shown in SEQ ID NO: 1 from position 1953 to 2775 or to the nucleotide sequence as shown in SEQ ID NO: 2 from position 1291 to 2137 may be comprised in a regulatory sequence that causes/drives expression in neuronal determined cells. It is also envisaged that the regulatory sequence merely comprises the nucleotide sequences as shown in the herein defined regions 2 and 4 (see FIG. 12) or homologues thereof which are at least 78% more preferably at least 80%, more preferably at least 85%, more preferably at least 90%, more preferably at least 95% and most preferably at least 99% identical to the regions 2 and 4 as defined herein. Said regions 2 and 4 may be directly linked on the nucleotide level but it is also envisaged that said regions are separated by a spacer sequence, which may be the spacer as shown between these two regions in SEQ ID Nos. 1 and 2 (or as depicted as "region 3 and exon 1 and 2) in FIG. 12 or which may be, more preferably unrelated to the spacer as shown in SEQ ID NOs 1 or 2 (and in FIG. 12). The prior art has provided and deposited a nucleotide sequence "AL450-490" in Genbank. Yet, in contrast to the present invention, in AL450-490 a gene defined as "DCX gene" comprises merely the coding region of DCX and a short 5' segment of 748 nucleotides upstream of the ATG present in exon 4.

Another aspect of the invention relates to the above defined uses of regulatory sequences which hybridize to one of the above-described regulatory sequences of the invention, preferably to the complementary strand thereof, and cause neuronal restricted/determined cell-specific expression of a nucleotide sequence controlled by them.

These hybridizing sequences may be promoters as defined above or regulatory elements imparting neuronal restricted/determined cell-specificity to minimal promoters.

The term "hybridize" as used refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 70° C., preferably at 65° C. (regarding the definition of SSPE, SSC and Denhardts solution see Sambrook, loc. cit.). Stringent hybridization conditions as for instance described in Sambrook, supra, are particularly preferred. Particularly preferred stringent hybridization conditions are for instance present if hybridization and washing occur at 65° C. as indicated above. Non-stringent hybridization conditions, for instance with hybridization and washing carried out at 45° C. are less preferred and at 35° C. even less.

Such regulatory sequences preferably show a homology, determined by sequence identity, of least 75%, preferably of at least 80%, more preferably of at least 85%, even more preferably of at least 90% and most preferably of at least 95% to a sequence as defined in (a) to (d) herein above. Yet, the invention also relates to regulatory sequences which comprise or is a nucleotide sequence which is at least 78%, more preferably at least 80%, even more preferably at least 90% and most preferably at least 95% identical to the nucleotide sequence as shown in SEQ ID NO: 1 from position 1166 to 1746 (or from position 1166 to 2049) or to the nucleotide sequence shown in SEQ ID NO: 2 from position 529 to 1079 (or from position 529 to 1390). Also envisaged are regulatory sequences which comprises or is a nucleotide sequence which is at least 82%, more preferably at least 85%, even more preferably at least 90% and most preferably at least 95% identical to the nucleotide sequence as shown in SEQ ID NO: 1 from position 1785 to 1843 or to the nucleotide sequence as shown in SEQ ID NO: 2 from position 1118 to 1175. Similarly, the invention provides for uses of regulatory sequences which comprise a nucleotide sequence which is at least 75%, more preferably at least 80%, even more preferably at least 90% and most preferably at least 95% identical to the nucleotide sequence as shown in SEQ ID NO: 1 from position 1953 to 2775 or to the nucleotide sequence as shown in SEQ ID NO: 2 from position 1291 to 2137.

The regulatory sequences to be employed in accordance with this invention preferably show a homology, determined by sequence identity, of at least 50%, preferably at least 60%, particularly preferably at least 70%, advantageously at least 80%, preferably at least 90% and especially preferably at least 95% to the sequences indicated under SEQ ID NO 1 to 4, preferably over the entire length of the sequences compared. The hybridizing sequences are preferably fragments having a length of at least 100, more preferably at least 200, more preferably at least 300, more preferably at lest 400 and most preferably at least 500 nucleotides which have an identity of at least 75%, preferably at least 80%, especially preferably at least 90% and particularly preferably at least 95% with the sequence shown under SEQ ID NO. 1, 2, 3 or 4, respectively. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson, Methods in Enzymology 183 (1990), 63-98, appended examples and http://workbench.sdsc.edu/). For this purpose, the "default" parameter settings may be used.

The techniques described in the appended examples may, inter alia, be used to determine whether hybridizing sequences mediate neuronal determined/neuronal-restricted cell-specific expression.

As pointed out above, the term "neuronal determined cell" relates, in accordance with this invention to cells which differentiate into neurons or which divide into neuronal restricted cells, i.e. into cells that generate merely neurons. Accordingly, the term "neuronal determined cell" as employed herein also comprises "neuronal restricted cells". Therefore, the "neuronal determined/restricted cells" as described in this invention lead during their differentiation or development merely and exclusively to neurons and not to other cells of the nervous system, like, oligodendrocytes, astrocytes, Schwann cells, microglia cells, glia cells or even cells like endothelial cells, fibroblasts and the like. However, the term "neuronal determined/restricted cell" does also comprise progenitor or stem cells, which activate the regulatory sequence of the present invention and, thereby, are on a restricted/determined differentiation/developmental pathway leading to (a) neuron(s). Stem cells can proliferate to give rise to daughter cells identical to the mother cells and thereby enlarge the stem cell population. Alternatively, they can divide into various cell types. A stem cell that can produce any cell type of an organism, for example an embryonic stem cell, is referred to as totipotent, whereas a stem cell that can produce only a defined subset of cell types is referred to as pluripotent. In several organs and systems, somatic stem cells have been described. These somatic stem cells have the potential to divide into daughter cells identical to the mother cells and thereby renew or enlarge the somatic stem cell population. Alternatively, a daughter cell can differentiate into various cell types relevant to this organ/system. For example, neural stem cells have been described in the central nervous system (CNS). These cells can differentiate into neurons, astrocytes and oligodendrocytes, i.e., the three major CNS cell types. The capacity of more or less differentiated cells to generate cell types present in another organ/system is referred to as trans-differentiation. Accordingly, the term "neuronal restricted/determined cell" as employed herein also refers to cells, like stem cells or trans-differentiating cells, which comprise an activated regulatory sequence of the present invention. Yet, the term "neuronal determined/restricted cell(s)" as used herein is to be delimited from multi/pluripotent undifferentiated stem cells that have not and or will not activate the regulatory sequence described herein. The term "neuronal restricted/determined cell" refers, therefore, to any cell/cell type that will exclusively lead, directly or via its progeny, to neurons in vivo or under experimental or in vitro settings/conditions selected. The term "neuronal restricted/determined cell" also comprises migrating cells, like migrating neuronal precursor cells. By providing the regulatory sequences of doublecortin (DCX), the present invention provides for a distinct tool to detect, track, select and/or isolate "neuronal restricted/determined cells". Accordingly, the present invention provides for specific advantageous uses and methods, wherein the regulatory sequences described herein or host cells/host organisms (like transgenic non-human animals, as well as organs, tissues or cells of such organisms) comprising the regulatory sequences or recombinant nucleic acid molecules as defined herein, are employed.

In a particular preferred embodiment, the regulatory sequence of the present invention is of human, rat or mouse origin. Corresponding human and mouse sequences are illustrated in SEQ ID NO. 1 and 2. The regulatory sequences of the invention are preferably DNA or RNA molecules, the DNA molecules being preferably genomic DNA.

The invention also relates to uses of recombinant nucleic acid molecules comprising the regulatory sequence described herein. Said recombinant nucleic acid molecule comprises the regulatory sequences in an "isolated" form, preferably in combination with a heterologous nucleic acid sequence to be expressed. As used herein, the term "isolated" when used in conjunction with a nucleic acid molecule/regulatory sequences of the present invention refers to a nucleic acid molecule which has been separated from an organism in a substantially purified form (i.e. substantially free of other substances originating from that organism), or a nucleic acid molecule having the same nucleotide sequence but not necessarily separated from the organism (i.e. synthesized or recombinantly produced nucleic acid molecules).

Preferably and most envisaged, the regulatory sequences described in the present invention are operatively linked to additional, heterologous nucleic acid sequences in a recombinant nucleic acid molecule. As detailed herein below, said additional nucleic acid sequence may be a coding gene as well as a nucleic acid sequence which, upon expression, leads to the production of an antisense construct, a ribozyme or the like.

As employed herein, the term "heterologous nucleic acid molecule", means a nucleic acid molecule which is preferably operatively linked to the regulatory sequence described above but is not a nucleic acid molecule which codes for doublecortin (DCX) or a fragment thereof. Therefore, said "heterologous nucleic acid molecule" originates from a different genetic context than the regulatory sequence described above. Non-limiting examples of such "heterologous nucleic acid molecules" are given herein below and comprise in particular marker molecules, like luciferase, galactosidase, GFP, EGFP, DsRed, etc. or tag-molecules, like Flag-tags, CBP and others. Yet, as detailed below, also receptor genes, anti-apoptotic genes, genes coding for determination/differentiation molecules, trophic factors, surface proteins, transcription factors, molecules directing neuronal migration or guidance are envisaged. Also nucleic acid molecules which do not encode proteins are envisaged as "heterologous nucleic acid molecules". Such nucleic acids comprise, but are not limited to, anti-sense molecules, aptamers, ribozymes, inhibiting RNA molecules and the like.

The term "recombinant nucleic acid molecule" relates to nucleic acid molecules originating from a different genetic context and combined by molecular biological methods. Here, the term "different genetic context" relates to genomes from different species, varieties or individuals or different positions within a genome. Recombinant nucleic acid molecules can contain not only natural sequences but also sequences, which, compared to the natural ones are mutated or chemically modified or else, the sequences are altogether newly synthesized sequences.

The recombinant nucleic acid molecules of the invention show one or more of the above-described regulatory sequences in combination with sequences from another genetic context. An example of a recombinant nucleic acid molecule contains one or more regulatory sequences of the invention or a minimal promoter derived and obtainable from the sequences disclosed herein in combination with a gene other than the DCX gene, preferably other than the human doublecortin gene. The term "recombinant nucleic acid molecule", therefore, does not relate to a nucleic acid molecules which comprises a DCX coding sequence under the control of the regulatory sequences provided herein. The regulatory sequences are regulatory promoter elements that impart a neuronal determined/neuronal-restricted cell-specific expression.

Moreover, the recombinant nucleic acid molecules can contain, apart from a promoter containing one or more regulatory sequences of the invention, a polylinker sequence located downstream thereof and comprising one or more restriction sites into which nucleotide sequences can be cloned by methods known to a skilled person, which thus come under the expression control of the promoter. Said polylinker lies preferably in a region that is situated directly behind the transcription starting point defined by the promoter.

Furthermore, the recombinant nucleic acid molecule described herein may contain a transcription termination signal downstream of the polylinker. Examples of suitable termination signals are described in the state of the art. The termination signal can, for instance, be the thymidine kinase polyadenylation signal. The herein-described recombinant nucleic acid molecules which preferably contain a nucleotide sequence to be expressed can be directly employed for uses within the meaning of the invention, such as DNA transfections, the generation of genetically modified host cells or non-human transgenic animals. Furthermore, said recombinant molecules can be employed in screening methods described herein as well as in medical and scientific settings. The recombinant nucleic acid molecules of the invention may, also, be multiplied by conventional in-vitro amplifications techniques, for instance PCR. However, they can also conventionally be multiplied in vivo in a vector, and after nucleic acid preparation and subsequent removal from the vector, for instance by restriction cleavage, can be provided for uses requiring for instance linearized expression units. Recombinant nucleic acid molecules, which preferably contain a nucleotide sequence to be expressed, can also constitute expression units which are often designated expression cassettes which can be easily cloned into different standard vectors and depending on the vector can thus exert different functions.

In a particular preferred embodiment, the recombinant nucleic acid molecule of the invention comprises the regulatory sequence of the invention which controls the expression of the additional nucleotide sequence.

Preferably, in context of this invention, the additional nucleotide sequence to be expressed is engineered "near" or in a certain distance to the 3'-end of the regulatory sequences defined herein. "Near" means that the additional nucleotide sequence(s) or parts thereof is(are) cloned directly or at a certain distance to the afore-mentioned regulatory sequences, upstream, downstream or intermittently. Cloning is carried out, however, preferably downstream because, as is known, the afore-mentioned regulatory sequences (promoters or functional parts thereof), require relatively defined distances from the transcription starting point and from the TATA box, respectively, for their way of functioning, that is to say for binding RNA polymerase or transcription factors. "At a certain distance" means a distance which is suitable to allow silencers or enhancers to exert their function. Corresponding examples are documented herein below, for example the engineering of constructs expressing selectable marker genes. It is of note that it is also envisaged that partial sequences of the above defined regulatory sequences be employed in context of this invention, i.e. that recombinant nucleic acid molecules are constructed which comprise one partial sequences or functional fragments of the regulatory sequences for DCX as defined herein. Such constructs may also be tested in the assays provided herein, e.g. transient expression assays for their expression function and level. For example, a construct comprising a partial sequence of the inventive regulatory sequence, and for comparison purposes, the same construct without said partial sequence, can be analyzed in a transient expression assay in cultured cells, (preferably a primary cell, like embryonic mouse day 12 neuronal precursor cells derived from forehead) and in cells not capable of or not expressing DCX (like HEK293 cells). If the difference of the expression level between cells capable of not expressing DCX is greater in the case of the construct with the partial sequence than in the case of the construct without the partial piece, then this partial sequence comprises a functional silencer or enhancer element. Additional techniques for delimiting such elements are available to a skilled person. A detailed example for such a technique is as follows: it is, inter alia, possible to deduce the minimal promoter element in the regulatory sequence described herein, by the construction of deletion mutants that express one of the fluorescent or luminescent proteins e.g. EGFP or DSRed etc. The minimal promoter should be sufficient and necessary to drive expression of a gene in neuronal precursor cells, neuronal determined/ restricted cells. Preferred minimal promoters comprise either alone or in combination the "region 2" and/or the "region 4" as defined in FIG. 12, corresponding to the nucleotide sequence of SEQ ID NO: 1 from position 1166 to 1746 (or from position 1166 to 2049) and from position 1953 to 2775 or the nucleotide sequence of SEQ ID NO: 2 from position 529 to 1079 (or from position 529 to 1390) and from position 1291 to 2137. Said desired minimal regulatory sequence does, preferably and in one embodiment, not comprise the nucleotide sequence comprising position 3169 to 3501/3509 of SEQ ID NO. 1, does not comprise the nucleotide sequence comprising position 2525 to 2859 of SEQ ID NO. 2 or does not comprise homologues thereof. These nucleotide sequences correspond to "region 5" as defined in FIG. 12. Yet, it is of note that regulatory sequence to be employed in the uses and methods of the present invention, as characterized herein, may also comprise said "region 5". A further optional part of the regulatory sequence described herein and to be employed is the "region 1" as defined in appended FIG. 12.

Functional constructs of the regulatory sequence causing transient, specific expression in neuronal determined cell may be, e.g., tested by transfection, into neuronal precursor cells derived from mouse embryonic day 10 to 14 forebrain and analyzed for expression as demonstrated in the appended examples. Transfections in non-neuronal cells e.g. HEK293 cells serve as negative controls, since the functional promoter should not be active in non-neuronal cells. In addition, transfections may be done using EGFP positive cells derived from the transgenic animal (Example 4). A functional promoter/promoter fragment should be active in these cells, however should be inactive in EGFP-negative cells from the same animals. Corresponding working examples are appended.

The embodiment comprises the above-described regulatory sequences which are combined with at least one nucleotide sequence, which can be provided by amplification from the insertion of the deposited clone DSM15111, using for instance PCR, or parts thereof. Such an additional sequence in the deposited clone DSM1511 encodes an enhanced green fluorescent protein. For amplification of said additional gene/nucleotide sequence (here EGFP), for instance pairs of oligonucleotides can be used. The sequences of indicated by the SEQ ID NOs: 13 and 14, i.e. the sequences ATG GTG AGC AAG GGC GAG GAG (SEQ ID No:13) or CTT GTA CAG CTC GTC CAT GCC (SEQ ID No:14) may be employed to amplify the EGFP in said DSM 15111 clone. Accordingly, the additional sequence coding for EGFP in deposited clone DSM 15111 may be replaced by any other desired sequence.

In accordance with this invention, it is also envisaged that more than one additional sequence is comprised in the recombinant nucleic acid molecule described herein. Accordingly, the invention also relates to the use of recombinant nucleic acid molecules which comprise, besides the DCX regulatory sequences, clusters genes, preferably in the same reading frame. For example, two nucleotide sequences can be located behind one another in one reading frame, that is to say, being translationally fused (if both nucleotide sequences encode a protein or a fragment thereof. These coding regions can be directly adjacent to one another or can be spaced apart by a spacer. A spacer separates the tertiary structure of the two proteins spatially from one another, in order to prevent their tertiary structures from negatively interacting. The spacer has, however, preferably the function of acting as a point of attack for a protease, preferably an endogenous protease of the transfected cell, with the result that the expressed proteins are separated in vivo. Alternatively, the spacer can contain an IRES sequence (internal ribosomal entry site). This allows both genes to be transcribed under the control of a single promoter, their translation occurring separately.

On the other hand, the two nucleotide sequences can also be encoded transcriptionally independently from each other. For this purpose, each nucleotide sequence is under the control of its own promoter, with at least one promoter, preferably both promoters, comprising the regulatory sequences of the present invention.

Such an embodiment would allow the particular advantages of co-transfection with expression constructs encoding an different proteins or fragments thereof.

Another preferred embodiment of the invention relates to uses of the above-described recombinant nucleic acid molecules or vectors, whereby these recombinant nucleic acid molecules additionally contain/comprise a nucleotide sequence to be expressed, wherein expression of the nucleotide sequence is controlled by the DCX regulatory sequence or a DCX promoter/enhancer comprising the regulatory sequence. In context of this invention, it is also envisaged that the regulatory sequence is employed in its inducible form.

The "nucleotide sequences to be expressed" encode either a protein or (poly)peptide or RNA molecules which display their function on the RNA level. Nucleotide sequences encoding a protein, polypeptide or peptide comprise a coding region which is characterized by a start codon (ATG), a sequence of base triplets encoding amino acids and a stop codon (TGA, TAG or TAA) if it concerns DNA. In the case of RNAs, the thymidine (T) is replaced with uracil (U). In the case of degenerated amino acid codons, the base triplets can be adapted in accordance with the codon usage of the target cells, using prior art techniques. Examples of nucleotide sequences which express RNA molecules are antisense RNA, inhibiting RNA, iRNA or ribozymes.

In a further embodiment, the invention relates to (a) recombinant nucleic acid molecule(s) described herein, wherein said nucleotide sequence to be expressed under the control of the regulatory sequence of the invention is a gene selected from the group consisting of a marker or receptor gene, an anti-apoptotic gene, a determination/differentiation gene, a gene capable of inducing and/or directing neuronal migration or guidance, a gene encoding a tag, a gene encoding for a trophic factor, a gene encoding a surface protein, a gene encoding for a transcription factor, a gene encoding an enzyme or wherein said nucleotide sequence to be expressed is an antisense sequence or encodes for a ribozyme or an inhibiting/interferring RNA molecule or the like. Accordingly, the invention relates in one embodiment said marker or receptor gene to be expressed under the control of the herein disclosed regulatory sequences are, e.g., fluorescent proteins (e.g. green fluorescent protein) or proteins which may, directly or indirectly, lead to a visible or measurable signal, when expressed (e.g chloramphenicol acetyltransferase, beta-galactosidase).

Examples of marker or reporter genes, which allow the expression activity of regulatory sequences, preferably promoters, to be detected, preferably in eukaryotic cells, are described in the literature. Examples of reporter genes encode luciferase, (green/red) fluorescent protein and variants thereof, like EGFP (enhanced green fluorescent protein), RFP (red fluorescent protein, like DsRed or DsRed2), CFP (cyan fluorescent protein), BFP (blue green fluorescent protein), YFP (yellow fluorescent protein), β-galactosidase or chloramphenicol acetyltransferase, and the like. For example, GFP can be from Aequorea victoria (U.S. Pat. No. 5,491, 084). A plasmid encoding the GFP of Aequorea victoria is available from the ATCC Accession No. 87451. Other mutated forms of this GFP including, but not limited to, pRSGFP, EGFP, RFP/DsRed, and EYFP, BFP, YFP, among others, are commercially available from, inter alia, Clontech Laboratories, Inc. (Palo Alto, Calif.). For example, DsRed2 is also available from Clontech Laboratories, Inc. (Palo Alto, Calif.); see appended examples. Also further luminescent proteins may be expressed under the control of the regulatory sequence provided herein. In this context, a nucleotide sequence coding, inter alia, for a protein of the luciferase family is envisaged.

The invention also relates to a recombinant nucleic acid molecule comprising the regulatory sequence of the invention and a gene under its control, whereby said gene encodes a tag. Said tag may be selected from the group consisting of a His-Tag, glutathione, a Strep-tag, a Flag-tag, CBP (Calmodulin-binding peptide), TAG-100 (available from Quiagen), E2-tag (from bovine papillomavirus type I transactivator protein E2) and Z-tag, but is not limited thereto. For example, the self-cleavable chitin-binding tag (e.g. from IMPACT-CN System) or influenza hemagglutinin (HA) may be employed in accordance with this invention. It is also envisaged that the recombinant nucleic acid molecule of this invention is capable of expressing a peptide or protein sequence which may be detected by a specific antibody (or antibody fragment or derivative) directed against said peptide or protein.

It is furthermore one embodiment of the invention that the recombinant nucleic acid molecule to be used in accordance with the invention codes for a (cell) surface protein, which may be detected by specific antibodies directed against said cell surface protein. A gene encoding a surface may for example be CD 24. This cell surface molecule was successfully employed for the selection of transduced cells, see Pawliuk, Blood 84 (1994), 2868-2877.

A gene encoding for a trophic factor and expressed under the control of the regulatory sequence of the present invention may be selected from the group consisting of NGF, BDNF, PDGF, NT-3, NT-4, NT-5, VEGF, PEDF, EGF, FGF, IGF, cardiotrophin, erythropoietin, leptin, LIF and TGF. These recombinant nucleic acid molecules are very useful in medical as well as scientific settings. For example, a NGF may be used in the treatment of Alzheimer's Disease (Winkler, J. Mol. Med. 76(8) (1998), 555-567), NT-3 in the treatment of Huntington's Disease (Perez-Navarro, J. Neurochem. 75(5) (2000), 2190-2199) or Parkinson's Disease (Espejo, Cell Transplant. 9(1) (2000), 45-53). Similarly, the expression of NT-4/5 may have beneficial effects in the treatment of Huntington's Disease (Perez-Navarro, J. Neurochem. 75(5) (2000), 2190-2199). VEGF may be desired in the treatment of stroke (Jin, Proc. Natl. Acad. Sci. USA 97(18) (2000), 10242-10247), whereas PEDF may have beneficial effects in Motor Neuron Diseases, like ALS (Bilak, J. Neuropathol. Exp. Neurol. 58(7) (1999), 719-728). It is also described that EGF, FGF and PDGF have beneficial effects in the treatment or prevention of stroke (Nakatomi, Cell. 110(4) (2002), 429-441 and Krupinski, Stroke 28(3) (1997), 564-573). IGF was studied in stroke intervention (Liu., Neurosci, Lett. 308(2) (2001), 91-94) and in the treatment of Huntington's Disease (Humbert, Dev Cell. 2(6) (2002), 831-837). Similarly, BDNF was employed in the medical intervention of Huntington's Disease (Perez-Navarro, J. Neurochem. 75(5) (2000), 2190-2199) and spinal cord injury (Hammond, Neuroreport 10(12) (1999), 2671-2675). GDNF was employed in Parkinson's Disease (Nakajima, Brain Res. 916(1-2) (2001), 76-84; Espejo, Cell Transplant. 9(1) (2000), 45-53) and HGF, like CNTF, were used in the treatment of amyotrophic lateral sclerosis, ALS (Sun, J. Neurosci. 22(15) (2002), 6537-6548 and Sendtner, Nature 358(6386) (1992), 502-504). Cardiotrophin (Toth, J. Neuroscience Res. 69(5) (2002), 622-632) protects PC12 cells against the excitatory damage, oxidative stress and apoptosis and erythropoietin (Juul, Acta. Peadiatr. Suppl. 91(438) (2002), 3642) was described to have neurotrophic and neuroprotective functions in the developing and injured brain. Leptin (Dicou, Neuroreport 12(18) (2001), 3947-3951) exerts neuroprotection against toxicity, whereas LIF (Marzella, Hear. Res. 138(1-2) (1999), 73-80) promotes survival of dissociated cultures of spinal ganglion cells. However, the use of the recombinant nucleic acid molecule expressing the trophic factors, especially the trophic factors listed above is not limited by the distinct disorders mentioned above and further medical uses are envisaged.

In a further embodiment of the recombinant nucleic acid molecule of the present invention, the anti-apoptotic gene to be expressed under the control of the inventive regulatory sequence is selected from the group consisting of bcl-2, Brn-3a, PTEN and (an) anti-caspase(s). Anti-apoptotic molecules and/or nucleic acid molecules inhibiting the apoptotic molecules, like caspases, such as antisense-caspase-3 are considered to reduce the cell death of neuronal determined cells. This is especially important, since apoptotic and neurogenic regions in the adult brain overlap (Biebi, Neurosci. Lett. 291(1) (2000), 17-20). Promoting the survival of neuronal determined cells might raise the total population of neurons in the adult brain. Brn-3a, for example, activates the expression of Bcl-x(L) and Bcl-2 and promotes neuronal survival in vivo as well as in vitro (Smith, Mol. Cell. Neurosci. 17(3) (2001), 460-470).

It is also envisaged that the determination/differentiation gene to be expressed under the control of the regulatory sequence described herein is the dopaminergic determination factor Nurr1. Nurr1 induces and promotes dopaminergic differentiation of stem cells (Chung, Eur. J. Neurosci. 16(10) (2002), 1829-1838).

The gene capable of inducing and/or directing neuronal migration or guidance and being expressed under the control of the regulatory sequence of the present invention may, inter alia, be netrin, neuropilin, CXCR4, SDF-1, DCC, slit, robo, a semaphorin, a plexin family member, an ephrin family member. These migration and/or guidance molecules are well known in the art and relate, e.g. to molecules attracting/repulsing growing axons in order to reestablish synaptic connection. Examples are CXCR4 and its ligand SDF-1 (Lu, PNAS 99(10) (2002), 7090-709. Without functional CXCR4, morphogenesis of the hippocampal DG (dentate gyrus) fails. In accordance with this invention, it is envisaged that loss of SDF-1/CXCR4 signaling could at least in part, mediate this migratory defect. Semaphorin/plexin family members have been described in Chen, Neuron 32 (2001), 249-263. For example, in vivo, PlexA3 is crucial for proper targeting of a subset of hippocampal afferents, but less important for guidance of peripheral axon of the superior cervical ganglion and DRG. The slit/robo guidance system is described in Zou, Cell 102 (2000), 363-375. Neuropilin receptors are expressed by commissural neurons and are required to navigate commissural axons across the midline of the CNS to their rostral targets after midline crossing. In this system, class 3 semaphorins act in concert with another class of repellent proteins, the Slits, to prevent commissural axons from recrossing or lingering at the midline. A small family of secreted proteins, termed netrins, which attract commissural axons before the midline crossing. Netrin-induced attraction is mediated by the DCC (deleted colorectal cancer) family of receptors that include Frazzled in *Drosophila*, UNC40 in *C elegans* and DCC and neurogenin in vertebrates, see Yu, Nat Neurosci 4 (2001), 1169-1176. Ephins and ephrin receptors (Eph) are also known in the art, see, e.g. Kullander, Genes Dev 15 (2001), 877-888. The knockout of ephrinsB3, an EphA4 ligand, provided strong evidence that EphA4 interacts with ephrinsB3, expressed at the midline, to prevent CST axons from aberrantly recrossing the midline.

In a further embodiment of the invention, the gene encoding a transcription factor and being controlled by the regulatory sequence described herein may be selected from the group consisting of NeuroD, BMP4, Nurr1 or ShcC.

The invention also provides for the above described uses of a recombinant nucleic acid molecule wherein an enzyme is expressed under the control of the DCX regulatory sequence. A preferred example, besides the above mentioned reported genes like β-galactosidase or luciferase is CRE (CRE-recombinase). It is, inter alia, envisaged that CRE is expressed under the control of the DCX regulatory sequence described herein and such a construct is employed in the generation of a non-human transgenic animal. Accordingly, the recombinant nucleic acid molecule may be used for transfection of, e.g. a zygote or an ES-cell, for the preparation of said transgenic animal for use in recombination studies and gene deletion systems. Such a CRE-positive transgenic animals or such CRE-positive cells are in particular useful for site- and time specific gene targeting, for example in mouse model systems or ES-cell systems; see, inter alia, Metzger, Methods 24

(2001), 71-80; Liu, Nat. Genet. 30 (2002), 66-72 or Yeh, PNAS 15 (2002), 13498-13503.

The recombinant nucleic acid molecule described and employed in this invention may also be a nucleic acid molecule comprising the DCX regulatory sequences described herein and nucleotide sequence to be expressed under its control, whereby said expression-controlled sequence is an antisense sequence, or encodes for a ribozyme or an inhibiting RNA-molecule.

The antisense sequences and ribozymes are molecules, the expression of which occurs on the RNA level. "Antisense sequences" are sequences which are complementary to an mRNA present in the target cell or a part thereof, the part possibly comprising the coding region, 5'- and/or 3'-nontranslated region. Antisense-RNAs, that is to say the transcripts of the antisense sequence, are capable of hybridizing in vivo to the complementary mRNA and thereby to inhibit its translation. "Ribozymes" are catalytic RNA molecules. In context of the present invention the ribozymes are preferably those which can bind specifically to an mRNA so as to render it inaccessible to successful translation by exerting a catalytic activity, preferably by hydrolytic cleavage. Instructions for selecting suitable antisense sequences and for constructing ribozymes with the desired sequence specificity are described in the literature and can be found for instance in "Antisense: From Technology to Therapy" (Schlingensiepen, R., Brysch, W., Schlingensiepen, K.-H., eds., Blackwell Science Ltd. Oxford, 1997) or Rossi (AIDS Research and Human Retroviruses 8 (1992), 183). Said ribozymes may also target DNA molecules encoding the corresponding RNAs. Ribozymes are catalytically active RNA molecules capable of cleaving RNA molecules and specific target sequences. By means of recombinant DNA techniques it is possible to alter the specificity of ribozymes. There are various classes of ribozymes. For practical applications aiming at the specific cleavage of the transcript of a certain gene, use is preferably made of representatives of two different groups of ribozymes. The first group is made up of ribozymes which belong to the group I intron ribozyme type. The second group consists of ribozymes which as a characteristic structural feature exhibit the so-called "hammerhead" motif. The specific recognition of the target RNA molecule may be modified by altering the sequences flanking this motif. By base pairing with sequences in the target molecule these sequences determine the position at which the catalytic reaction and therefore the cleavage of the target molecule takes place. Since the sequence requirements for an efficient cleavage are low, it is in principle possible to develop specific ribozymes for practically each desired RNA molecule. In order to produce DNA molecules encoding a ribozyme which specifically cleaves transcripts of a gene encoding a protein to be inhibited or inactivated, a DNA sequence encoding a catalytic domain of a ribozyme is bilaterally linked with DNA sequences which are homologous to sequences encoding the target protein. In accordance with this invention said sequence encoding a ribozyme or its catalytic domain is under the control of the regulatory sequences (or functional parts or fragments thereof) of the invention. The expression of ribozymes in order to decrease the activity in certain proteins is also known to the person skilled in the art and is, for example, described in EP-B1 0 321 201 or EP-B1 0 360 257.

Antisense technology can be used to control gene expression through triple-helix formation or antisense DNA or RNA, whereby the inhibitory effect is based on specific binding of a nucleic acid molecule to DNA or RNA. The antisense oligonucleotide of, e.g., at least 10 nucleotides in length may be under the control of the regulatory sequences described herein. The antisense DNA or RNA oligonucleotide hybridises to the desired mRNA (which should be inactivated or inhibited) in vivo and blocks translation of said mRNA and/or leads to destabilization of the mRNA molecule (Okano, J. Neurochem. 56 (1991), 560; Oligodeoxynucleotides as antisense inhibitors of gene expression, CRC Press, Boca Raton, Fla., USA (1988)).

For applying a triple-helix approach, a DNA oligonucleotide can be designed to be complementary to a region of the gene to be inhibited or inactivated according to the principles laid down in the prior art (see for example Lee, Nucl. Acids Res. 6 (1979), 3073; Cooney, Science 241 (1988), 456 and Dervan, Science 251 (1991), 1360). Such a triple helix forming oligonucleotide can then be used to prevent transcription of the specific gene. The oligonucleotides described above can be delivered, inter alia, via a gene delivery vector as described below. Also this approach leads to in vivo inhibition of gene expression of the respective protein. The corresponding oligonucleotides have a length of preferably at least 10, in particular at least 15, and particularly preferably of at least 50 nucleotides. They are characterized in that they specifically hybridize to said polynucleotide, that is to say that they do not or only to a very minor extent hybridize to other nucleic acid sequences.

A particularly preferred embodiment relates to the use of the recombinant nucleic acid molecules or vectors, wherein the antisense sequence, RNAi or the ribozyme is specific for to an inhibition and/or down-regulation of an apoptosis-protein, like a caspase. This is of particular interest in context of this invention, since apoptotic and neurogenic regions in the adult brain overlap; see Biebl, Neurosci Lett 291 (2000), 17-20. Promoting the survival of neuronal determined cells by means and methods provided herein raises the total population of neuronal determined cells and neurons in nervous tissue, in in vitro cultures or in the adult brain. For example, the inhibition of caspase 3 by the recombinant molecule described above is considered to lead to reduced cell death of neuronal determined cells in vivo and in vitro.

Preferred inhibiting RNA molecules (RNAi/iRNA) may be selected from the group consisting of RNAi, siRNA, shRNA and stRNA.

The term RNA interference (RNAi) is very well known in the art and usually describes the use of double-stranded RNA to target specific mRNAs for degradation, thereby silencing their expression. Double-stranded RNA (dsRNA) matching a gene sequence is synthesized in vitro and introduced into a cell. The dsRNA feeds into a natural, but only partially understood process including the highly conserved nuclease dicer which cleaves dsRNA precursor molecules into short interfering RNAs (siRNAs). The generation and preparation of siRNA(s) as well as the method for inhibiting the expression of a target gene is, inter alia, described in WO 02/055693, Wei, Dev. Biol. 15 (2000), 239-255; La Count, Biochem. Paras. 111 (2000), 67-76; Baker, Curr. Biol. 10 (2000), 1071-1074; Svoboda, Development 127 (2000), 4147-4156 or Marie, Curr. Biol. 10 (2000), 289-292. These siRNAs built then the sequence specific part of an RNA-induced silencing complex (RISC), a multicomplex nuclease that destroys messenger RNAs homologous to the silencing trigger). Elbashir, EMBO J. 20 (2001), 6877-6888 showed that duplexes of 21 nucleotide RNAs may be used in cell culture to interfere with gene expression in mammalian cells. It is already known that RNAi is mediated very efficiently by siRNA in mammalian cells but the generation of stable cell lines or non-human transgenic animals was limited. However, new generations of vectors may be employed in order to stably express, e.g. short hairpin RNAs (shRNAs). Stable Expression of Short Interfering RNAs in Mammalian Cells is inter alia shown in Brummelkamp, Science 296 (2002), 550-553. Also Paul, Nat. Biotechnol. 20 (2002), 505-508 documented the effective expression of small interfering RNA in human cells. RNA interference by expression of short-interfering RNAs and hairpin RNAs in mammalian cells was also shown by Yu, Proc. Natl. Acad. Sci. U.S.A 99 (2002), 6047-6052. The shRNA approach for gene silencing is well known in the art and may comprise the use of st (small temporal) RNAs; see, inter alia, Paddison, Genes Dev. 16 (2002), 948-958.

As mentioned above, approaches for gene silencing are known in the art and comprise "RNA"-approaches like RNAi or siRNA. Successful use of such approaches has been shown in Paddison (2002), loc. cit., Elbashir, Methods 26 (2002), 199-213; Novina, Mat. Med. Jun. 3 (2002), 2002; Donze, Nucl. Acids Res. 30 (2002), e46; Paul, Nat. Biotech 20 (2002), 505-508; Lee, Nat. Biotech. 20 (2002), 500-505; Miyagashi, Nat. Biotech. 20 (2002), 497-500; Yu, PNAS 99 (2002), 6047-6052 or Brummelkamp, Science 296 (2002), 550-553. These approaches may be vector-based, e.g. the pSUPER vector, or RNA polIII vectors may be employed as illustrated, inter alia, in Yu (2002), loc. cit.; Miyagishi (2002), loc. cit. or Brummelkamp (2002), loc. cit. It is envisaged that the regulatory sequences of the present invention are used in similar fashion as the systems based on PSUPER or RNA polIII vectors.

Another preferred embodiment of the invention relates to the above described uses of nucleotide sequences comprising a fragment having a length of at least 15 nucleotides which specifically hybridizes under stringent conditions to a strand of a DCX regulatory sequence described in context of the invention.

Hybridizing nucleotide sequences according to the present embodiment can for instance serve as probes which for instance contribute to identify homologous promoters, preferably regulatory sequences of other genes which, on account of certain corresponding sequence elements, induce an expression pattern comparable to that of the regulatory sequences of the invention. Moreover, these sequences can be used to design suitable oligonucleotides, for instance as PCR primers.

The term "hybridization" has already been defined further above. The nucleotide sequences preferably hybridize under stringent conditions. The fragments have a length of at least 15 nucleotides, preferably of at least 20 nucleotides, particularly preferably of at least 50 nucleotides, especially preferably of at least 100 nucleotides, advantageously of at least 200 nucleotides and most preferably of at least 500 nucleotides.

The invention also provides for the use of a vector comprising the inventive regulatory sequence or the recombinant nucleic acid molecule described herein above, whereby said vector is preferably used for the early transient expression of heterologous nucleotide sequences in proliferative neuronal determined cells.

The term "vector" relates to circular or linear nucleic acid molecules which can autonomously replicate in host cells into which they are introduced. The vectors may contain the above-characterized recombinant nucleic acid molecules in their full length or may contain, apart from the regulatory sequences of the invention, the components described for the recombinant nucleic acid molecules, such as minimal promoter, polylinker and/or termination signal.

The vectors of the invention may be suitable for replication in prokaryotic and/or eukaryotic host cells. They contain a corresponding origin of replication. The vectors are preferably suitable for replication in mammalian cells, particularly preferably in human cells.

The vectors of the invention preferably contain a selection marker. Examples of selection marker genes are known to a skilled person. Selection marker genes which are suitable for selection in eukaryotic host cells are for instance genes for dihydrofolate reductase, G418 or neomycin resistance.

The vectors of the invention are preferably expression vectors for expression in eukaryotic cells. Such vectors can be constructed starting from known expression vectors by replacement of their promoter or the sequences not belonging to a minimal promoter with the regulatory sequences of the invention or by supplementation with regulatory sequences (regulatory elements) of this invention. Examples of expression vectors which can be modified in this way are pcDV1 (Pharmacia), pRC/CMV, pcDNA1 or pcDNA3 (Invitrogen).

As document in the appended examples, the vector of the present invention may, inter alia, comprise (a) marker or receptor gene(s) which is GFP, EGFP or RFP.

In particular preferred embodiment of the invention the vector to be used comprises a nucleotide sequence selected from the group consisting of
(a) a nucleotide sequence as shown in SEQ ID NO: 5, 6 or 26 or as shown in SEQ ID NO: 7, 8 or 27;
(b) a nucleotide sequence coding for the regulatory sequence and the heterologous gene as comprised in the construct deposited under accession number DSM 15111; and
(c) a nucleotide sequence which is at least 80%, more preferably at least 85%, more preferably at least 90% and most preferably at least 95% identical to the nucleotide sequence as shown in SEQ ID NOS: 5 to 8, 26 or 27 and which comprises a regulatory sequence of claim 1 or 2.

The corresponding sequences (SEQ ID NOs 5 to 8, 26 or 27) are also illustrated in the appended figures, examples or in the sequence listing. Sequence identities of the vectors described herein may be deduced by methods known in the art and also illustrated herein above.

It is of note that the vectors to be employed in accordance with the invention may also comprise functional parts or fragments of the regulatory sequence as disclosed herein. Functional fragments and parts may also be deduced by methods described above and comprise, e.g. transfection studies with partial/fragmented regulatory sequences linked, inter alia to expressible marker/reporter genes.

In a particularly preferred embodiment, the above-described vectors are viruses. In the state of art, a great number of viral vectors for transfection of mammalian cells ex vivo or in vivo is described. These are derivatives of mammalian or human pathogenic viruses, which have been deprived of their pathogenic properties by genetic modification. For transfection, viral vectors are packaged in vitro according to methods known to a skilled person, i.e. are provided with viral envelope proteins. DNA and RNA viruses can be used. Examples of viruses for transfection of mammalian, preferably human cells, are Herpes virus, lentivirus, retroviruses, adenoviruses and adeno-associated viruses.

In another embodiment of the invention, the above-described vectors are suitable for gene therapy or vaccination with a nucleic acid. Gene therapy and nucleic acid vaccination are based on the introduction of therapeutic or immunizing genes into cells ex vivo or in vivo. Suitable vectors or vector systems and methods for using them for gene therapy or DNA/RNA vaccination are described in the literature and are known to a skilled person, see for instance Giordano, Nature Medicine 2 (1996), 534-539; Schaper, Circ. Res. 79 (1996), 911-919; Anderson, Science 256 (1992), 808-813; Isner, Lancet 348 (1996), 370-374; Muhlhauser, Circ. Res. 77 (1995), 1077-1086; Wang, Nature Medicine 2 (1996), 714-716; WO 94/29469; WO 97/00957; Schaper, Current Opinion in Biotechnology 7 (1996), 635-640; or Verma, Nature 389 (1997), 239-242 Geddes, Front Neuroendocrinol. 20 (1999), 296-316 and the references cited therein. Of particular interest is the fact that gene delivery systems/gene therapy approaches in neurology have also been described by Tuszyski, J. Neurosci. 19 (2002), 207 or Blesch, Brain Res Bull. 57 (2002), 833-833. Global gene and cell replacement strategies via stem cells and the like have been proposed and described by Park, Gene Therapy 9 (2002), 613-624. The above-described recombinant nucleic acid molecules or vectors can for instance be designed for the direct introduction or for introduction via liposomes or viral vectors, e.g. adenoviral, lentiviral, adeno-associated viral (AAV), herpes vectors or retroviral vectors.

In a further preferred embodiment, the invention relates to a genetically modified cell/host cell which comprises the regulatory sequence, the recombinant nucleic acid molecule or the vector as described above. Also provided is/are (a) method(s) for preparing genetically modified host cells, characterized in that the host cells are transfected with one of the above-described vectors and the transfected host cell is cultured in a culture medium.

The term "genetically modified" means that the host cell or the host contains, in addition to the natural genome, a nucleic acid molecule or a vector of the present invention, which has been introduced into the host cell or the host or into a precursor. The nucleic acid molecule or the vector can be present in the genetically modified host cell/host either as an independent molecule outside the genome, preferably as a replicable molecule, or may be stably integrated in the genome of the host cell or host.

The introduction of a vector into host cells can be carried out according to known standard methods as for instance described in Sambrook (loc. cit.). Examples of applicable transfection techniques are calcium phosphate transfection, DEAE dextran-mediated transfection, electroporation, transduction, infection, lipofection or biolistic transfer. Subsequent culturing can be carried out using standard methods too, or in the case of the genetic modification of neuronal cells, preferably the methods described in the Examples and the references cited therein.

In another preferred embodiment, the invention relates to host cells which are genetically modified with a regulatory sequence, a recombinant nucleic acid molecule or a vector of the present invention or are obtainable by the above-described method. Most preferably the host cell is capable of proliferation and is able to acquire (for example under experimental in vivo or in vitro conditions) a neuronal phenotype.

The host cell of the present invention can in principle be any prokaryotic or eukaryotic cell and includes, inter alia, mammalian cells, fungal cells, plant cells, insect cells or bacterial cells.

The host cells of the present invention should be able to be mitotically active and should be able to acquire a neural phenotype, in particular under in vitro conditions. Suitable bacterial cells are those which are generally used for cloning, such as E. coli or Bacillus subtilis. Examples of fungal cells are yeast cells, preferably those of the genera Saccharomyces or Pichia, particularly preferably of Saccharomyces cerevisiae or Pichia pastoris. Suitable animal cells include for instance insect cells, vertebrate cells, preferably mammalian cells, such as CHO, COS7, Hela, NIH3T3, MOLT-4, Jurkat, K562, HepG2, PC12, Neuro 2A, P19 teratocarcinoma and the like. Yet, also cultured primary cells are envisaged, like cultured hippocampal cells or cultured RPE-cells. Further suitable cell lines are described in the art and can for instance be obtained from the Deutsche Sammlung für Mikroorganismen und Zellkulturen (DSMZ, Braunschweig). In this context it is of note that also non-neuronal cells may be transfected with a regulatory sequence, a recombinant nucleic acid sequence or a vector of the invention. These transfected cells are particularly useful in methods described herein below relating, inter alia, to screening methods for compounds capable of inducing differentiation/determination programs in cells which lead, either directly or indirectly, to a neuron or a neuron-like phenotype. As illustrated in the appended examples, a non-stimulated COS7 cell, transfected with a construct described herein, i.e. an EGFP-gene under the control of the regulatory sequence of the present invention, does, under normal culturing conditions, not express said marker/reporter. Yet, these cells may be employed in screening systems, for example high-throughput screenings, were compounds are tested for their capacity to activate the regulatory sequence of the invention.

The embodiment of the host cells which are brain or neuronal cells is particularly preferred.

Neuronal progenitor or stem cells as well as general embryonic stem cells (ES cells) are the primary site of application of the regulatory sequences, recombinant nucleic acid molecules or vectors of the invention. In particular embryonic stem cells transfected with the regulatory sequences, recombinant nucleic acid molecules or vectors are useful in methods described herein below and in high-throughput screenings. The isolated cells can also be precursor or a stem cells which can be converted into neuronal determined cells by suitable in vitro culturing. Corresponding methods are described in the art. Host cells of mammalian, most preferably human origin are particularly preferred in the present invention.

Accordingly, the host cell of the invention may be a neuronal cell, an ES-cell, a germ cell (for example a zygote which is particularly useful for the preparation of non-human transgenic animals as detailed in the appended examples) or, a cultured cell line as defined above or a primary cell, like hippocampal cells, RPE-cells or olfactory bulb cells.

The invention also relates to a method for preparing a genetically modified host cell, characterized in that the host cell is transfected with a nucleic acid molecule which is or which comprises the DCX regulatory sequence, the recombinant nucleic acid molecule or the vector described above.

Various methods are known in the art for introducing nucleic acid molecules into host cells. These include but are not limited to microinjection, in which DNA is injected directly into the nucleus of cells through fine glass needles; dextran incubation, in which DNA is incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell; calcium phosphate coprecipitation, in which cells efficiently take in DNA in the form of a precipitate with calcium phosphate; electroporation, in which cells are placed in a solution containing DNA and subjected to a brief electrical pulse that causes holes to open transiently in their membranes. DNA enters through the holes directly into the cytoplasm, bypassing the endocytic vesicles through which they pass in the DEAE-dextran and calcium phosphate procedures (passage through these vesicles may sometimes destroy or damage DNA); liposomal mediated transformation, in which DNA is incorporated into artificial lipid vesicles, liposomes, which fuse with the cell membrane, delivering their contents directly into the cytoplasm; biolistic transformation, in which DNA is absorbed to the surface of gold particles and fired into cells under high pressure using a ballistic device; and viral-mediated transformation, in which nucleic acid molecules are introduced into cells using viral vectors. Since viral growth depends on the ability to get the viral genome into cells, viruses have devised efficient methods for doing so. These viruses include, as mentioned above, retroviruses and lentivirus, adenovirus, herpesvirus, and adeno-associated virus. As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture. The DNA sequences are cloned into the plasmid vector using standard cloning procedures known in the art, as described by Sambrook (1989), loc. cit.

In accordance with one of the below-described methods, a nucleic acid molecule encoding, e.g. GFP under the control of a regulatory sequence of the present invention is thus introduced into a plurality of cells. The regulatory sequence which controls expression of the GFP, however, only functions in the cell type of interest (i.e. neuronal determined cells). Therefore, the GFP is only expressed in the cell type of interest. Since GFP is a fluorescent protein, the cells of interest can therefore be identified from among the plurality of cells by the fluorescence of the GFP.

Any suitable means of detecting the fluorescent cells can be used. The cells may be identified using epifluorescence optics, and can be physically picked up and isolated by mechanical devices such as Quixell (Stoelting, Inc., St. Louis, Mo.) or Laser Tweezers (Cell Robotics Inc., Albuquerque, N. Mex.). They can also be separated in bulk through fluorescence-activated cell sorting, a method that effectively separates the fluorescent cells from the non-fluorescent cells (e.g., Wang (1998)).

As will be further explained below, one embodiment of the present invention thus provides for the isolation and enrichment of neuronal determined cells from embryonic and adult nervous tissue, in particular brain of both rodent and human derivation. Specifically, fluorescence-activated cell sorting of human hippocampal cells, transfected with the fluorescent protein of choice driven by the DCX promoter/enhancer described herein is provided.

As also illustrated in the appended examples, one of the basic findings of the invention is the fact that herein generated non-human transgenic animals express heterologous nucleic acid sequences under the control of the regulatory sequences provided herein and that said expression is limited to cells which are neuronal determined/restricted and mitotically active.

Therefore, the present invention also provides a non-human transgenic animal which comprises host cells of the present invention and/or which comprises in its cells at least one additional copy of the regulatory sequence of the invention or which comprises in its cells a recombinant nucleic acid molecule of the invention. As shown in the examples, the generation of such a transgenic animal is within the skill of a skilled artisan. Corresponding techniques are, inter alia, described in "Current Protocols in Neuroscience" (2001), John Wiley&Sons, Chapter 3.16. Accordingly, the invention also relates to a method for the generation of a non-human transgenic animal comprising the step of introducing a regulatory sequence or a recombinant nucleic acid molecule of the invention into an ES-cell or a germ cell. The transgenic non-human animal may be selected from a plurality of transgenic animals e.g. non-vertebrates like *C. elegans, Drosophila* or vertebrates, like chicken. Yet, more preferred is a non-human transgenic which is a mammal, more preferably a rat or a pig, and most preferably mouse.

Preferably, the non-human transgenic animal comprises in its cells a recombinant nucleic acid molecule expressing a marker gene under the control of the regulatory sequence of this invention. Most preferably, the non-human transgenic animal comprises in its cells a recombinant nucleic acid molecule comprising the regulatory sequence of the invention and additionally a nucleotide sequence under the control of said regulatory sequence and encoding a marker/reporter gene, like green fluorescent protein (GFP or EGFP). Further corresponding embodiments are in the Examples. The non-human transgenic animal provided and described herein is particular useful in screening methods and pharmacological tests described herein below. In particular the non-human transgenic animal described herein may be employed in drug screening assays as well as in scientific and medical studies wherein neuronal determined cells and/or are tracked, selected and/or isolated.

In a further embodiment the invention provides for a composition comprising the regulatory sequence, the recombinant nucleic acid molecule, the vector or a genetically modified host cell described herein. Said composition may also comprise cells or tissue derived and/or obtained from a transgenic animal described above. Such cells or tissue may be particularly useful in xenografts. Most preferably, said composition is a pharmaceutical composition, optionally comprising a pharmaceutically acceptable carrier or diluent or a diagnostic composition, optionally further comprising suitable means of detection.

For formulating cells for administration as a pharmaceutical composition, the cells are suspended in a pharmaceutically acceptable carrier material. This applies, inter alia to neuronal determined cells obtained or selected by the methods described herein. Examples of carrier material are water, sodium chloride solution, dextrose, glycerol etc. or combinations thereof. In addition, the cell suspension to be administered may contain further substances, such as emulsifying agents, pH buffer, adjuvants or also neurotrophic factors, such as BDNF or NT-3 and the like.

Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal or intranasal administration and the like. Particularly preferred is intra-cerebral administration. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Proteinaceous pharmaceutically active matter may be present in amounts between 1 μg and 10 mg per dose; however, doses below or above this exemplary range are envisioned, especially considering the aforementioned factors. If the regimen is a continuous infusion, it should also be in the range of 1 μg to 10 mg units per kilogram of body weight per minute, respectively. Progress can be monitored by periodic assessment. The compositions of the invention may be administered locally or systemically. The compositions of the invention may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents depending on the intended use of the pharmaceutical composition.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, that is combined with buffer prior to use. After pharmaceutical compositions have been prepared, they can be placed in an appropriate container and labeled for treatment of an indicated condition. Pharmaceutical compositions suitable for use in the invention include compositions wherein the active ingredients are contained in an effective amount to achieve the intended purpose. The determination of an effective dose is well within the capability of those skilled in the art. For any compounds, the therapeutically effective dose can be estimated initially either in cell culture assays, e.g., of cultured neuronal cells, cell lines, or in animal models, usually mice, rabbits, dogs, or pigs. The animal model may also be used to determine the appropriate concentration range and route of administration. Such information can then be used to determine useful doses and routes for administration in humans. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration. The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy.

Modes of administering nucleic acid pharmaceuticals are described in the art, e.g. (Fynan, Proc. Natl. Acad. Sci. USA 90 (1993), 11478-11482; Boyer, Nat. Med. 3 (1997), 526-532; Webster, Vaccine 12 (1994), 1495-1498; Montgomery, DNA Cell Biol. 12 (1993), 777-783; Barry, Nature 311 (1995), 632-635; Xu and Liew, Immunology 84 (1995), 173-176; Zhoug, Eur. J. Immunol. 26 (1996), 2749-2757; Luke, J. Inf. Dis. 175 (1997), 91-97; Mor, Biochem. Pharmacology 55 (1998), 1151-1153; Donelly, Annu. Rev. Immun. 15 (1997), 617-648; MacGregor, J. Infect. Dis. 178 (1998), 92-100). Particular examples from the neurological field comprise Blits, Cell Transplant 11 (2002), 593-613; Boulis, J. Neurosurg. 96 (2002), 212-219. As mentioned above, gene therapy approaches are currently under way for certain disorders and offer novel treatment methods, see, inter alia, Frank, Surg. Oncol. Clin. N. Am. 11 (2002), 589-606 or Hull, Nurs. Stand. 17 (2002), 39-42.

For use the nucleic acid molecules described herein can be formulated in a neutral form or as a salt. Pharmaceutically effective salts are known to a skilled person. The nucleic acid molecules, in particular the recombinant nucleic acid molecules described above can be used inter alia to treat and/or to prevent neurological disorders and are administered in doses which are pharmacologically effective for prophylaxis or treatment.

Pharmaceutical compositions for injection are typically prepared as a liquid solution or suspension. The preparations can be emulsified or the active ingredient can be encapsulated in liposomes. The active ingredients are often mixed with carrier materials which are compatible with the active ingredient. Examples of carrier materials are water, sodium chloride solution, dextrose, glycerol, ethanol etc or combinations thereof. The vaccine as well as other nucleic acid pharmaceuticals of the invention may also contain auxiliary substances, such as emulsifiers, pH buffers and/or adjuvants.

DNA can be administered by biolistic transfer instead of by injection (U.S. Pat. No. 5,100,702; Kalkbrenner, Meth. Mol. Biol. 83 (1996), 203-216). For this purpose, DNA, that is to say recombinant nucleic acid molecules or vectors of the present invention, are bound to small particles, for instance gold particles or particles of biocompatible material, and, accelerated by gas pressure, are introduced into the brain. DNA can also be administered orally or sublingually or applied to the mucosa of the respiratory tract by nasal or intratracheal application. (for this, examples are given in Etchart, J. Gen. Virol. 78 (1997), 1577-1580 or McCluskie, Antisense and Nucleic Acid Drug Development 8 (1998), 401-414).

Of particular interest in context of this invention is also a pharmaceutical composition comprising proliferative neuronal determined/restricted cells as isolated and/or obtained by methods described herein below.

A "patient" or "subject" for the purposes of the present invention includes both humans and other animals, particularly mammals, and other organisms. Thus, the methods are applicable to both human therapy and veterinary applications. In the preferred embodiment the patient is a mammal, and in the most preferred embodiment the patient is human. Most preferably, the pharmaceutical composition to be prepared in accordance with this invention is to be administered by one or several of the following modes: Administration can be oral, intravenous, intraarterial, intratracheal, intranasal, subcutaneous, intramuscular, intracranial (i.e. intraventricular), intra-cerebral or intraspinal (intrathecal), epidermal or transdermal, pulmonary (e.g. inhalation or insufflation of aerosol or powder), by delivery to the oral or rectal mucosa as well as ophthalmic delivery.

In another embodiment, the present invention provides for a kit comprising the regulatory sequence, the recombinant nucleic acid molecule, the vector of any one or a genetically modified host cell described herein.

The invention furthermore provides for the use of a recombinant nucleic acid molecule, of a vector or of a genetically modified host cell (all expressing or capable of expression of a heterologous nucleic acid molecule under the control of the DCX promoter described herein) for the preparation of a pharmaceutical composition for the treatment of a neurological disorder or disease. Said neurological disorder or disease is preferably a neurodegenerative disease, an injury of the CNS or PNS, hypoxia, ischemia, epilepsy, stroke, CNS trauma, a tumorous disorder of the nervous system, a neural disorder caused by toxicological insult, a neuro-ophthalmological disorder, a psychiatric disorder, an age-related neurological loss or damage, or is neurological disorder caused by a developmental malformation, a brain malformation or a neural migration disorder. Neurodegenerative diseases in this context are, inter alia, Parkinson's disease, Alzheimer's disease, ALS, Creutzfeld-Jacobs disease or dementia, like HIV-related dementia. As mentioned above, also other neurological disorders, like Huntington's disease, stroke, ischemia, injuries, like spinal cord injuries or brain injuries, or toxic insults may be treated with the compounds of the present invention.

It is also envisaged that the recombinant nucleic acid molecule, the vector or the genetically modified host cell as described herein and capable of expressing a heterologous nucleic acid sequence is employed in the preparation of a pharmaceutical composition for the treatment of learning and/or memory disorders or for the enhancement of memory or learning skills. Memory or learning disorder comprise, but are not limited to, dementias, traumas, syphilis or apraxias. It is envisaged that, for example a recombinant nucleic acid molecule as described herein and consisting of the DCX promoter (or a functional fragment thereof) and a heterologous gene (driven by said promoter and expressing an anti-apoptotic gene is employed.

Accordingly, the present invention also provides for a method for treating and/or preventing a neurological disorder or disease comprising the administration of a compound of the present invention to a subject in need of such a treatment. Preferably said subject is a human patient. As will be discussed herein below, the present invention also provides for means and methods for the detection and/or isolation of neuronal determined/restricted cells. These cells are also particularly useful in medical settings and may also be comprised in pharmaceutical compositions of the invention and be employed in treatment and/or prevention regimes on, preferably, human patients.

Therefore, and as illustrated herein below, the invention also provides for the use of a recombinant nucleic acid molecule or of a vector of the invention for the preparation of a diagnostic composition for the detection of (a) neuronal determined cell(s). Furthermore, the use of a recombinant nucleic acid, of a vector or a genetically modified host cell described herein for the preparation of a diagnostic composition for the isolation of (a) proliferating neuronal determined cell(s) is an embodiment of the present invention.

In yet a further embodiment, the invention relates to a method for the detection of (a) neuronal proliferating determined cell(s) comprising the steps of (a) expressing in a plurality of cells a recombinant nucleic acid or a vector of the invention; and (b) selecting cells which express a heterologous nucleotide sequence under the control of the regulatory sequence as defined herein. In one embodiment said method comprises in step (b) the detection of an expressed, heterologous marker or reporter gene. Said method may comprise the detection of an expressed fluorescent marker, like GFP and derivatives thereof or gene coding for an enzyme, like β-Gal, CAT or luciferase. As illustrated herein below, the methods provided herein may comprises a FACS (Fluorescence activated cell sorting) analysis, MACS (Magnetic cell sorting via, inter alia, MS separation columns) analysis or affinity isolation (for example with magnetic beads and the like) of cells to be selected and isolated. Such methods are known by the person skilled in the art, see, e.g. Kawaguchi, Mol. Cell. Neurosci. 17 (2001), 259-273; WO 00/23571 or WO 01/53503.

As pointed out herein above, the present invention provides for the first time means for the detection and isolation of proliferative, neuronal-determined/restricted cells in vivo. Since DCX is an intracellularly expressed protein, selection systems based on detection of expressed DCX-mRNA or DCX-protein may only be carried out when cells are fixed and/or permeabilized and, accordingly, destroyed. Yet, the present invention provides for detection/selection systems allowing for an in vivo detection/selection of proliferative neuronal restricted/determined cells, in particular neuronal restricted/determined stem or progenitor cells. Due to the provision of specific DCX-regulatory sequences the invention, therefore, allows for unique and simple isolation approaches for desired neuronal cells, i.e. neuronal restricted cells which do not develop into undesired cells, like, e.g. astrocytes, oligodendrocytes or even non-neural cells, like cells of the hematopoetic system or epithelial cells. Accordingly, the invention also provides for a method for the detection of (a) proliferative neuronal restricted determined cell(s) comprising the step of selecting in a plurality of cells (a) cell(s) which comprise(s) an activated DCX regulatory sequence. Said method may additionally comprise a step of separating (a) cell(s) which express(es) a heterologous nucleotide sequence under the control of the regulatory sequence described herein from (a) cell(s) which is/are not capable of expressing said heterologous nucleotide sequence or may comprise an additional step of separating (a) cell(s) which comprise an activated regulatory sequence as defined herein. The activation of said regulatory sequence may, inter alia, be determined by the expression of a gene or a nucleic acid sequence encoding for a marker or a reporter as defined above. Said marker/reporter may, e.g. comprise a fluorescent protein or an enzyme, like luciferase or β-gal and the like.

Accordingly, the invention also provides for a method of separating proliferative neuronal determined cells from a mixed population of cell types from nervous tissue, based upon cell type-selective expression of the specific regulatory sequences/"promoters" for DCX. This method includes selecting the DCX regulatory sequence as defined herein which functions selectively in the neuronal determined cells, introducing a nucleic acid molecule encoding a marker, marker protein like a fluorescent protein under control of said promoter into all cell types of the mixed population of cell types from nervous tissue, e.g. hippocampal tissue allowing only the neuronal determined cells, but not other cell types, within the mixed population to express said marker protein, identifying cells of the mixed population of cell types that express said marker/marker protein, which are restricted to neuronal determined cells, and separating the marked/labelled cells from the mixed population of cell types, wherein the separated cells are restricted to neuronal determined cells. The person skilled in art is readily in a position to carry out the methods provided herein. Methods for separating cells are described in WO 98/32879, WO 00/23571 or WO 01/53503.

Due to the methods provided herein, it is now possible to obtain a distinct population of proliferative neuronal determined/restricted cells. Accordingly, in one embodiment, the present invention relates to an isolated neuronal determined cell or an enriched or purified preparation of isolated neuronal determined cells and progeny thereof. In context of the embodiments provided herein, the term "isolated" relates to (a) proliferative neuronal determined cell(s) which are obtained by methods described herein and have been separated from (nervous) tissue and/or cell populations/suspensions which comprise other neural cells, like glial cells, microglia cells, endothelial cells oligodendrocytes or mature, fully developed neurons and the like. Also envisaged is the isolation and separation of (a) proliferative neuronal determined cell(s) from multi/pluripotent undifferentiated stem cells.

The distinct all population of proliferative neuronal determined/restricted cells as obtained by the methods of this invention are particularly useful I screening assays (for example for neuroactive substances) as well as for medical purposes.

The invention relates to a detection of mitotically active neuronal determined/restricted cells or to an isolated and/or enriched or purified preparation of isolated, proliferative neuronal restricted/determined cells. The invention also relates to a method of separating proliferative neuronal restricted/determined cells from a mixed population of cells from nervous tissue or other tissues of an organism, such as chicken, rodent or human, based upon cell-type specific expression of a neuronal restricted/determined cells specific promoter/regulatory element, as disclosed herein. This invention comprises, e.g. the selective expression of a nucleic acid molecule encoding a detectable marker (fluorescent protein, luminescent protein, surface antigen, tag, etc.) under the control of the DCX regulatory sequence described herein. When using a fluorescent protein, the fluorescent cells of a mixed population of cell types are mitotically active neuronal determined/restricted cells and can be identified and separated from the rest of the cells. The hereby separated cells are neuronal determined/restricted cells, as documented in the appended examples. The promoter/regulatory sequence described herein specifically drives expression in neuronal determined/restricted cells, but not in other cells from the organism or from the mixed population of cells.

The regulatory sequence of the invention driving the expression of a detectable marker can be introduced into a plurality of cells, organs and organisms. This includes, but is not limited to, the introduction into cells by various methods known to those of ordinary skill in the art, for example transfection (liposomal based, electroporation, ballistic based, etc.) or viral mediated transduction (adenoviral, retroviral, etc.), and the introduction into organisms by various methods known to those of ordinary skill in the art, for example transfection (liposomal based, electroporation, biolistic based), viral mediated transduction (adenoviral, retroviral) and transgenic technology.

After cell specific expression of the detectable marker protein, e.g. green fluorescent protein (GFP) or enhanced green fluorescent protein (EGFP), the cells expressing the fluorescent protein are detected and/or separated by appropriate means, such as fluorescent activated cell sorting. Methods for isolation and separating cells expressing a detectable marker are available and known by skilled persons (Roy, J. Neuroscience 59 (2000), 321-331; Kawaguchi 2001, loc. cit.).

In spite of the embodiment described above, the invention also relates to the one of herein described regulating sequences for the expression of other heterologous nucleic acid sequences besides marker or reporter genes.

In another preferred embodiment, the present invention relates to the use of the regulatory sequences or the recombinant nucleic acid molecules or vectors of the invention, which preferably express a reporter gene, for identifying and isolating cis-elements from the regulatory sequence which mediate neuronal determined/restricted cell-specific expression.

In another preferred embodiment, the present invention relates to the use of the regulatory sequences or the recombinant nucleic acid molecules or vectors of the invention, which preferably express a reporter gene, for determining the degree of maturation of neuronal determined/restricted cells or for determining the influence of candidate compounds/drugs and the like on their differentiation program and/or their development. This embodiment can be used for instance to determine the degree of maturation of in vitro cultured neuronal cells or neural stem cells which are to be used in clinical studies. Yet, it is also envisaged that the degree of maturation of other cells (human and non-human cells) be assayed by the uses and methods provided herein. For example, it is envisaged that cells, e.g. non-neuronal/neural cells, like HEK293-cells, fibroblasts, are transfected/transduced with recombinant nucleic acid molecules as described above and said cells are employed in screening methods as provided herein. Accordingly, these transfected/transduced (host) cells may provide valuable tools in drug screening assays. As documented in the appended examples expression driven by the regulatory sequences of doublecortin provides for unique means to determine the developmental stage of a neuron-restricted cell, since doublecortin is merely transiently expressed during a restricted early phase during neuron development or differentiation.

Another embodiment of the invention relates to the use of the regulatory sequences, the recombinant nucleic acid molecules, the vectors, the host cells or the transgenic non-human animals (or their cells, tissues or organs) described herein for identifying and isolating factors which mediate neuron-restricted/neuronal determined cell-specific expression. Detailed methods for such an use are described herein below.

As already mentioned above, the neuronal determined/restricted cells which may be detected and isolated by methods provided herein are also useful in medical settings and in the prevention and/or treatment of neurological disorders and/or the treatment or prevention of learning or memory disorders. Therefore, the invention relates, in one embodiment, to the use of (a) neuronal determined cell(s) detected or as isolated by the method described herein for the preparation of a pharmaceutical composition for the treatment of a neurological disorder or disease. The present invention also provides means for the isolation and separation of proliferative neuronal restricted/determined cells from a mixed population of cells or from organs or organisms of different species. These isolated cells can be used for different purposes, including studying the molecular and cellular properties of this cell population, and for medical transplantation. Transplantation strategies for the diseased central nervous system (CNS) require non-tumorigenic, well characterized cells which are able to differentiate into the appropriate cell types. For neuronal cell replacement, neuronal determined/restricted cells are most suitable since they are already determined to become neurons, but are not yet fully differentiated and still flexible enough to acquire the neuronal phenotype required.

The recombinant nucleic acid molecule or of a vector of the invention may also be used for determining the degree of maturation of a neuronal cell. The person skilled in the art may for example employ transfection studies wherein the recombinant nucleic acid molecule or of a vector of the invention drives the expression of a marker or reporter gene. By analyzing the degree of expression of said marker or reporter gene, the skilled artisan is readily in a position to determine the developmental state of a cell transfected or transduced with said recombinant nucleic acid molecule or said vector. A positive signal indicates that the cell to be analyzed has the neuronal determination/differentiation program switched on, since the herein disclosed DCX regulatory sequence is active.

The recombinant nucleic acid molecule, the vector, the genetically modified host cell or the non-human transgenic animal (or organs, tissue or cells thereof of the present invention may also be employed and used for identifying and/or isolating factors and/or compounds capable of regulating neuronal determined cell activity, neurogenesis and/or neuronal differentiation or migration. Accordingly, the recombinant nucleic acid molecule, the vector, the genetically modified host cell or the non-human transgenic animal (or parts like isolated organs and cells of said animal) of the present invention may, inter alia, be employed in screening methods as described. Said recombinant nucleic acid molecule, said vector, and/or said genetically modified host cell of the invention are particularly useful for the generation of a non-human transgenic animal.

Therefore, the invention also provides for non-human transgenic animals as well as to the use of said transgenic, non-human animal for identifying and/or obtaining a molecule which is capable of modifying the cell fate of a neuronal stem cell or a neuronal progenitor. Preferably, said transgenic animal comprises in its somatic and/or germ cells at least one additional copy of the DCX regulatory sequence (or a functional part or a fragment thereof which controls the expression or non-expression of a selectable marker/reporter gene or of any further heterologous nucleic acid molecule. Such an animal may be a "knock-in" animal, expressing, e.g., a marker/reporter gene, like GFP, EGFP or DsRed, under the control of a regulatory sequence provided herein. Yet, an inventive transgenic animal may also be a transgenic animal which does not express a nucleic acid sequence under the control of the regulatory sequence described herein. Such animal may be a transgenic animal in which the corresponding, endogenous doublecortin (DCX) regulatory sequence has been inactivated or deleted (e.g. a "knock-out animal" or an animal comprising a mutated, non-functional version of the corresponding DCX regulatory sequences). In said "knock-out animal" the herein described regulatory sequences are inactivated or suppressed. The appended examples illustrate how such transgenic animals may be obtained and employed in the methods of the present invention.

A most preferred non-human transgenic animal of the present invention comprises in its cells at least one additional copy of the regulatory linked sequence described herein, preferably operatively linked to a heterologous gene, like a gene coding for a marker/reporter (e.g. luciferase, GFP, DsRed, EGFP and the like).

In a particular preferred embodiment of the invention, a method for screening of compounds capable of regulating neuronal determined cell activity, neurogenesis and/or neuronal differentiation is disclosed, said method comprising the steps of: (a) contacting a recombinant nucleic acid molecule, a vector or a genetically modified host cell or a non-human transgenic animal of the invention or a non-human transgenic animal as generated by the method of the invention with (a) compound(s) suspected to directly or indirectly interact with the regulatory sequence as defined herein; and (b) it is detected whether said compound(s) is/are capable of interacting with said regulatory sequence.

Said "contacting" may be carried out in vivo as well as in vitro. It is, e.g. envisaged that said transgenic animal is contacted in vivo with the compound/candidates to be tested. Said compound(s) may, inter alia, be injected to said animal, for example by inter-cerebral/inter-cranial injection. Similarly, cells transfected with a recombinant nucleic acid molecule as disclosed herein may be contacted in vitro with the compounds to be tested, for example by introducing the test compounds into the culture medium. The detection, whether said compound(s) is/are capable of interacting with regulatory sequence of the invention, may involve the detection, whether the regulatory sequence is activated. Corresponding, non limiting models are given herein below and in the appended examples.

The term "contacting a recombinant nucleic acid molecule of the invention with (a) compound(s) suspected to directly or indirectly interact said the regulatory sequence" may comprise tests of interaction. Such tests may be carried out by specific immunological, biochemical assays and/or genetic assays which are known in the art and comprise homogenous and heterogeneous assays. For example, in the method of the present invention, the interaction assays to be employed in accordance with this invention may be used to detect as a response the direct or indirect interaction of the regulatory sequence with the candidate molecule. Said interaction assays employing read-out systems are well known in the art and comprise, inter alia, two hybrid screenings, (as, described, inter alia, in EP-0 963 376, WO 98/25947, WO 00/02911 and modified for detection of interaction partners for the regulatory sequences of the invention), GST-pull-down columns, co-precipitation assays from cell extracts as described, inter alia, in Kasus-Jacobi, Oncogene 19 (2000), 2052-2059, "interaction-trap" systems (as described, inter alia, in U.S. Pat. No. 6,004,746), in vitro binding assays and the like. Further interaction assay methods and corresponding read out systems are, inter alia, described in U.S. Pat. No. 5,525,490, WO 99/51741, WO 00/17221, WO 00/14271, WO 00/05410. Of particular relevance in accordance with this invention are interaction assays which comprise biochemical/genetic methods like, e.g. band shift assays which are employed to deduce, inter alia, proteineous compounds capable of interacting with regulatory sequences/promoters.

Furthermore, the above recited method for screening of compounds capable of regulating neuronal determined cell activity, neurogenesis and/or neuronal differentiation may comprise the screening for substances which are capable to induce a differentiation program in a test/host cell comprising the regulatory sequence of the present invention. Said screening methods may also comprise the screening of compounds which activate, directly or indirectly, the regulatory sequence of DCX as defined herein and lead to a migration of a cell wherein said regulatory sequence is activated. The present invention provides for drug screening methods, as will be detailed below.

A difference in the expression profile of a nucleic acid molecule under the control of a regulatory sequence (or a functional part of fragment thereof) in the absence of the candidate agent as compared with the expression profile in the presence of the candidate agent indicates that the agent modulates the expression of DCX. Said agent is, accordingly, capable of "interacting with the regulatory sequence" of the present invention, when a corresponding readout scores positively. For example, a candidate agent may provoke the expression of a marker or reporter gene, like EGFP, DsRed or GFP under the control the herein described DCX-regulatory sequence. In this case, the candidate compound has, either directly or indirectly, interacted with said regulatory sequence. A direct interaction is, inter alia, envisaged from a specific transcription factor capable of binding to the regulatory sequence of the invention and of eliciting the transcription. An example of indirect interaction of the candidate compound comprises, but does not limited to, the involvement of a signal transduction pathway. Similarly, it is also envisaged that difference in the physiological response, for example of the electrophysiological response, in absence or in presence of the candidate molecule to be tested for specific modulation the activity of the regulatory sequence of the present invention indicates that the candidate agent/molecule/compound is capable of modifying said activity. The difference, as used herein, is statistically significant and preferably represents at least a 30%, more preferably at least 50%, more preferably at least a 90% difference. Accordingly, the DCX-specific promoter disclosed herein may be linked to a suitable reporter gene, e.g. DsRed, luciferase or GFP and the like, and used in cell-based assays to screen for compounds capable of modulating, via up- or down-regulation of DCX, a molecule which is transiently expressed in neurogenesis, as detailed in the appended examples.

The above mentioned comparison between the response upon contacting the regulatory sequence of the invention with said candidate molecule and the standard response as measured in the absence of said candidate molecule may provide for the presence, the absence, the decrease or the increase of a specific signal in the readout system. Said readout system, as described herein may be a, e.g., a biochemical or a physiological readout system, like a electrophysiological readout system. Genetic readout systems are also envisaged. A specific signal which is increased over the standard signal/response may thereby be classified as being an activator of the DCX regulatory sequence provided herein, whereas a decreased signal may be classified as being diagnostic for an inhibitor of DCX regulatory sequence function or expression.

As will be detailed below, the invention also relates to the use of a recombinant nucleic acid molecule, of a vector, of a genetically modified host cell or of a non-human transgenic animal of the invention or a non-human transgenic animal as generated by the method of the invention or to the use of (a) neuronal determined cell(s) as isolated by the method invention or of (an) isolated neuronal determined cell or an enriched or purified preparation of isolated neuronal determined cells and progeny thereof as described herein for in vivo or in vitro tracking of newly generated neurons, of transplanted neuronal determined cells or of migrating neuronal determined cells.

As described above, the present invention relates, inter alia, to the specific uses of recombinant nucleic acid molecules encoding marker genes or reporter activities whereby the expression of said markers and reporters is driven by the regulatory sequence described in the invention as DCX promoter. For example, a enzymatic activity may be used as marker or reporter activity that can be detected in a host of the present invention, e.g. a host cell or a transgenic animal, as well as in tissues and organs of said animal. The systems provided in this invention allow also the in vivo and in vitro tracking of newly generated neuron. For example, in vivo imaging of newly generating neurons during their "statu nascendi" is possible due to the provisions of the present invention. Accordingly, an ideal in vivo system is provided, which allows, inter alia, the test of environmental conditions, psycho- and physiological conditions and lesions on neurongeneration and migration. Furthermore, substances/compounds and mixtures of compounds, such as potential therapeutics, may be tested for their potential to influence neurogenesis during development and in the adult by employing, inter alia, the transgenic animals of the invention. Since marker/reporter molecules are expressed in the host cells or transgenic animals of the invention, their expression is specifically detectable in proliferative neuronal determined/restricted cells and their expression is down-regulated in mature neurons. In vivo imaging of the marker/reporter or of the marker/reporter activity enables a qualitative and quantitative analysis of the neurogenic activity in the host cell or the transgenic animal of the invention. In particular in the transgenic animal of the invention, migration of neuronal precursor cells may be studied. However, it is also possible to employ cells expressing the recombinant nucleic acid molecule of the invention in such studies. For example, such a host cell or isolated neuronal determined cell may be transplanted to a test animal and the fate of the transplanted cell may be visualized or measured in vivo. Accordingly, the methods of the invention allow in vivo tracking of transplanted cells that carry the recombinant nucleic acid as described in the invention, and their process of migration and neuronal determination/restriction/differentiation may be followed by means known in the art. In addition to in vivo experiments, the invention can be used to follow migrating or neuronal determined/restricted cells in an in vitro/ex situ tissue preparation which comprises cells comprising a recombinant nucleic acid molecule of the invention. In this context, a preferred molecule to be expressed under the control of the regulatory sequence of the invention is luciferase or its derivatives.

The method of noninvasive optical imaging of, e.g. luciferase activity in living animals, such as transplanted or transgenic mice or rats, is available and known by skilled persons (Bhaumik and Gambhir, PNAS 99 (2002), 377-382; Wu, Molecular Therapy 4 (2001), 297-306) and described in Examples. Here, a cooled charged-coupled device (CCD) camera for continuous in vivo assessment is used. The CCD camera is mounted on a light-tight imaging chamber, that houses the host organism such as transgenic mouse expressing luciferase under the regulatory sequence of the invention. The advantages of using luciferase-based non-invasive optical imaging are several: 1. compared to colorimetric and fluorescent reporter proteins that require an external source of light for excitation, bioluminoescent luciferase gene(s), such as firefly luciferase, does not need external light excitation, it self emits light from yellow to green wavelengths in the presence of luciferin, ATP, magnesium and oxygen. Therefore, cells that activate expression of, e.g. luciferase under the regulatory sequence of the invention (neuronal restricted/determined cells) are only luminescent for a transient period of time and therefore allow multiple real-time measurements in one and the same animal. 2. The fast rate of luciferase turnover (T $\frac{1}{2}$=3 h) in the presence of the substrate luciferin allows real time measurements. 3. There is a linear relationship between luciferase concentration and the emitted light in 7 to 8 orders of magnitude.

Therefore, the invention provides for in vivo and in vitro means and methods which allow the screening of substances/candidate compounds capable of influencing and/or modifying the fate and development of neuronal cells, like neuronal precursor cells as well as neuronal restricted/determined cells. Furthermore, with the means and methods provided herein, in particular the host cells and the transgenic non-human animals, it is now possible to screen for substances/candidate corresponds which promote neurogenesis. The substances are not only useful in the prevention and therapy of neurological disorders and diseases but are also useful in treating psychosis, learning or memory disorders. Additionally, in vivo, in vitro and ex situ methods are provided which allow the tracking of cells comprising an activated regulatory sequence described in the invention. It is also envisaged that cell migration assays be carried out, employing the recombinant nucleic acid molecule, the vectors, the host cells as well as cells or tissues derived from the transgenic animals of the invention. These assays may comprise grafting experiments. As a non-limiting example, it is envisaged that grafting experiments from one species to another are carried out, e.g., the cells obtained from a transgenic mouse comprising in its cells a recombinant nucleic acid molecule as described above (for example the transgene luciferase, GFP. DsRed or the like) may be grafted into, e.g., rat (brains) and migration behaviour, survival and/or differentiation of said grafted cells may be tested.

As mentioned above, in particular cell systems or transgenic animals (or cells, tissues or organs thereof comprising the recombinant nucleic acid molecule described above may be employed in drug screenings, for example in screenings for the detection and/or isolation of substances and drugs which, either directly or indirectly activate the DCX regulatory sequence and which promote, inter alia, differentiation/determination programs in cells towards a neuron-phenotype or towards a neuron. As non-limiting example, a transgenic mouse model (or its cells, tissues or organs, like the brain) as described in the appended examples and expressing a marker gene (e.g. luciferase, DsRed, EGFP and the like) under the control of the regulatory sequence described herein may be used in drug screening experiments, in order to test the neurogenic potential (i.e. the potential to generate new neurons in the adult brain) of a compound. The dentate gyrus and the lateral ventricle/rostral migratory stream/olfactory bulb system are the two prominent regions of the adult brain, which produce new neurons. Therefore, these two regions may be analyzed in these mice for enhanced production of new neurons. Other brain regions, such as the neocortex, striatum, cerebellum, substantia nigra and spinal cord, which have very low or undetectable adult neurogenesis, may be analyzed in order to test the ability of a compound to induce de novo neurogenesis. In an exemplified experiment, the animals receive a compound or a mixture of compounds to be tested either by, e.g., intracerebroventricular infusion via osmotic minipumps (Kuhn, J. Neurosci. 17 (1997), 5820-5829) or by peripheral administration (such as intraperitoneal, subcutaneous or intravenous route). After several days of treatment the animals will be sacrificed and the brains are removed. In order to measure the amount of marker (for example GFP) producing cells, several different detection methods may be used: For example, histological cell counting may be employed. Brains will be sliced on a microtome and mounted on slides for histological analysis. With this method the number of marker (for example GFP) expressing cells in the above mentioned brain areas may be counted either manually using a fluorescent microscope or with assistance of automatic or semiautomatic morphometric analysis systems. The goal is to generate the number of marker-expressing cells per brain structure. The data from animals, which received a drug, may be compared to control animals or animals, which received a reference drug. Similarly, histological fluorescence detection may be employed. In order to avoid time-consuming manual cell counting, a direct fluorescence intensity measurement may be taken to assess the expression level. Brains will be processed for histological analysis and individual images from certain brain areas are analyzed for marker (here fluorescence intensity using morphometric software such as NIH Image. The goal is to generate a marker (e.g. GFP) intensity index for each mouse in order to compare animals, which received a compound, to control animals or animals, which received a reference drug. Biochemical methods may also be used: after tissue homogenization, this procedure may allow the determination of total marker fluorescence per analyzed sample. Microdissected brain areas or whole brain may be used to quantify the amount of green fluorescence marker (e.g. GFP, EGFP and the like) from supernatant of tissue homogenates. Supernatants may be analyzed in a fluorometer, such as a fluorescent ELISA plate reader. Also, FACS-analysis may be employed. As illustration, the brains of the transgenic animal expressing the marker under control of the regulatory sequence of the invention are microdissected to analyze the above mentioned brain areas for marker-expressing cells. After tissue homogenization, single cell suspension may be injected into a fluorescence-activated cell analyzer in order to determine the fraction of marker (e.g. GFP) expressing cells among the total population of cells in a given brain structure.

The non-human transgenic animals as well as the isolated cells and organs from said animal are partially useful (like the host cells described herein) for the screening methods disclosed in this invention. They are partially useful in in vivo and in vitro assays for testing the neurogenic properties of candidate compounds.

Candidate agents for compounds capable of regulating neuronal determined cell activity, neurogenesis and/or neuronal differentiation encompass numerous chemical classes. It is, e.g. envisaged that antidepressants or growth factors be employed in the screening systems provided herein. Typical candidate agents are also typically organic compounds; preferably small organic compounds. Small organic compounds have a molecular weight of more than 50 Da yet less than about 2.500 Da, preferably less than about 1.000 Da, more preferably, less than about 500 Da. Candidate agents comprise functional chemical groups necessary for structural interactions with lipids, proteins and/or DNA, and typically include at least an amine, carbonyl, hydroxyl or carboxyl group, preferably at least two of the functional chemical groups, more preferably at least three. The candidate agents often comprise cyclical carbon or heterocyclic structures and/or aromatic or polyaromatic structures substituted with one or more of the aforementioned functional groups. Candidate agents are also found among biomolecules including peptides, proteins, saccharides, fatty acids, steroids, purines, pyrimidines, derivatives, structural analogues or combinations thereof, and the like. Where the agent is or is encoded by a transfixed nucleic acid, said nucleic acid is typically DNA or RNA. The candidate compound itself may be an nucleic acid molecule, e.g. a DNA or an RNA encoding a potential candidate. Such candidates comprise for example nucleic acid molecules encoding transcription factors or proteins/peptides involved in neuro-development and the like. Such a candidate may, however, also be a compound which inhibits the expression of proteins. Such inhibiting candidates may, inter alia, be nucleic acid molecules comprising, e.g., antisense oligonucleotides, RNAi and the like. Candidate molecules which can be used in accordance with the method of the present invention also include, inter alia, peptides, proteins, lipids, antibodies, aptamers, intramers or small organic compounds.

As mentioned above, candidate agents may be obtained from a wide variety of sources including libraries of synthetic or natural compounds. For example, numerous means are available for random and directed synthesis of a wide variety of organic compounds and biomolecules. Alternatively, libraries of natural compounds in the form of bacterial, fungal, plant, and animal extracts are available or readily produced. Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc., to produce structural analogues.

The candidate molecule to be tested in the method of the present invention may be a single isolated substance as well as a plurality of substances which may or may not be identical. Said candidate molecules/compound(s) may be comprised in, for example, samples, e.g., cell extracts from, e.g., plants, animals or microorganisms. Furthermore, said compound(s) may be known in the art but hitherto not known to be capable of influencing the activity of DCX regulatory sequences or not known to be capable of influencing the expression of the DCX regulatory sequences, respectively. The plurality of compounds may be, e.g., added to a sample in vitro, to the culture medium or injected into the cell or a test animal, preferably a non-human transgenic test animal.

If a sample (collection of candidate molecules) containing (a) compound(s) is identified in the method(s) of the invention, then it is either possible to isolate the compound from the original sample identified as containing the compound in question or one can further subdivide the original sample, for example, if it consists of a plurality of different compounds, so as to reduce the number of different substances per sample and repeat the method with the subdivisions of the original sample. It can then be determined whether said sample or compound displays the desired properties by methods known in the art such as described herein. Depending on the complexity of the samples, the steps described above can be performed several times, preferably until the sample identified according to the method of the invention only comprises a limited number of or only one substance(s). Preferably said sample comprises substances of similar chemical and/or physical properties, and most preferably said substances are identical. The methods of the present invention can be easily performed and designed by the person skilled in the art, for example in accordance with other cell based assays described in the prior art (see, e.g., EP-A-0 403 506). Furthermore, the person skilled in the art will readily recognize which further compounds and/or cells may be used in order to perform the methods of the invention, for example, transfected/transduced host cells as described herein above. It is also envisaged that the methods of the present invention are employed on cells, tissues or organs of the transgenic animal as described above.

The compounds/candidate molecules to be tested may also be functional derivatives or analogues of known activators or inhibitors. Methods for the preparation of chemical derivatives and analogues are well known to those skilled in the art and are described in, for example, Beilstein, loc. cit. Furthermore, said derivatives and analogues can be tested for their effects according to methods known in the art and/or as described herein. Furthermore, peptidomimetics and/or computer aided design of appropriate activators or inhibitors of the expression the DCX regulatory sequence can be used, for example, according to the methods described herein. Appropriate computer systems for the computer aided design of, e.g., proteins and peptides are described in the prior art, for example, in Berry, Biochem. Soc. Trans. 22 (1994), 1033-1036; Wodak, Ann. N.Y. Acad. Sci. 501 (1987), 1-13; Pabo, Biochemistry 25 (1986), 5987-5991. The results obtained from the above-described computer analysis can be used in combination with the method of the invention for, e.g., optimizing known compounds, substances or molecules. Appropriate compounds/candidate molecules can also be identified by the synthesis of peptidomimetic combinatorial libraries through successive chemical modification and testing the resulting compounds, e.g., according to the methods described herein. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715.

In a further embodiment, the present invention provides for a method for the preparation of a pharmaceutical composition for the treatment of a neurological disorder or disease comprising the steps of the method(s) described herein and, additionally, the formulation of (a) compound(s) capable of regulating neural stem cell activity, neurogenesis and/or neuronal differentiation as detected and/or obtained obtained by said method(s) with a pharmaceutically acceptable carrier, excipients and/or diluent. Examples of suitable pharmaceutical carriers, excipients and/or diluents are mentioned herein above.

The methods described herein are particularly suited for automated high-throughput drug screening using robotic liquid dispensing workstations. Similar robotic automation is available for high-throughput cell plating and detection of various assay read-outs.

Generally a plurality of assay mixtures are run in parallel with different agent concentrations to obtain a differential response to the various concentrations. Typically, one of these concentrations serves as a negative control, i.e. at zero concentration or below the limits of assay detection.

These and other embodiments are disclosed and obvious to a skilled person and embraced by the description and the Examples of the present invention. Additional literature regarding one of the above-mentioned methods, means and uses, which can be applied within the meaning of the present invention can be obtained from the prior art, for instance in public libraries, e.g. with the use of electronic means. For this purpose, public data bases, such as "Medline", can be accessed via the internet, for instance under the address http://www.ncbi.nim.nih.gov/PubMed/medline.html Additional data bases and addresses are known to a skilled person and can be taken from the internet, for instance under the address http://www.lycos.com. An overview of sources and information regarding patents or patent applications in biotechnology is given in Berks, TIBTECH 121 (1994), 352-364.

The Figures show:

FIG. 1: Western blot analysis of antibodies directed against doublecortin (DCX)

Tissue homogenate from an adult rat olfactory bulb was separated on a 12% polyacrylamide SDS-PAGE and transferred onto a nitrocellulose membrane. Each lane, containing 2 μg of proteins, was incubated into a different antibody solution. Lane 1 was incubated in a solution containing goat anti-doublecortin C-18 antibody (Santa Cruz Laboratories), lane 2 was incubated in a solution containing goat anti-doublecortin N-19 antibody (Santa Cruz Laboratories) and the lane 3 was incubated in a solution containing mouse anti-doublecortin antibody (Transduction Laboratories). The immune complex was detected by chemiluminescence. The goat anti-doublecortin C-18 antibody was the more specific and recognized a single band of approximately 40 kDa, which corresponds to the expected molecular weight of doublecortin.

Figure 2A:
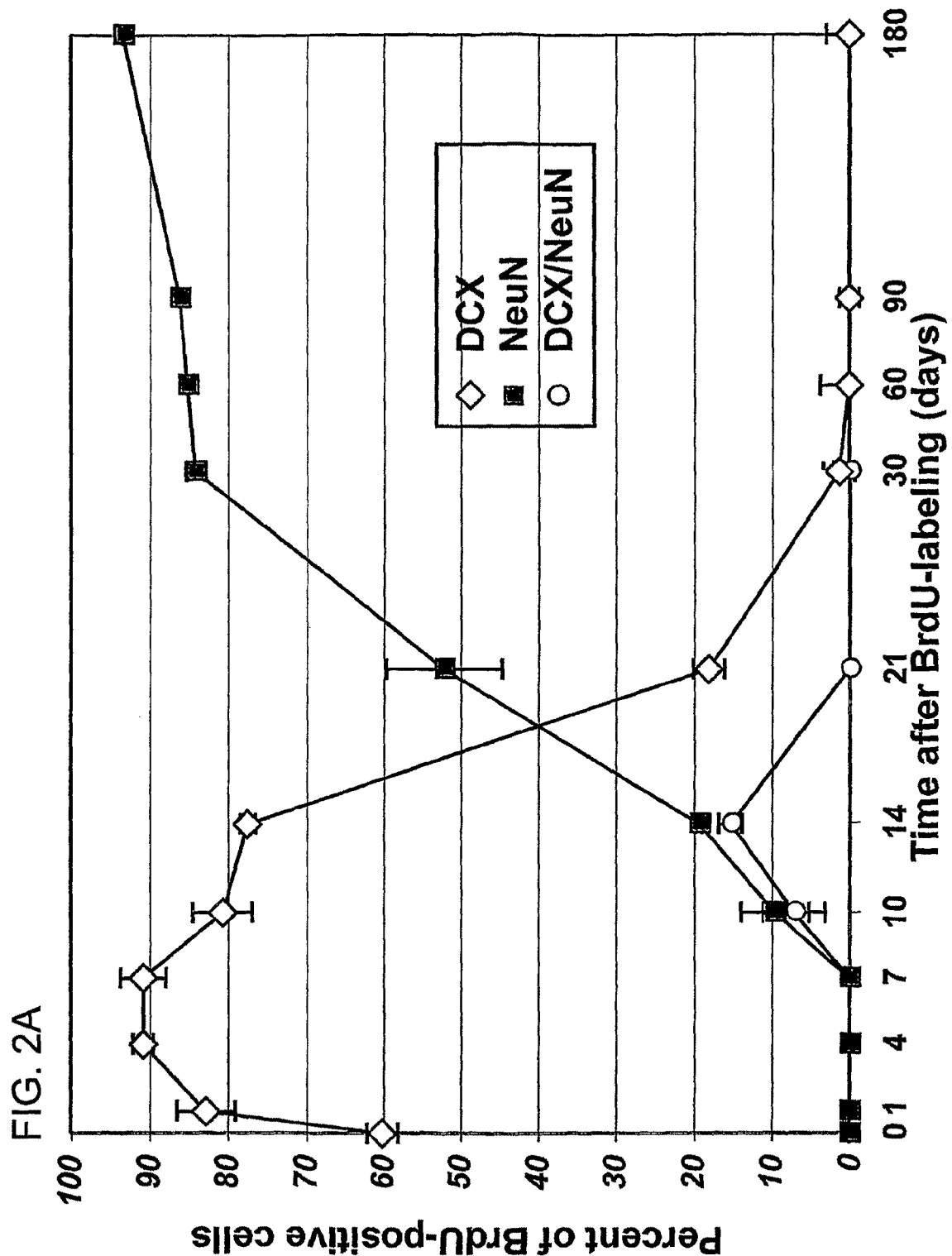

FIG. 2: Time course of DCX expression in newly generated cells of the adult dentate gyrus After injecting BrdU into 2 month-old rats, we determined in the dentate gyrus granule cell layer over a period of 180 days the changes in co-labeling of BrdU with DCX and NeuN. The time course in (A) depicts the percentage of BrdU immuno-positive cells co-labeling for DCX (diamonds), NeuN (squares) or DCX+NeuN (circles). The data are presented as the percentages of BrdU-positive per region, for each time point post BrdU injection (n=4 animals per group, mean±S.E.M). (B-G) Representative images from the dentate gyrus granule cell layer depicting BrdU immunodetection (central block)(nuclear immuno-reactivity), DCX (cytoplasmic immuno-reactivity detected in the perikaryal regions and in the processes crossing the granule cell layer (left block) and NeuN (right block) (nuclear immuno-reactivity) at 2 hours (B), 4 days (C), 7 days (D), 10 days (E), 21 days (F), 60 days (G). Arrows indicate examples of double labeling of BrdU with DCX and asterisks indicate double labeling of BrdU with NeuN.

Figure 3:
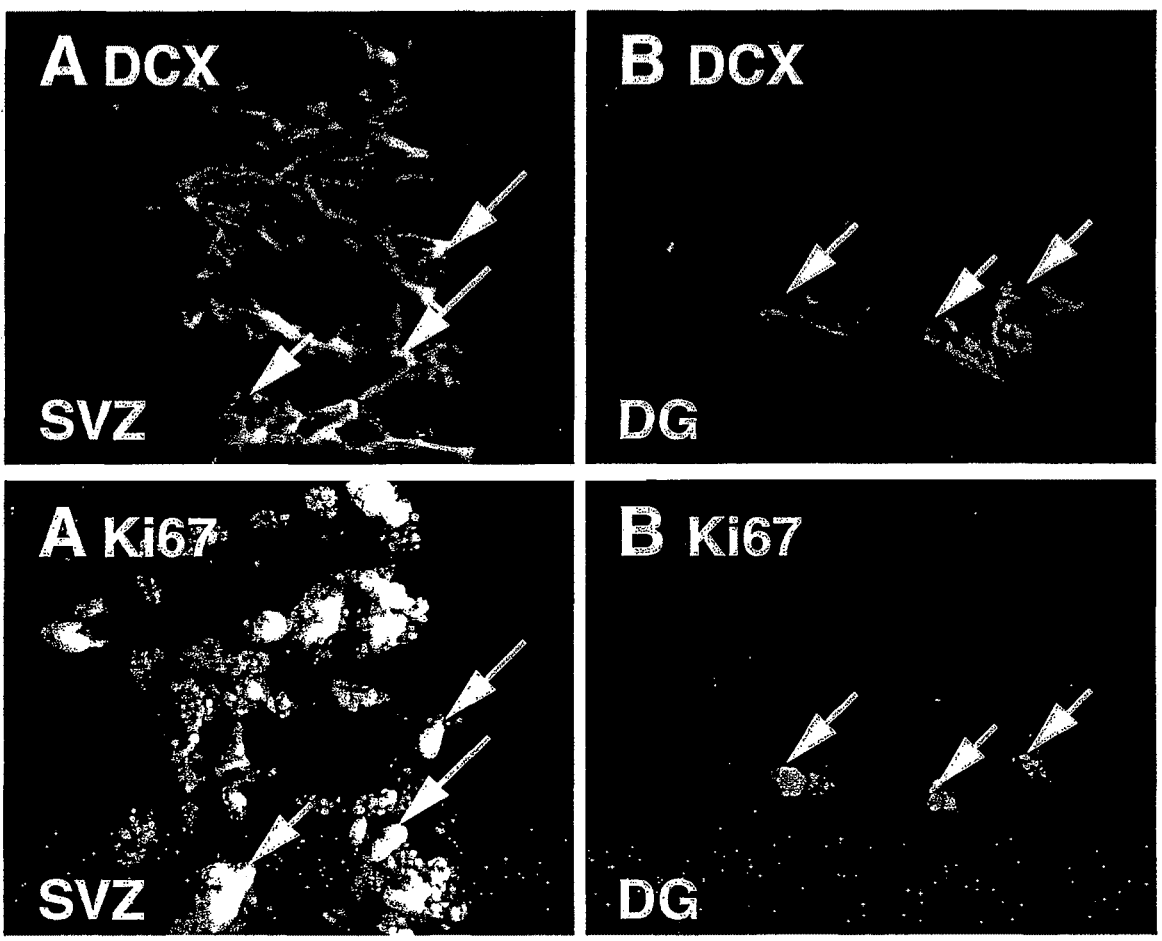

FIG. 3: DCX expression in proliferating cells

To confirm that DCX is expressed in proliferating cells, we used co-labeling DCX with Ki-67, a marker for cells undergoing cell division. (A) In the subgranular zone of the dentate gyrus (SVZ) and (B) in the subventricular zone of the lateral ventricle wall (DG) DCX/Ki-67 double labeling can be readily detected as proliferative cell clusters. The Ki67 immuno-reactivity is located in the nucleus, whereas the DCX immuno-reactivity is cytoplasmic. Some of the Ki67 immuno-reactive nuclei are indicated with arrows.

Figure 4:
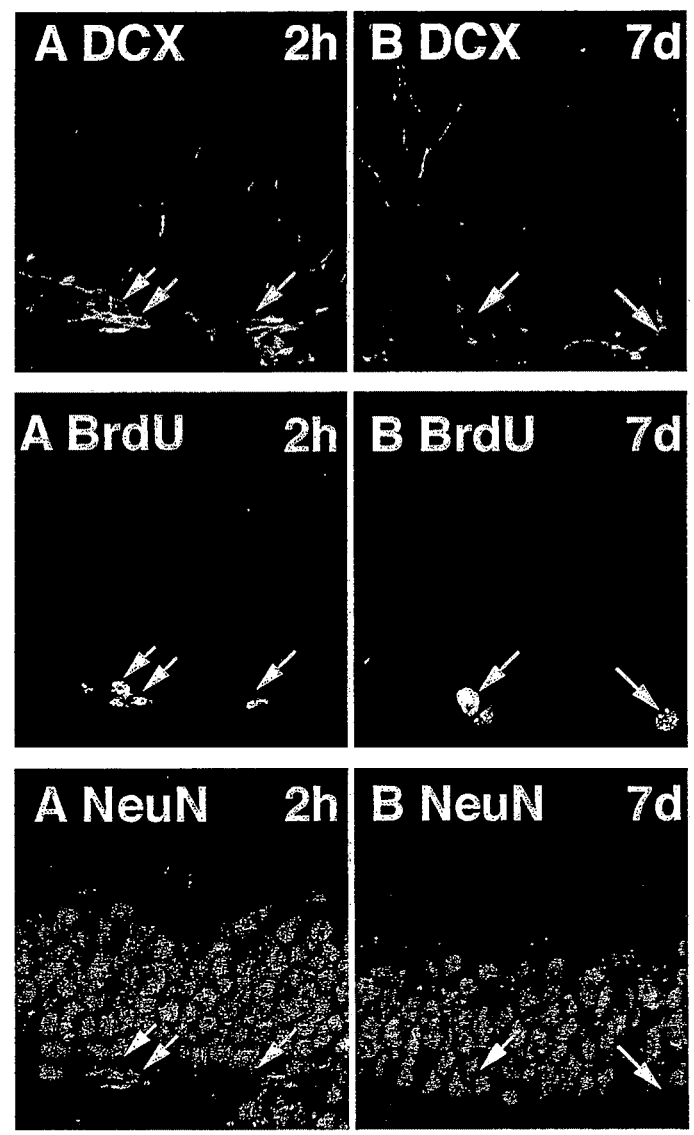

FIG. 4: Morphology of DCX expressing cells in the dentate gyrus

Two different phenotypes of DCX positive cells were found in the dentate gyrus, which correlate with double labeling of BrdU at certain time points after BrdU application: (A) Amorphous and short branched cells in the subgranular zone with a tangential orientation along the granule cells layer and (B) cells situated at the base of the granule cell layer, with processes oriented perpendicular reaching into the molecular layer. Arrows point to cells co-labeled with BrdU and DCX.

Figure 5:
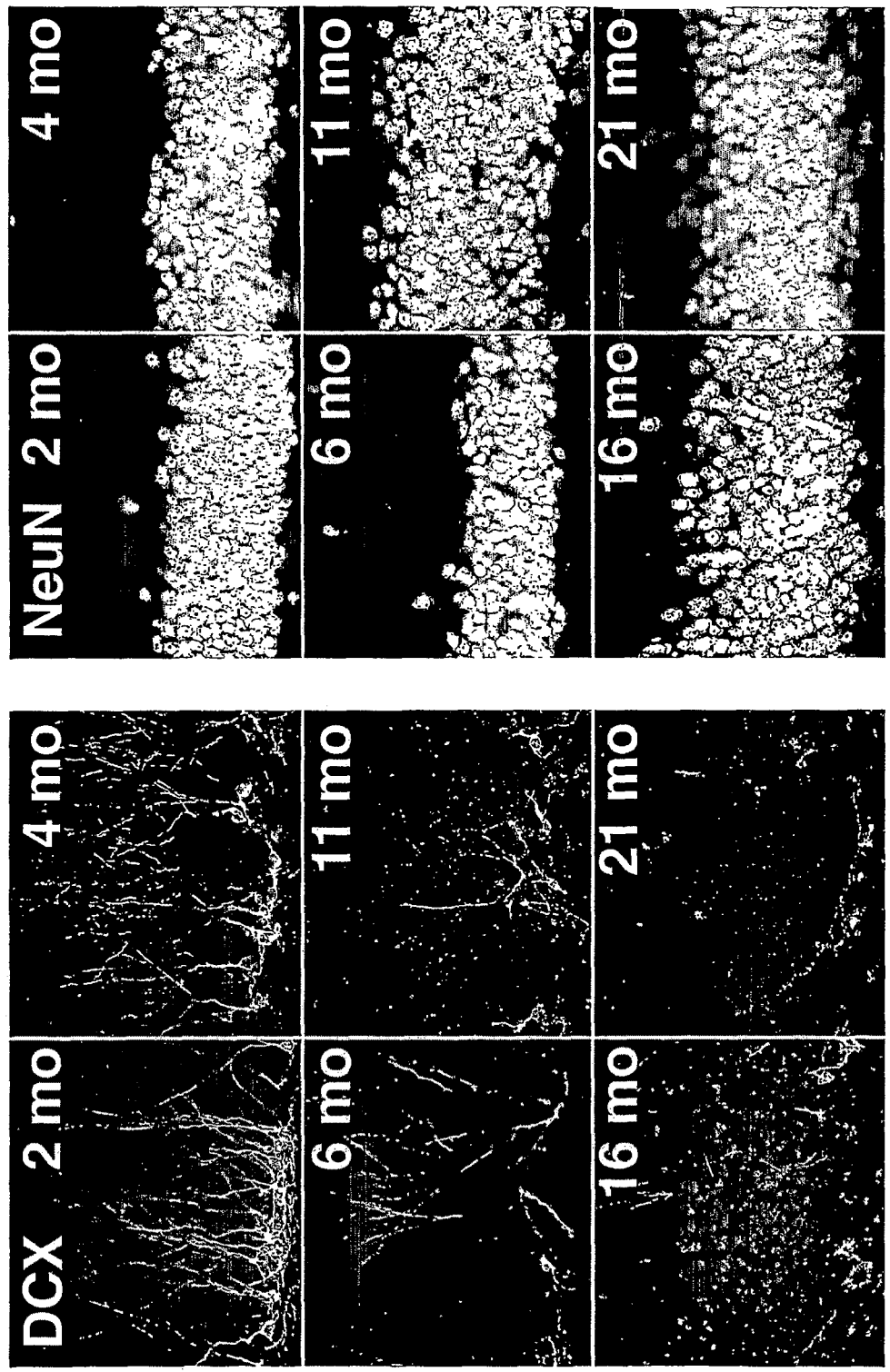

FIG. 5: Doublecortin expression decreases in the aging dentate gyrus

Six time points ranging from 2 month-old animals to 21 month-old animals were selected for analysis. These time points cover the range over which the age dependent decrease in hippocampal neurogenesis has been previously described (Kuhn, J, Neurosci, 16 (1996), 2027-2033). Images were obtained by confocal microscopy using representative sections from the dentate gyrus. Areas of greatest intensity of DCX were chosen from each section for imaging. The DCX immunoreactivity can be appreciated in the numerous processes crossing the granule cell layer. The NeuN immunoreactivity is present in most of the granule cells nuclei, thereby highlighting the granule cell layer.

Figure 6:
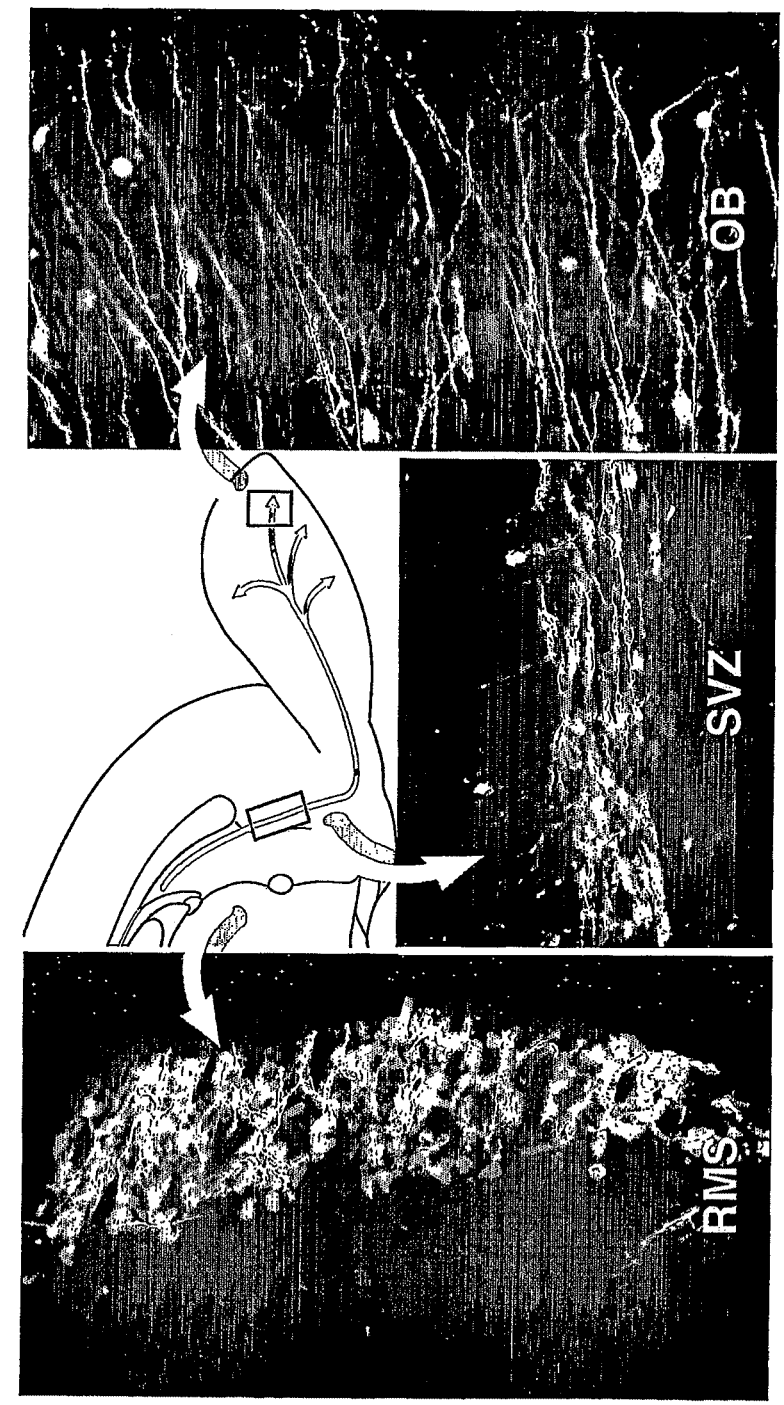

FIG. 6: Morphology of DCX expressing cells during olfactory bulb neurogenesis

Similar to the dentate gyrus, multiple morphological phenotypes of DCX immuno-reactive cells can be found in the subventricular zone (RMS), rostral migratory stream (SVZ) and olfactory bulb (OB), which correlate with double labeling of BrdU and DCX at different time points after BrdU application: amorphous and short branched cells in the subventricular zone undergoing cell division, tangentially oriented cells in the rostral migratory stream, representing migrating neuroblasts and cells in the olfactory bulb extending neurites into the plexiform layer, indicative of differentiating neuroblasts and young neurons. A schematic anatomical drawing (center) depicts the anatomical position from which the pictures were taken.

FIG. 7: Time course of DCX expression in newly generated cells of the adult olfactory bulb After injecting BrdU into 2 month-old rats, we determined in the olfactory bulb granule cell layer over a period of 180 days the changes in co-labeling of BrdU with DCX and NeuN. The time course in (A) depicts the percentage of BrdU immunopositive cells co-labeling for DCX (diamonds), NeuN (squares) or DCX+NeuN (circles). The data are presented as the percentages of BrdU-positive per region for each time point post BrdU injection (n=4 animals per group, mean±S.E.M.). (B-G) Representative images of from the olfactory bulb granule cell layer depicting BrdU (central block) (nuclear immuno-reactivity), DCX (left block) (cytoplasmic immuno-reactivity detectable in the cell soma and processes) and NeuN (right block) (nuclear immuno-reactivity) at 2 hours (B), 4 days (C), 7 days (D), 10 days (E), 21 days (F), 60 days (G). Arrows indicate examples of double labeling of BrdU with DCX. Note that no BrdU/DCX double labeling can be found at 2 hrs and 4 days after labeling, since the BrdU-positive neuronal precursor cells of the SVZ have to migrate through the RMS and arrive in the olfactory bulb at after approximately 4 days.

Figure 8B:
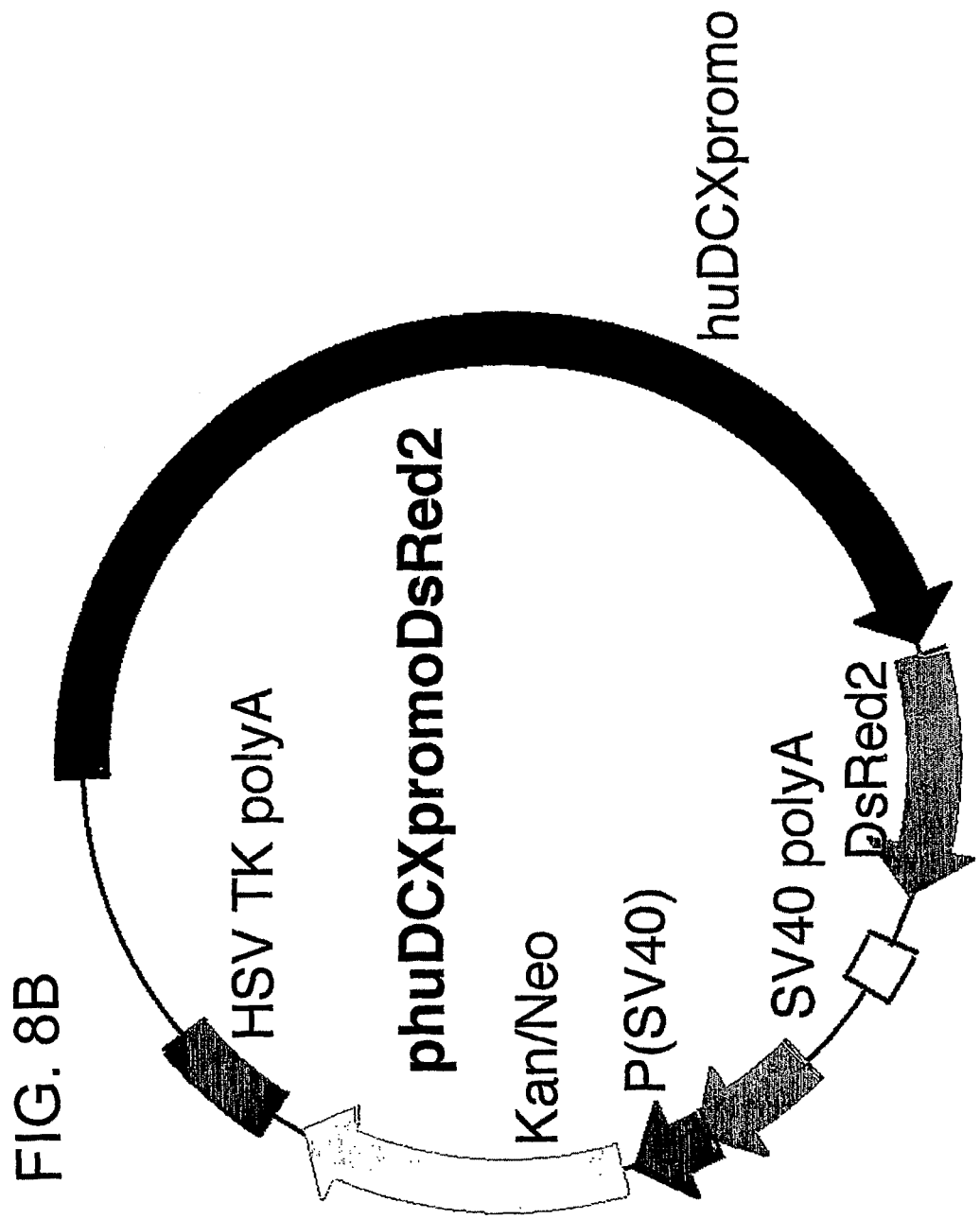

FIG. 8: Diagrams of the plasmids phuDCXpromoEGFP1 and phuDCXpromoDsRed2

The regulatory sequence of the DCX gene was subcloned in the pEGFP-N1 and the pDsRed2-1 from BD Biosciences Clontech. The cytomegalovirus (CMV) promoter was removed from the pEGFP-N1 vector prior to the insertion of the DCX regulatory sequences. The regulatory sequence was subcloned in order to control the expression of the fluorescent proteins EGFP (A) or DsRed2 (B). Examples of the EGFP reporter gene under the control of the human DCX regulatory sequence are the Seq ID NO:5 and 7. Examples of the DsRed2 reporter gene under the control of the human DCX regulatory sequence are the Seq ID NO:6 and 8.

FIG. 9: Alignment #1. Human vs Mouse regulatory sequences

Optimal global alignment between Sequence ID no: 1 and Sequence ID no: 2 using the "fasta20u66, version 2.0u66" alignment function available at Biology Workbench of the San Diego Supercomputer Center.

FIG. 10: Diagram of the human vs mouse regulatory DCX sequences

A) The two sequences (SEQ ID NO 1: Human and SEQ ID NO 2: Mouse) are illustrated with the exon sequences as black boxes. Only the putative non-translated exon fragments are represented, i.e. exon 1, exon 2, exon 3 and the beginning of exon 4. B) The nucleic acid sequence outside the exons can be subdivided into regions. The diagram illustrates the positions of these regions and exons. The table gives the nucleotide positions of these regions and exons in the mouse and human regulatory DCX sequences, as well as the percentage of identity between the corresponding regions and exons of the two sequences. The fragment of the human DCX regulatory sequence comprised between the nucleotide number 1166-3509 corresponds to the diagnostic region.

FIG. 11: Alignment #2. Alignment of the diagnostic regions of the human vs mouse DCX regulatory sequences Optimal global alignment between Sequence ID no: 3 (human) and Sequence ID no: 4 (mouse) using the "fasta20u66, version 2.0u66" alignment function available at Biology Workbench of the San Diego Supercomputer Center.

FIG. 12: Cloning strategy of the human DCX regulatory sequence

Schematic representation of the cloning of the human DCX regulatory sequence using a PCR amplification approach (as described in the Example II).

FIG. 13: Expression of the EGFP gene under the control of the human DCX regulatory sequence A) Mouse embryonic day 14.5 dissociated forebrain cultures, containing neuronal-restricted precursor cells, were plated over poly-ornithin/laminin matrix for one week in the presence of NT3 and fetal calf serum. The culture were then transfected with the phuDCXpromoEGFP1 vector. Two days after the end of the transfection, the cultures were examined for the expression of the EGFP reporter gene. In the right panel DAPI was used as a nuclear counterstain. This photograph documents the presence of cells with the morphology of young neuroblasts expressing the reporter EGFP gene. Insert documents the various morphologies of cells transfected with the reporter EGFP gene expressed under an ubiquitous promoter (CMV; cytomegalovirus promoter).

B) Human fetal cortical stem cell cultures were treated and transfected as in (A). The photograph documents the presence of cells with the morphology of young neuroblasts expressing the reporter EGFP gene.

C) Cultures of the COS7 cell line (ATCC number CRL-1651), derived from SV40 transformed kidneys cells of Cercopithecus aethiops and therefore not containing neuronal-restricted precursor cells, were plated over poly-ornithin/laminin matrix for 24 hours and transfected with the phuDCXpromoEGFP1 vector.

Two days after the end of the transfection, the cultures were examined for the expression of the EGFP reporter gene. Few cells expressed the EGFP reporter gene at the lower limit of detection. In the right panel DAPI was used as a nuclear counterstain. In contrast, identical culture transfected with vector encoding the EGFP reporter gene under the control of an ubiquitous promoter, i.e. the CMV promoter, strong expression of the reporter gene could be detected in numerous cells (see C inset).

Figure 14:
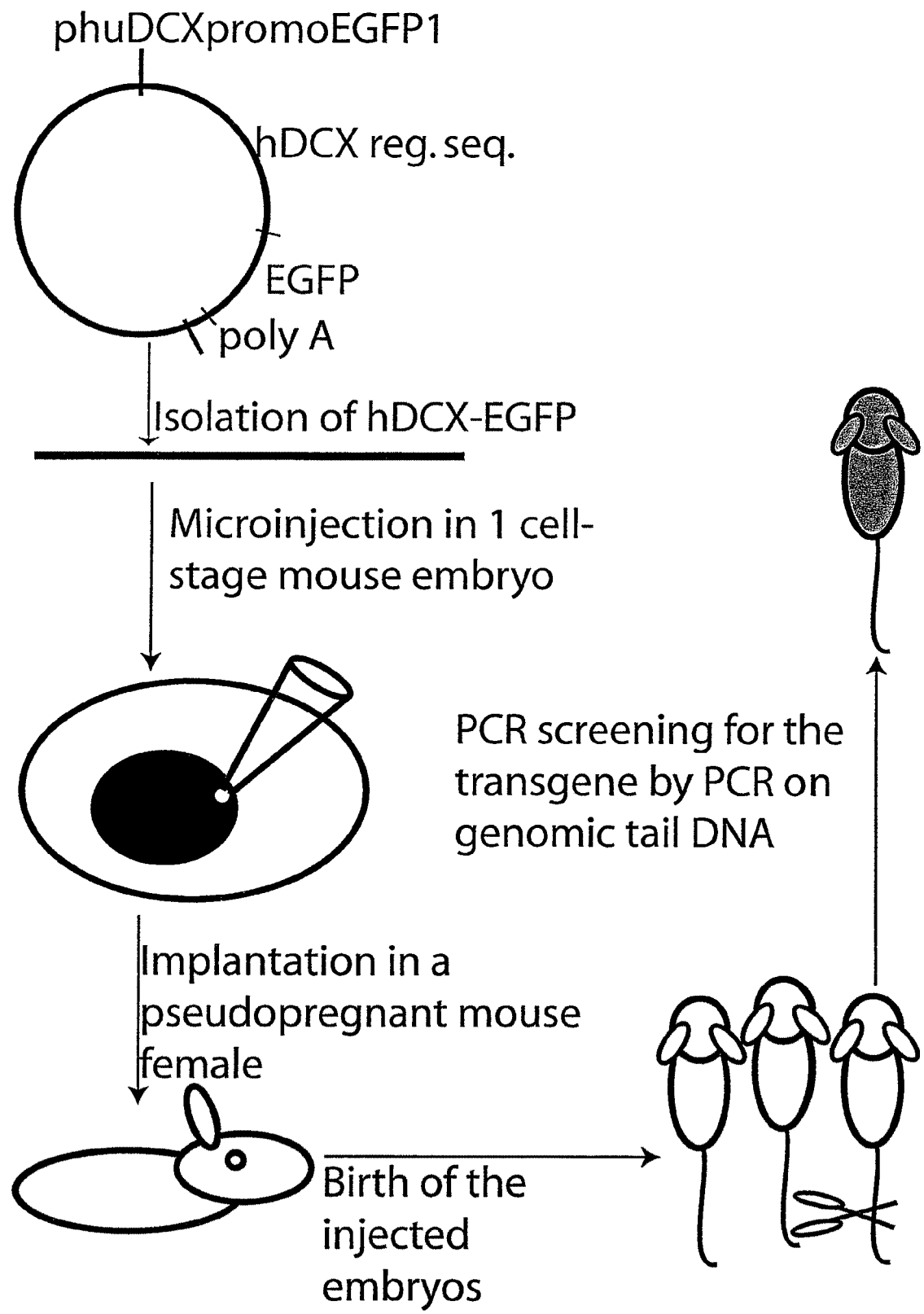

FIG. 14: Strategy for the generation of transgenic mice expressing the EGFP gene under the control of the human DCX regulatory sequence Schematic description of the generation of transgenic mice expressing the EGFP reporter gene under the control of the human DCX regulatory sequence (as described in the Example IV).

FIG. 15: Expression pattern of EGFP under the control of the human DCX regulatory sequence in two lines of transgenic mouse Detection of the EGFP fluorescent signal in sagital brain sections of 1 month-old huDCXpromoEGFP1 transgenic mice from the line 299 and line 303. The EGFP reporter gene signal can be detected in newly generated neuronal restricted precursors, in particular in regions involved in active neurogenesis, i.e. in the dentate gyrus and in the subventricular zone-olfactory bulb axis. A-F) transgenic mouse from line 299. A-C) EGFP signal detected in the olfactory bulb (A), cortex (B), dentate gyrus (C), respectively. D-F) counterstain using the DNA binding fluorochrome, DAPI, in the same visual fields as in A-C. G-L, transgenic mouse from line 303. G-1) EGFP signal detected in the olfactory bulb (G), cortex (H), dentate gyrus (I), respectively. J-L) counterstain using the DNA binding fluorochrome, DAPI, in the same visual fields as in G-I.

Figure 16:
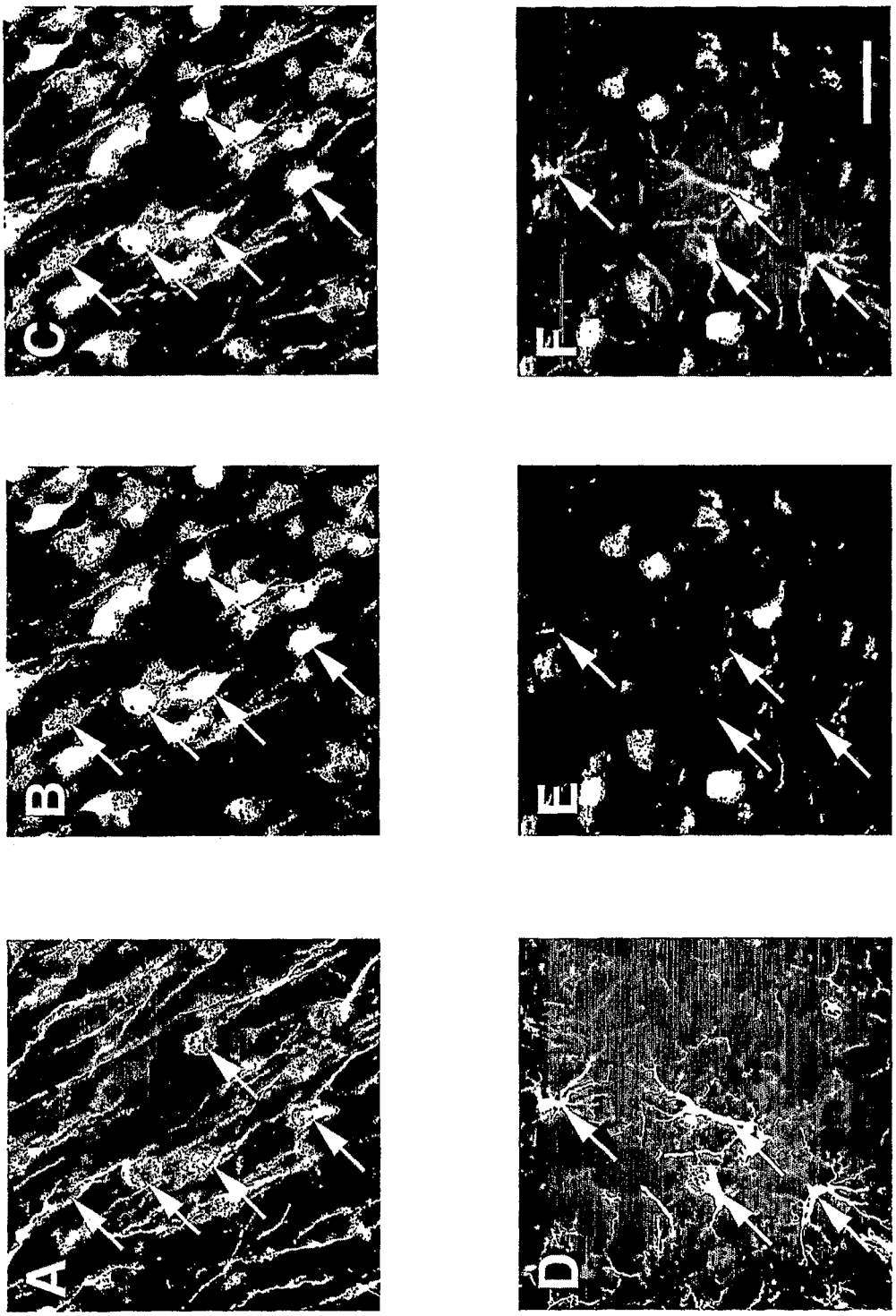

FIG. 16: Immunocharacterization of the huDCXpromoEGFP1 transgenic mouse

The olfactory bulb of a one month-old huDCXpromoEGFP1 transgenic mouse from the line 303 was processed for immunohistochemistry using antibodies directed against the doublecortin polypeptide or the GFAP polypeptide. Photographs A to C document the co-localization of the EGFP reporter gene expression, under the control of the human DCX regulatory sequence, with the endogenous expression of the mouse doublecortin. The arrows point to some cell somata to allow for the comparison of the (B) EGFP reporter signal with the (A) mouse endogenous doublecortin expression. C) shows an overlay of the signals documented in panels A and B. The EGFP reporter polypeptide is localized preferentially in the cell soma, whereas the doublecortin polypeptide distributes more significantly in the cell processes. Photographs D to F document the absence of co-localization of the EGFP reporter gene expression, under the control of the human DCX regulatory sequence, with the expression of GFAP, a polypeptide expressed in astrocytes. The arrows point to (D) astrocytes detected by the anti-GFAP antibody. These cells did not express the EGFP reporter gene as revealed by the absence of EGFP fluorescent signal at the corresponding coordinates (E). F) shows an overlay of the signals documented in panels D and E.

Figure 17:
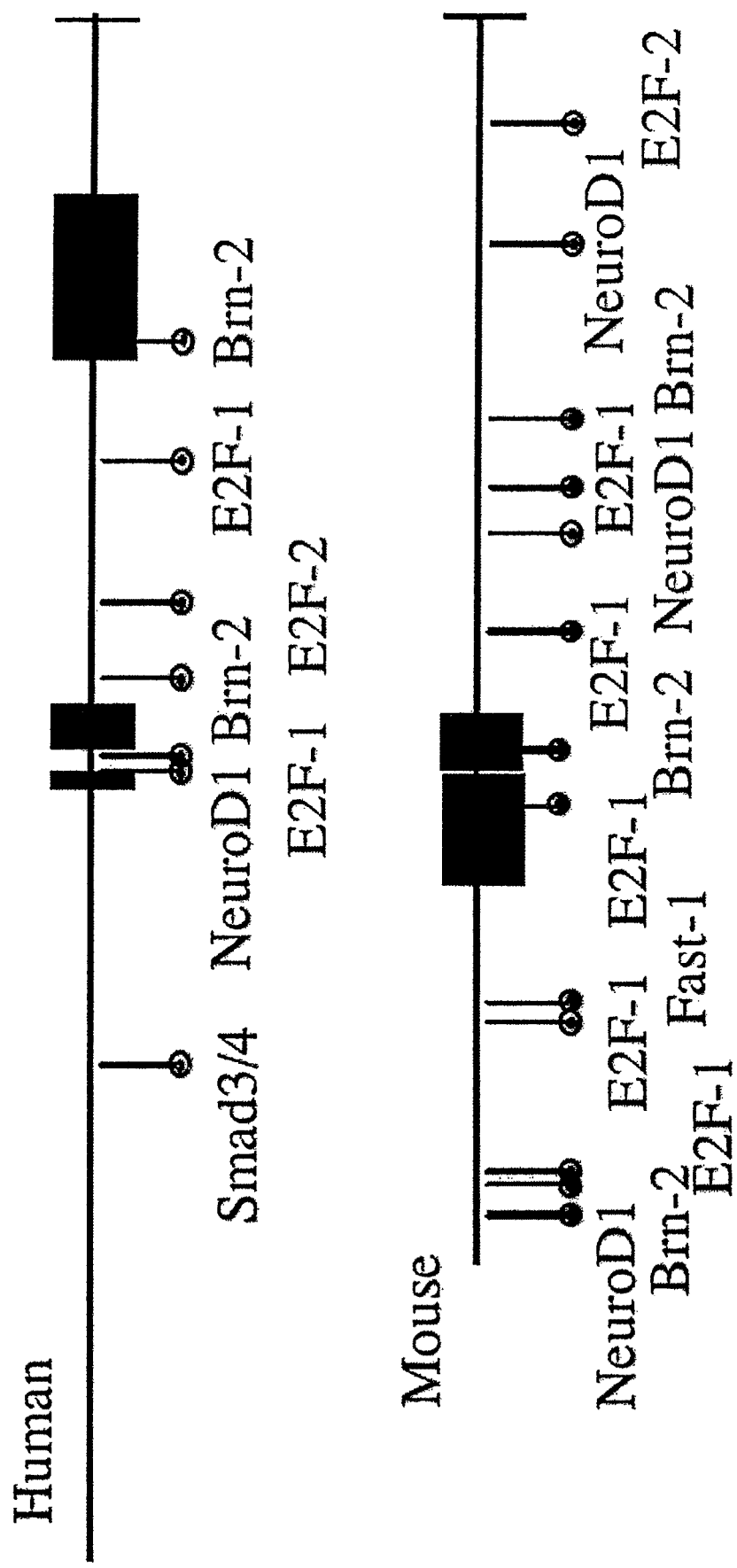

FIG. 17: Putative binding sites for transcription factors on SEQ ID NO.: 1 and SEQ ID NO.: 2

Putative binding sites for transcription factors on SEQ ID NO:1 and SEQ ID NO:2 as determined by computer analysis are shown (as described in the text).

Figure 18:
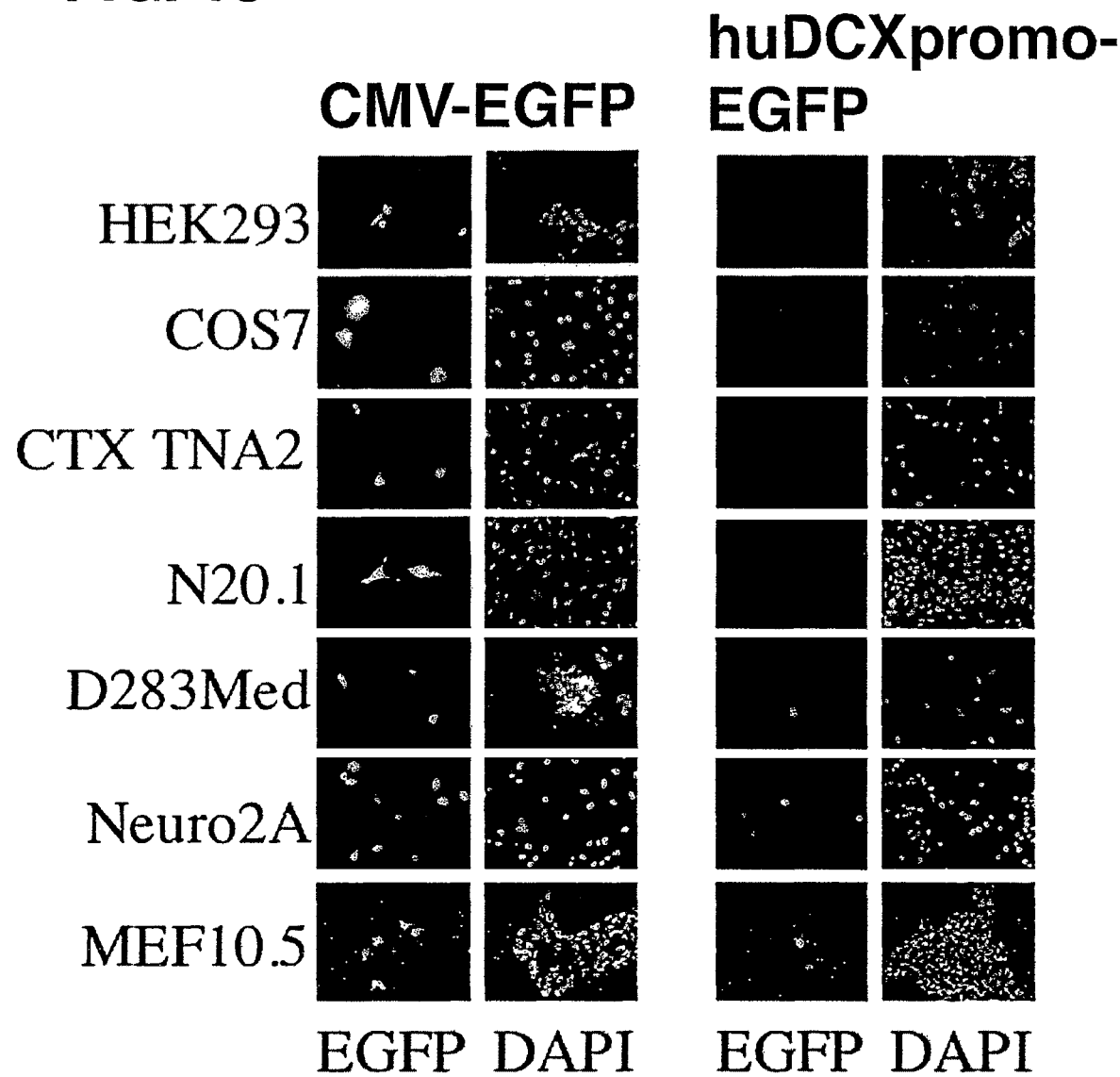

FIG. 18: Specific activity of the human DCX regulatory sequence in cells of neuronal lineage Different cell types (HEK293, COS7, CTX TNA2, N20.1, D283Med, Neuro2A and MEF E10,5) were transiently transfected with pEGFP-N1 or phuDCXpromoEGFP1 and analyzed for expression of EGFP. Whereas all the cell types can be transfected and express EGFP under control of the ubiquitous CMV promoter (left block), the DCX regulatory sequence drives reporter gene expression specifically in cells of neuronal lineage (right block).

Figure 19A:
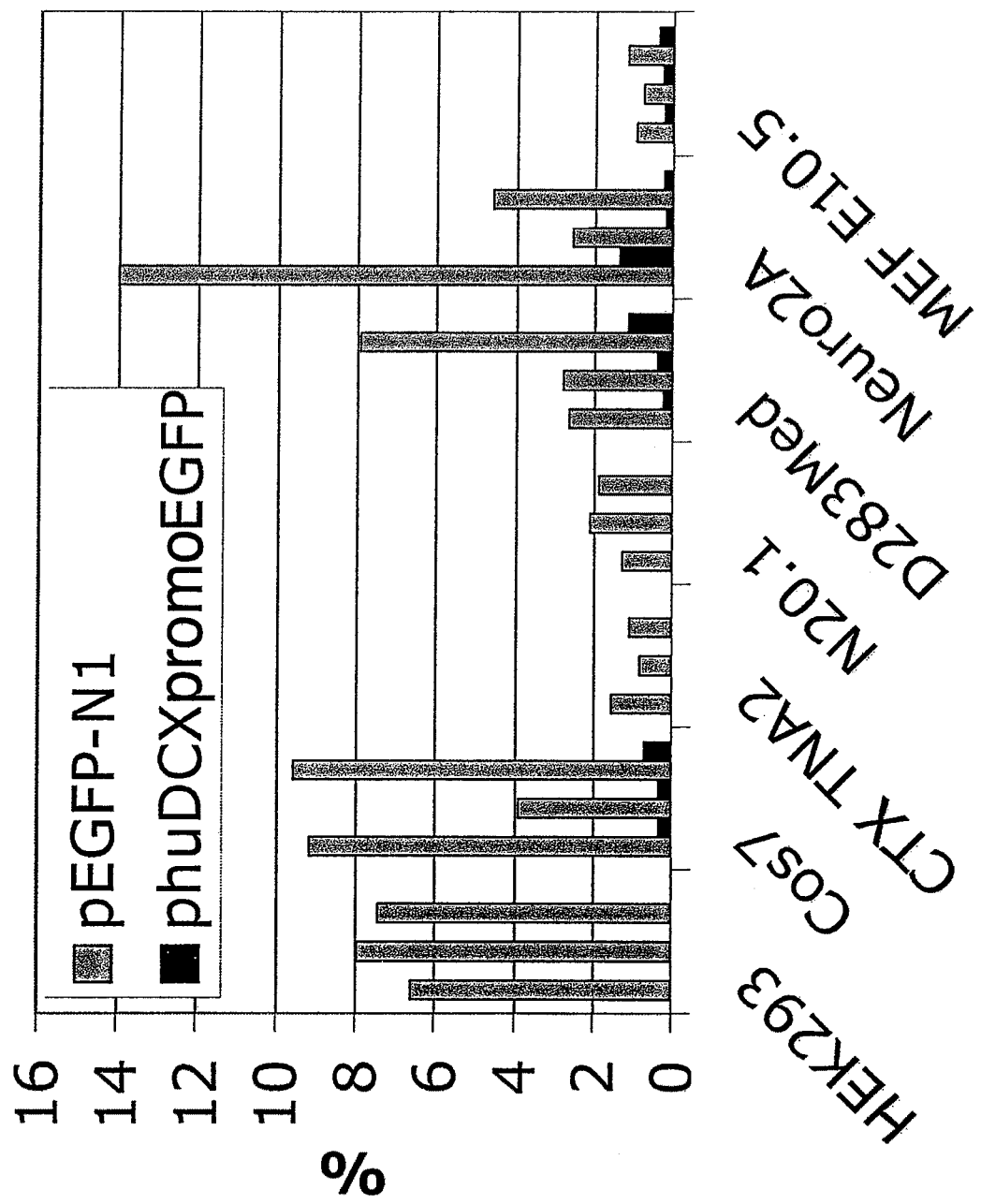
Figure 19B:
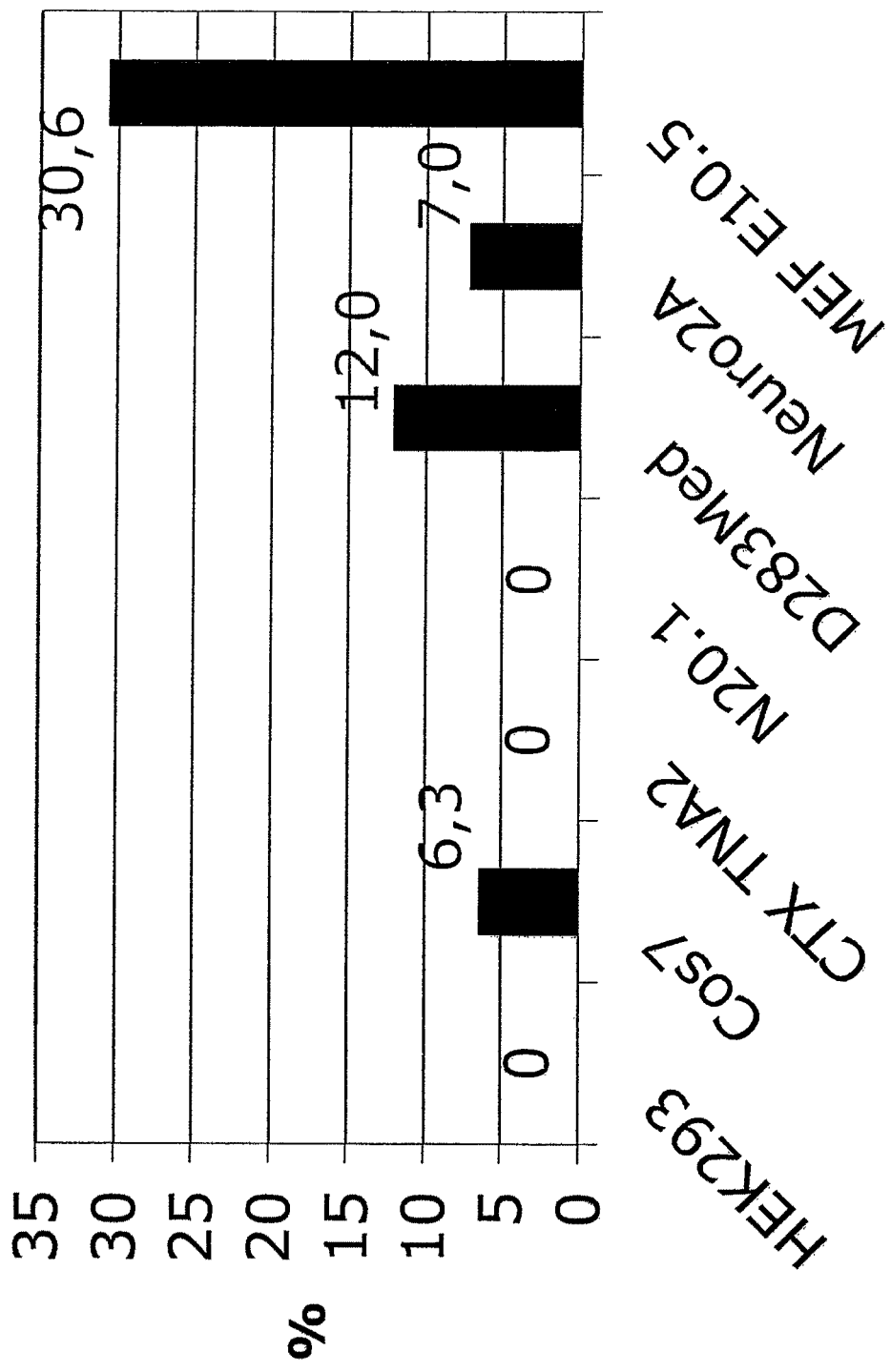

FIG. 19: Quantitative analysis of promoter activity

Different cell types (HEK293, COS7, CTX TNA2, N20.1, D283Med, Neuro2A and MEF E10,5) were transiently transfected with pEGFP-N1 or phuDCXpromoEGFP1 and analyzed for expression of EGFP. A) The percentage of cells that express EGFP is analyzed and shown. B) The expression efficacy (calculated as the percentage of cells that express EGFP after transfection with phuDCXpromoEGFP1 relative to the percentage of cells that express EGFP after transfection with pEGFP-N1) is shown. Note the high level of expression efficacy in cells of neuronal lineage.

FIG. 20: Cell type analysis of cells present in MEF E10,5 cells

MEF E10,5 cells are analyzed for marker expression after one week of differentiation. A) shows immunofluorescence staining of different markers present in the culture. B) shows a quantitative analysis of the percentages of cells expressing the various markers in MEF E10,5 cell cultures.

Figure 21:
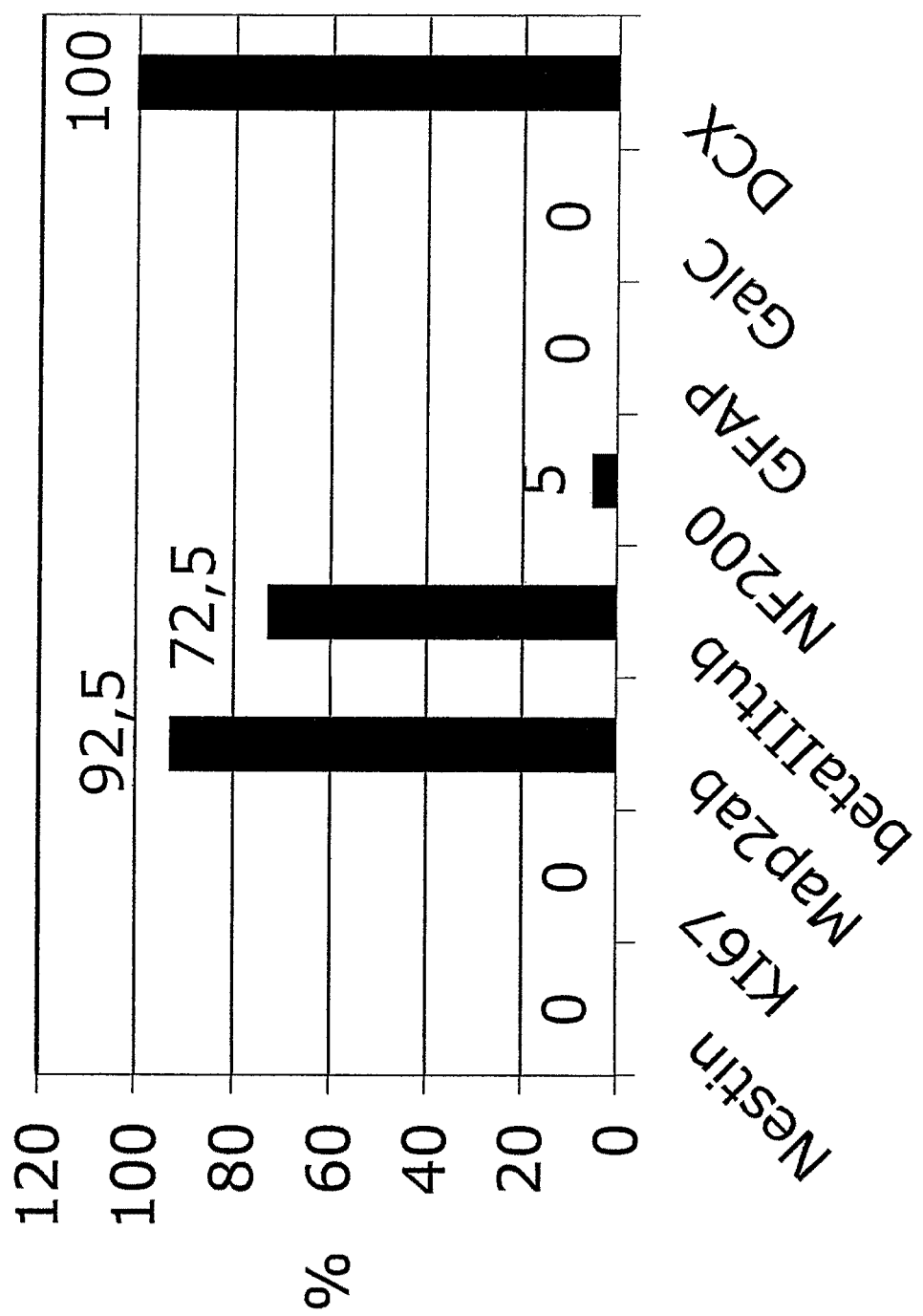

FIG. 21: Frequency of DCX co-expression with various markers in MEF E10,5 cells after 1 week of differentiation Note that DCX expression colocalizes with neuronal determined cell types, and not glia (GFAP, GalC) or not stem cells (Nestin).

Figure 22:
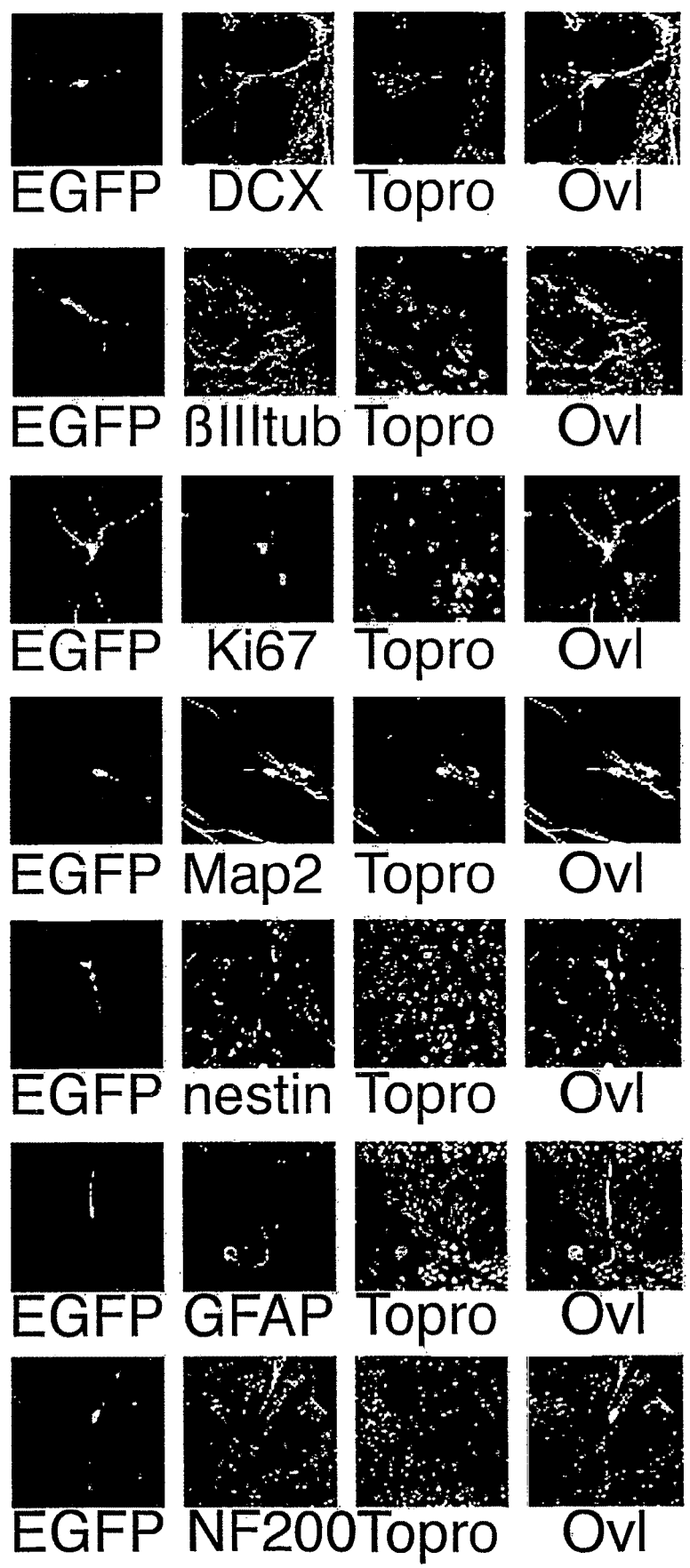

FIG. 22: Cell type analysis of cells in which the human DCX regulatory sequence is active MEF E10,5 were transiently transfected with phuDCXpromoEGFP1 and immunostained for different markers. EGFP positive cells colabeled with endogenous markers for neuronal determined cells, but not with stem cells or glial markers.

Figure 23:
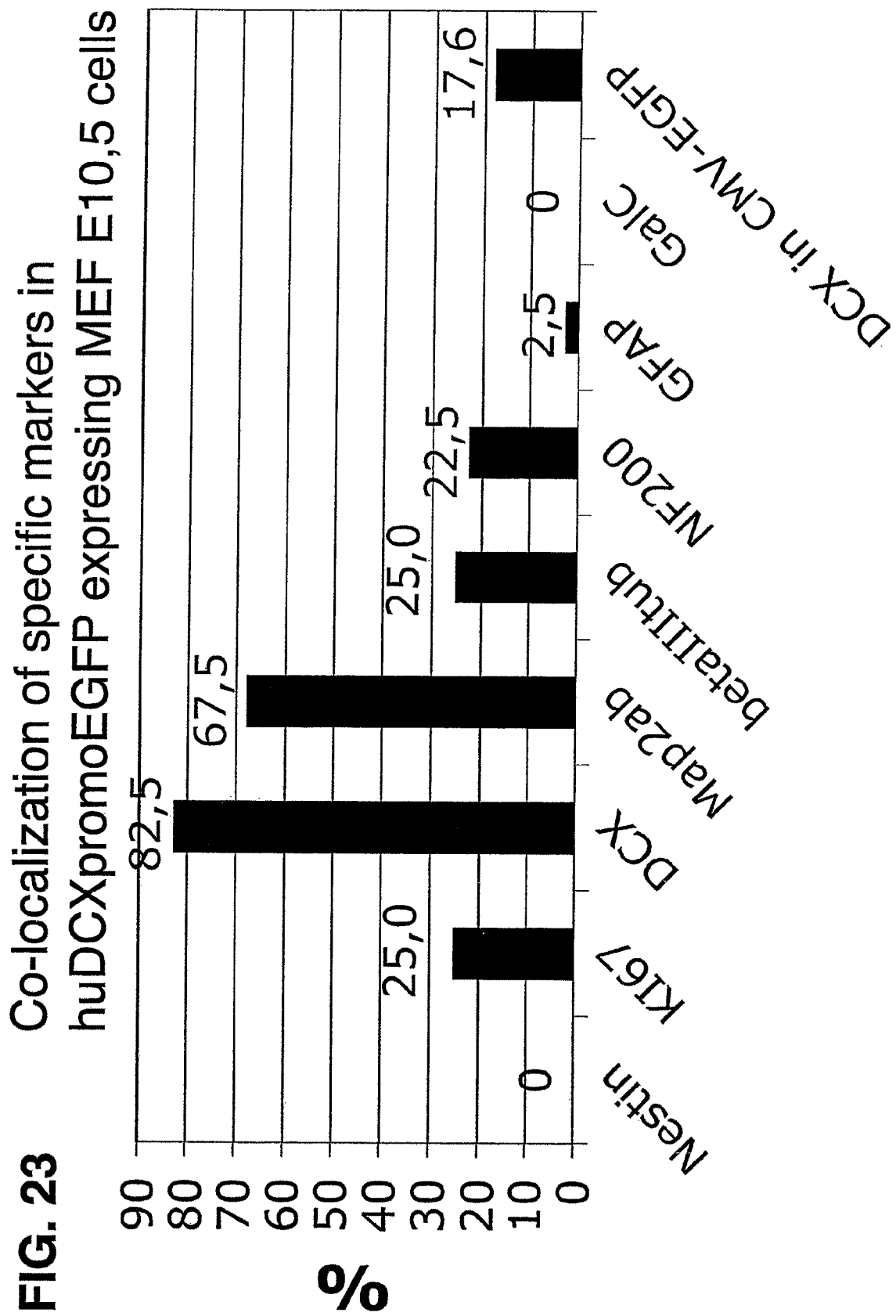

FIG. 23: Quantitative analysis of experiments in FIG. 22

The frequency of presence of the various markers shown in FIG. 22 was quantified in MEF 10,5 cell expressing EGFP following transfection with phuDCXpromoEGFP1. Additionally, for comparative purposes, the frequency of DCX-EGFP expression in MEF 10,5 cells after pEGFP-N1 transfection is shown.

Figure 24:
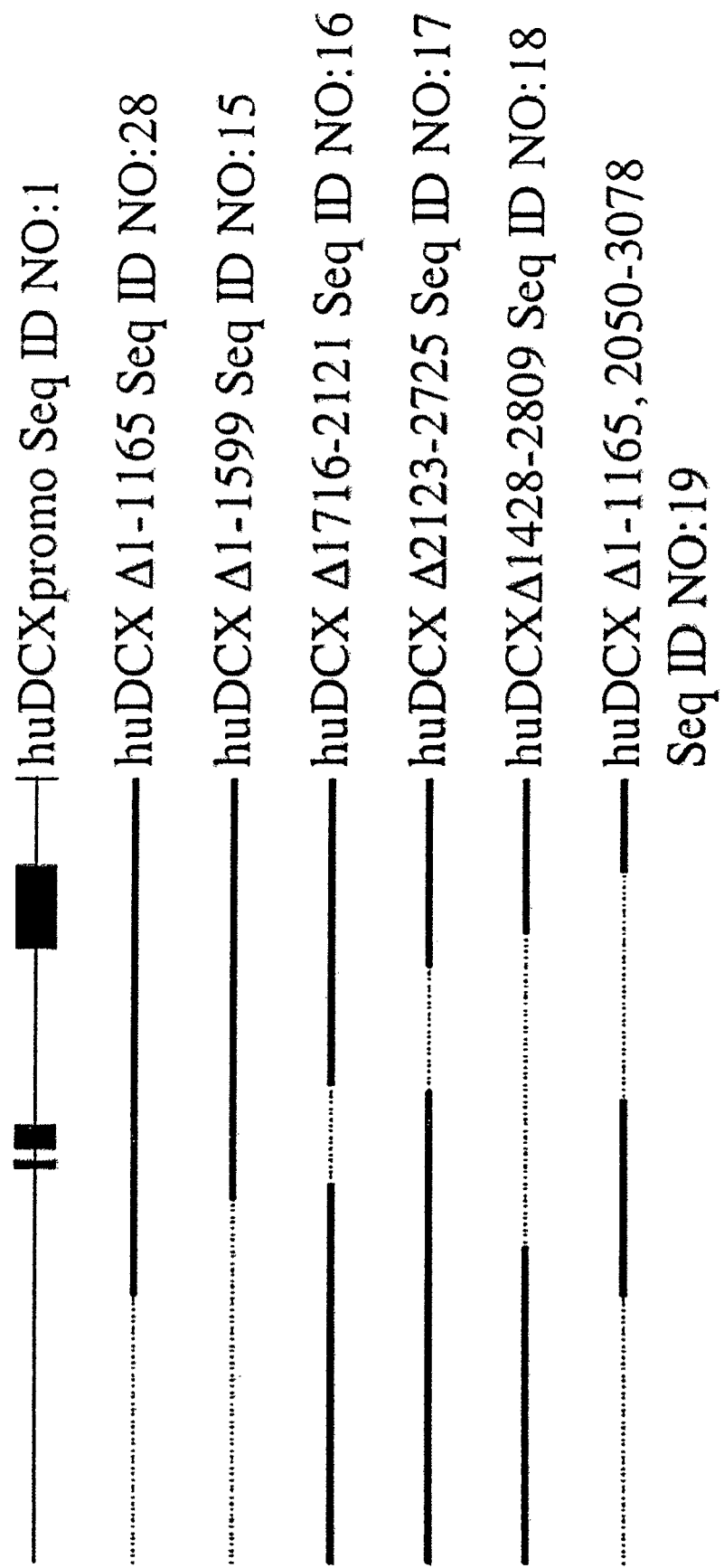

FIG. 24: Deletion constructs of SEQ ID NO.: 1

The deletion fragments presented in this figure were used to control the expression of the EGFP reporter gene as shown in the Seq ID NO: 20 to 25.

Figure 25:
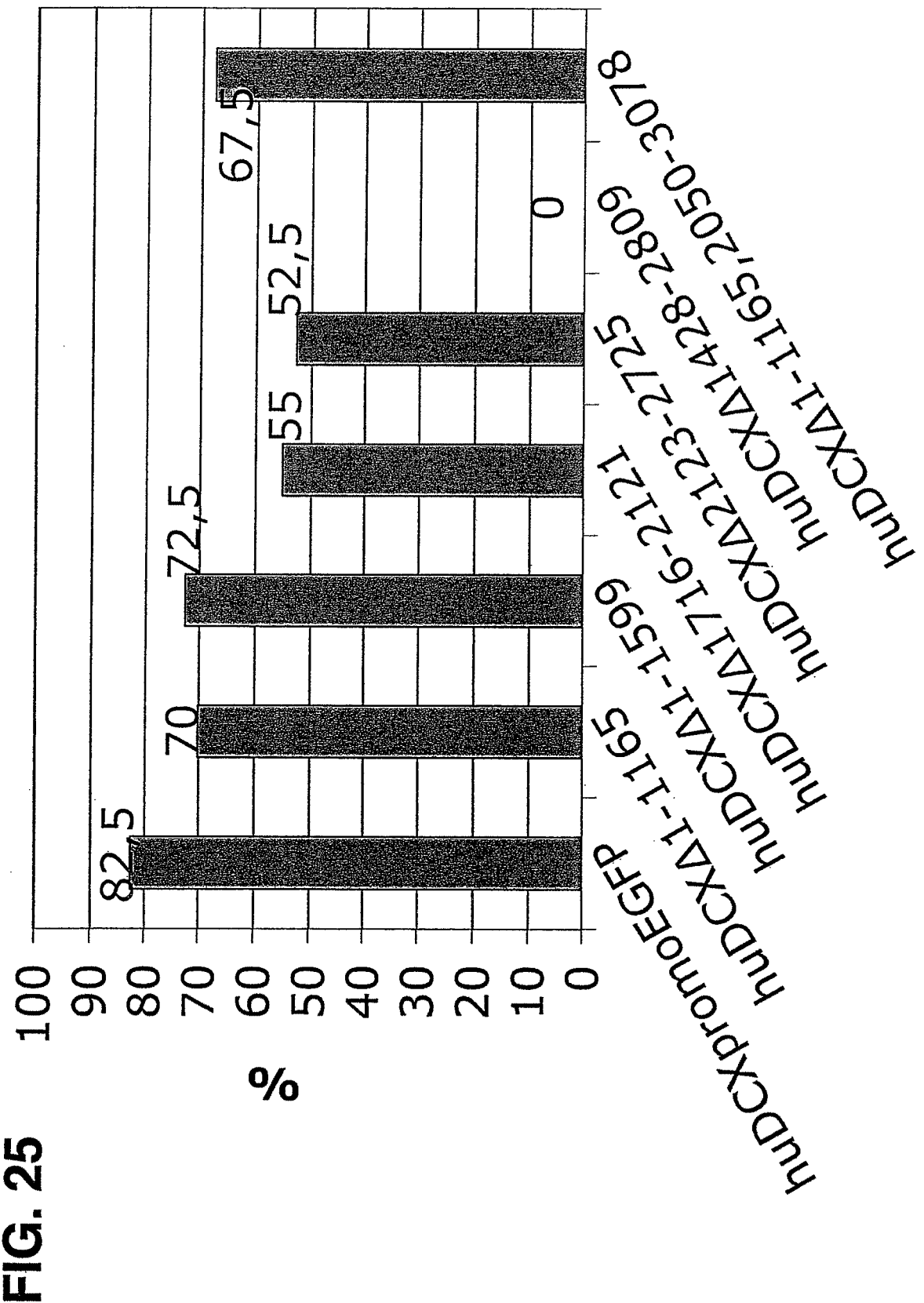

FIG. 25: Specific activity of the deletions constructs of FIG. 24 when transfected in MEF E10,5 cells MEF E10,5 were transiently transfected with different deletion constructs and the percentage of EGFP positive cells that co-label with DCX was analyzed.

Figure 26:
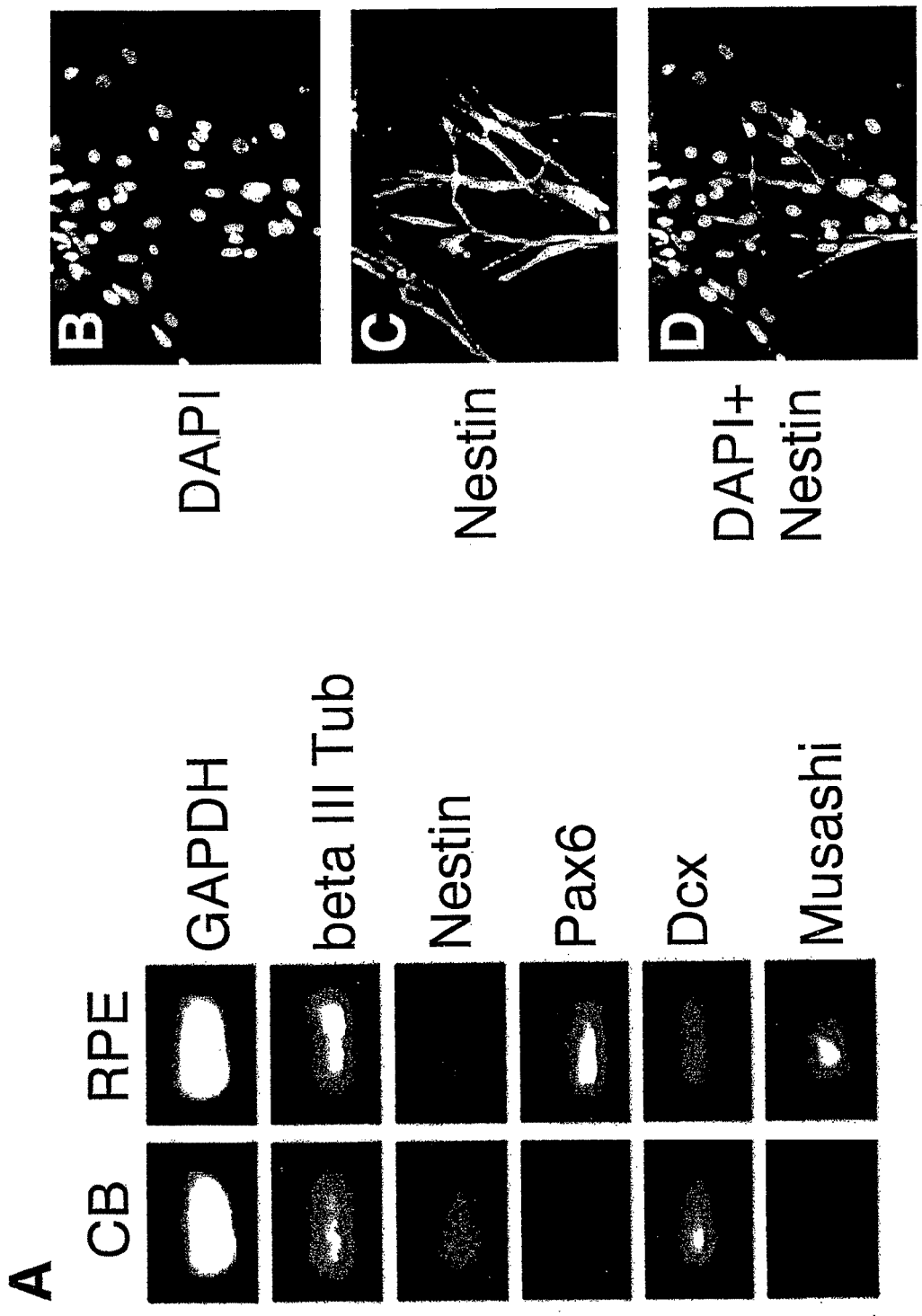

FIG. 26: Ciliary body and RPE derived cells express progenitor markers in vitro (A) RT-PCR for βIII Tubulin, nestin, Pax6, Dcx and musashi with GAPDH as standard. Products are 140 bp for each primer pair. (B)-(D) Immunostaining for the neural stem cell marker nestin with nuclear counterstain DAPI on RPE derived cells after 21 DIV under differentiation conditions (NB/B27+5% FCS).

Figure 27:
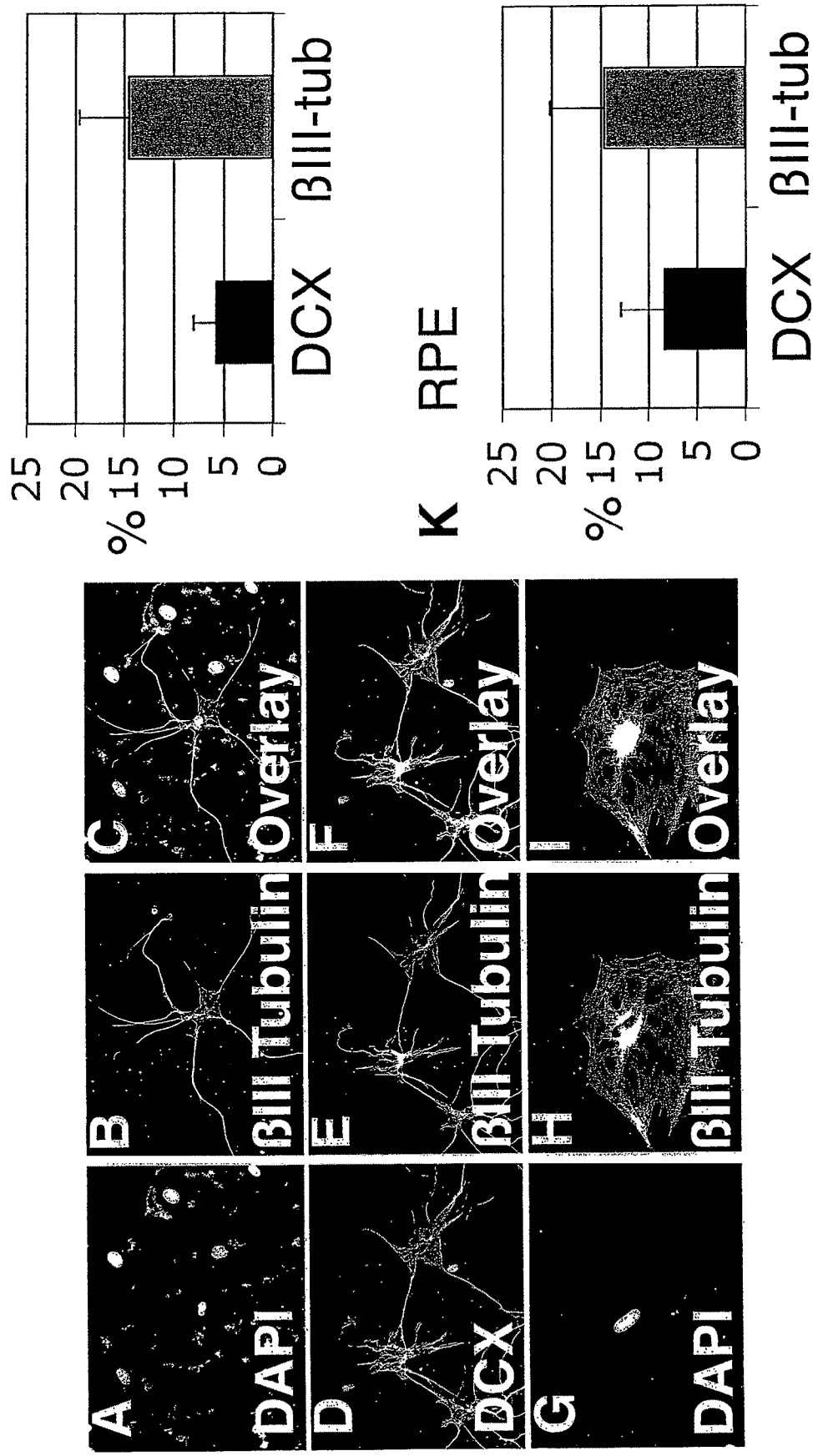

FIG. 27: Neuronal phenotype and morphology in RPE derived cells and quantification of differentiation in CB and RPE cells Cell derived from RPE cultures of passage number 3 grown for 7 days on laminin coated glass cover slips are shown. (A)-(C) Immunostaining for βIII Tubulin with nuclear counterstain DAPI. The morphology of the cell is of neuronal character. (D)-(F) Double immunostaining for 111 Tubulin and the neuronal precursor marker Dcx with nuclear counterstain DAPI. (G)-(I) Immunostaining for βIII Tubulin (H) and Dcx (G) with nuclear counterstain DAPI in RPE cells grown under proliferation conditions on collagen coated plastic. The cell displays a more epithelial morphology and does not coexpress Dcx. (J), (K) Quantification of the percentage of cells expressing Dcx and βIII Tubulin in CB and RPE cultures after 7 DIV under differentiation conditions. Data is expressed as mean value+/−standard error of the mean (S.E.M.).

Figure 28:
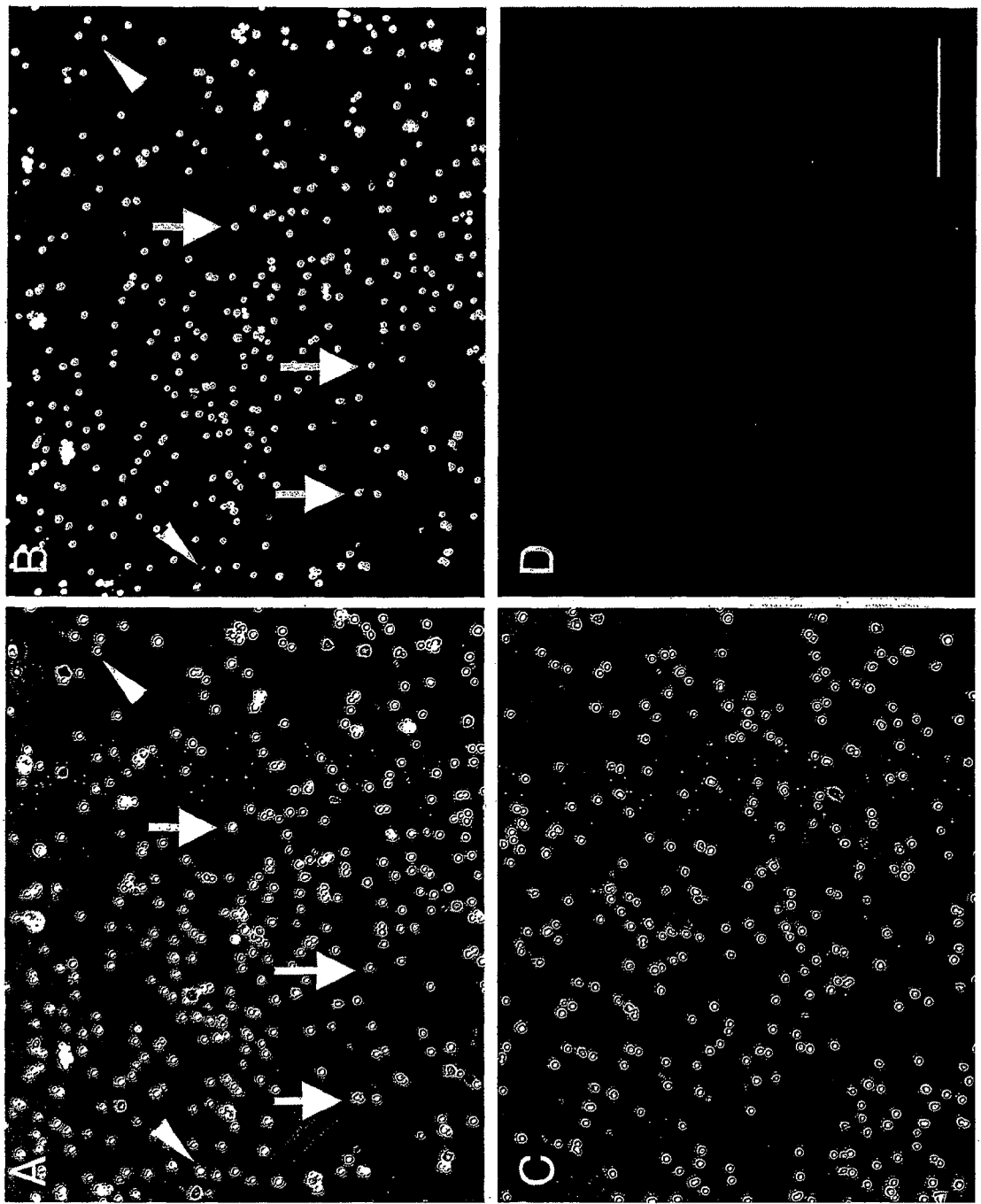

FIG. 28: Enrichment of cells expressing DsRed2 derived from an animal as described in Example IV by FACS-sorting Cell cultures originating from dissociated brains of neonatal huDCXpromoDsRed2 transgenic mice analyzed immediately after FACS-sorting. (A) Phase contrast photograph of a culture composed of cells FACS-sorted for the presence of DsRed2 fluorescence. (B) Fluorescence signal obtained from the DsRed2 reporter protein detected in the same observation field as in A. Some cells expressing the DsRed2 reporter gene are marked with arrows, whereas some cells devoid of DsRed2 are marked with an arrow head. Note that more the 99% of the cells are expressing the DsRed2 reporter gene. (C) Phase contrast photograph of a culture composed of cells FACS-sorted for the absence of DsRed2 fluorescence. (D) Fluorescence signal obtained from the DsRed2 reporter protein detected in the same observation field as in C. Note that more the 99% of the cells are negative, i.e. do not express the DsRed2 reporter gene. Scale bar in D represents 200 μm.

Figure 29:
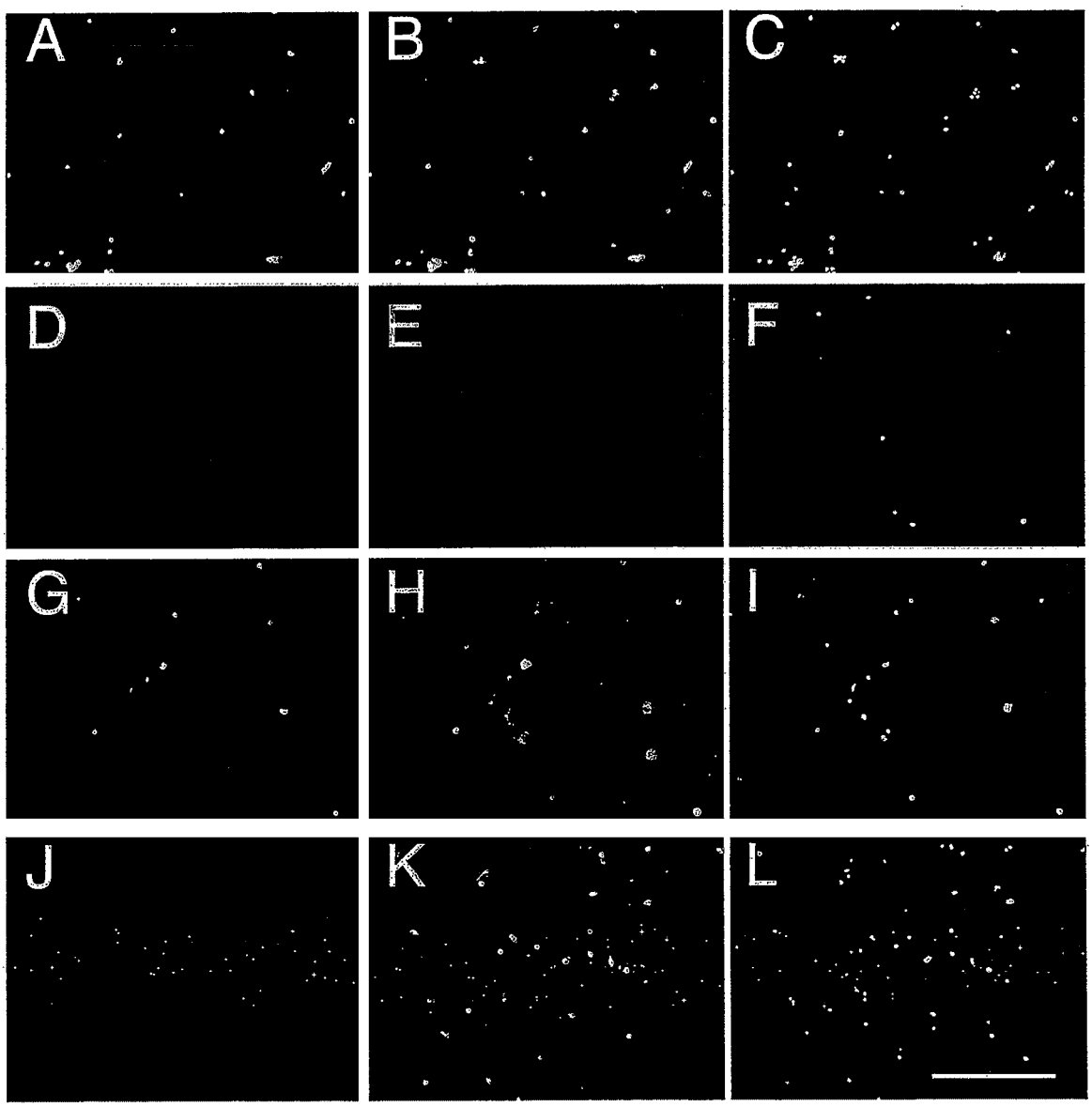

FIG. 29: Cells expressing a fluorescent gene (EGFP or DsRed2) derived from an animal as described in Example IV enriched by FACS yields Doublecortin-positive cells Cell cultures originating from dissociated neonatal brains of huDCXpromoDsRed2 or nestin-EGFP transgenic mice. Cells were FACS-sorted into positive and negative populations in respect to their expression of the reporter genes DsRed2 and EGFP respectively. The sorted populations were maintained in culture for 1 day before fixation as described in EXAMPLE VI. Panels A to C document that cells derived from the huDCXpromoDsRed2 transgenic mice sorted for the presence the DsRed2 reporter (A) resulted in a culture with >90% of cells expressing doublecortin (B), nuclear counterstaining with Dapi is shown in (C). Panels D to F document that cells derived from the huDCXpromoDsRed2 transgenic mice sorted for the absence the DsRed2 reporter (D) resulted in a culture with <5% of cells expressing doublecortin (B), nuclear counterstaining with Dapi is shown in (F). Panels G to I document that cells derived from the nestin-EGFP transgenic mice sorted for the presence the EGFP reporter (G) resulted in a mixed culture with some of cells expressing doublecortin (H), nuclear counterstaining with Dapi is shown in (I). Panels J to L document that cells derived from the nestin-EGFP transgenic mice sorted for the absence the EGFP reporter (J) also resulted in a mixed culture with some of the cells expressing doublecortin (K), nuclear counterstaining with Dapi is shown in (L). The level of expression of the EGFP reporter gene in the nestin-EGFP FACS-sorted cells is significantly downregulated after 1 day of culture on coverslip. The presence of cellular debris is responsible for some unspecific binding of the doublecortin antibody. Only cells with a normal nuclear morphology were considered. Scale bar in (L) represents 100 μm.

FIG. 30: huDCXpromoEGFP transgenic mice to study variations in neurogenesis levels EGFP fluorescence in the dentate gyrus of different huDCXpromoEGFP1 transgenic mice is shown. A) shows a section from a 1 month-old mouse, B) shows a section of a 2 month-old mouse, C) shows a section of a 12 month-old mouse. Note the decline of EGFP fluorescence intensity as a function of age according to the reported age-related decrease of neurogenesis. D and E) show sections of three month-old mice D) a control mouse, and E) a mouse 7 days after experimentally-induced epileptic seizures. Note the seizure-related up-regulation of EGFP signal in E) according to the reported increase of neurogenesis occurring after seizure activity. F) shows the results of a quantitative analysis.

The examples illustrate the invention.

EXAMPLE I

Transient Expression Of Doublecortin (DCX) During Adult Neurogenesis a) Methods and Materials Used in this Study:
Animals and BrdU Injections Female Wistar rats (Charles River-Wiga, Sulzfeld, Germany) were kept in normal light dark cycle (12 hour light/12 hour dark) and had free access to food and water. All animal experiments were approved by the university's animal care commission and by local government and were conform with NIH guidelines and German law. Animals received at 2 month of age intraperitoneal injections with BrdU (50 mg/kg body weight). Animals perfused at 2 hours, 4 and 7 days after BrdU treatment received only a single BrdU injection. The animals that were sacrificed at 10, 14, and 21 days, 1, 2, 3, 4, 6, 9, 14, and 19 months after BrdU injection received daily injections on 4 consecutive days. Each time point consisted of 3 animals.

SDS-PAGE/Western Blot

The olfactory bulb from a 2 month-old female Wistar rat (Charles-River-Wiga, Sulzfeld, Germany) was homogenized in SUB buffer (0.5% SDS, 8 M urea, 2% β-mercaptoethanol) and centrifuge at room temperature for 10 minutes at 12 000×g to remove the insoluble debris. The protein concentration in the supernatant was determined using Bradford reagent (Sigma, St. Louis, Mo., USA). The sample (2 μg/lane) was electrophoresed in a 12% polyacrylamide SDS-PAGE and transferred onto a nitrocellulose membrane (Schleicher and Schuell, Dassel, Germany).

Membranes were placed into blocking buffer (20 mM Tris-HCl, pH 7.3, 0.9% NaCl, 1% Teleostean gelatin (Sigma, St. Louis, Mo., USA), and 0.1% Tween-20) for 1 hour at room temperature. The same buffer served for antibody dilutions, as well as for washes. For detection of DCX, the following primary antibodies were used: goat anti-DCX C-18 (1:500, Santa Cruz Labs, Santa Cruz, USA), goat anti-DCX N-19 (1:500, Santa Cruz Labs, Santa Cruz, USA), and mouse anti-DCX (1:500, Transduction Labs, Lexington, USA). The blots were incubated in primary antibody solutions overnight at 4° C. on a shaking table. The following day, the blots were washed and further incubated with peroxidase-conjugated species-specific secondary antibody for 2 hours at room temperature (rabbit anti-goat 1:5000 (Sigma, Taufkirchen, Germany) and donkey anti-mouse 1:5000 (Jackson ImmunoResearch, West Grove, USA). Blots were washed and the immune complex was detected using the SuperSignal West Pico chemiluminescent substrate (Perbio, Bonn, Germany) according to the manufacturer's protocol.

Histology

The animals were deeply anesthetized and perfused transcardially with 4% paraformaldehyde in 100 mM phosphate buffer, pH 7.4. The brains were dissected, immersed overnight in fixative, and transferred to 30% sucrose/100 mM phosphate buffer, pH 7.4 for at least 48 hours. Brains were cut into 40 μm sagittal sections using a sliding microtome. Sections were stored at −20° C. in cryoprotectant solution until staining (25% v/v glycerol, 25% v/v ethylene glycol, and 0.05M phosphate buffer, pH 7.4).

Immunofluorescence

To allow for a better penetration of antibodies in areas of high neuronal density, free-floating sections were placed in 1% Triton X-100/TBS (Tris-buffered saline: 0.1M Tris-HCl pH 7.4/0.9% NaCl) solution for 15 minutes followed by three consecutive 5 minute washes with TBS. For detection of incorporated BrdU, the sections were subjected to the following procedure: incubation in 0.3M NaCl/30 mM Citrate Buffer pH 7.0/50% (v/v) formamide at 65° C. for 2 hours, rinse in 0.3M NaCl/30 mM Citrate Buffer pH 7.0, incubation in 2N HCl at 37° C. for 30 minutes, rinse in 0.1M borate buffer (pH 8.5) for 10 minutes, rinse in TBS. Sections were blocked in TBS/3% donkey serum/0.1% Triton-X 100 (TBS-DS-TX) for 30 min, followed incubation with primary antibodies in TBS-DS-TX for 48 hours at 4° C. The following primary antibody dilutions were used: rat anti-BrdU (1:500 Accurrate, Westbury, USA), mouse anti-NeuN (1:500, Chemicon, Temecula, USA), goat anti-DCX C-18 (1:500, Santa Cruz Labs, Santa Cruz, USA), rabbit anti-KI67 (1:500, Novacastra Laboratories Ltd., Newcastle Upon Tyne, UK). The sections were then rinsed in TBS three times for 10 minutes, and then incubated with secondary antibodies in TBS-DS-TX for 2 hours. The following fluorochrome-conjugated secondary antibodies were used: donkey anti-rat-CY5 F(ab)$_2$ fragment, donkey anti-mouse-rhodamineX F(ab)$_2$ fragment, donkey anti-goat-FITC F(ab)$_2$ fragment and donkey anti-rabbit-FITC (all 2 μg/ml, Jackson ImmunoResearch, West Grove, USA). After several washes in TBS, sections were mounted on gelatin-coated glass slides and coverslipped using Prolong (Molecular Probes, Eugene, Oreg.).

Quantification

Analysis was performed using a confocal microscope (TCS-NT, Leica Microsystems, Bensheim, Germany) equipped with a 40×PL APO oil objective (1.25 NA) and a pinhole setting that corresponded to a thickness of the focal plane of less than 2 μm. Randomly selected BrdU-positive cells were analyzed in their entire z-axis in order to exclude false double-labeling due to an overlay of signals from different cells (Kuhn (1997), loc. cit.). A minimum of 50 BrdU-positive cells per region of interest were examined for co-labeling with DCX and NeuN in each animal and time point. Data are presented as the average percentage of BrdU-positive cells, which co-labeled for DCX, NeuN or DCX/NeuN (Mean+/−S.E.M.).

b) Selection of Doublecortin Antibody by Western Blot Analysis

The specificity of three commercially available antibodies directed against DCX was examined by western Blot analysis. A band of 40 kDa, consistent with the molecular weight of the DCX protein, was detected by all three antibodies (FIG. 1). Nevertheless, the antibody directed against the C-terminus of DCX (Santa Cruz Labs, Santa Cruz, USA) proved to be the most specific (FIG. 1, Lane 1). The two other antibodies (FIG. 1 lane 2 and 3) detected several other proteins at higher molecular weights. One such band could be doublecortin-like kinase (DCLK), a related protein sharing 85% homology with the N-terminus of DCX (Ohara, DNA Res. 4 (1997), 53-59). DCLK is a microtubule-associated protein kinase also expressed in brain. Because of its higher specificity, the goat anti-DCX C-18 antibody was chosen for immunohistological analysis of the tissue sections. Accordingly, the present study documents that only highly specific antibodies directed against DCX can be employed in order to elucidate temporal and spatial expression of said DCX.

c) Doublecortin Expression During Adult Hippocampal Neurogenesis

Time Course Analysis

The pattern of DCX expression within newly generated cells was examined by immunofluorescence labeling of DCX and BrdU in the neurogenic regions of the adult rat brain different time points after BrdU administration. We first quantified the number of BrdU-positive cells that expressed DCX within the dentate gyrus (FIG. 2). At the earliest time point analyzed, i.e. 2 hours post-BrdU administration, we observed co-labeling of DCX within 60% of the newborn cells (FIG. 2). The fact that the majority of BrdU-positive cells were expressing DCX at the earliest time point strongly suggested that proliferating cells were already expressing DCX. To further substantiate this observation, frequent co-labeling of DCX with Ki67 could be demonstrated. Ki67 is an antigen enriched in proliferating cells during DNA synthesis and mitosis, in the hippocampus and lateral ventricle wall (FIG. 3). Between the seventh and tenth day post-labeling the percentage of BrdU-positive cells expressing DCX further increased to more than 90% (FIG. 2). Thereafter, DCX expression was rapidly downregulated. It was observed in only 2% of the BrdU-positive cells by one month and became undetectable by two months after labeling.

Towards the final stage of neuronal differentiation, the newborn cells begin to express proteins typically present in mature neurons such as the nuclear neuronal marker NeuN, neuronal-specific enolase (NSE), or calbindin (Cameron (1993), loc. cit.; Kuhn (1996), loc. cit and Kuhn, J. Neurosci, 17 (1997), 5820-5829). Once induced, these markers are expressed throughout the lifetime of the neuron. For that reason, we used NeuN to determine when newly generated neuronal precursors become mature and to what extent NeuN and DCX expressions overlap. BrdU-labeled cells immunoreactive for NeuN were first detected in the hippocampus at 10 days after BrdU injection (FIG. 2). The majority of the NeuN positive cells co-expressed DCX between Day 10 and 14, thereafter NeuN/DCX co-labeling was not detectable anymore. The percentage of BrdU-positive cells expressing NeuN increased to about 80% one month after labeling and increased further to more than 90% at later time points analyzed (FIG. 2). Adjacent non-neurogenic regions, the hilus and molecular layers of the dentate gyrus, were analyzed as control areas. The co-localization of BrdU-positive cell bodies with DCX or NeuN was not detected within these regions.

Morphology of DCX Expressing Cells

It is interesting to note that the morphology of DCX-expressing cells changed as neuroblasts matured (FIG. 4). Two cellular morphologies were observed. Within the first days after BrdU-labeling, DCX-positive cells formed clusters in the subgranular zone adjacent to the inner margin of the granule cell layer. Some of these cells were without defined processes, whereas others resembled neuroblasts with processes oriented parallel to granule cell layer (FIG. 4a). Later, at about 10 days after BrdU labeling, DCX-positive cells were integrated into the granule cell layer and displayed processes spanning the entire layer and further into the molecular layer (FIG. 4b).

d) Doublecortin Expression in the Aging Dentate Gyrus

An age-dependent decrease of neurogenesis within the granule cell layer of the dentate gyrus has previously been reported (Kuhn (1996), loc. cit.). Consequently, we performed an analysis of DCX expression as a function of age. The highest incidence of DCX immunoreactivity was observed in the younger animals examined, i.e. 2 month-old rats. The total amount of cells expressing DCX notably decreased by 11 months of age, and very few DCX positive cells were detectable in 21 month-old rats (FIG. 5). The reduction of DCX-expressing cells in the dentate gyrus is consistent with and substantiates the reported age-dependent neurogenesis decrease.

The current study analyzed the time course of DCX expression in adult born cells of the dentate gyrus and the lateral ventricle wall/olfactory bulb. DCX is to a high degree expressed in dividing cells (FIG. 2 and FIG. 3). DCX is not detected in the embryonic ventricular zone during cortex development (Gleeson, Neuron 23 (1999), 257-271), but it is expressed in proliferating cells of the adult SVZ and hippocampus. Apparently, fetal and adult neural progenitors cells have different molecular identities and properties.

e) Doublecortin Expression in the Granule Cell Layer of the Olfactory Bulb

Newly generated neuroblasts of the olfactory bulb arise in the subventricular zone (SVZ) of the lateral ventricle wall, where proliferation of neural stem cells and neuronally committed progenitors takes place (Doetsch (1997), loc. cit.). The new cells form chains of migrating cells, which converge to form the rostral migratory stream. After reaching the olfactory bulb (OB) the cells integrate into the granule cell layer and periglomerular region and begin to express mature neuronal markers.

Subventricular Zone/Rostral Migratory Stream

DCX is already strongly expressed in the subventricular zone (FIG. 6). Similar to the hippocampus, numerous cells in the subventricular zone were double-labeled for DCX and the proliferation marker Ki-67, indicating frequent cell division of neuroblasts (FIG. 3). The morphology of the DCX-expressing cells in the subventricular zone is mostly bipolar with short processes (FIG. 6). The DCX-positive cells are organized in chain-like structures, which has been previously been described for migratory neuroblasts (Lois, Science 271 (1996), 978-981). In the rostral migratory stream, the DCX-expressing neuroblasts have an elongated morphology with a leading process, consistent with neuroblast migration towards the OB (FIG. 6).

Olfactory Bulb

Finally, in the OB the DCX-expressing cells adopt a more complex morphology, similarly to the one observed for the cell integrating into the cell granular layer of the hippocampus (FIG. 6). Consequently, BrdU-labeled cells coming from the SVZ were first detected in the olfactory bulb four days after BrdU injection. This interval reflects the time required for neuroblasts to migrate from the SVZ, where they arise and incorporate BrdU, to the OB. At four days after labeling, only 2% of the BrdU-labeled cells in the OB were found to express DCX. At this time point, the percentage is relatively low since most to the BrdU-labeled cells observed in the OB result from in situ cell division of non-neuronal cells. Over the next days, as the bulk of newly generated neuroblasts from the SVZ reach the OB, this percentage increased rapidly. Ten days after labeling, approximately 70% of the BrdU-positive cells in the OB were expressing DCX (FIG. 7). Similar to the hippocampus, the number of BrdU-positive cells expressing DCX within the OB decreased to very low levels by 1 month after labeling and remained undetectable throughout the subsequent time points. The co-localization of BrdU with NeuN was first detected at 14 days after BrdU injection. At this time, 24% of the BrdU-labeled cells expressed NeuN (FIG. 7). The percentage of BrdU-labeled cells expressing NeuN increased to nearly 90% by 1 month and remained at this level in the later time points analyzed.

f) Doublecortin is a Useful Marker for Neuronal Determined Cells and the Detection of Neurogenesis, Independent from Pre-Labeling Methods Within the first 10 day after BrdU-labeling, the percentage of DCX positive cells among the new cells increased to about 90%. However, once the cells become older and begin to express markers for mature neurons DCX is downregulated to undetectable levels. Although it is not possible to predict the fate of individual DCX positive cells from histological analysis, it is very intriguing that the percentage of BrdU/DCX co-labeling is almost identical to the percentage of new cells which later differentiate into neurons (>90% BrdU/NeuN co-labeling, see FIGS. 2 and 7). This shows that DCX is transiently expressed in neuronally committed cells and therefore can serve as an indicator for adult neurogenesis.

DCX immunoreactivity is not exclusively found in immature neurons, but has been reported to be occasionally present in neurons with differentiated morphology within non-neurogenic regions, including cortex, striatum and corpus callosum (Nacher (2001), loc. cit.). However, in the current study only very low levels of DCX expression outside the neurogenic regions was observed. One reason for this discrepancy might be the use of different antisera against DCX between studies. As shown by comparative western blot analysis, antibodies recognize to a different degree additional antigens and may therefore not reflect DCX alone (FIG. 1). Another explanation for occasional DCX expression outside the neurogenic regions could be that neurogenesis may perhaps exist in these regions.

This hypothesis is supported by recent evidences that induction of neurogenesis in the cortex and striatum under pathological conditions is associated with the migration of DCX-positive neuronal progenitors from the lateral ventricle wall. (Magavi, Naute 405 (2000), 951-955; Arvidsson, Nat. Med. 8 (2002), 963-970). Moreover, it has been suggested by other studies that adult neurogenesis is a common feature of several brain regions, including the cortex and amygdala (Gould, PNAS 96 (1999), 5263-5267; Pencea, Exp. Neurol. 172 (2001), 1-16; Bernier PNAS 99 (2002), 11464-11469) although at very low levels.

Since DCX is a protein, which binds, bundles and stabilizes microtubules, it could play a role into various neuronal cytoskeleton depending scenarios including migration of neuronal precursor cells, nuclear translocation, and axonal and dendritic maturation. Here, it was surprisingly found and documented that, due to the time course of DCX expression during neuronal maturation in the adult brain, DCX is present not only in proliferating and migrating but also differentiating neuronal progenitors, e.g. during dendritic elongation and arborization (FIGS. 2, 4 and 6). LIS1, a protein functionally similar to DCX and associated with neuronal migration, has been shown to regulate neuroblast proliferation, nuclear translocation and positioning as well as dendritic elaboration and axonal transport in drosophila (Swan, Nat. Cell Biol 1 (1999), 444-449; Lei, Dev. Biol. 226 (2000), 57-72; Liu, Nat Cell Biol. 2 (2000), 776-783 as well as Leveter Trends Neurosci 24 (2001), 489-492) indicating that microtubule-associated proteins play important roles in most cellular function involving cytoskeletal rearrangement.

In addition to characterizing the role of DCX in the adult brain, results documented here improve neurogenesis-tests and -analysis on a methodological level. Traditional techniques to study neurogenesis have utilized labeling with tritiated thymidine, BrdU or retrovirus, in conjunction with various neuronal markers to address the nature and fate of neural stem cell population. The limitations of these protocols, in particular the need to perform in vivo pre-labeling, have made the identification of a specific and early marker for neuronal lineage of great importance. In this study, it is shown that DCX is detected in neuroblasts within the first month after their emergence. The temporal expression pattern and specificity of DCX within the adult neurogenic regions suggest that DCX is a useful marker for the detection of neurogenesis independent from pre-labeling methods, like BrdU incorporation. Such a neurogenesis marker provides a valuable tool especially under circumstances that prohibit the use of BrdU, for instance in postmortem analysis of human brain tissue.

EXAMPLE II

Cloning of the Human DCX Regulatory Sequence

PCR Amplification of the Genomic Fragment Comprising the Human DCX Regulatory Sequence Using the partial human X chromosome sequence available under the GenBank accession number AL450490, two oligonucleotides (oligo no: 1: AAC ACC TAT TAA TGC CCA; SEQ ID NO.: 9 and oligo no: 2: TCA GAG ACC TGA GCG TGG GAG AA; SEQ ID NO.: 10) were designed for the PCR amplification of an approximately 3.5 kilobase pairs fragment. The sequence of the amplified fragment was chosen in order to comprise approximately 1.5 kilobase pairs of genomic sequence upstream the DCX putative exon 1, the genomic sequence corresponding to the DCX first three putative exons, the genomic sequence corresponding to the three first DCX introns and a few base pairs upstream from the start position of DCX protein coding sequence located in the putative exon 4.

The PCR amplification on human genomic DNA was performed using Expand High Fidelity PCR System kit (Roche) according to the manufacturer's protocol. The following PCR protocol was used:

| | | |
|---|---|---|
| 94° C. | 3 minutes | 1 cycle |
| 94° C. | 45 seconds | 30 cycles |
| 59° C. | 30 seconds | |
| 72° C. | 3 minutes | |
| 72° C. | 8 minutes | 1 cycle |

Preparation of the PCR Product Comprising the Human DCX Regulatory Sequence for Subcloning.

A single PCR product of approximately 3.5 kilobase pairs was obtained as visualized on a 1% agarose gel electrophoresis. The DNA present in the band of 3.5 kilobase pairs was recovered using the MiniElute Gel Extraction kit (Qiagen). The purified fragment was blunt-ended with the DNA polymerase I Klenow fragment without the addition of free dNTPs. The blunt-ended fragment was then phosphorylated using the T4 polynucleotide kinase in the presence of ATP. This processed DNA fragment corresponds to the Sequence ID no: 1 and was further used for subcloning.

Preparation of the Cloning Vector Containing the Reporter Gene EGFP

The CMV promoter from the plasmid pEGFP-N1 (Clontech) was deleted using the restriction enzymes AseI and NheI. A DNA fragment of approximately 4.1 kilobase pairs corresponding to the linearized pEGFP-N1 vector without the CMV promoter was isolated from a 1% agarose gel following electrophoresis using the MiniElute Gel Extraction kit (Qiagen). The isolated DNA fragment was blunt-ended using the DNA polymerase I Klenow fragment in the presence of 33 microM of free dNTPs. The resulting DNA fragment was further re-circularized using the T4 DNA ligase resulting in a promoterless pEGFP-N1 vector of approximately 4.1 kilobase pairs.

Subcloning of the PCR Fragment Comprising the Human DCX Regulatory Sequence into the Promoterless pEGFP-N1 Vector For the insertion of the human DCX regulatory sequence, the promoterless pEGFP-N1 vector was linearized using with the restriction enzyme SmaI. The DNA fragment was dephosphorylated using calf intestinal alkaline phosphatase. The linearized fragment was isolated by electrophoresis in a 1% agarose gel followed by extraction using the MiniElute Gel Extraction kit (Qiagen). The resulting linear vector and the DNA fragment corresponding to the human DCX regulatory sequence were ligated together into a circular plasmid using the T4 DNA ligase according to the manufacturer's protocol (New England Biolabs). In this construct of approximately 7.7 kilobase pairs, phuDCXpromoEGFP1 Sequence ID no: 7, the human DCX regulatory sequence controls the expression of the EGFP gene (FIG. 8A).

Subcloning of the PCR Fragment Comprising the Human DCX Regulatory Sequence into the pDsRed2-1 Vector The pDsRed2-1 vector (Clontech) was digested with the restriction enzymes SalI and BamHI. A DNA fragment of approximately 4.1 kilobase pairs, was purified by electrophoresis in an 1% agarose gel followed by an extraction using the MiniElute Gel Extraction kit (Qiagen). The DNA fragment was dephosphorylated using calf intestinal alkaline phosphatase. The phuDCXpromoEGFP1 vector was digested with the restriction enzymes SalI and BamHI. A DNA fragment of approximately 3.5 kilobase pairs, encoding the human DCX regulatory sequence, was purified by electrophoresis in an 1% agarose gel followed by an extraction using the MiniElute Gel Extraction kit (Qiagen). The purified fragment was ligated to the prepared pDsRed2-1 vector using the T4 DNA ligase according to the manufacturer's protocol (New England Biolabs). In the resulting vector, phuDCXpromoDsRed2 Sequence ID no: 8, of approximately 7.6 kilobase pairs, the human DCX regulatory sequence controls the expression of the DsRed2 reporter gene. The cloning protocol is schematized in FIG. 12.

EXAMPLE III

Expression of the phuDCXpromoEGFP1 Vector in Cell Cultures

Mouse Embryonic Forebrain Cell Cultures

Pregnant C57BL/6NcrI mouse females (Charles River Laboratories) were sacrificed by cervical dislocation. The uterus were removed and immersed in ice cooled Dulbecco's phosphate buffered saline solution (DBPS). Embryonic day 12.5 to 14.5 embryos were released from the uterus, the forebrain was dissected and separated from surrounding tissues. The dissected forebrain was washed once in ice-cooled DPBS, transferred to a petri dish and dissociated mechanically with a scalpel blade. The resulting preparation was washed in DPBS. Following 5 minutes centrifugation at 120× g, the pellet was resuspended in PPD-solution containing 0.01% Papain (Worthington Biochemicals, England), 0.1% dispase II (Boehringer, Germany), 0.01% DNaseI (Worthington Biochemicals, England) and 12.4 mM $MgSO_4$ in HBSS without $Mg^{++}/Ca^{++}$ (PAA, Germany) and incubated for 30 to 40 minutes at 37° C. The cell preparation was triturated every 10 minutes through a pipette. Dissociated cells were collected by 5 minutes centrifugation at 120×g. The pellet was resuspended in Neurobasal medium (Gibco BRL, Germany) and washed three times. Finally, the cell preparation was resuspended in Neurobasal medium supplemented with B27 (Gibco BRL, Germany), 2 mM L-Glutamine (PAN, Germany), 100 U/mL penicillin, 0.1 mg/mL streptomycin (PAN, Germany), 2 µg/mL heparin (Sigma, Germany), 20 ng/mL bFGF-2 (R&D Systems, Germany) and 20 ng/mL EGF (R&D Systems, Germany) and maintained at 37° C. in a 5% $CO_2$ containing humidified atmosphere. Growing suspension cultures formed cell aggregates referred to as neurospheres. In order to dissociate these neurospheres for passaging, cultures were centrifuged for 5 minutes at 120×g and the pellet was resuspended in Accutase (Innovative Cell Technologies, Inc.). The suspension was incubated at 37° C. for 10 minutes. The dissociated aggregates were recovered by centrifugation for 5 minutes at 120× and the cells reseeded in the growing media described above.

Human Fetal Cortical Cell Cultures

These cultures originate from an 8 weeks post conception human brain. Description of the culture conditions have been previously described in Svendsen, Journal of Neuroscience Methods 85 (1998), 141-152.

Preparation of the Forebrain Cell Cultures for Transfection

Following dissociation of the cell aggregates with Accutase (Innovative Cell Technologies, Inc.) at 37° C. for 10 minutes, cells were seeded on coverslips coated with poly-ornithin and laminin at a density of $7.5 \times 10^4$ cells per $cm^2$, in Neurobasal medium supplemented with B27 (Gibco BRL, Germany), 2 mM L-Glutamine (PAN, Germany), 100 U/mL penicillin, 0.1 mg/mL streptomycin (PAN, Germany), 10 ng/mL NT3 and 1% fetal calf serum and maintained for 1 week at 37° C. in a 5% $CO_2$ humidified atmosphere.

COS7 Cell Cultures

COS7 cell were obtained from ATCC U.S.A. (number CRL-1651) and maintained in culture in Dulbecco's modified Eagle's medium (DMEM), containing 10% fetal calf serum, 4.5 g/L glucose, 100 U/mL penicillin, 0.1 mg/mL streptomycin and 4 mM glutamine at 37° C. in a 5% $CO_2$ humidified atmosphere. The cells were seeded on coverslip coated with poly-ornithin and laminin at a density of $7.5 \times 10^4$ cells per $cm^2$, 1 day before proceeding to the transfection. As shown in FIG. 13, only a faible, non-specific expression of some green fluorescence may be detected in COS7-cells transfected with phuDCXpromoEGFP1 vector.

Transfection of the Cell Cultures with the phuDCXpromoEGFP1 Vector

Transfection was performed using 3 µg of phuDCXpromoEGFP1 vector in the presence of 5 µl of the cationic lipid reagent Metafectene (Biontex Laboratories, Germany) in a final volume of 1 mL according to the manufacturers protocol. Two days after the end of the transfection, the cultures were examined for the expression of the EGFP reporter gene using an Olympus IX70 inverted-fluorescent microscope. Nuclear counterstaining was performed with 4'6'diamidino-2-phenylindole dihydrochloride hydrate at 0.25 µg/µL (DAPI, Sigma, Germany).

As documented in FIG. 13, the human DCX regulatory sequences are activated to drive the expression of the EGFP reporter gene specifically in neuronal restricted/determined cells.

EXAMPLE IV

Analysis of Transgenic Mouse Lines Expressing the EGFP Reporter Gene Under the Control of the Human DCX Regulatory Sequence Generation of Transgenic Mouse Lines Expressing the EGFP Reporter Gene Under the Control of the Human DCX Regulatory Sequence For the generation of transgenic mouse lines, 100 micrograms of phuDCXpromoEGFP1 vector was digested using the restriction enzymes AflII and XhoI. A DNA fragment of approximately 4.5 kilobase pairs, Sequence ID no: 5, bearing the human DCX regulatory sequence, the EGFP gene and a SV40 poly adenylation signal, was obtained by agarose gel electrophoresis followed by an extraction using the Geneclean kit (Bio 101, Carlsbad, Calif., USA). A solution of 10 mM Tris; 0.1 mM EDTA containing the purified the DNA fragment at 1 ng/microL was injected into the pronucleus of B6C3 µl mouse (Harland) embryos at the 1-cell stage. The surviving embryos were transferred the same day into the oviduct of 0.5 day post coitum pseudopregnant CD-1 recipient mice. The protocol for the generation of transgenic mouse lines is schematized in FIG. 14.

Mice bearing the huDCXpromoEGFP1 transgene were mated with C57BL/6NcrI mice (Charles River Laboratories) to expand the colony.

Identification of the huDCXpromoEGFP1 Transgenic Mice

An approximately 5 mm tail piece was cut from the mice in order to gain genomic DNA. The DNA was purified from the piece of tail using the DNeasy Tissue kit (Qiagen). PCR amplification was performed on mouse genomic DNA to detect the presence of the EGFP reporter gene. The PCR was performed using the Amplitaq polymerase (Roche) and the following oligonucleotide: oligo no. 3: AAG TTC ATC TGC ACC ACC GGC (SEQ ID NO. 11) and oligo no. 4: CTT TAC TTG TAC AGC TCG TCC (SEQ ID NO.: 12).

The following PCR protocol was used:

| 94° C. | 2 mintues | 1 cycle |
|---|---|---|
| 94° C. | 45 seconds | 30 cycles |
| 59° C. | 45 seconds | |
| 72° C. | 2 minutes | |
| 72° C. | 8 minutes | 1 cycle |

The PCR amplification product was analysed by electrophoresis in agarose gel. Transgenic mice can be identified by the presence of an approximately 600 base pairs PCR product.

Analysis of the huDCXpromoEGFP1 Transgene Expression

One month-old transgenic mouse from the line 299 and the line 303 were deeply anesthetized and perfused transcardially with 4% paraformaldehyde in 100 mM phosphate buffer, pH 7.4. The brains were dissected, immersed overnight in fixative, and transferred to 30% sucrose/100 mM phosphate buffer, pH 7.4 for at least 48 hours. Brains were cut into 40 µm sagittal sections using a sliding microtome. Sections were stored at −20° C. in cryoprotectant solution until staining (25% v/v glycerol, 25% v/v ethylene glycol, and 0.05M phosphate buffer, pH 7.4).

For direct observation of the transgene expression pattern, sections were counterstained with 4'6'diamidino-2-phenylindole dihydrochloride hydrate at 0.25 µg/µL (DAPI, Sigma, Germany) in Tris-buffered saline (TBS: 0.1M Tris-HCl pH 7.4/0.9% NaCl) for 10 minutes. The DAPI staining labels every nucleus of the section. The sections were washed twice for 10 minutes in TBS and mounted on gelatin-coated glass slides. The slides were coverslipped using Prolong (Molecular Probes, Eugene, U.S.A.). Documentation was performed using a Leica DMR microscope (Leica Mikroskopie und Systeme GmbH, Germany) equipped with a Spot digital camera (Diagnostic Instrument Inc. U.S.A.).

For immuno-histological analysis, sections were blocked in Tris-buffered saline (TBS: 0.1M Tris-HCl pH 7.4/0.9% NaCl) containing 3% donkey serum and 0.1% Triton-X 100 (TBS-DS-TX) for 30 min, followed incubation with primary antibodies in TBS-DS-TX for 48 hours at 4° C. The following primary antibody dilutions were used: goat anti-DCX C-18 (1:500, Santa Cruz Labs, Santa Cruz, USA) and rabbit anti-GFAP (1:1000, Dako, Danemark). The sections were then rinsed in TBS three times for 10 minutes, and then incubated with secondary antibodies in TBS-DS-TX for 2 hours. The following fluorochrome-conjugated secondary antibodies were used: Alexa fluor 568 donkey anti-goat and Alexa fluor 568 goat anti-rabbit antibodies (4 micrograms/mL, Molecular Probes, Eugene, U.S.A.). Nuclear counterstain was performed with 0.5 microM TO-PRO-3 (Molecular Probes, Eugene, U.S.A.) for 10 minutes. After several washes in TBS, sections were mounted on gelatin-coated glass slides and coverslipped using Prolong (Molecular Probes, Eugene, U.S.A.).

Analysis was performed using a confocal microscope (TCS-NT, Leica Microsystems, Bensheim, Germany) equipped with a 40×PL APO oil objective (1.25 NA) and a pinhole setting that corresponded to a thickness of the focal plane of less than 2 µm.

From the mouse embryos that were microinjected with the DNA fragment encoding the EGFP reporter gene under the control of the human DCX regulatory sequence, 101 mice survived and developed into a mature mouse. PCR Screening of the genomic DNA isolated from the tail of the mouse revealed that 8 animals were transgenic, 5 males and 3, females. The pattern of the EGFP reporter gene expression in the CNS was analyzed by observing brain sections from 1 month-old huDCXpromoEGFP1 transgenic mice from line 299 and from line 303 under a microscope for fluorescence. The high expression of the EGFP reporter was observed in the dentate gyrus of the hippocampal formation, in the subventricular zone, in the rostral migratory stream and in the olfactory bulb (FIG. 15). These regions are known to contain neuronal-restricted precursor cells and doublecortin expressing cells. Therefore, the expression of the EGFP reporter gene occurs in the relevant regions expected from the use of the human DCX regulatory sequence. Immunohistology was performed on brain sections from huDCXpromoEGFP1 transgenic mice of the line 303 to define what type of cell expressed the DCX reporter gene. FIG. 16 shows a co-localization of the endogenous doublecortin expression in the olfactory bulb with the expression of the EGFP reporter gene. We also observed an absence of co-localization within astrocytes, here detected with an anti-GFAP antibody, and the expression of the EGFP reporter gene. Therefore the EGFP reporter gene is expressed in neuronal-restricted precursor cells expressing the endogenous doublecortin and not is not expressed in other cell types, like astrocytes.

EXAMPLE V

Enrichment of Cells Expressing a Fluorescent Gene (EGFP or DsRed2) Derived from an Animal as Described in Example IV by FACS-Sorting Brain tissue from transgenic mice of different developmental stages, comprising embryonic, postnatal and adult stages, are removed and transferred into 4° C. DPBS (PAN, Germany) with or without 4.5 g/L glucose (DPBS-glu solution). Overlying meninges and blood vessel are removed as much as possible and the brain tissue is cut in small pieces with a scalpel. Alternatively, specific brain regions, such as hippocampus, olfactory bulb, lateral ventricle wall, striatum, cerebellum or cortex are dissected. The tissue is washed in DPBS or DPBS-glu in order to rinse off the excess of blood and resuspended in PPD-solution composed of 0.01% Papain (Worthington Biochemicals, England), 0.1% dispase II (Roche, Germany), 0.01% DNase I (Worthington Biochemicals, England) 12.4 mM $MgSO_4$ in Hank's Balanced Salt Solution (HBSS, PAN, Germany) without $Ca^{++}/Mg^{++}$ and digested for 30 to 40 minutes at 37° C. with gentle trituration every 5 to 10 minutes. The cell suspension is then centrifuged at 200×g for 5 minutes, wash two times with HBSS without $Ca^{++}/Mg^{++}$ and resuspended in 1 ml of HBSS without $Ca^{++}/Mg^{++}$. The cell suspension is passed through a 30 µm cell-strainer (Becton-Dickinson, Germany).

The cell suspension is further sorted using a FACS Vantage flow cytometer equipped with a cell sorter (Becton-Dickinson, Germany) using the CELLQuest software. The cells population is analyzed using the light forward and right-angle (side) scatter, the EGFP fluorescence through a 530±15 nm bandpass filter and the DsRed fluorescence through a 575±13 nm bandpass filter, as they traverse the beam of an argon ion laser (488 nm 100 mW). Additionally, dead cells could be excluded using substances labeling cells with damaged membranes, for example using a solution of propidium iodide at 10 µg/ml. Cells derived from a wild type mice can be use to define the background fluorescence level. A sorting error level under 5%, resulting from false sorting or the presence of doublet/multiplex of cells composed of positive and negative cells, is expected and acceptable. FIG. 28 illustrated sorted cell populations obtained from dissociated brains of neonatal huDCXpromoDsRed2 transgenic mice. FACS-sorting of these dissociated brains for the presence of DsRed2 fluorescence, resulted in a population of cells in which more than 99% of the cells expressed the DsRed2 reporter gene as visualized directly after sorting with an Olympus IX70 inverted-fluorescence microscope. Similarly, sorting for the absence of fluorescence in cells of the dissociated brains resulted in a cell population in which less than 1% of the cells were expressing the DsRed2 reporter gene as visualized directly after sorting with an Olympus IX70 inverted-fluorescence microscope.

EXAMPLE VI

Cells Expressing a Fluorescent Gene (EGFP or DsRed2) Derived from an Animal as Described in Example IV Enriched by FACS Yields Doublecortin-Positive Cells Sorted viable cells from EXAMPLE V (above) are cultivated into Neurobasal medium (Gibco BRL, Germany) supplemented with B27 (Gibco BRL, Germany), 5% fetal calf serum (PAN, Germany), 2 mM L-glutamine (PAN, Germany), 100 U/ml penicillin, 0.1 mg/ml streptomycin (PAN, Germany) into 12 wells/plate at different densities, e.g. $1\times10^5$ cells per well and ml of medium, over glass coverslips pre-coated sequentially with a solution of 250 µg/ml poly-ornithin followed by a solution of 5 µg/ml laminin. Following different periods in culture, e.g. 1 day to 7 days, cells are fixed using a phosphate-buffered 4% paraformaldehyde solution pH 7.4 (4% w/v paraformaldehyde, 100 mM $NaH_2PO_4$, 0.4 mM $CaCl_2$, 50 mM sucrose) for 30 minutes at room temperature. Sample are washed two times with DPBS (PAN, Germany) for 10 minutes at room temperature and blocked using a fish-skin gelatin containing solution (0.1M Tris-HCl pH 7.5, 0.15M NaCl, 1% bovine serum albumin, 0.2% Teleostean gelatin (Sigma, Germany), 0.1% Triton X-100 (Sigma, Germany)) for one hour at room temperature. The fish-skin gelatin containing solution is also used for the antibody dilutions and the washing steps. The specimens are incubated overnight at 4° C. with the primary antibodies at the following dilutions: goat anti-DCX C-18 1:100 to 1:1000 (Santa Cruz Labs, USA); mouse anti-galactocerebrosides 1:500 (Chemicon, USA); rabbit anti-GFAP 1:1000 (Dako, Danemark); rabbit anti-Ki67 1:500 (Novocastra, UK); rabbit anti-nestin 1:200 (Chemicon, USA); mouse anti-nestin 1:200 (Pharmingen International, USA); mouse anti-βIII-tubulin 1:500 (clone 5G8, Promega, USA); mouse anti-βIII-tubulin 1:500 (clone TUJ1, Babco, USA). The secondary fluochrome-conjugated antibodies are diluted 1:500 (donkey anti-mouse or rabbit or goat, Dianova, Germany). Nuclear counterstaining is performed with 4',6'-diamidino-2-phenylindole dihydrochloride hydrate at 0.25 µg/µl (Dapi, Sigma, Germany). Following the last wash, the samples are briefly rinsed with PBS and mounted on slides using Prolong (Molecular Probes, The Netherlands). In cases where antigens are sensitive to detergents, e.g. galactocerebrosides, Triton X-100 is omitted from the fish-skin gelatin containing solution.

Dissociated cells from neonatal transgenic mice expressing the EGFP reporter gene under the control of the neural nestin promoter (Kawaguchi, Mol Cell Neurosci 17 (2001), 259-273) can be used as a FACS-sorting control in a similar manner as described in the EXAMPLE V. Cells expressing nestin (in this transgenic model=expressing EGFP) constitute the population of neural stem cells. Upon differentiation, these cells have the potential to generate the three major types of cells found in the central nervous system, namely neurons, astrocytes and oligodendrocytes. The cell population sorted for the presence of the EGFP reporter protein should have the potential in the experiment described above to become neurons, astrocytes and oligodendrocytes. The cell population sorted for the absence of EGFP reporter protein has also this potential, since it can be constitute from precursors cells for neurons and glia that are already more differentiated than the stem cells population and therefore do not express nestin (EGFP) anymore. Therefore, the two populations (positive and negative) of sorted cells for the expression of EGFP under the control of the neural nestin promoter should generate mixed population of neurons and glia upon differentiation.

FIG. 29 illustrates an immunostaining for doublecortin performed on cell cultures originating from dissociated brains of neonatal huDCXpromoDsRed2 transgenic mice and from neonatal nestin-EGFP transgenic mice that were FACS-sorted for the presence/absence of fluorescent reporter protein. The cultures were fixed after one day of culture in Neurobasal medium (Gibco BRL, Germany) supplemented with B27 (Gibco BRL, Germany), 5% fetal calf serum (PAN, Germany), 2 mM L-glutamine (PAN, Germany), 100 U/ml penicillin, 0.1 mg/ml streptomycin (PAN, Germany) into 12 wells/plate over glass coverslips pre-coated sequentially with a solution of 250 µg/ml poly-ornithin followed by a solution of 5 µg/ml laminin, as described above. FIG. 29 documents that FACS-sorting single cells suspension of dissociated brains from neonatal huDCXpromoDsRed2 transgenic mice for cells expressing the reporter gene DsRed2 resulted in an enrichment of the population of cells expressing doublecortin. FACS-sorting of the cells not-expressing the reporter gene DsRed2 resulted in a culture with very few doublecortin expressing cells after 1 day in culture. FIG. 29 also documents that FACS-sorting of a single cells suspension of dissociated brains from neonatal nestin-EGFP transgenic mice for cells expressing the reporter gene EGFP did not result in an enrichment of the population of cells expressing doublecortin as compared to the cells sorted for the absence of EGFP expression.

EXAMPLE VII

Cells Expressing a Fluorescent Reporter Gene (EGFP or DsRed2) Derived from an Animal as Defined in Example IV Enriched by FACS Yields in Neuronal Precursors-Enriched Cultures Sorted viable cells from EXAMPLE V (above) are cultivated into Neurobasal medium (Gibco BRL, Germany) supplemented with B27 (Gibco BRL, Germany), 5% fetal calf serum (PAN, Germany), 2 mM L-glutamine (PAN, Germany), 100 U/ml penicillin, 0.1 mg/ml streptomycin (PAN, Germany) into 12 wells/plate at different densities, e.g. $1\times10^5$ cells per well and ml of medium, over glass coverslips pre-coated sequentially with a solution of 250 µg/ml poly-ornithin followed by a solution of 5 µg/ml laminin. Following different periods in culture, e.g. 1 day to 7 days, cells are fixed using a phosphate-buffered 4% paraformaldehyde solution pH 7.4 (4% w/v paraformaldehyde, 100 mM $NaH_2PO_4$, 0.4 mM $CaCl_2$, 50 mM sucrose) for 30 minutes at room temperature. Sample are washed two times with DPBS (PAN, Germany) for 10 minutes at room temperature and blocked using a fish-skin gelatin containing solution (0.1M Tris-HCl pH 7.5, 0.15M NaCl, 1% bovine serum albumin, 0.2% Teleostean gelatin (Sigma, Germany), 0.1% Triton X-100 (Sigma, Germany)) for one hour at room temperature. The same fish-skin gelatin containing solution is used for the antibody dilutions and the washing steps. The specimens are incubated overnight at 4° C. with the primary antibodies at the following dilutions: goat anti-DCX C-18 1:100 to 1:1000 (Santa Cruz Labs, USA); mouse anti-galactocerebrosides 1:500 (Chemicon, USA); rabbit anti-GFAP 1:1000 (Dako, Danemark); rabbit anti-Ki67 1:500 (Novocastra, UK); rabbit anti-nestin 1:200 (Chemicon, USA); mouse anti-nestin 1:200 (Pharmingen International, USA); mouse anti-βIII-tubulin 1:500 (clone 5G8, Promega, USA); mouse anti-βIII-tubulin 1:500 (clone TUJ1, Babco, USA). The secondary fluochrome-conjugated antibodies are diluted 1:500 (donkey anti-mouse or rabbit or goat, Dianova, Germany). Nuclear counterstaining is performed with 4',6'-diamidino-2-phenylindole dihydrochloride hydrate at 0.25 µg/µl (Dapi, Sigma, Germany). Following the last wash, the samples are briefly rinsed with PBS and mounted on slides using Prolong (Molecular Probes, The Netherlands). In cases where antigens are sensitive to detergents, e.g. galactocerebrosides, Triton X-100 is omitted from the fish-skin gelatin containing solution.

Dissociated cells from neonatal transgenic mice expressing the EGFP reporter gene under the control of the neural nestin promoter (Kawaguchi, Mol Cell Neurosci 17 (2001), 259-273) can be used as a FACS-sorting control in a similar manner as described in the EXAMPLE V. Cells expressing nestin (in this transgenic model=expressing EGFP) constitute the population of neural stem cells. Upon differentiation, these cells have the potential to generate the three major types of cells found in the central nervous system, namely neurons, astrocytes and oligodendrocytes. The cell population sorted for the presence of the EGFP reporter protein should have the potential in the experiment described above to become neurons, astrocytes and oligodendrocytes. The cell population sorted for the absence of EGFP reporter protein has also this potential, since it can be constitute from precursors cells for neurons and glia that are already more differentiated than the stem cells population and therefore do not express nestin (EGFP) anymore. Therefore, the two populations (positive and negative) of sorted cells for the expression of EGFP under the control of the neural nestin promoter should generate mixed population of neurons and glia upon differentiation.

Immunodetection of βIII-tubulin performed on cell cultures originating from dissociated brains of neonatal huDCX-promoDsRed2 transgenic mice and from neonatal nestin-EGFP transgenic mice that are FACS-sorted for the presence/absence of fluorescent reporter protein. The cultures are fixed after one day of culture in Neurobasal medium (Gibco BRL, Germany) supplemented with B27 (Gibco BRL, Germany), 5% fetal calf serum (PAN, Germany), 2 mM L-glutamine (PAN, Germany), 100 U/ml penicillin, 0.1 mg/ml streptomycin (PAN, Germany) into 12 wells/plate over glass coverslips pre-coated sequentially with a solution of 250 µg/ml poly-ornithin followed by a solution of 5 µg/ml laminin, as described above. FACS-sorting of single cells suspension of dissociated brains from neonatal huDCXpromoDsRed2 transgenic mice for cells expressing the reporter gene DsRed2 results in an enrichment of the population of cells expressing βIII-tubulin. Since βIII-tubulin is expressed in neuronal precursors, FACS-sorting of cells expressing the huDCXpromoDsRed2 vector is an efficient mean generate from a mixed cell population a cell culture enriched in neuronal precursors. FACS-sorting of the cells not-expressing the reporter gene DsRed2 results in a culture containing very few of βIII-tubulin expressing cells after 1 day in culture. FACS-sorting of a single cells suspension of dissociated brains from neonatal nestin-EGFP transgenic mice for cells expressing the reporter gene EGFP does not result in an enrichment of the population of cells expressing βIII-tubulin as compared to the culture of cells FACS-sorted for the absence of EGFP reporter gene expression.

EXAMPLE VIII

Enrichment of EGFP-Positive Cells by Transfection and FACS-Sorting

Cell Culture Preparation
Embryonic Rat, Mouse and Chicken Forebrain Cultures:

Embryonic mouse, rat or chicken forebrain cultures are prepared as follows: pregnant rats such Sprague-Dawley, Whistar, Fisher 344, or pregnant mice, such as C57/bl6 are sacrificed at gestation day 10.5 by pentobarbital overdose, their fetuses removed, decapitated, and their brains dissected, Special care is taken not to contaminate with meningeal tissue and skull osteoid. For chicken brain cultures, the forebrain is dissected from freshly decapitated embryos after 6, 8, 10 or 12 days of gestation. In each case, the tissue is collected in 4° C. DPBS (PAN, Germany) with 4.5 g/L glucose (Merck, Germany) (DPBS/glu). The tissue is enzymatically treated in PPD-solution containing 0.01% Papain (Worthington Biochemicals, England), 0.1% dispase II (Boehringer, Germany), 0.01% DNase I (Worthington Biochemicals, England) and 12.4 mM $MgSO_4$ in HBSS (PAN, Germany) without $Mg^{++}/Ca^{++}$ (PAA, Germany) and digested for 20 min at 37° C. with gentle trituration every 5 min. The cell suspension is then centrifuged at 200 g for 5 Min, wash 2× with HBSS —Ca/—Mg and resuspended in 2 ml HBSS —Ca/—Mg. Cells are dissociated by triturating sequentially 20/10/5, through serially-narrowed glass pasteur pipette, and resuspended in NB medium (Gibco BRL, Germany) supplemented with B27 (Gibco BRL, Germany) (NB/B27), 5% FCS (PAN, Germany), 2 mM L-glutamine (PAN, Germany), 100 µg/ml penicillin/0.1 mg/mL streptomycin (PAN, Germany). Cells are plated on poly-ornithine (250 µg/ml) and laminin (5 µg/ml) coated 12 well plates at different cell densities (10E5 to 10E7 cells/well and ml) and grown for two to seven days.
Adult Cultures Brains from mice, such as C57/bl6 or rats, such as Sprague-Dawley, Whistar, Fisher 344, elder than 1 month are removed after sacrificing, Overlying meninges and blood vessels are removed and the brain tissue is cut in small pieces with a scalpel. Alternatively, specific brain regions, such as hippocampus, olfactory bulb, lateral ventricle wall, striatum, cerebellum or cortex are dissected. The tissue is washed in DPBS/glu in order to rinse off excess blood and resuspended in PPD-solution containing 0.01% Papain (Worthington Biochemicals, England), 0.1% dispase II (Boehringer, Germany), 0.01% DNase I (Worthington Biochemicals, England) and 12.4 mM $MgSO_4$ in HBSS (PAN, Germany) without $Mg^{++}/Ca^{++}$ (PAA, Germany) and digested for 30 to 40 min at 37° C. with gentle trituration every 10 min. The cell suspension is then centrifuged at 200 g for 5 Min, wash 2× with HBSS —Ca/—Mg and resuspended in 2 ml HBSS —Ca/—Mg. Cells are dissociated by triturating sequentially 20/10/5, through serially-narrowed glass pasteur pipette and passed through a 30 µm cell strainer (Becton-Dickinson). and resuspended in NB medium (Gibco BRL, Germany) supplemented with B27 (Gibco BRL, Germany) (NB/B27), 5% FCS (PAN, Germany), 2 mM L-glutamine (PAN, Germany), 100 µg/ml penicillin/0.1 mg/mL streptomycin (PAN, Germany). Cells are plated on poly-ornithine (250 µg/ml) and laminin (5 µg/ml) coated 12 well plates at different cell densities (10E5 to 10E7 cells/well and ml) and grown for two to seven days.
Explant Cultures:

Alternatively to dissociated monolayer cultures, tissue explants is also used for transfection experiments. Here, adult mouse, rat or human brain tissue, such as hippocampus, ventricle wall or olfactory bulb are isolated and dissected as described above and cut in small pieces with a scalpel. Additional dissection in 200 µm pieces is performed automatically using a McIllwain tissue chopper. Explants are than plated onto poly-ornithine (250 µg/ml) and laminin (5 µg/ml) coated 35 mm Falcon dishes in NB medium (Gibco BRL, Germany) supplemented with B27 (Gibco BRL, Germany) (NB/B27), 5% FCS (PAN, Germany), 2 mM L-glutamine (PAN, Germany), 100 µg/ml penicillin/0.1 mg/mL streptomycin (PAN, Germany).

Transfection Methods:

Liposomal transfection: Cells derived from different sources, such as embryonic or adult, such as chicken, mouse rat and human are plated as described above. Two to seven days after plating, medium is exchanged to transfection medium comprising of NB medium (Gibco BRL, Germany) supplemented with B27 (Gibco BRL, Germany) (NB/B27), 2 mM L-glutamine (PAN, Germany) to remove serum and Pen/Strep for 1 h. 3 µg DNA (SEQ ID NO. 7; EGFP-vector under the control of DCX regulatory sequence) and 5 µl of kationic lipid reagent (Metafectene) are each diluted in 50 µl transfection medium. Dilutions of DNA and Metafectene are gently mixed, mixture is incubated at room temperature for 20 min before pipetting on the cells in the 12-well-plate. Transfection lasts 8 to 10 hours, then the supernatant is exchanged by fresh, antibiotic and serum containing medium. Imaging for EGFP is performed 12-38 hrs after transfection, using an OlympusIX70 microscope with epifluorescence optics. Particel-mediated gene transfer: Alternatively to liposomal-based transfection, genes can be introduced into different kind of cells by particle-mediated delivery, using a Biolistics particle delivery system (Bio-Rad PDS1000). Explant cultures are prepared as described above. After an overnight incubation, the brain explants are well adherent on the dish. Medium is removed during, and readded after gene delivery. For gene delivery, gold particles (0.6 or 1 µm, 50 ml of 60 mg/ml, Bio-Rad) are coated with 5 µg of plasmid DNA, such as (SEQ ID NO. 7; EGFP-vector under the control of DCX regulatory sequence) for 1 h, after which the particles are collected by centrifugation, washed and resuspended in 50 µl 100% ethanol. A total of 8 µl of gold particle/DNA suspension is added on a sterile macrocarrier disc (Bio-Rad) and the ethanol is evaporated. The macrocarrier is then mounted in a Biolistic particle delivery system and the samples are placed in 5 to 10 cm distance from the stopping screen. Helium with pressure of 1500 psi, and a rupture pressure of 1000-1200 psi is provided by using a 1100 psi rupture disk. Bombardment is performed at chamber vacuum of 20-25 Hg.

Alternatively to liposomal-based or particle-mediated gene delivery methods, viral mediated gene delivery using vectors such as adenoviral, adeno-associated viral, lenti viral, or retroviral vectors can be conceived to deliver a marker-gene under the control of the DCX regulatory sequence. Different cell types including embryonic or adult, mouse, rat, chicken or human may be used for gene delivery of the EGFP reporter gene under the control of the human DCX promoter using the different viral vectors. Using an adenoviral vector at a concentration of 10 pfu/cell, roughly 20% of cultures forebrain cells express EGFP 3 days after infection. At 1000 pfu/cells, over 50% of cells express EGFP.

FACS-Sorting: Cells are dissociated by using Accutase (PAA) and loaded with 10 µg/ml propidium iodide (PI) and passed through a 30 µm cell strainer (Becton-Dickinson). Cells are analyzed and sorted using a FACS Vantage flow cytometer/cell sorter (Becton-Dickinson) equipped with CELLQuest software). Cells (2×10E6 cells/ml) are analyzed by light forward and right-angle (side) scatter, PI fluorescence, and EGFP fluorescence through a 510±20 nm bandpass filter, as they traverse the beam of an with an argon ion laser (488 nm 100 mW). Dead cells are excluded by gating on forward and side scatter, and by eliminating propidium iodide-positive events. Cells that were not transfected are used to set the background fluorescence. A false positive rate of 0.02±0.05% is accepted so as to ensure an adequate yield.

EXAMPLE IX

Cells Expressing a Fluorescent Gene (EGFP) Derived from an Transfection Experiment Enriched by FACS Yields Doublecortin-Positive Cells Viable cells form EXAMPLE VIII (above) are sorted into NB medium (Gibco BRL, Germany) supplemented with B27 (Gibco BRL, Germany), (NB/B27), 5% FCS (PAN, Germany), 2 mM L-glutamine (PAN, Germany), 100 µg/ml penicillin/0.1 mg/mL streptomycin (PAN, Germany) at a speed of 3000 events/s. Sorted cells are plated on poly-ornithine (250 µg/ml) and laminin (5 µg/ml) coated glass coverslips in 12 well plates at different cell densities (10E5 to 10E7 cells/well and ml and grown for two to seven days. Cells are fixed with phosphate-buffered 4% prewarmed 37° C. paraformaldehyde pH 7.4 (4% w/v paraformaldehyde, 100 mM $NaH_2PO_4$, 0.4 mM $CaCl_2$, 50 mM sucrose) for 30 min and processed for immunohistochemistry. Following 30 min of fixation at room temperature with phosphate-buffered 4% paraformaldehyde, samples are blocked for a minimum of 1 hour in fish skin gelatin buffer (0.1M Tris-HCl pH 7.5, 0.15M NaCl, 1% bovine serum albumin, 0.2% Teleostean gelatin (Sigma, Germany), 0.1% Triton X-100) at room temperature. The specimens are incubated overnight at 4° C. with the primary antibodies at the following dilutions: goat anti-DCX C-18 (1:500, Santa Cruz Labs, Santa Cruz, USA); mouse anti-galactocerebroside 1:500 (Chemicon, USA); rabbit anti-GFAP 1:1000 (Dako, Danemark); rabbit anti-Ki67 1:500 (Novocastra, UK); rabbit anti-nestin 1:200 (Chemicon, USA); mouse anti-nestin 1:200 (Pharmingen International, USA); mouse anti-βIII-tubulin 1:500 (clone 5G8, Promega, USA); mouse anti-βIII-tubulin 1:500 (clone TUJ1, Babco, USA). The secondary fluorochrome-conjugated antibodies are diluted 1:500 (donkey anti-mouse or rabbit, Dianova, Germany). All antibody dilutions and washes are performed with the fish skin gelatin buffer. Nuclear counterstaining is performed with 4',6'-diamidino-2-phenylindole dihydrochloride hydrate at 0.25 µg/µl (DAPI, Sigma, Germany). Following the last wash, the samples are briefly rinsed with PBS and mounted on slides using Prolong (Molecular Probes, The Netherlands). In cases where antigens are sensitive to detergents (GalC), Triton X-100 is omitted from the fish skin gelatin buffer.

Dissociated cells are sorted into one of two fractions, a EGFP negative and a EGFP positive one. Sorted cells are cultured and analyzed by immunohistochemistry as described above. 2 days after sorting, most cells of the EGFP positive fraction continued to express EGFP and immunostaining for doublecortin revealed that more than 90% of cells express doublecortin. In contrast, very few of the cells from the EGFP negative fraction expresses doublecortin.

Two days after cell sorting, less than 5% of the cells derived from the EGFP positive population expresses the neuroectodermal progenitor marker Nestin, non of the cells express the glial marker GFAP or the oligodendroglial marker GalC, however, more than 90% of the cells expressed βIII tubulin, a neuronal marker that is turned on early during neuronal differentiation. Doublecortin expressing cells co-express βIII tubulin. Very few of the cells derived from the EGFP negative fraction, doublecortin is expressed. However, we find that less than 1% of the cells express Nestin, more than 30% of the cells express GFAP, no GalC staining can be detected, but 10% of the cells express βIII tubulin. These are likely to be mature neurons, since some cells express also the neuronal marker MAP2.

Seven days after sorting and plating, the EGFP signal in cells derived from the EGFP positive fraction decreases and is only hardly detectable. At the same time, doublecortin expression decreases in the culture as determined by immunostaining. None of the cells in these cultures in positive for Nestin, but most cells do now express βIII tubulin. Many of these cells (more than 20%) express MAP2 and GAP-43, marker for maturing neurons. In cultures derived from the EGFP negative fraction, the number of GFAP positive glial cells increases probably due to glial growth, whereas the number of neurons does not change.

EXAMPLE X

Transplantation Experiments Using Cells Enriched in EGFP-DCX Expressing Cells Cells can be derived either from an transgenic animal as described in Example IV or from transfected cells as described in Example III.

Transplantations are conducted according to protocols previously established. Single cell suspensions are prepared for transplantation by FACS sorting as described above and sorted into HBSS. Cells are resuspended in HBSS at a concentration of 100,000 cells/μl. The specific injection parameters need to be determined depending on the animal model, but initially cells are injected at specific sites with each infusion site receiving 0.5 μl (50,000 cells). A single volumetric pressure injection of the cell suspension into the brain is performed using a digitally controlled microinjector via a pulled-glass micropipette with tip diameter of approximately 100 μm.

Grafting of human or mouse cells into rodents requires immunosuppression in order to prevent rejection of grafts by the host. This is achieved by continuous treatment with cyclosporine or FK506.

Animal Models

Alzheimer's Disease (AD). The cholinergic neurons of the cholinergic forebrain system are significantly affected in AD and their progressive cell death leads to cognitive impairment and dementia. Animals with discrete lesions of the forebrain cholinergic system exhibit similar deficits in learning and memory tasks. Lesion are performed on cholinergic cells in the medial septum, diagonal band and nucleus basalis by intraventricular injection of a specific neurotoxin (192-IgG-Saporin). This neurotoxin is selectively taken up by cholinergic neurons and leads to cell death within 7 days after application. When the lesion is complete the levels of cholinergic activity in the cortex and hippocampus are reduced to less than 20% of preoperative values. In brief, intraventricular infusions of the immunotoxin is performed by injecting 3.5 μg 192IgG-saporin in a final volume of 5 μl saline over a period of 5 min into the right lateral ventricle. Transplantations are performed about 2 weeks after lesion in order to test the ability of cells to replace the lost cholinergic neurons and to improve function in learning tasks.

Parkinson's Disease. A mouse model that is widely used as an animal model of PD is based on the systemic application of the compound I-methyl-4-phenyl-1,2,3,6-tetrahydropyridine (MPTP) for review see, (Kaakkola and Teravainen (1990); Langston (1985). Major steps in the expression of neurotoxicity involve the conversion of MPTP to the toxic agent 1-methyl-4-phenylpyridinium ion (MPP+) by type B monoamine oxidase (MAO-B) in glial cells, the specific uptake of MPP+ into nigro-striatal dopaminergic neurons and the intraneuronal accumulation of MPP+. It induces selectively cell death of the dopaminergic cells in the substantia nigra and produces severe motor deficits. Briefly, C57BL/6 mice (8 weeks-old) receive a single s.c. injection of 40 mg/kg MPTP. This regimen has been shown typically to induce a reproducible 80% striatal dopamine depletion in C57BL/6 mice (Chan (1997)) within 7 days after injection. One week after inducing Parkinson-like symptoms in mice cells are grafted into the striatum to improve dopamine release in this structure, and the substantia nigra for reconstruction of the nigro-striatal projection.

Stroke: the medial cerebral artery occlusion (MCAO) model. Briefly, male Wistar rats weighing 250-270 g are anesthetized with 4% isoflurane in a mixture of 70% $N_2O$ and 30% $O_2$ and intubated orotracheally for mechanical ventilation. A thermostatically regulated heating lamp and pad are used to maintain body temperature at 37° C. Local cortical blood flow in each hemisphere is monitored in the cerebral artery by laser-doppler flowmetry. After exposure of the right carotid bifurcation and ligation of the branches of the internal carotid artery (ICA) under the operating microscope, the external carotid artery is ligated and cut distal to the superior thyreoid artery. Then, a silicone-coated 4-0 nylon monofilament is introduced into the ECA and gently advanced through the ICA until its tip occludes the origin of the MCA. By this, local cortical blood flow in the MCA territory drops to about 20% of baseline. The endovascular suture remains in place until reperfusion is allowed by withdrawal of the filament. Transplantation sites for cells include the basal ganglia and subcortical white matter (ischemic core) and the overlying cortex (ischemic penumbra) of the ischemic hemisphere.

Morphology

Transplantation of cells into animal models of neurological diseases provide information about the integration and survival of grafted cells, their differentiation potential under pathological conditions and their capability to functionally replace dying neurons. For morphological evaluation the brains are removed at predetermined time points after grafting. Specific antibody immunohistochemical staining will determine the number and distribution of grafted cells. In combination with cell marker for neurons, astrocytes and oligodendrocytes, the differentiation fate for cells is determined via multiple-immunofluorescence and confocal laser microscopy. When necessary, characterization of individual neuronal phenotypes will be conducted using transmitter specific antibodies.

Also envisaged are grafting experiments from other species, e.g., mouse cells may be grafted into, e.g., rat (brains) and migration behaviour, survival and/or differentiation of said grafted cells may be tested.

Tissue preparation. Animals are killed at different time points after grafting with an overdose of anesthetics and perfused transcardially with 4% paraformaldehyde in phosphate buffer. The brains are removed, stored in the fixative overnight, and then transferred to 30% sucrose. For free-floating immunohistochemistry, 40-μm sections are cut on a sliding microtome and stored at −20° C. in cryoprotectant solution. Quantitative stereology. Sections through the grafted regions are stained immunohistochemically for the protein that is expressed under the control of the DCX regulatory sequence.

EXAMPLE XI

Deletion- and Transfection Studies Generation of Deletion Mutants from the Human DCX Regulatory Sequence in Order to Define the Human DCX Minimal Promoter and its Regulatory Elements Generation of Deletions Mutants:

Using the subcloned human DCX regulatory sequence, for example the phuDCXpromoEGFP1 vector, it is possible to design deletion protocols using restriction enzymes. By digesting the vector with appropriate restriction enzymes, it is possible to cut apart a segment of the human DCX regulatory sequence. The remaining piece of the vector can possess compatible ends for recircularization using T4 DNA ligase or may need to be first blunt-ended. In order to generate a fragment of DNA with compatible blunt ends, one may make use of the DNA polymerase I Klenow fragment in the presence of an excess of free dNTPs.

Alternatively, segments of the human DCX regulatory sequence can be amplified by PCR and subcloned in the promoterless EGFP-N1 vector, as described in the Example II. This strategy allows for a more precise selection of the regions to be analyzed, without the requirement of sites for restriction enzymes. Several of these amplified fragments can be easily subcloned in tandem in front of a reporter gene, such as the EGFP reporter gene.

Analysis of the Expression Promoting Activity of the Human DCX Regulatory Sequence and its Sub-Regions:

The expression promoting activity of the human DCX regulatory sequence, as well as from the various deletion mutants, can be assess by transfecting neuronal-restricted progenitor cells. These cells can be gained from the dissociation of forebrains from embryonic day 10.5 to 12.5 mouse embryo. The cells suspensions obtained from these embryonic forebrains contain several cell-types, including neuronal-restricted precursor cells. Parallel transfections of these dissociated forebrain cultures can be performed using the EGFP reporter gene under the control of an ubiquitous promoter, such as CMV, under the control of the human DCX regulatory sequence or under the control of any fragments of the human DCX regulatory sequence. Comparison of the levels of EGFP reporter gene expression, as visualized under a microscope for fluorescence, allows for the analysis of the expression promoting activity of the sequence controlling the expression of the EGFP reporter gene. Alternatively, the transfected cells can be analyzed by FACS, allowing for a rapid quantification of the percentage of cells expressing the EGFP reporter gene as well as the relative intensity of expression.

The neuronal-restricted precursor cells can also be gained by the use of huDCXpromoEGFP1 transgenic mice. Dissociation of regions of the CNS bearing neurogenesis will provide a cell suspension containing several cell types, including neuronal-restricted precursor cells. This cell suspension can be divided into EGFP reporter expressing cells and EGFP reporter non-expressing cells fractions by FACS-sorting using the fluorescent signal of the EGFP reporter protein as the sorting criteria. The EGFP positive cells would correspond to neuronal-restricted precursor cells, and the EGFP negative cells to all the other cell types. These two populations can then be transfected, for example, with the DsRed2 fluorescent reporter gene under the control of the human DCX regulatory sequence and under the control of fragments of the human DCX regulatory sequence.

The cell-specificity of regulatory sequences is often the result of expression inducing elements, that induce the expression of the gene in a specific desired cell type, and expression inhibitory elements, that blocks the expression of the gene in cell types other then the desired cell type. The use of the two sorted cells fractions permits for the identification of inducing and inhibitory elements. Analysis of the expression of the DsRed2 reporter gene in the transfected EGFP positive cells, allows to determined if the regulatory sequence is able to induce the expression of the DsRed2 reporter gene in cells which are neuronal-restricted, revealing the presence of sufficient expression-inducing elements. Analysis of the expression of the DsRed2 reporter gene in the transfected EGFP negative cells allows to determine if some expression inhibitory elements have been deleted. In this case, DsRed2 expression would be observed in EGFP negative cells.

The use of established cell lines, such as COS7 cells, can also be used to assess the deletion of expression inhibitory elements in the human DCX regulatory sequence, resulting in the expression of the reporter gene in cells other than neuronal-restricted precursor cells.

EXAMPLE XII

Putative Transcription Factor Binding Sites in the DCX Regulatory Sequences

For sequence analysis the following programs were applied: fasta20u66, version 2.0u66 available at Biology Workbench of the San Diego Supercomputer Center (http://workbench.sdsc.edu) for alignment; MatInspector, version 6.2.1, available at Genomatix Software GmbH (Munich, Germany, www.genomatix.de) for analysis of transcription factor binding sites (Quandt (1995) Nucleic Acids Research 23, 4878-4884).

The analysis of the SEQ ID NO:1 revealed putative binding sites for Brn-2 (position 1985-2001; 2774-2790), NeuroD1 (position 1821-1833), E2F-1 (positions 1831-1845; 2675-2689; 2761-2775), E2F-2 (positions 2309-2323), Smad3 (position 1397-1405), Smad4 (position 1397-1405) (FIG. 17). The analysis of the SEQ ID NO: 2 revealed a similar pattern like binding sites for Brn-2 (positions 153-166; 2136-2152), Brn-3 (position 926-942), NeuroD1 (positions 178-190; 1154-1166; 2468-2480), E2F-1 (positions 196-210; 561-575; 1136-1150; 1616-1630; 1800-1814), E2F-2 (position 2578-2592) and Fast1 (positions 574-588; 646-660) (FIG. 17).

EXAMPLE XIII

The DCX Regulatory Sequence is Active Specific in Neuronal Determined Cells In Vitro Cells and Cell Culture If not otherwise cited, solutions for cell culture were obtained from PAN Biotech GmbH (Aidenbach, Germany), plastic culture vessels from TPP (Trasadingen, Switzerland). HEK293 cells (Clontech, Heidelberg, Germany) and COS7 cells (ATCC U.S.A., #CRL-1651) were maintained in Dulbecco's modified Eagles's medium adjusted to contain 10% fetal calf serum, 100 U/ml penicillin, 0.1 mg/ml streptomycin, 4 mM L-glutamine, 1.5 g/l sodium bicarbonate and 4.5 g/l glucose at 37° C. in a 5% $CO_2$. containing humidified atmosphere. CTX TNA2 (rat astrocyte line, ECACC #98102213) were maintained in DMEM adjusted to contain 10% fetal calf serum, 100 U/ml penicillin, 0.1 mg/ml streptomycin, 2 mM L-glutamine, 1.5 g/l sodium bicarbonate and 1 mM sodium pyruvate at 37° C. in a 5% $CO_2$ containing humidified atmosphere. N20.1, a mouse oligodendrocyte line, was kindly provided by Anthony T. Campagnoni, University of California, Los Angeles, USA. For proliferation, N20.1 cells were maintained in HAM's-F12/DMEM 1:1 supplemented with 2.4 g/l glucose, 0.18 g/l L-Glutamine, 100 U/ml penicillin, 0.1 mg/ml streptomycin and 22.5 mg/l Gentamicin at 33° C. in a 5% $CO_2$ containing humidified atmosphere. In order to differentiate this line into a oligodendroglial phenotype, cells were maintained in the same medium, but at 39° C. for 7 days. D283Med (ATCC U.S.A. #HTB-185) and Neuro2A (ATCC U.S.A. #CCL-131) were maintained in Minimal essential medium (Eagle) with Earle's BSS adjusted to contain 10% fetal calf serum, 100 U/ml penicillin, 0.1 mg/ml streptomycin, 2 mM L-glutamine, 1.5 g/l sodium bicarbonate, 1 mM sodium pyruvate and 0.1 mM non-essential amino acids at 37° C. in a 5% $CO_2$. containing humidified atmosphere. Cells were seeded on plastic culture plates at a density of $2.5 \times 10^4$ cells per $cm^2$ one day before proceeding to the transfection. Before seeding D283Med cells, culture dishes were coated with poly-ornithin (250 µg/ml) and laminin (15 µg/ml). 1 day after transfection, cells were reseeded on glass coverslips coated with poly-ornithin (250 µg/ml) and laminin (15 µg/ml) at a density of $7.5 \times 10^4$ cells per $cm^2$. Mouse embryonic forebrain (MEF) cultures were prepared as follows: pregnant C57BI/6NcrI mouse females (Charles River Laboratories, Sulzfeld, Germany) were sacrificed by cervical dislocation. The uteri were removed an immersed in ice-cold Dulbecco's phosphate buffered saline solution (DBPS). Embryonic day 10.5 to 12.5 embryos were released from the uteri, the forebrains were dissected and separated from surrounding tissues. The dissected forebrains were washed once in ice-cold DPBS, transferred to a petri dish and dissociated mechanically with a scalpel blade. The resulting preparation was washed in DPBS. Following 5 min centrifugation at 120×g, the pellet was resuspended in PPD-solution containing 0.01% Papain (Worthington Biochemicals, England), 0.1% dispase II (Roche, Germany), 0.01% DNase I (Worthington Biochemicals, England) and 12.4 mM $MgSO_4$ in HBSS (PAN, Germany) without $Mg^{++}/Ca^{++}$ (PAA, Germany) and incubated for 30 to 40 min at 37° C. The cell solution was triturated every 10 min through a pipette. Dissociated cells were collected by 5 min centrifugation at 120×g. The pellet was resuspended in serum-free neurobasal medium (Gibco BRL, Germany) and washed three times. Finally, the cell preparation was resuspended in Neurobasal medium supplemented with B27 (Gibco BRL, Germany), 2 mM L-glutamine, 100 U/ml penicillin, 0.1 mg/ml streptomycin, 5% fetal calf serum, seeded on coverslips coated with poly-ornithin (250 µg/ml) and laminin (15 µg/ml) at a density of $2.5 \times 10^5$ cells per $cm^2$ and maintained for four days at 37° C. in 5% $CO_2$. containing humidified atmosphere before transfection.

Transfections:

Transfections of cell lines were performed in 10 $cm^2$ culture dishes (6-well-plates) using 3 µg of plasmid (phuDCXpromoEGFP1 or phuDCXpromoDsRed2) per dish in the presence of 5 µl Metafectene (Biontex Laboratories, Munich, Germany) in a final volume of 2 ml according to the manufacturer's protocol. Medium was exchanged after 12 hours. One day after the end of transfection, cells were trypsinized and reseeded on Poly-Ornithin/Laminin coated glass coverslips for another 24 h before immunohistological analysis. MEF cells were transfected directly on the coated glass coverslips they had been seeded on to form a differentiated culture. Transfections of MEF cells were performed using 1.2 µg of plasmid per 4 $cm^2$ culture surface in the presence of 3 µl Metafectene in a final volume of 1 ml according to the manufacturer's protocol. Medium was exchanged after 12 hours, cells were incubated for another 4 days under cell culture conditions before immunohistological analysis. After the end of transfection, all cultures were examined for the expression of the EGFP or DsRed2 reporter gene using an Olympus IX70 inverted fluorescent microscope. To prepare cell extracts of transfected cell lines or transfected MEF primary cultures, cells were seeded and transfected on 10-$cm^2$ dishes and harvested directly from the culture vessel with a cell scraper.

Immunostainings

Following 30 min of fixation at room temperature with phosphate-buffered 4% paraformaldehyde, samples were blocked for a minimum of 1 hour in fish skin gelatin buffer (0.1M Tris-HCl pH 7.5, 0.15M NaCl, 1% bovine serum albumin, 0.2% Teleostean gelatin (Sigma-Aldrich, Taufkirchen, Germany), 0.1% Triton X-100) at room temperature. The specimens were incubated overnight at 4° C. with the primary antibodies at the following dilutions: goat anti-doublecortin C18 1:1000 (Santa Cruz Biotechnology, Santa Cruz, Calif., USA); rabbit anti-galactocerebroside 1:250 (AB142, Chemicon, Temecula, Calif., USA); rabbit anti-GFAP 1:1000 (Dako, Glostrup, Denmark); rabbit anti-Ki67 1:500 (Novocastra, Newcastle upon Tyne, UK); mouse anti-nestin 1:500 (BD Biosciences Pharmingen, San Diego, Calif., USA); mouse anti-βIII-tubulin 1:500 (clone 5G8, Promega, Madison, Wis., USA); rabbit anti-neurofilament 200 (Chemicon, Temecula, Calif., USA); mouse anti-map-2a/b (Sigma-Aldrich, Taufkirchen, Germany). The secondary fluorochrome-conjugated antibodies were diluted 1:500 (Rhodamine Red™-X-conjugated-, Cy™5-conjugated-, Fluorescein (FITC)-conjugated donkey anti-mouse, rabbit and goat anti IgG from dianova GmbH, Hamburg, Germany). All antibody dilutions and washes were performed with the fish skin gelatin buffer. Nuclear counterstaining was performed with 4',6'-diamidino-2-phenylindole dihydrochloride hydrate at 0.25 µg/µl (DAPI, Sigma-Aldrich, Taufkirchen, Germany) or TO-PRO-3 (Molecular Probes, Eugene, Oreg., USA). Following the last wash, the samples were briefly rinsed with PBS and mounted on slides using Fluoromount (Southern Biotechnology Associates, Birmingham, Ala., USA). In cases where antigens were sensitive to detergents, Triton X-100 was omitted from the fish skin gelatin buffer.

Western Blot Analysis

To prepare protein extracts of transfected cell lines or transfected MEF primary cultures, cells were seeded and transfected on 10-$cm^2$ dishes. Cells were harvested from the culture vessel in phosphate buffered saline using a cell scraper and collected by 5 min centrifugation at 200×g. Proteins were extracted by homogenizing the cell pellet in SUB-buffer (0.5% sodium-dodecyl-sulfate, 8M urea, 2% β-mercaptoethanol), passing the suspension at least 5 times through a 20 gauge needle fitted to a 2 ml-plastic-syringe and separating the lysate from debris by centrifugation at 10.000×g for 10 min. Concentration of total protein in the supernatant was assayed using Bradford's method. 5 µg of total protein per lane was run on a 12.5% SDS-PAGE gel at 2 mA/cm and blotted at 2.5 mA/$cm^2$ for 0.7 h on a nitrocellulose membrane (0.45 µm pore size, Protran BA 85; Schleicher+Schuell, Dassel, Germany). Blocking of the membrane, incubation with antibodies and washing steps were performed in fish-skin-gelatine western buffer (20 mM Tris-HCl pH 7.3, 0.9% NaCl, 1% fish skin gelatine, 0.1% Tween-20). To detect doublecortin, EGFP or actin immunologically, the membrane was blocked for 2 hours at room temperature, probed with anti-DCX (goat IgG, 1:1000 dilution, Santa Cruz, Santa Cruz, Calif., USA), anti-EGFP (goat IgG, 1:1000 dilution, Rockland, Gilbertsville, Pa., USA) or anti-actin (rabbit IgG, 1:5000 dilution, Sigma, Taufkirchen, Germany) antibody overnight at 4° C. Blots were rinsed and incubated with a horseradish peroxidase-conjugated donkey anti goat IgG (1:50.000 dilution, Sigma, Taufkirchen, Germany) or anti rabbit IgG secondary antibody (1:50.000 dilution, Dianova, Hamburg, Germany) for 2 hours at room temperature and rinsed before performing ECL detection of protein-antibody conjugates (ECL-Plus Western Blotting Detection System, Amersham-Pharmacia, Freiburg, Germany) according to the manufacturer's protocol.

Quantitative Analysis

Immunostainings of cultured cells were examined using confocal laser microscopy. In order to determine the ratio of cells expressing a certain marker or a reporter protein, five randomly picked visual fields were examined under a magnification of 200×. First, the total cell number in the field was determined according to a nuclear counterstain, then the number of cells positive for the marker or the transgene was determined. In order to detect colabeling of endogenous markers or colabeling of marker and reporter, cells expressing marker or reporter were picked randomly and examined for co-expression with the other marker. For this purpose, a magnification of 400× was used, a total number of 40 cells positive for the reporter or the marker was examined in each paradigm.

Specific activity of the human DCX regulatory sequence in cells of neuronal lineage. To test the activity of the SEQ ID NO.:1 as promoter, the expression vector phuDCXpromoEGFP1 (SEQ ID NO: 7) (FIG. 8A) was transiently transfected into different cell types. HEK293 and COS7 cells were used as examples for non-neural cells, glial lineage restricted cells were represented by the astrocytic cell line CTX TNA2 and by the oligodendroglial line N20.1, mixed neural population by the mouse neuroblastoma cell line Neuro-2a and by human medulloblastoma D283 Med cells, and for a most physiological relevant cell type, primary mouse embryonic forebrain cells of embryonic day 10.5 to 12.5 (MEF) were used. Expression was analyzed by Western-blot analysis and qualitative and quantitative fluorescence microscopy. Expression of EGFP driven by SEQ ID NO:1 was not or barely detected in the non-neural cells HEK293 and COS7 and not in the CTX TNA2 and the N20.1, weakly detectable in the neural cell lines D283 Med and Neuro-2a, and strongly detectable in MEF cells (FIG. 18). The few non-neuronal cells expressing EGFP under the human DCX regulatory sequence expressed EGFP only at low levels, compared to expression driven by the CMV enhancer in these cell lines or compared to expression driven by the human DCX regulatory sequence in the neuronal Neuro-2a and MEF cells (FIG. 18). The activity of the DCX promoter fragment correlated well with expression of endogenous DCX, as demonstrated by Western-blot analysis. Control transfections with pEGFP-N1 to drive EGFP expression via the ubiquitous CMV promoter demonstrated that all cell types were transfectable and expressed EGFP (FIG. 18). These transfected cells expressed EGFP at high levels (FIG. 18). However, transfection rates varied between the different cell types, so that HEK293, COS7 and Neuro-2a cells showed transfection efficiencies from 6% to 14%, whereas CTX TNA2, D283 and primary MEF had transfection efficiencies below 3% (FIG. 19). Calculating the relative promoter activity coefficient by (% cells expressing phuDCXpromoEGFP1 divided by % cells expressing pEGFP-N1)×100 indicates that in up to 30.6% of transfected MEF cells, the human DCX regulatory sequence is active (FIG. 19). Lower specific activity was found in Neuro-2a and D283 cells (approx. 7 to 12%), and no activity was found in the non-neuronal cell lines HEK293, CTX TNA2 and N20.1. COS7 cells activated the human DCX regulatory sequence rarely and weakly. As compared to the strong expression observed in neuronal cells, this level is considered non-significant. In summary, these experiments suggest that the human DCX regulatory sequence is predominantly active in proliferative cells of neuronal lineage.

The human DCX regulatory sequence is predominantly active in young neuronal determined cells.

The next sets of experiments were targeted towards the question, whether, in transient transfection experiments, the SEQ ID NO: 1 has a similar activity compared to the endogenous DCX promoter. For that, we made use of the MEF cells. This culture system is comprised of different cell types of the developing nervous system. The immunocytochemical analysis revealed a low percentage of nestin positive neural stem cells (1.17%) and KI67 positive proliferating cells (2.24%) (FIG. 20). The vast majority of cells expressed markers for young neurons, such as DCX (16.43%), Map2ab (16.08%) and βtubIII (24.31%), few cells expressed the mature neuronal marker NF200 (2.34%) (FIG. 20). GFAP was expressed in 12.87% of the cells, and the oligodendrocytic marker GalC was detected in only 0.32% of the cells. DCX colocalized with cells expressing Map2ab (92.5%), βtubIII (72.5%) and NF200 (5%), not with the neural stem cell marker nestin and not with cells expressing the mature neuronal marker NF200, the astrocytic marker GFAP or the oligodendrocytic marker GalC (FIG. 21).

In cells expressing EGFP after transient transfection with SEQ ID NO.: 7 a similar pattern was observed (FIG. 22, FIG. 23). None of the EGFP positive cells were immunoreactive for nestin nor for the glial marker GalC, a minor percentage of EGFP expressing cells stained for the glial marker GFAP (2.5%), 25% of EGFP expressing cells were positive for KI67, 67.5% for Map2ab, 25% for tubIII, 22.5% for NF200. Most importantly, the vast majority of EGFP expressing cells were immunoreactive for DCX (82.5%) (FIG. 23), indicating that the human DCX regulatory sequence activity correlates with the endogenous DCX gene expression. In addition to the marker expression that suggests a young neuronal phenotype for the EGFP expressing cells, the cells display a morphology characteristic for young neuronal or neuronal precursor cells, indicated by a small cell soma and a bipolar to oligopolar neurite pattern (FIG. 22).

Deletions in the DCX promoter define regions required for expression and for specificity.

The sequence analysis of the human DCX regulatory sequence defined several possible important regions (FIG. 10). To analyze the relevance of some of these regions, several deletion mutations were constructed and tested for their activity in MEF cells (FIG. 24). Accordingly, Region 2 comprises a critical part of the regulatory sequence (FIG. 25).

EXAMPLE XIV

DCX Expression as a Marker for Neuronal Trans-Differentiation

Retinal pigment epithelium (RPE) cells of higher mammals are fully differentiated epithelial cells that do not express neuronal markers in vivo (Zhao, Int. Rev. Cytol. 171 (1997), 225-266). Substantial evidence, however, exists for de- or trans-differentiation of RPE cells. In vivo, experimentally induced retinal detachment causes focal proliferation of RPE cells at the site of detachment in a number of mammalian species (Anderson, Invest. Opthalmol. Vis. Sci. 21 (1981), 10-16). In this paradigm, RPE cells round up, loose their apical processes and divide to form a three to four cells thick layer. In vitro, de- and trans-differentiation of mammalian RPE cells is well documented. Primary cultures of RPE cells loose differentiation markers such as pigmentation and the differentiation markers RPE10 and RPE65 (Neill. Invest. Opthalmol. Vis. Sci. 34 (1993), 453-462; Hamel, J. Neurosci. Res. 34 (1993), 414-425). Neuronal trans-differentiation was found in human RPE cultures by expression of the early neuronal marker beta III-tubulin and in a minor population of cultured human RPE cells that express the neuron-specific enolase and the neuronal marker neurofilament 200 (Vinores, Exp. Eye Res. 60 (1995), 385-400). In addition, the mRNA for the neuronal specific microtubule-associated protein MAP 1B is induced in human cultured RPE cells (Esser, Invest. Opthalmol. Vis. Sci. 38 (1997), 2852-2856). This example demonstrates DCX expression in trans-differentiating RPE cells.

Adult Long Evans rats were briefly sedated and sacrificed by decapitation. Eyes were removed and stored in ice cold DPBS (PAN, Germany). Eyes were dissected by first opening the eye shortly behind the border of the sclera and the rest of the eye. For preparation of ciliary body derived stem cells (CB), the frontal part of the eye was dissected clean of the surrounding tissues, including the vitreus, RPE cells, iris and neural retina and pieces of the ciliary body were digested in PPD solution (0.01% Papain (Worthington Biochemicals, USA), 0.1% Dispase II (Boehringer Mannheim, Germany), 0.01% Dnase I (Worthington Biochemicals, USA) and 149 mg $MgSO_4*7H_2O$ in Hank's Balanced Salt Solution w/o $Ca^{2+}/Mg^{2+}$ (PAN, Germany) for 100 ml). For preparation of RPE cells, the neural retina was taken out of the eye cup and then 2% Dispase II solution was applied to the cup. The cups were collected in 96 well plates and incubated at 37° C. for 30 min. After that the RPE cells were gently washed from the underlying choroid tissue and harvested in ice-cold PBS. After a 15 min incubation step in PPD solution, the cells were processed equally to the CB derived cells. Typically, the tissue of 10 eyes was digested and the PPD solution containing the cells were triturated every 10 min. Dissociated cells were collected by centrifugation (188 rcf) and resuspended in 5 ml cold DMEM/F12. Cells were washed three times with thorough trituration. Finally, cells were plated at $1 \times 10^5$ cells/2 ml in Neurobasal (NB) medium supplemented with B27, 0.1 g/L Penicilline/Streptavidine, 2 mM L-Glutamine, 20 ng/ml EGF, 20 ng/ml FGF-2 and 2 µg/ml Heparin plus 1% fetal calf serum (FCS, PAA, Germany). Cells were seeded in 6 well plates (each well at 35 mm) and cultures were maintained at 37° C. in an incubator with 95% air, 5% $CO_2$. Single cells began to form spheres within 2 to 3 days in culture and continued to grow in mass and number over the next weeks. Half of the medium was changed every 4 days. For passaging of cells, the culture medium containing the floating spheres was collected in a 15 ml centrifuge tube and centrifuged at 188 rcf for 5 min. The pellet was resuspended in 200 µl of Accutase™ and triturated 5 times. Additionally the cell suspension was placed at 37° C. for 10 min. After dissociation, the cells were again triturated, centrifuged at 188 rcf and resuspended in NB/B27 medium. To visualize proliferation in immunohistochemical studies, the thymidin-analogue Bromodeoxyuridin (BrdU) was used. Cells after passage #3 were supplemented with 10 µM BrdU in NB/B27 for 24 hrs prior to seeding on coated glass cover slips. During the time of differentiation (7 days), medium was changed every 3 days, but no new BrdU was added.

Dissociated cells from the adult ciliary margin (CB) or retinal, pigment epithelium (RPE) were placed in culture and analyzed for their proliferative potential. When first plated after dissociation, the cultures were composed of single, mostly pigmented cells that occasionally appeared in small clusters, probably due to a not complete dissociation during the preparative process. After an initial growth phase of approximately 3-4 days, the cells started to form aggregates, so called spheres. The very same process has been detected for adult-derived stem cells from other neurogenic regions of the central nervous system, e.g. the hippocampus (HC) or the subventricular zone (SVZ). The spheres grew in size over the next 4 weeks. Spheres grew by cell proliferation as indicated by BrdU incorporation and a quantitative analysis of the cell number showed that the cultures expanded over time. In addition, a clonal analysis revealed that both CB and RPE derived cells are able to clonally expand under limited dilution conditions and therefore indicate a similarity to known stem cell cultures from e.g. the HC or the SVZ. In cultures derived from the CB, the cell number initially increased by three-fold during the first two weeks. Then, cell proliferation ceased and the number of cells reached a plateau, suggesting that the generated cells did survive in culture. The increase in cell number was slightly delayed in RPE derived cells, but basically showed the same kinetics as the CB cells and eventually also reached a plateau with a cell count that could not be increased by longer cultivation. Both CB and RPE derived cells could be kept in culture for up to 12 weeks (or 6 passages) before a change in the morphology of the cells indicated an arrest of growth and proliferation. Dissociated and passaged cells readily reformed spheres with similar growth kinetics compared to primary spheres. Cells were tested for expression of the neural stem cells markers Nestin and Musashi, the proneural gene Pax6, the neuronal precursor marker DCX and early neuronal marker βIII Tubulin. CB and RPE derived cells were grown under proliferation conditions (NB/B27 medium with EGF/FGF/Heparin and 1% FCS). RT-PCR analysis was performed and showed that these cells express the neuronal precursor marker DCX (FIG. 26), indicating that indeed, adult and fully differentiated CB and RPE cells can transdifferentiate into a neuronal cell. Approximately 8% of cells were found to be immunoreactive for DCX by immunostaining (FIG. 27). In addition, βIII Tubulin was expressed in up to 15% of cells (FIG. 27). Suprisingly, βIII Tubulin was expressed in two types of cells: one with flat epithelial appearance, and one with a neuronal morphology including bi- or pluripolar structure, elongating processes. Doublelabeling for DCX illustrates that DCX identifies the βIII Tubulin subpopulation with neuronal morphology, indicating that DCX is indeed a marker for neuronal restriction and neuronal determination/differentiation in these cells and suggesting that DCX is a reliable indicator for neuronal differentiation and neuronal trans-differentiation.

EXAMPLE XV

Enrichment of Neuronal Trans-Differentiating Cells Expressing a Fluorescent Gene (EGFP) Under the Regulatory Sequence of the Human DCX Gene as Described Herein by FACS-Sorting RPE cells are prepared from eyes of huDCXpromoEGFP1 transgenic mice of embryonic, postnatal and adult stages, and cultured as described in Example XIV. Cells are dissociated by using Accutase (PAA) and loaded with lop/ml propidium iodide (PI) and passed through a 30 microm cell strainer (Becton-Dickinson). Cells are analyzed and sorted using a FACS Vantage flow cytometer/cell sorter (Becton-Dickinson) equipped with CELLQuest software. Cells ($2 \times 10E6$ cells/ml) are analyzed by light forward and right-angle (side) scatter, PI fluorescence, and EGFP fluorescence through a 510±20 nm bandpass filter, as they traverse the beam of an with an argon ion laser (488 nm 100 mW). Dead cells are excluded by gating on forward and side scatter, and by eliminating propidium iodide-positive events. Cells from wild type animals are used to set the background fluorescence. A false positive rate of 0.02±0.05% is accepted so as to ensure an adequate yield.

Viable cells are sorted into NB medium (Gibco BRL, Germany) supplemented with B27 (Gibco BRL, Germany) (NB/B27), 5% FCS (PAN, Germany), 2 mM L-glutamine (PAN, Germany), 100 U/ml penicillin/0.1 mg/ml streptomycin (PAN, Germany) at a speed of 3000 events/s. Sorted cells are plated on poly-ornithine (250 µg/ml) and laminin (5 µg/ml) coated glass coverslips in 12 well plates at different cell densities (10E5 to 10E7 cells/well and ml and grown for two to seven days. Cells are fixed with phosphate-buffered 4% prewarmed 37° C. paraformaldehyde pH 7.4 (4% w/v paraformaldehyde, 100 mM $NaH_2PO_4$, 0.4 mM $CaCl_2$, 50 mM sucrose) for 30 min and processed for immunohistochemistry. Following 30 min of fixation at room temperature with phosphate-buffered 4% paraformaldehyde, samples are blocked for a minimum of 1 hour in fish skin gelatin buffer (0.1M Tris-HCl pH 7.5, 0.15M NaCl, 1% bovine serum albumin, 0.2% Teleostean gelatin (Sigma, Germany), 0.1% Triton X-100) at room temperature. The specimens are incubated overnight at 4° C. with the primary antibodies at the following dilutions: goat anti-DCX C-18 (1:500, Santa Cruz Labs, Santa Cruz, USA); mouse anti-galactocerebroside 1:500 (Chemicon, USA); rabbit anti-GFAP 1:1000 (Dako, Danemark); rabbit anti-Ki67 1:500 (Novocastra, UK); rabbit anti-nestin 1:200 (Chemicon, USA); mouse anti-nestin 1:200 (Pharmingen International, USA); mouse anti-βIII-tubulin 1:500 (clone 5G8, Promega, USA); mouse anti-βIII-tubulin 1:500 (clone TUJ1, Babco, USA). The secondary fluorochrome-conjugated antibodies are diluted 1:500 (donkey anti-mouse or rabbit, Dianova, Germany). All antibody dilutions and washes are performed with the fish skin gelatin buffer. Nuclear counterstaining is performed with 4',6'-diamidino-2-phenylindole dihydrochloride hydrate at 0.25 µg/µl (DAPI, Sigma, Germany). Following the last wash, the samples are briefly rinsed with PBS and mounted on slides using Prolong (Molecular Probes, The Netherlands). In cases where antigens are sensitive to detergents (GalC), Triton X-100 is omitted from the fish skin gelatin buffer.

Dissociated cells are sorted into one of two fractions, a EGFP negative and a EGFP positive one. Sorted cells are cultured and analyzed by immunohistochemistry as described above. Two days after sorting, most cells of the EGFP positive fraction continued to express EGFP and immunostaining for DCX revealed that more than 90% of cells express DCX. In contrast, none of the cells from the EGFP negative fraction expresses DCX.

EXAMPLE XVI

In Vivo Imaging of Adult Neurogenesis Using a Transgenic Mouse Comprising SEQ ID NO: 26 (Human DCX Regulatory Sequence-Luciferase)

In vivo imaging of physiological events by EGFP and/or luciferase reporter genes is becoming more and more interesting, since it allows the analysis of physiological and/or pathophysiological dynamic changes in a longitudinal and real time manner (Gambhir, Neoplasia 2 (1-2) (2000), 118-38; Wu, Mol. Ther. 4(4) (2001), 297-306). In this example, changes in the level of adult neurogenesis are detected in vivo by luminometric measurements.

Transgenic mice are generated as in the Examples above, but instead of expressing EGFP or DSRed2, the luciferase gene is placed under control of the human DCX regulatory sequence as defined herein (see SEQ ID NO: 26 and SEQ ID NO: 27). Coelenterazine (Hayward, Calif., USA), a substrate for *renilla* luciferase, and D-luciferin firefly potassium salt (Xenogen, California, USA), the substrate for firefly luciferase, are used. The in vivo Imaging System (IVIS, Xenogen) consists of a cooled CCD camera mounted on a light-tight specimen chamber (dark box), a camera controller, a camera cooling system, and a Windows computer system. The transgenic mouse is placed in the specimen chamber mounted with the CCD camera cooled to −120° C., with a field of view set at 25 cm above the sample shelf. The photon emission is measured. The grey scale photographic images and bioluminescent color images are superimposed using the LIVINGIMAGE V. 2.11 software overlay (Xenogen) and IGOR image analysis software (V. 4.02 A, Wave Metrics, Lage Oswego, Origon). A region of interest (e.g. the head) is manually selected.

Mice are anesthetized by i.p injection of a ketamine/xylazine (4:1) solution. Mice are injected by tail-vein injection with 0.7 mg/kg body weight of coelenterazine or 150 mg/kg body weight D-luciferin and scanned with fifteen 1-min scans using the cooled CCD camera.

Bioluminescence is specifically detected in the two neurogenic regions, dentate gyrus of the hippocampus and the subventricular zone—rostramigratory stream—olfactory bulb axis. No other brain region is bioluminescent, and so is the rest of the body, when scans from other body regions are performed. In the next set of experiments, neurogenesis in the adult brain is up-regulated by the experimental conditions such as physical activity, administration of anti-depressants and of experimentally-induced seizures. Here the changes in bioluminescence correlate with the described changes in neurogenesis. There is a clear decline in the level of bioluminescence in the dentate gyrus of the hippocampus with animals of increasing age. The decrease in bioluminescence can also be observed within one and the same animal in a longitudinal study. Similarly, the up-regulation of neurogenesis in the hippocampus after seizure can easily be detected by the elevated level of bioluminescence.

EXAMPLE XVII

Use of huDCXpromoEGFP1 Transgenic Mice to Study Variation in Neurogenesis Levels The level of neurogenesis in the dentate gyrus has been reported to decrease during aging (Kuhn, J. Neurosci. 6 (1996), 2027-2033). Using huDCXpromoEGFP1 transgenic mice from Example IV, the quantification of EGFP fluorescence intensity in the neurogenic areas can serve as a reporter of the level of neurogenesis in these regions.

For the study of the age-related decrease in neurogenesis occurring in the dentate gyrus, mice of the huDCXpromoEGFP1 line 303 of 1, 2 and 12 months of age were deeply anesthetized and perfused with 4% paraformaldehyde in 100 mM phosphate buffer pH 7.4. The brains were dissected, immersed overnight in fixative and transferred to 30% sucrose/100 mM phosphate buffer pH 7.4 for 24 hours. Brains were cut into 40 µm sagittal sections using a sliding microtome. Sections were stored at −20° C. in cryoprotectant solution until use (25% v/v glycerol, 25% v/v ethylene glycol, 0.05M phosphate buffer pH 7.4).

For comparison of the fluorescence intensity between the transgenic mice of different ages, sections were put on microscope slides (SuperFrost Plus, Menzel-Glaser, Germany) and mounted using Fluoromount-G (Southern Biotechnology Associates, Inc., USA). The fluorescence signal was recorded using a Leica microscope (Leica Mikroskopie und Systeme GmbH, Wetzlar, Germany) equipped with a Spot™ digital camera and software (Diagnostic Instrument, Inc., Sterling Heights, USA). The fluorescence intensity was quantified by measuring the mean gray value of the pixels within the granular cells area of the dentate gyrus using the ImageJ software (Image J 1.29, National Institutes of Health, USA). The level of fluorescence observed in the cortex of the 1 month-old animal was used as the background fluorescence level and was subtracted from mean gray values calculated for dentate gyri. FIG. 30 (Panels A to C) documents the levels of fluorescence detected in the dentate gyrus of the young versus the old huDCXpromoEGFP1 line 303 transgenic mice. The picture acquisitions were performed using the same illumination, exposure time and image post-processing for all transgenic mice, allowing therefore for a direct comparison. FIG. 30 documents a significant decrease in the level of EGFP fluorescence detected in the dentate gyrus of the aged transgenic mice as compare to the levels observed in the young transgenic mice, hence confirming that the use of huDCXpromoEGFP1 transgenic mice provides an efficient mean to monitor the variation in the levels of neurogenesis between individuals. FIG. 30F presents the result of the quantification performed using ImageJ on the dentate gyrus of four mice, i.e. the three presented in FIGS. 30A-C and a fourth animal of 2 months of age. For every animal, 4 sections containing a segment of dentate gyrus were quantified in order to generate an average and a standard deviation. Quantification demonstrates that the reduction of neurogenesis observed during aging is accompanied by a reduction of the EGFP fluorescent signal as a function of aging, i.e. 1 month>2 months>12 months. Also, comparison of the two mice of 2 months of age demonstrate that the variation inter-individual in minimal.

Epileptic seizures have been reported to provoke an increase of neurogenesis level in the dentate gyrus (Parent, J. Neurosci. 17 (1997), 3727-3738). Using huDCXpromoEGFP1 transgenic mice, comparison of EGFP fluorescence intensities in the dentate gyrus of control animals and animals in which epileptic seizures were experimentally induced allows for the measurement of variation of neurogenesis.

To this end, huDCXpromoEGFP1 transgenic mice of 3 months of age received 1 mg of scopolamine per kilogram of body weight i.p. (Sigma, St. Louis, Mo., USA). Twenty minutes later, these animals were injected with 340 mg of pilocarpine per kilogram of body weight i.p. (Sigma, St. Louis, Mo., USA). Seizure activity was monitored behaviourally, and after 120 minutes, the seizures were terminated using 10 mg of diazepam per kilogram of body weight i.p. (Sigma, St. Louis, Mo., USA). Only mice that displayed continuous, convulsive seizure activity after pilocarpine treatment were used in this experiment. Control mice received saline injections in replacement to scopolamine and pilocarpine, but nevertheless received diazepam injections. All animals received food and water ad libitum. The animals were processed for histological analysis 7 days after the seizure induction. Animals were deeply anesthetized and perfused with 4% paraformaldehyde in 100 mM phosphate buffer pH. 7.4. The brains were dissected, immersed overnight in fixative and transferred to 30% sucrose/100 mM phosphate buffer pH 7.4 for 24 hours. Brains were cut into 40 μm sagittal sections using a sliding microtome. Sections were stored at −20° C. in cryoprotectant solution until use (25% v/v glycerol, 25% v/v ethylene glycol, 0.05M phosphate buffer pH 7.4).

For comparison of the fluorescence intensity between the transgenic mice, sections from animals of the same age were put on microscope slides (SuperFrost Plus, Menzel-Glaser, Germany) and mounted using Fluoromount-G (Southern Biotechnology Associates Inc., USA). The fluorescence signal was recorded using a Leica microscope (Leica Mikroskopie und Systeme GmbH, Wetzlar, Germany) equipped with a Spot™ digital camera and software (Diagnostic Instrument Inc, Sterling Heights, USA). The fluorescence intensity was quantified by measuring the mean gray value of the pixels within the granular cells area of the dentate gyrus using the ImageJ software (Image J. 1.29, National Institutes of Health, USA). The level of fluorescence observed in the cortex of the control animal was used as the background fluorescence level and was subtracted from mean gray values calculated for dentate gyri. FIGS. 30D-E documents an increase in the level of EGFP fluorescence detected in the dentate gyrus of the transgenic mice in which epileptic seizures have been experimentally-induced as compare to the level observed in the control transgenic mice, confirming that the use of huDCXpromoEGFP1 transgenic mice provides an efficient mean to monitored the variation in the levels of neurogenesis between individuals. FIG. 30F presents the result of the quantification performed using ImageJ on the dentate gyrus of the control mouse and the one in which seizures was experimentally induced. For every animal, 4 sections containing a segment of dentate gyrus were quantified in order to generate an average and a standard deviation. Quantification (FIG. 30F) demonstrates that the increase in neurogenesis occurring in the animal in which seizures have been experimentally induced is accompanied by an increase of the EGFP fluorescent signal. Therefore, quantification of the EGFP fluorescence signal in the huDCXpromoEGFP1 transgenic mice may easily be employed to quantify modulation in neurogenesis.

The invention claimed is:

1. A method for the detection of (a) proliferative neuronal determined cells comprising the steps of:
expressing in a plurality of cells a recombinant nucleic acid molecule comprising a heterologous nucleotide sequence to be expressed, said sequence under the control of a regulatory sequence selected from the group consisting of:
(a) regulatory sequences comprising the nucleotide sequence shown in SEQ ID NO: 1, as shown in SEQ ID NO: 2, as shown in SEQ ID NO: 3 or as shown in SEQ ID NO: 4;
(b) regulatory sequences comprising the nucleotide sequence contained in the insertion of clone DSM 15111 and obtainable by amplification using two oligonucleotides having the sequences indicated under SEQ ID NO: 9 and SEQ ID NO: 10;
(c) regulatory sequences comprising at least one nucleotide sequence of SEQ ID NO: 1 from position 1166 to 1746, from position 1166 to 2049, from position 1785 to 1843 or from position 1953 to 2775;
(d) regulatory sequences comprising at least one nucleotide sequence of SEQ ID NO: 2 from position 529 to 1079, from position 529 to 1390, from position 1118 to 1175 or from position 1291 to 2137; regulatory sequences comprising a nucleotide sequence which is at least 75% identical to a sequence as defined in (a) to (d) or which comprises a nucleotide sequence which is at least 78% identical to the nucleotide sequence as shown in SEQ ID NO: 1 from position 1166 to 1746 or from position 1166 to 2049 or to the nucleotide sequence shown in SEQ ID NO: 2 from position 529 to 1079 or from position 529 to 1390, which comprises a nucleotide sequence which is at least 82% identical to the nucleotide sequence as shown in SEQ ID NO: 1 from position 1785 to 1843 or to the nucleotide sequence as shown in SEQ ID NO: 2 from position 1118 to 1175 or which comprises a nucleotide sequence which is at least 75% identical to the nucleotide sequence as shown in SEQ ID NO: 1 from position 1953 to 2775 or to the nucleotide sequence as shown in SEQ ID NO: 2 from position 1291 to 2137; and
(f) regulatory sequences comprising a nucleotide sequence which hybridizes under stringent conditions with a complementary strand of the regulatory sequence as defined in (a) to (e) and which provides early, transient expression of a heterologous nucleotide sequence in proliferative neuronal determined cells; and
selecting cells which express a heterologous nucleotide sequence under the control of the regulatory sequence.

2. The method of claim 1, which comprises in step (b) the detection of an expressed, heterologous marker or reporter gene.

3. The method of claim 1, wherein said regulatory sequence is of human, mouse or rat origin.

4. The method of claim 2, wherein said heterologous nucleotide sequence to be expressed is a gene selected from the group consisting of a marker gene, a receptor gene, an anti-apoptotic gene, a determination/differentiation gene, a gene capable of inducing and/or directing neuronal migration or guidance, a gene encoding a tag, a gene encoding for a trophic factor, a gene encoding a surface protein, a gene encoding for a transcription factor ora gene encoding an enzyme, or wherein said nucleotide sequence to be expressed is an antisense sequence or encodes for a ribozyme or an inhibiting RNA molecule.

5. The method of claim 4, wherein said marker or receptor gene is selected from the group consisting of GFP, EGFP, RFP, CFP, BFP, YFP, DsRed, f3-galactosidase, luciferase or chloramphenicol acetyltransferase.

6. The method of claim 4, wherein said gene encoding a tag is selected from the group consisting of a His-Tag, glutathione, a Strep-tag, a Flag-tag, CBP, TAG-100, E2-tag and Z-tag.

7. The method of claim 4, wherein said gene encoding a surface protein is CD24.

8. The method of claim 4, wherein said gene encoding for a trophic factor is selected from the group consisting of NGF, BDNF, PDGF, NT-3, NT-4, NT-5, VEGF, PEDF, EGF, FGF, IGF, cardiotrophin, erythropoietin, leptin, LIF, and TGF.

9. The method of claim 4, wherein said anti-apoptotic gene is selected from the group consisting of bcl-2, Brn-3a, PTEN and (an) anti-caspase(s).

10. The method of claim 4, wherein said determination/differentiation gene is the dopaminergic determination factor Nurr1.

11. The method of claim 4, wherein said gene capable of inducing and/or directing neuronal migration or guidance is selected from the group consisting of netrin, neuropilin, CXCR4, SDF-1, DCC, slit, robo, a semaphorin, a plexin family member, and an ephrin family member.

12. The method of claim 4, wherein said gene encoding a transcription factor is selected from the group consisting of NeuroD, BMP4, Nun 1 or ShcC.

13. The method of claim 4, wherein said gene encoding an enzyme is CRE.

14. The method of claim 4, wherein said heterologous nucleotide sequence to be expressed is an antisense sequence, or encodes for a ribozyme or an inhibiting RNA-molecule.

15. The method of claim 14, wherein said inhibiting RNA is selected from the group consisting of RNAi, siRNA, shRNA and stRNA.

16. The method of claim 2, wherein said recombinant nucleic acid molecule is further defined as a recombinant vector comprising said a regulatory sequence and heterologous nucleotide sequences to be expressed positioned under the control of said regulatory sequence.

17. The method of claim 16, wherein said vector is further defined as a virus.

18. The method of claim 16, wherein said vector is further defined as vector is suitable for gene therapy or vaccination with a nucleic acid molecule.

19. The method of claim 1, wherein the regulatory sequence comprises the nucleotide sequence shown in SEQ ID NO: 1, as shown in SEQ ID NO: 2, as shown in SEQ ID NO: 3 or as shown in SEQ ID NO: 4.

20. The method of claim 1, wherein the regulatory sequence comprises the nucleotide sequence contained in the insertion of clone DSM 15111 and obtainable by amplification using two oligonucleotides having the sequences indicated under SEQ ID NO: 9 and SEQ ID NO: 10.

21. The method of claim 1, wherein the regulatory sequence comprises at least one nucleotide sequence of SEQ ID NO: 1 from position 1166 to 1746, from position 1166 to 2049, from position 1785 to 1843 or from position 1953 to 2775.

22. The method of claim 1, wherein the regulatory sequence comprises at least one nucleotide sequence of SEQ ID NO: 2 from position 529 to 1079, from position 529 to 1390, from position 1118 to 1175 or from position 1291 to 2137.

23. The method of claim 1, wherein the regulatory sequence comprises a nucleotide sequence which is at least 75% identical to the regulatory sequences set forth in SEQ ID NOs 1 through 4, or which comprises a nucleotide sequence which is at least 78% identical to the nucleotide sequence as shown in SEQ ID NO: 1 from position 1166 to 1746 or from position 1166 to 2049 or to the nucleotide sequence shown in SEQ ID NO: 2 from position 529 to 1079 or from position 529 to 1390, which comprises a nucleotide sequence which is at least 82% identical to the nucleotide sequence as shown in SEQ ID NO: 1 from position 1785 to 1843 or to the nucleotide sequence as shown in SEQ ID NO: 2 from position 1118 to 1175 or which comprises a nucleotide sequence which is at least 75% identical to the nucleotide sequence as shown in SEQ ID NO: 1 from position 1953 to 2775 or to the nucleotide sequence as shown in SEQ ID NO: 2 from position 1291 to 2137.

24. The method of claim 1, wherein the regulatory sequence comprises a nucleotide sequence which hybridizes with a complementary strand of the regulatory sequence as defined in claim 22 under stringent conditions and which provides early, transient expression of a heterologous nucleotide sequence in proliferative neuronal determined cells.

* * * * *

SEQUENCE LISTING

<160> NUMBER OF SEQ ID NOS: 28

<210> SEQ ID NO 1
<211> LENGTH: 3509
<212> TYPE: DNA
<213> ORGANISM: homo sapiens

<400> SEQUENCE: 1

```
aacacctatt aatgcccaca tatctcaaac aaggaaatat tgatcctgcc tatccctctg      60
ctctctatta tatataaagc aaacaaagtc atttatccta ggctgtctca taaaaacatt     120
ttgtagcttc cacagtagca ttgcaaagcc tatattatga ggaattttcc tctgaaatac     180
```

```
attccaaatg gttcgtgttt aagttttatt atcccatcca ttgttgtatc ttcaccagaa    240
ataaaatgat tttttagttct gatgcaaaat taattgctac atatttactg aatgcttatg    300
atgtgcaaga aagaagtttt aagacattag ctttgttgga atttccatat tttcctgccc    360
ttattccttg attttttcttt gcctctagcc tgaataatgt tgattttttca tgaggttgcc    420 acaaggtaag gcaacaacac atggaagaaa acagggcaga cacatgcatt cccctgaggt    480
acttgtatag taaccaagaa atcagcagca aggtgttggg gggacttaac taggtaggtt    540
gcacatttga ggctatccac tcaactaaca gacagttcca ggctttgctg agtcaacacc    600
tttcacagaa gaaagaccat catatatttt atcccacttg gtggcagctt acaataaaac    660
acatgcagag aaaatgctta aatataaaag ttcaacagca ctatataaaa ggaagggtta    720
attatactag gaatcagata taaaataatt actgagcatg ctcttagctc tgagcttcct    780
ggaagccaag caaaaataga accatgatag ttcaaggctg ctacatattg atgcatgtag    840
cttcaattgt gaagatggta gcatcccccct accccattta acctctcacc tttctctttt    900
gttttatagt tcggcctgat ctaattagtt caatttggat gcttccttga gttttttttg    960
taacatattt tatataaaga agtcagttag tgacaaataa gcagtttgag gagaaatctg   1020
ttaatattta ttttgtagcc atcagattta cttcacatag aaaggtcttt gggttgggtt   1080
tgaacttcca aactctcaaa ggtaaatgcc acattaacct ttcattaacc aaattcttac   1140
accaagctga tagatttggg atgtcctttt tacttctatc ttccataata ttctaaaatt   1200
attttccctt gttttgttcc tatcctactt cctcttagtc tactttgttg acttcattaa   1260
aaaacaaaaa accagttgtt ggatacttga gctaaactgc cttaaagaat ctgcagattt   1320 tatttttattt tttttctctc aagagggtaa aaggaagaga gctacaattt ctaagaagcc   1380
tggcttggct gtctgagtct ggcccccagg cagattaggc caaggttttg gccaagtgaa   1440
attgccaatt ttctaaaaga aagggctagc acattgctca ttagagcatt ctgattttgt   1500
ctgcgcaatc tttttgctac cccgcaattt cctgttggtt ataaatgaaa cctttctagc   1560
tgttaatgca gcctgtgaat tttttttaaaa gcatgtaatt aatcatagga ggttgggggg   1620
attcactaag cctgagttac atgggagaag ctggacaagg cactaggacc tagaaggcat   1680
ctatccaccc tggcaggaat ttcttgcttg gagctcagac aacaaaggca tagagagatt   1740
ggttttcttt ctctcagcat ctccacccaa ccagcagaaa accggtgagt ggggctttta   1800
agtgattttc aagaagaatg taacagatgt caaacgggaa aagcacaagg caaagcctgc   1860
tctctctgtc tctctgtctc ctcttctcct ttttgccttt attctatccg attttttccc   1920
taagcttcta cctgggattt tccttttggaa aagtgagttt gatgttcctt tgttttcact   1980
gtgatgttaa tttagaataa tactacctct gatcctaaag caaagcaaag ccttactggc   2040
atgcctgggg aaatgtttgc tgcttgcctt gaggaggtgg ggtctcttac cactgcaggt   2100
tgtctgacag agacaatgct gagctcagca taggtcatgg tgacattgga aaaaaggcgg   2160
aattgagcct ggcagaccca ttaggcacca gtctttctta tctcctgtcc tcctggtccc   2220
ttgcaaatat attgatgtgg cagtgtgtag cagctgagcc ctgcttgctt tgtgagtcct   2280
tttatcccca tctgtgagat gcatgttaat agtttggctc gtaggatgtc actacatttg   2340
ctagcatttg tggcttcagt tgtattgggt ttcatgtttt gattgtttgg ggttcttggt   2400
gggggagggg gttcaacaga agggagaaaa gcaaagcctg acaaatgacc atctttttctc   2460 agctaatgca cctgggcaat atacaagttt ggggtgaatt gcctgctgtg agggtaaatg   2520
```

-continued

```
tcacttcaat taaggtagaa acccagaaca atgaaaggtg tgcttccttc taaaggtccc    2580
gtatgctgtt cggagagtca tttgtgaatc tttcaacaat taaattattc cattaagagg    2640
tgttgctgca tcagtgggga gggggtggag cacctggggg ggaaaaaaaa ggattttgtg    2700
aacaaatgga accggggggaa gacagagcta gtaacttgtt aaataactta ttttttctaat   2760
ccttttttccc cccagcttat ttcttatgaa tgtcggatag ctgcaccagc ttggtgggga    2820
aagggtttga tgaatagcac aaagacactg gctgttccct ggaggctgtc cctttaaagg    2880
agaatcttag tttattctgg ggggagggga tgcacacatt agagtaggaa agagggcttg    2940
gaataaaatg aaaacactcc cccttcatag tcattgtact gaaatgcaaa gactgcttcc    3000
taagctggag atgctaacct tgggtagctc cttctgttct cttcaagggg aattttgtca    3060
ggctatggat tcatttacaa ctgttagtca tgtgggcatg tgtgaggaaa cagatgccag    3120
ttttaatgta tttagcccga agttccaatt tgataggagc cactgtcagt aagtctcagg    3180
attttcagct atttcaaaat ctccccttct cctctgtctg gaacagtgcc aagagtgcct    3240
ccctctctat ctcttactcc caacccccac aaccaccagc accccgcccc agcccctcct    3300
tcttctctat taagatcaat attcctgcag gtcagggcca agcagcagat gggtcacagg    3360
cttttttcaa ccagttcttt tcacaagcag cagattgcag atctggatct ggctaatatt    3420
taaaatccct tcttttttcc ttctccttgt cccttttgt ttttgcctct cttccccc      3480
atccctttct cccacgctca ggtctctga                                     3509
```

<210> SEQ ID NO 2
<211> LENGTH: 2881
<212> TYPE: DNA
<213> ORGANISM: mus musculus

<400> SEQUENCE: 2

```
tcccatatga agaaagaaa ataaatcctt ttgtctctct cagcctcgga tacttcactc      60
agtatatcat tttcggttcc acacaatttc ttgcaaatct cataatttca cattttactg   120
atgggtgatt aaaatcatgc atatatcttg cattttcatt acccattcat ctgttaacag    180
acatctgggc tgtttctatt ttctggcttt tgtgaataga gcagccataa acacagatat    240
gcaagtgtct ctatggtagg ttatagtctc ctttgggtat atgcccagga gtgggaaggt    300
gaaacattaa ccaatgtttt acatcagtct aaaatgtttt ggagtcatgc tgggcctaga    360
gacctaagtg ctggcaaatt ttagtagcca agaagcagaa cagaggctga aaattttcag    420
caaatgagag gtcagcctgg gctacacagc gagttccaga acaactatca ctataaagct    480
ggaccctgac tcgataaaac aactgaacaa aaacttggag aagtgccact tttcaattcc    540
agccttcatg attcctgcaa ctattttccc gtgtactgtc aatttactat tcctgctgac    600
ttcgtttaaa aaacaaccag tgttggatgc atgagccgaa atgttaaaaa atttacatat    660
ttttattttt ctttgaagaa gataaaaaga ggagatctgt aatttctaag aaacttgatt    720
tggcctgctg agtccagcca ctaggcagaa ggttttagcc aagtaaaatt gccaattttc    780
taagagaaag ggctagcaca ttgctcatta gagcattctg agcttgcctg tgcaatcttt    840
tttttcctac cctgcaattt cctgtgcgtt ataaacgaaa cctttctagc tgttaatgca    900
ggctgtgaat tgaagaaaaa aaagcatgta attaatcata ggaggttggg ggtgttcgct    960
aagcttcagt tacaggggag aagctggaca aggcactagg acctagaagg caactatcca   1020
ccctggcagg aatttcttgc ttggagctca gacaacaaag gcatagagag attggttttc   1080
tttctctcag catctccacc caaccagcag aaaaccggtg agtggggctt tcgagtgatt   1140
```

-continued

```
ttcaagcaga atgtaacaga tgtcaaccgg gaaagcacaa ggcacacggc tttctttctc    1200
tgtgtgttcg cctctttctt ctcttttatt tgccttattc tataggattt ttgtcctcta    1260
agattctacc tgggattttc ctttggaaaa gtgagtttgt tgttcctttg ttttcactat    1320
gatgctaatt tagaataata gcacttctga ttctaaagct agctttattt gcacagcctg    1380
cctggggaaa atgcttgcta ctcatcttga ggaggtgggc tcttactact gcaggttgtc    1440
tgacagagac aatgctgagc tcagcatagg tcatggtgac actggaaaaa aaggggggtac   1500 tgagcctggc aaatatacca actaccagtc ctcctttatc tcctttctcc ctggtttctt    1560
gcaaatctcg atgtggcagt atatatatag cagctgagcc ctcttgcttt gtgagtcttt    1620 ttcccccat ttgtgagatg aatgttaata gtttggtttc ttggatgtca cattacctttt   1680 gtaaggggtt agggctttgg ttgtattatt gggttgcatg ttttcattgt tttgacgtt     1740 tttttttctg gtgggggacg ggttcagggg ggttgaaatc caagcttgac agatgacttt    1800 tttttccct ccatcaatac acctaagcaa tagacaagtt tgaagtgaat tgcctgcttc     1860
gagggcaaaa tattccttca gtcaggggag aaacccagaa caatgaaagg tgtacctact    1920
tggaaaggtc ccatgtgcta ttcagggacc catttgggaa tctttccaca attattccat    1980
taagaggtgt tgctgcattc attggtcggg gaggggatga acacctgaa aggagaaaaa    2040 ggattctgtg atcaaatgga aatgaaaggg aagcagagct aatagcttgc taaataactg    2100
ggttttttcg acaatccctc cccttttag accccagctt atttcttatg gatgccgtat     2160
agcggcacca gcttgatggg gagagggttt gatgaatagc acaaaggcac tgggtattcc    2220
ctggaggctg tcccttttaaa agagaatcct agtttattct gggggagggg atacacatat   2280
tagagcaggc aaaaaaggac aaggaataaa agtaattcac cccctttccta gccattgtat  2340 tgagatgcaa aggctgcttc ctacaggagg gtgctaacct tggctagctc cctctgtttc    2400
tctttgaggg aatttagtca ggctatggat tcatttacaa ctgttagtca tgtggccatg    2460
tgtgaaggag cagatgccag ttttaatgta ttttgcccga agttacaatt tgataggagc    2520
cactgtcagg aagctccagg tttttaagct atttcaacac gccctcccca aattggaaca    2580
gtgccaaaag tgccacccctt tctatctctt cctcctatcc cctcccac cattcagtcc    2640 tcagcctact gcccagcccc ctccttcttc tctattaaga tcaatattcc tgcaggtcag    2700
ggacaagcag cagatgggtc acaggctttt ttcaaccagt tcttttcaca ggcagcagat    2760
tgcagctctg gatctggcta atattttaat tctccccccct cccttatcca tccttattct   2820
ttgcctctcc ttatctccac ccttttctct aacaatcagg ttgctgtggt tccaccaaaa    2880
t                                                                     2881
```

<210> SEQ ID NO 3
<211> LENGTH: 2344
<212> TYPE: DNA
<213> ORGANISM: homo sapiens

<400> SEQUENCE: 3

```
ctttttactt ctatcttcca taatattcta aaattatttt cccttgtttt gttcctatcc     60
tacttcctct tagtctactt tgttgacttc attaaaaaac aaaaaaccag ttgttggata    120
cttgagctaa actgccttaa agaatctgca gatttttattt tatttttttt ctctcaagag   180
ggtaaaagga agagagctac aatttctaag aagcctggct tggctgtctg agtctggccc   240
ccaggcagat taggccaagg ttttggccaa gtgaaattgc caattttcta aaagaaaggg   300
```

```
ctagcacatt gctcattaga gcattctgat tttgtctgcg caatcttttt gctaccccgc    360
aatttcctgt tggttataaa tgaaacctt ctagctgtta atgcagcctg tgaattttt     420
taaaagcatg taattaatca taggaggttg gggggattca ctaagcctga gttacatggg    480
agaagctgga caaggcacta ggacctagaa ggcatctatc caccctggca ggaatttctt    540
gcttggagct cagacaacaa aggcatagag agattggttt ctttctctc agcatctcca    600
cccaaccagc agaaaaccgg tgagtggggc ttttaagtga ttttcaagaa gaatgtaaca    660
gatgtcaaac gggaaaagca caaggcaaag cctgctctct ctgtctctct gtctcctctt    720
ctcctttttt gccttattct atccgatttt ttccctaagc ttctacctgg gattttcctt    780
tggaaaagtg agtttgatgt tccttttgttt tcactgtgat gttaatttag aataatacta    840
cctctgatcc taaagcaaag caaagcctta ctggcatgcc tggggaaatg tttgctgctt    900
gccttgagga ggtgggtct cttaccactg caggttgtct gacagagaca atgctgagct     960
cagcataggt catggtgaca ttggaaaaaa ggcggaattg agcctggcag acccattagg   1020
caccagtctt tcttatctcc tgtcctcctg gtcccttgca aatatattga tgtggcagtg   1080
tgtagcagct gagccctgct tgctttgtga gtcctttat ccccatctgt gagatgcatg   1140
ttaatagttt ggctcgtagg atgtcactac atttgctagc atttgtggct tcagttgtat   1200
tgggtttcat gttttgattg tttggggttc ttggtgggg aggggggttca acagaaggga   1260
gaaaagcaaa gcctgacaaa tgaccatctt ttctcagcta atgcacctgg gcaatataca   1320
agtttggggt gaattgcctg ctgtgagggt aaatgtcact tcaattaagg tagaaaccca   1380
gaacaatgaa aggtgtgctt ccttctaaag gtcccgtatg ctgttcggag agtcatttgt   1440
gaatctttca acaattaaat tattccatta agaggtgttg ctgcatcagt ggggaggggg   1500
tggagcacct ggggggaaa aaaaaggatt ttgtgaacaa atggaaccgg gggaagacag   1560
agctagtaac ttgttaaata acttattttt ctaatccttt ttcccccccag cttatttctt   1620
atgaatgtcg gatagctgca ccagcttggt ggggaaaggg tttgatgaat agcacaaaga   1680
cactggctgt tccctggagg ctgtcccttt aaaggagaat cttagtttat tctgggggga   1740
ggggatgcac acattagagt aggaaagagg gcttggaata aaatgaaaac actccccctt   1800
catagtcatt gtactgaaat gcaaagactg cttcctaagc tggagatgct aaccttgggt   1860
agctccttct gttctcttca agggaattt tgtcaggcta tggattcatt tacaactgtt   1920
agtcatgtgg gcatgtgtga ggaaacagat gccagtttta atgtatttag cccgaagttc   1980
caatttgata ggagccactg tcagtaagtc tcaggatttt cagctatttc aaaatctccc   2040
cttctcctct gtctggaaca gtgccaagag tgcctccctc tctatctctt actcccaacc   2100
cccacaacca ccagcacccc cgcccagccc ctccttcttc tctattaaga tcaatattcc   2160
tgcaggtcag gggcaagcag cagatgggtc acaggctttt ttcaaccagt tcttttcaca   2220
agcagcagat tgcagatctg gatctggcta atatttaaaa tcccttcttt tttccttctc   2280
cttgtccctt tttgttttg cctctcttca cccccatccc tttctcccac gctcaggtct   2340
ctga                                                                2344
```

<210> SEQ ID NO 4
<211> LENGTH: 2353
<212> TYPE: DNA
<213> ORGANISM: mus musculus

<400> SEQUENCE: 4

```
cttttcaatt ccagccttca tgattcctgc aactattttc ccgtgtactg tcaatttact     60
```

```
attcctgctg acttcgttta aaaaacaacc agtgttggat gcatgagccg aaatgttaaa    120
aaatttacat attttttatt ttctttgaag aagataaaaa gaggagatct gtaatttcta    180
agaaacttga tttggcctgc tgagtccagc cactaggcag aaggttttag ccaagtaaaa    240
ttgccaattt tctaagagaa agggctagca cattgctcat tagagcattc tgagcttgcc    300
tgtgcaatct ttttttttcct accctgcaat ttcctgtgcg ttataaacga aacctttcta    360
gctgttaatg caggctgtga attgaagaaa aaaaagcatg taattaatca taggaggttg    420
ggggtgttcg ctaagcttca gttacagggg agaagctgga caaggcacta ggacctagaa    480
ggcaactatc caccctggca ggaatttctt gcttggagct cagacaacaa aggcatagag    540
agattggttt tctttctctc agcatctcca cccaaccagc agaaaaccgg tgagtggggc    600
tttcgagtga ttttcaagca gaatgtaaca gatgtcaacc gggaaagcac aaggcacacg    660
gctttctttc tctgtgtgtt cgcctctttc ttctctttta tttgccttat tctataggat    720
ttttgtcctc taagattcta cctgggattt tcctttggaa aagtgagttt gttgttcctt    780
tgttttcact atgatgctaa tttagaataa tagcacttct gattctaaag ctagctttat    840
ttgcacagcc tgcctgggga aaatgcttgc tactcatctt gaggaggtgg gctcttacta    900
ctgcaggttg tctgacagag acaatgctga gctcagcata ggtcatggtg acactggaaa    960 aaaaggggggt actgagcctg gcaaatatac caactaccag tcctccttta tctcctttct   1020
ccctggtttc ttgcaaatct cgatgtggca gtatatatat agcagctgag ccctcttgct   1080
ttgtgagtct ttttcccccc atttgtgaga tgaatgttaa tagtttggtt tcttggatgt   1140
cacattacct ttgtaagggg ttagggcttt ggttgtatta ttgggttgca tgttttcatt   1200
gttttggacg ttttttttttc tggtgggggga cgggttcagg ggggttgaaa tccaagcttg   1260
acagatgact tttttttttcc ctccatcaat acacctaagc aatagacaag tttgaagtga   1320
attgcctgct tcgagggcaa aatattcctt cagtcagggg agaaacccag aacaatgaaa    1380
ggtgtaccta cttggaaagg tcccatgtgc tattcaggga cccatttggg aatctttcca    1440
caattattcc attaagaggt gttgctgcat tcattggtcg gggaggggat gaaacacctg    1500
aaaggagaaa aaggattctg tgatcaaatg gaaatgaaag ggaagcagag ctaatagctt    1560
gctaaataac tgggttttttt cgacaatccc tcccccttt agaccccagc ttatttctta    1620
tggatgccgt atagcggcac cagcttgatg gggagagggt ttgatgaata gcacaaaggc    1680
actgggtatt ccctggaggc tgtcccttta aaagagaatc ctagtttatt ctgggggagg    1740
ggatacacat attagagcag gcaaaaaagg acaaggaata aaagtaattc accccccttcc    1800 tagccattgt attgagatgc aaaggctgct tcctacagga gggtgctaac cttggctagc    1860
tccctctgtt tctctttgag ggaatttagt caggctatgg attcatttac aactgttagt    1920
catgtggcca tgtgtgaagg agcagatgcc agttttaatg tattttgccc gaagttacaa    1980
tttgatagga gccactgtca ggaagctcca ggttttttaag ctatttcaac acgccctccc    2040
caaattggaa cagtgccaaa agtgccaccc tttctatctc ttcctcctat cccctcccc    2100 accattcagt cctcagccta ctgcccagcc ccctccttct tctctattaa gatcaatatt    2160
cctgcaggtc agggacaagc agcagatggg tcacaggctt ttttcaacca gttcttttca    2220
caggcagcag attgcagctc tggatctggc taatatttta attctccccc ctcccttatc    2280 catcctttatt ctttgcctct ccttatctcc acccttttct ctaacaatca ggttgctgtg   2340
gttccaccaa aat                                                       2353
```

<210> SEQ ID NO 5
<211> LENGTH: 4532
<212> TYPE: DNA
<213> ORGANISM: artificial sequence
<220> FEATURE:
<223> OTHER INFORMATION: fusion construct homo sapiens and EGFP

<400> SEQUENCE: 5

| | | | | | |
|---|---|---|---|---|---|
| tcgagctcaa | gcttcgaatt | ctgcagtcga | cggtaccgcg | ggaacaccta | ttaatgccca | 60 |
| catatctcaa | acaaggaaat | attgatcctg | cctatccctc | tgctctctat | tatatataaa | 120 |
| gcaaacaaag | tcatttatcc | taggctgtct | cataaaaaca | ttttgtagct | tccacagtag | 180 |
| cattgcaaag | cctatattat | gaggaatttt | cctctgaaat | acattccaaa | tggttcgtgt | 240 |
| ttaagtttta | ttatcccatc | cattgttgta | tcttcaccag | aaataaaatg | attttttagtt | 300 |
| ctgatgcaaa | attaattgct | acatatttac | tgaatgctta | tgatgtgcaa | gaaagaagtt | 360 |
| ttaagacatt | agctttgttg | gaatttccat | attttcctgc | ccttattcct | tgattttttct | 420 |
| ttgcctctag | cctgaataat | gttgattttt | catgaggttg | ccacaaggta | aggcaacaac | 480 |
| acatggaaga | aaacagggca | gacacatgca | ttcccctgag | gtacttgtat | agtaaccaag | 540 |
| aaatcagcag | caaggtgttg | gggggactta | actaggtagg | ttgcacattt | gaggctatcc | 600 |
| actcaactaa | cagacagttc | caggctttgc | tgagtcaaca | cctttcacag | aagaagacc | 660 |
| atcatatatt | ttatcccact | tggtggcagc | ttacaataaa | acacatgcag | agaaaatgct | 720 |
| taaatataaa | agttcaacag | cactatataa | aaggaagggt | taattatact | aggaatcaga | 780 |
| tataaaataa | ttactgagca | tgctcttagc | tctgagcttc | ctggaagcca | agcaaaaata | 840 |
| gaaccatgat | agttcaaggc | tgctacatat | tgatgcatgt | agcttcaatt | gtgaagatgg | 900 |
| tagcatcccc | ctaccccatt | taacctctca | ccttctctt | ttgttttata | gttcggcctg | 960 |
| atctaattag | ttcaatttgg | atgcttcctt | gagttttttt | tgtaacatat | tttatataaa | 1020 |
| gaagtcagtt | agtgacaaat | aagcagtttg | aggagaaatc | tgttaatatt | tattttgtag | 1080 |
| ccatcagatt | tacttcacat | agaaaggtct | ttgggttggg | tttgaacttc | caaactctca | 1140 |
| aaggtaaatg | ccacattaac | ctttcattaa | ccaaattctt | acaccaagct | gatagatttg | 1200 |
| ggatgtcctt | tttacttcta | tcttccataa | tattctaaaa | ttattttccc | ttgttttgtt | 1260 |
| cctatcctac | ttcctcttag | tctactttgt | tgacttcatt | aaaaaacaaa | aaaccagttg | 1320 |
| ttggatactt | gagctaaact | gccttaaaga | atctgcagat | tttattttat | ttttttttctc | 1380 |
| tcaagagggt | aaaaggaaga | gagctacaat | ttctaagaag | cctggcttgg | ctgtctgagt | 1440 |
| ctggccccca | ggcagattag | gccaaggttt | tggccaagtg | aaattgccaa | ttttctaaaa | 1500 |
| gaaagggcta | gcacattgct | cattagagca | ttctgatttt | gtctgcgcaa | tcttttttgct | 1560 |
| accccgcaat | ttcctgttgg | ttataaatga | aacctttcta | gctgttaatg | cagcctgtga | 1620 |
| atttttttaa | aagcatgtaa | ttaatcatag | gaggttgggg | ggattcacta | agcctgagtt | 1680 |
| acatgggaga | agctggacaa | ggcactagga | cctagaaggc | atctatccac | cctggcagga | 1740 |
| atttcttgct | tggagctcag | acaacaaagg | catagagaga | ttggttttct | ttctctcagc | 1800 |
| atctccaccc | aaccagcaga | aaaccggtga | gtggggcttt | taagtgattt | tcaagaagaa | 1860 |
| tgtaacagat | gtcaaacggg | aaaagcacaa | ggcaaagcct | gctctctctg | tctctctgtc | 1920 |
| tcctcttctc | ctttttttgcc | ttattctatc | cgatttttct | cctaagcttc | tacctgggat | 1980 |
| tttcctttgg | aaaagtgagt | ttgatgttcc | tttgttttca | ctgtgatgtt | aatttagaat | 2040 |
| aatactacct | ctgatcctaa | agcaaagcaa | agccttactg | gcatgcctgg | ggaaatgttt | 2100 |

```
gctgcttgcc ttgaggaggt ggggtctctt accactgcag gttgtctgac agagacaatg    2160
ctgagctcag cataggtcat ggtgacattg gaaaaaaggc ggaattgagc ctggcagacc    2220
cattaggcac cagtctttct tatctcctgt cctcctggtc ccttgcaaat atattgatgt    2280
ggcagtgtgt agcagctgag ccctgcttgc tttgtgagtc cttttatccc catctgtgag    2340
atgcatgtta atagtttggc tcgtaggatg tcactacatt tgctagcatt tgtggcttca    2400
gttgtattgg gtttcatgtt ttgattgttt ggggttcttg gtgggggagg gggttcaaca    2460
gaagggagaa aagcaaagcc tgacaaatga ccatctttc tcagctaatg cacctgggca     2520
atatacaagt ttggggtgaa ttgcctgctg tgagggtaaa tgtcacttca attaaggtag    2580
aaacccagaa caatgaaagg tgtgcttcct tctaaaggtc ccgtatgctg ttcggagagt    2640
catttgtgaa tctttcaaca attaaattat tccattaaga ggtgttgctg catcagtggg    2700 gaggggtgg agcacctggg gggaaaaaa aaggattttg tgaacaaatg gaaccggggg      2760
aagacagagc tagtaacttg ttaaataact tatttttcta atcctttttc cccccagctt    2820
atttcttatg aatgtcggat agctgcacca gcttggtggg gaaagggttt gatgaatagc    2880
acaaagacac tggctgttcc ctggaggctg tcccttttaaa ggagaatctt agtttattct   2940 gggggaggg gatgcacaca ttagagtagg aaagagggct tggaataaaa tgaaaacact     3000 ccccttcat agtcattgta ctgaaatgca aagactgctt cctaagctgg agatgctaac     3060
cttgggtagc tccttctgtt ctcttcaagg ggaattttgt caggctatgg attcatttac    3120
aactgttagt catgtgggca tgtgtgagga aacagatgcc agttttaatg tatttagccc    3180
gaagttccaa tttgatagga gccactgtca gtaagtctca ggattttcag ctatttcaaa    3240
atctcccctt ctcctctgtc tggaacagtg ccaagagtgc ctccctctct atctcttact    3300
cccaaccccc acaaccacca gcaccccgc ccagcccctc cttcttctct attaagatca     3360
atattcctgc aggtcagggg caagcagcag atgggtcaca ggctttttc aaccagttct     3420 tttcacaagc agcagattgc agatctggat ctggctaata tttaaaatcc cttcttttt     3480 ccttctcctt gtccctttt gtttttgcct ctcttcaccc ccatccctt ctcccacgct      3540 caggtctctg agggatccac cggtcgccac catggtgagc aagggcgagg agctgttcac    3600
cggggtggtg cccatcctgg tcgagctgga cggcgacgta aacggccaca agttcagcgt    3660
gtccggcgag ggcgagggcg atgccaccta cggcaagctg accctgaagt tcatctgcac    3720
caccggcaag ctgcccgtgc cctggcccac cctcgtgacc accctgacct acggcgtgca    3780
gtgcttcagc cgctacccg accacatgaa gcagcacgac ttcttcaagt ccgccatgcc    3840
cgaaggctac gtccaggagc gcaccatctt cttcaaggac gacggcaact acaagacccg    3900
cgccgaggtg aagttcgagg gcgacaccct ggtgaaccgc atcgagctga agggcatcga    3960
cttcaaggag gacggcaaca tcctggggca caagctggag tacaactaca acagccacaa    4020
cgtctatatc atggccgaca agcagaagaa cggcatcaag gtgaacttca gatccgccaa    4080
caacatcgag gacggcagcg tgcagctcgc cgaccactac cagcagaaca ccccatcgg    4140 cgacggcccc gtgctgctgc ccgacaacca ctacctgagc acccagtccg ccctgagcaa    4200
agaccccaac gagaagcgcg atcacatggt cctgctggag ttcgtgaccg ccgccgggat    4260
cactctcggc atggacgagc tgtacaagta aagcggccgc gactctagat cataatcagc    4320
cataccacat ttgtagaggt tttacttgct ttaaaaaacc tcccacacct cccctgaac     4380 ctgaaacata aaatgaatgc aattgttgtt gttaacttgt ttattgcagc ttataatggt    4440
```

```
tacaaataaa gcaatagcat cacaaatttc acaaataaag cattttttc actgcattct    4500 agttgtggtt tgtccaaact catcaatgta tc                                4532

<210> SEQ ID NO 6
<211> LENGTH: 4488
<212> TYPE: DNA
<213> ORGANISM: artificial sequence
<220> FEATURE:
<223> OTHER INFORMATION: fusion construct homo sapiens and DsRed2

<400> SEQUENCE: 6
tcgagctcaa gcttcgaatt ctgcagtcga cggtaccgcg ggaacaccta ttaatgccca      60
catatctcaa acaaggaaat attgatcctg cctatccctc tgctctctat tatatataaa    120
gcaaacaaag tcatttatcc taggctgtct cataaaaaca ttttgtagct tccacagtag    180
cattgcaaag cctatattat gaggaatttt cctctgaaat acattccaaa tggttcgtgt    240
ttaagtttta ttatcccatc cattgttgta tcttcaccag aaataaaatg attttagtt     300 ctgatgcaaa attaattgct acatatttac tgaatgctta tgatgtgcaa gaaagaagtt    360
ttaagacatt agctttgttg gaatttccat attttcctgc ccttattcct tgattttct    420 ttgcctctag cctgaataat gttgattttt catgaggttg ccacaaggta aggcaacaac    480
acatggaaga aaacagggca gacacatgca ttcccctgag gtacttgtat agtaaccaag    540
aaatcagcag caaggtgttg gggggactta actaggtagg ttgcacattt gaggctatcc    600
actcaactaa cagacagttc caggctttgc tgagtcaaca cctttcacag aagaaagacc    660
atcatatatt ttatcccact tggtggcagc ttacaataaa acacatgcag agaaaatgct    720
taaatataaa agttcaacag cactatataa aaggaagggt taattatact aggaatcaga    780
tataaaataa ttactgagca tgctcttagc tctgagcttc ctggaagcca agcaaaaata    840
gaaccatgat agttcaaggc tgctacatat tgatgcatgt agcttcaatt gtgaagatgg    900
tagcatcccc ctaccccatt taacctctca ccttctctt tgttttata gttcggcctg      960 atctaattag ttcaatttgg atgcttcctt gagtttttt tgtaacatat tttatataaa    1020
gaagtcagtt agtgacaaat aagcagttg aggagaaatc tgttaatat tattttgtag     1080 ccatcagatt tacttcacat agaaaggtct ttgggttggg tttgaacttc caaactctca    1140
aaggtaaatg ccacattaac ctttcattaa ccaaattctt acaccaagct gatagatttg    1200
ggatgtcctt tttacttcta tcttccataa tattctaaaa ttattttccc ttgttttgtt    1260
cctatcctac ttcctcttag tctactttgt tgacttcatt aaaaaacaaa aaaccagttg    1320
ttggatactt gagctaaact gccttaaaga atctgcagat tttattttat ttttttctc    1380 tcaagagggt aaaaggaaga gagctacaat ttctaagaag cctggcttgg ctgtctgagt    1440
ctggccccca ggcagattag gccaaggttt tggccaagtg aaattgccaa ttttctaaaa    1500
gaaagggcta gcacattgct cattagagca ttctgatttt gtctgcgcaa tcttttttgct   1560 accccgcaat ttcctgttgg ttataaatga aacctttcta gctgttaatg cagcctgtga    1620
atttttttaa aagcatgtaa ttaatcatag gaggttgggg ggattcacta agcctgagtt    1680
acatgggaga agctggacaa ggcactagga cctagaaggc atctatccac cctggcagga    1740
atttcttgct tggagctcag acaacaaagg catagagaga ttggttttct ttctctcagc    1800
atctccaccc aaccagcaga aaaccggtga gtggggcttt taagtgattt tcaagaagaa    1860
tgtaacagat gtcaaacggg aaaagcacaa ggcaaagcct gctctctctg tctctctgtc    1920
tcctcttctc ctttttttgcc ttattctatc cgattttttc cctaagcttc tacctgggat   1980
```

```
tttcctttgg aaaagtgagt ttgatgttcc tttgttttca ctgtgatgtt aatttagaat   2040
aatactacct ctgatcctaa agcaaagcaa agccttactg gcatgcctgg ggaaatgttt   2100
gctgcttgcc ttgaggaggt ggggtctctt accactgcag gttgtctgac agagacaatg   2160
ctgagctcag cataggtcat ggtgacattg gaaaaaaggc ggaattgagc ctggcagacc   2220
cattaggcac cagtctttct tatctcctgt cctcctggtc ccttgcaaat atattgatgt   2280
ggcagtgtgt agcagctgag ccctgcttgc tttgtgagtc cttttatccc catctgtgag   2340
atgcatgtta atagtttggc tcgtaggatg tcactacatt tgctagcatt tgtggcttca   2400
gttgtattgg gtttcatgtt ttgattgttt ggggttcttg gtggggagg gggttcaaca    2460
gaagggagaa aagcaaagcc tgacaaatga ccatctttc tcagctaatg cacctgggca    2520
atatacaagt ttggggtgaa ttgcctgctg tgagggtaaa tgtcacttca attaaggtag   2580
aaacccagaa caatgaaagg tgtgcttcct tctaaaggtc ccgtatgctg ttcggagagt   2640
catttgtgaa tctttcaaca attaaattat tccattaaga ggtgttgctg catcagtggg   2700
gagggggtgg agcacctggg ggggaaaaaa aaggattttg tgaacaaatg gaaccggggg   2760
aagacagagc tagtaacttg ttaaataact tattttctca atcctttttc cccccagctt   2820
atttcttatg aatgtcggat agctgcacca gcttggtggg gaaagggttt tgatgaatagc  2880
acaaagacac tggctgttcc ctggaggctg tcccttaaa ggagaatctt agtttattct    2940
gggggagggg gatgcacaca ttagagtagg aaagagggct tggaataaaa tgaaaacact   3000
cccccttcat agtcattgta ctgaaatgca aagactgctt cctaagctgg agatgctaac   3060
cttgggtagc tccttctgtt ctcttcaagg ggaattttgt caggctatgg attcatttac   3120
aactgttagt catgtgggca tgtgtgagga acagatgcc agttttaatg tatttagccc    3180
gaagttccaa tttgatagga gccactgtca gtaagtctca ggattttcag ctatttcaaa   3240
atctcccctt ctcctctgtc tggaacagtg ccaagagtgc ctccctctct atctcttact   3300
cccaaccccc acaaccacca gcaccccgc ccagccctc cttcttctct attaagatca     3360
atattcctgc aggtcagggg caagcagcag atgggtcaca ggcttttttc aaccagttct   3420
tttcacaagc agcagattgc agatctggat ctggctaata tttaaaatcc cttcttttt    3480
ccttctcctt gtccctttt gttttgcct ctcttcaccc ccatccctt ctcccacgct      3540
caggtctctg agggatccac cggtcgccac catggcctcc tccgagaacg tcatcaccga   3600
gttcatgcgc ttcaaggtgc gcatggaggg caccgtgaac ggccacgagt tcgagatcga   3660
gggcgagggc gagggccgcc cctacgaggg ccacaacacc gtgaagctga aggtgaccaa   3720
gggcggcccc ctgcccttcg cctgggacat cctgtccccc cagttccagt acggctccaa   3780
ggtgtacgtg aagcaccccg ccgacatccc cgactacaag aagctgtcct tcccgaggg    3840
cttcaagtgg gagcgcgtga tgaacttcga ggacggcggc gtggcgaccg tgacccagga   3900
ctcctccctg caggacggct gcttcatcta caaggtgaag ttcatcggcg tgaacttccc   3960
ctccgacggc cccgtgatgc agaagaagac catgggctgg gaggcctcca ccgagcgcct   4020
gtacccccgc gacggcgtgc tgaagggcga gacccacaag gccctgaagc tgaaggacgg   4080
cggccactac ctggtggagt tcaagtccat ctacatggcc aagaagcccg tgcagctgcc   4140
cggctactac tacgtggacg ccaagctgga catcacctcc cacaacgagg actacaccat   4200
cgtggagcag tacgagcgca ccgagggccg ccaccacctg ttcctgtagc ggccgcgact   4260
ctagatcata atcagccata ccacatttgt agaggtttta cttgctttaa aaaacctccc   4320
```

```
acacctcccc ctgaacctga acataaaat gaatgcaatt gttgttgtta acttgtttat    4380
tgcagcttat aatggttaca aataaagcaa tagcatcaca aatttcacaa ataaagcatt    4440
tttttcactg cattctagtt gtggtttgtc caaactcatc aatgtatc                4488

<210> SEQ ID NO 7
<211> LENGTH: 7660
<212> TYPE: DNA
<213> ORGANISM: artificial sequence
<220> FEATURE:
<223> OTHER INFORMATION: fusion construct homo sapiens and EGFP

<400> SEQUENCE: 7
tagttattac tagcgctacc ggactcagat ctcgagctca agcttcgaat tctgcagtcg      60
acggtaccgc gggcccaaca cctattaatg cccacatatc tcaaacaagg aaatattgat     120
cctgcctatc cctctgctct ctattatata taaagcaaac aaagtcattt atcctaggct     180
gtctcataaa aacattttgt agcttccaca gtagcattgc aaagcctata ttatgaggaa     240
ttttcctctg aaatacattc caaatggttc gtgtttaagt tttattatcc catccattgt     300
tgtatcttca ccagaaataa aatgattttt agttctgatg caaaattaat tgctacatat     360
ttactgaatg cttatgatgt gcaagaaaga agttttaaga cattagcttt gttggaattt     420 ccatatttc ctgcccttat tccttgattt ttctttgcct ctagcctgaa taatgttgat     480
ttttcatgag gttgccacaa ggtaaggcaa caacacatgg aagaaaacag gcagacaca      540 tgcattcccc tgaggtactt gtatagtaac caagaaatca gcagcaaggt gttgggggga     600
cttaactagg taggttgcac atttgaggct atccactcaa ctaacagaca gttccaggct     660
ttgctgagtc aacaccttc acagaagaaa gaccatcata tattttatcc cacttggtgg     720
cagcttacaa taaaacacat gcagagaaaa tgcttaaata taaagttca acagcactat     780 ataaaaggaa gggttaatta tactaggaat cagatataaa ataattactg agcatgctct     840
tagctctgag cttcctggaa gccaagcaaa atagaaccca tgatagttca aggctgctac     900
atattgatgc atgtagcttc aattgtgaag atggtagcat cccctaccc catttaacct     960 ctcacctttc tcttttgttt tatagttcgg cctgatctaa ttagttcaat ttggatgctt    1020
ccttgagttt tttttgtaac atattttata taaagaagtc agttagtgac aaataagcag    1080
tttgaggaga atctgttaa tatttatttt gtagccatca gatttacttc acatagaaag    1140
gtctttgggt tgggtttgaa cttccaaact ctcaaggta aatgccacat taacctttca    1200
ttaaccaaat tcttacacca agctgataga tttgggatgt ccttttact tctatcttcc    1260 ataatattct aaaattattt tcccttgttt tgttcctatc ctacttcctc ttagtctact    1320
ttgttgactt cattaaaaaa caaaaaacca gttgttggat acttgagcta aactgcctta    1380
aagaatctgc agattttatt ttattttttt tctctcaaga gggtaaaagg aagagagcta    1440
caatttctaa gaagcctggc ttggctgtct gagtctggcc cccaggcaga ttaggccaag    1500
gttttggcca agtgaaattg ccaattttct aaaagaaagg ctagcacat tgctcattag    1560 agcattctga ttttgtctgc gcaatctttt tgctaccccg caatttcctg ttggttataa    1620
atgaaacctt tctagctgtt aatgcagcct gtgaattttt ttaaaagcat gtaattaatc    1680
ataggaggtt gggggggattc actaagcctg agttacatgg gagaagctgg acaaggcact    1740
aggacctaga aggcatctat ccaccctggc aggaatttct tgcttggagc tcagacaaca    1800
aaggcataga gagattggtt ttcttttctct cagcatctcc acccaaccag cagaaaaccg    1860
gtgagtgggg cttttaagtg attttcaaga agaatgtaac agatgtcaaa cgggaaaagc    1920
```

```
acaaggcaaa gcctgctctc tctgtctctc tgtctcctct tctccttttt tgccttattc    1980
tatccgattt tttccctaag cttctacctg ggattttcct ttggaaaagt gagtttgatg    2040
ttcctttgtt ttcactgtga tgttaattta gaataatact acctctgatc ctaaagcaaa    2100
gcaaagcctt actggcatgc ctggggaaat gtttgctgct tgccttgagg aggtggggtc    2160
tcttaccact gcaggttgtc tgacagagac aatgctgagc tcagcatagg tcatggtgac    2220
attggaaaaa aggcggaatt gagcctggca gacccattag gcaccagtct ttcttatctc    2280
ctgtcctcct ggtcccttgc aaatatattg atgtggcagt gtgtagcagc tgagccctgc    2340
ttgctttgtg agtccttta tccccatctg tgagatgcat gttaatagtt tggctcgtag     2400
gatgtcacta catttgctag catttgtggc ttcagttgta ttgggtttca tgttttgatt    2460
gtttggggtt cttggtgggg gaggggttc aacagaaggg agaaaagcaa agcctgacaa     2520
atgaccatct tttctcagct aatgcacctg gcaatatac aagtttgggg tgaattgcct     2580
gctgtgaggg taaatgtcac ttcaattaag gtagaaaccc agaacaatga aaggtgtgct    2640
tccttctaaa ggtcccgtat gctgttcgga gagtcatttg tgaatctttc aacaattaaa    2700
ttattccatt aagaggtgtt gctgcatcag tggggagggg gtggagcacc tgggggggaa    2760
aaaaaaggat tttgtgaaca atggaaccg ggggaagaca gagctagtaa cttgttaaat     2820
aacttatttt tctaatcctt ttccccccca gcttatttct tatgaatgtc ggatagctgc    2880
accagcttgg tggggaaagg gtttgatgaa tagcacaaag acactggctg ttccctggag    2940 gctgtcccctt taaggagaa tcttagttta ttctgggggg aggggatgca cacattagag    3000
taggaaagag ggcttggaat aaaatgaaaa cactcccct tcatagtcat tgtactgaaa     3060
tgcaaagact gcttcctaag ctggagatgc taaccttggg tagctccttc tgttctcttc    3120 aagggggaatt ttgtcaggct atggattcat ttacaactgt tagtcatgtg ggcatgtgtg   3180
aggaaacaga tgccagtttt aatgtattta gcccgaagtt ccaatttgat aggagccact    3240
gtcagtaagt ctcaggattt tcagctattt caaaatctcc ccttctcctc tgtctggaac    3300
agtgccaaga gtgcctccct ctctatctct tactcccaac ccccacaacc accagcaccc    3360
ccgcccagcc cctccttctt ctctattaag atcaatattc ctgcaggtca ggggcaagca    3420
gcagatgggt cacaggcttt tttcaaccag ttcttttcac aagcagcaga ttgcagatct    3480
ggatctggct aatatttaaa atcccttctt ttttccttct ccttgtccct ttttgttttt    3540
gcctctcttc accccatcc ctttctccca cgctcaggtc tctgagggat ccaccggtcg     3600
ccaccatggt gagcaaggc gaggagctgt tcaccgggt ggtgcccatc ctggtcgagc      3660
tggacggcga cgtaaacggc cacaagttca gcgtgtccgg cgagggcgag ggcgatgcca    3720
cctacggcaa gctgacctg aagttcatct gcaccaccgg caagctgccc gtgccctggc     3780
ccaccctcgt gaccaccctg acctacggcg tgcagtgctt cagccgctac cccgaccaca    3840
tgaagcagca cgacttcttc aagtccgcca tgcccgaagg ctacgtccag gagcgcacca    3900
tcttcttcaa ggacgacggc aactacaaga cccgcgccga ggtgaagttc gagggcgaca    3960
ccctggtgaa ccgcatcgag ctgaagggca tcgacttcaa ggaggacggc aacatcctgg    4020
ggcacaagct ggagtacaac tacaacagcc acaacgtcta tatcatggcc gacaagcaga    4080
agaacggcat caaggtgaac ttcaagatcc gccacaacat cgaggacggc agcgtgcagc    4140
tcgccgacca ctaccagcag aacacccca tcggcgacgg ccccgtgctg ctgcccgaca    4200
accactacct gagcacccag tccgccctga gcaaagaccc caacgagaag cgcgatcaca    4260
```

```
tggtcctgct ggagttcgtg accgccgccg ggatcactct cggcatggac gagctgtaca    4320
agtaaagcgg ccgcgactct agatcataat cagccatacc acatttgtag aggttttact    4380
tgctttaaaa aacctcccac acctcccct gaacctgaaa cataaaatga atgcaattgt     4440
tgttgttaac ttgtttattg cagcttataa tggttacaaa taaagcaata gcatcacaaa    4500
tttcacaaat aaagcatttt tttcactgca ttctagttgt ggtttgtcca aactcatcaa    4560
tgtatcttaa ggcgtaaatt gtaagcgtta atattttgtt aaaattcgcg ttaaattttt    4620
gttaaatcag ctcatttttt aaccataggc cgaaatcgg caaaatccct tataaatcaa    4680
aagaatagac cgagataggg ttgagtgttg ttccagtttg gaacaagagt ccactattaa    4740
agaacgtgga ctccaacgtc aaagggcgaa aaaccgtcta tcagggcgat ggcccactac    4800
gtgaaccatc accctaatca agttttttgg ggtcgaggtg ccgtaaagca ctaaatcgga    4860
accctaaagg gagcccccga tttagagctt gacggggaaa gccggcgaac gtggcgagaa    4920
aggaagggaa gaaagcgaaa ggagcgggcg ctagggcgct ggcaagtgta gcggtcacgc    4980
tgcgcgtaac caccacaccc gccgcgctta atgcgccgct acaggcgcg tcaggtggca     5040
cttttcgggg aaatgtgcgc ggaacccta tttgtttatt tttctaaata cattcaaata     5100
tgtatccgct catgagacaa taaccctgat aaatgcttca ataatattga aaaggaaga    5160
gtcctgaggc ggaaagaacc agctgtggaa tgtgtgtcag ttagggtgtg aaagtcccc    5220
aggctcccca gcaggcagaa gtatgcaaag catgcatctc aattagtcag caaccaggtg    5280
tggaaagtcc ccaggctccc cagcaggcag aagtatgcaa agcatgcatc tcaattagtc    5340
agcaaccata gtcccgcccc taactccgcc catcccgccc ctaactccgc ccagttccgc    5400
ccattctccg ccccatggct gactaatttt ttttatttat gcagaggccg aggccgcctc    5460
ggcctctgag ctattccaga agtagtgagg aggctttttt ggaggcctag cttttgcaa     5520
agatcgatca agagacagga tgaggatcgt ttcgcatgat tgaacaagat ggattgcacg    5580
caggttctcc ggccgcttgg gtggagaggc tattcggcta tgactgggca acagacaa     5640
tcggctgctc tgatgccgcc gtgttccggc tgtcagcgca ggggcgcccg gttcttttg     5700
tcaagaccga cctgtccggt gccctgaatg aactgcaaga cgaggcagcg cggctatcgt    5760
ggctggccac gacgggcgtt ccttgcgcag ctgtgctcga cgttgtcact gaagcgggaa    5820
gggactggct gctattgggc gaagtgccgg gcaggatct cctgtcatct caccttgctc     5880
ctgccgagaa agtatccatc atggctgatg caatgcggcg gctgcatacg cttgatccgg    5940
ctacctgccc attcgaccac caagcgaaac atcgcatcga gcgagcacgt actcggatgg    6000
aagccggtct tgtcgatcag gatgatctgg acgaagagca tcaggggctc gcgccagccg    6060
aactgttcgc caggctcaag gcgagcatgc ccgacggcga ggatctcgtc gtgacccatg    6120
gcgatgcctg cttgccgaat atcatggtgg aaaatggccg cttttctgga ttcatcgact    6180
gtggccggct gggtgtggcg gaccgctatc aggacatagc gttggctacc cgtgatattg    6240
ctgaagagct tggcggcgaa tgggctgacc gcttcctcgt gctttacggt atcgccgctc    6300
ccgattcgca gcgcatcgcc ttctatcgcc ttcttgacga gttcttctga gcgggactct    6360
ggggttcgaa atgaccgacc aagcgacgcc caacctgcca tcacgagatt tcgattccac    6420
cgccgccttc tatgaaaggt tgggcttcgg aatcgttttc cgggacgccg gctggatgat    6480
cctccagcgc ggggatctca tgctggagtt cttcgcccac cctaggggga gctaactga    6540
aacacggaag gagacaatac cggaaggaac ccgcgctatg acggcaataa aaagacagaa    6600
taaaacgcac ggtgttgggt cgtttgttca taaacgcggg gttcggtccc agggctggca    6660
```

```
ctctgtcgat accccaccga gacccccattg gggccaatac gcccgcgttt cttccttttc    6720 cccacccccac cccccaagtt cgggtgaagg cccagggctc gcagccaacg tcggggcggc    6780
aggccctgcc atagcctcag gttactcata tatactttag attgatttaa aacttcattt    6840
ttaatttaaa aggatctagg tgaagatcct ttttgataat ctcatgacca aaatccctta    6900
acgtgagttt tcgttccact gagcgtcaga ccccgtagaa aagatcaaag gatcttcttg    6960
agatcctttt tttctgcgcg taatctgctg cttgcaaaca aaaaaaccac cgctaccagc    7020
ggtggtttgt ttgccggatc aagagctacc aactcttttt ccgaaggtaa ctggcttcag    7080
cagagcgcag ataccaaata ctgtccttct agtgtagccg tagttaggcc accacttcaa    7140
gaactctgta gcaccgccta catacctcgc tctgctaatc ctgttaccag tggctgctgc    7200
cagtggcgat aagtcgtgtc ttaccgggtt ggactcaaga cgatagttac cggataaggc    7260
gcagcggtcg ggctgaacgg ggggttcgtg cacacagccc agcttggagc gaacgaccta    7320
caccgaactg agatacctac agcgtgagct atgagaaagc gccacgcttc ccgaagggag    7380
aaaggcggac aggtatccgg taagcggcag ggtcggaaca ggagagcgca cgagggagct    7440
tccaggggga aacgcctggt atctttatag tcctgtcggg tttcgccacc tctgacttga    7500
gcgtcgattt ttgtgatgct cgtcaggggg gcggagccta tggaaaaacg ccagcaacgc    7560
ggccttttta cggttcctgg ccttttgctg gccttttgct cacatgttct ttcctgcgtt    7620
atcccctgat tctgtggata accgtattac cgccatgcat                          7660

<210> SEQ ID NO 8
<211> LENGTH: 7616
<212> TYPE: DNA
<213> ORGANISM: artificial sequence
<220> FEATURE:
<223> OTHER INFORMATION: fusion construct homo sapiens and DsRed 2

<400> SEQUENCE: 8
tagttattac tagcgctacc ggactcagat ctcgagctca agcttcgaat tctgcagtcg      60
acggtaccgc gggcccaaca cctattaatg cccacatatc tcaaacaagg aaatattgat     120
cctgcctatc cctctgctct ctattatata taaagcaaac aaagtcattt atcctaggct     180
gtctcataaa aacattttgt agcttccaca gtagcattgc aaagcctata ttatgaggaa     240
ttttcctctg aaatacattc caaatggttc gtgtttaagt tttattatcc catccattgt     300
tgtatcttca ccagaaataa aatgattttt agttctgatg caaaattaat tgctacatat     360
ttactgaatg cttatgatgt gcaagaaaga agttttaaga cattagcttt gttggaattt     420
ccatattttc ctgcccttat tccttgattt ttctttgcct ctagcctgaa taatgttgat     480
ttttcatgag gttgccacaa ggtaaggcaa caacacatgg aagaaaacag gcagacaca     540 tgcattcccc tgaggtactt gtatagtaac caagaaatca gcagcaaggt gttgggggga     600
cttaactagg taggttgcac atttgaggct atccactcaa ctaacagaca gttccaggct     660
ttgctgagtc aacacctttc acagaagaaa gaccatcata tattttatcc cacttggtgg     720
cagcttacaa taaacacat gcagagaaaa tgcttaaata taaagttca acagcactat       780 ataaaaggaa gggttaatta tactaggaat cagatataaa ataattactg agcatgctct     840
tagctctgag cttcctggaa gccaagcaaa aatagaacca tgatagttca aggctgctac     900
atattgatgc atgtagcttc aattgtgaag atggtagcat ccccctaccc catttaacct     960
ctcacctttc tcttttgttt tatagttcgg cctgatctaa ttagttcaat ttggatgctt    1020
```

```
ccttgagttt tttttgtaac atattttata taaagaagtc agttagtgac aaataagcag    1080
tttgaggaga aatctgttaa tatttatttt gtagccatca gatttacttc acatagaaag    1140
gtctttgggt tgggtttgaa cttccaaact ctcaaggta aatgccacat taacctttca    1200
ttaaccaaat tcttacacca agctgataga tttgggatgt ccttttact tctatcttcc    1260 ataatattct aaaattattt tcccttgttt tgttcctatc ctacttcctc ttagtctact    1320
ttgttgactt cattaaaaaa caaaaaacca gttgttggat acttgagcta aactgcctta    1380
aagaatctgc agatttattt ttatttttt tctctcaaga gggtaaaagg aagagagcta    1440
caatttctaa gaagcctggc ttggctgtct gagtctggcc cccaggcaga ttaggccaag    1500
gttttggcca agtgaaattg ccaattttct aaaagaaagg gctagcacat tgctcattag    1560
agcattctga ttttgtctgc gcaatctttt tgctaccccg caatttcctg ttggttataa    1620
atgaaacctt tctagctgtt aatgcagcct gtgaattttt ttaaaagcat gtaattaatc    1680
ataggaggtt ggggggattc actaagcctg agttacatgg gagaagctgg acaaggcact    1740
aggacctaga aggcatctat ccaccctggc aggaattct tgcttggagc tcagacaaca    1800
aaggcataga gagattggtt ttcttctct cagcatctcc acccaaccag cagaaaaccg    1860
gtgagtgggg cttttaagtg attttcaaga agaatgtaac agatgtcaaa cgggaaaagc    1920
acaaggcaaa gcctgctctc tctgtctctc tgtctcctct tctcctttt tgccttattc     1980 tatccgattt tttccctaag cttctacctg ggattttcct ttggaaaagt gagtttgatg    2040
ttcctttgtt ttcactgtga tgttaattta gaataatact acctctgatc ctaaagcaaa    2100
gcaaagcctt actggcatgc ctggggaaat gtttgctgct tgccttgagg aggtggggtc    2160
tcttaccact gcaggttgtc tgacagagac aatgctgagc tcagcatagg tcatggtgac    2220
attggaaaaa aggcggaatt gagcctggca gacccattag gcaccagtct ttcttatctc    2280
ctgtcctcct ggtcccttgc aaatatattg atgtggcagt gtgtagcagc tgagccctgc    2340
ttgctttgtg agtccttta tccccatctg tgagatgcat gttaatagtt tggctcgtag    2400
gatgtcacta catttgctag catttgtggc ttcagttgta ttgggtttca tgttttgatt    2460
gtttggggtt cttggtgggg gaggggttc aacagaaggg agaaaagcaa agcctgacaa    2520
atgaccatct tttctcagct aatgcacctg gcaatatac aagtttgggg tgaattgcct    2580
gctgtgaggg taaatgtcac ttcaattaag gtagaaaccc agaacaatga aggtgtgct    2640 tccttctaaa ggtcccgtat gctgttcgga gagtcatttg tgaatctttc aacaattaaa    2700
ttattccatt aagaggtgtt gctgcatcag tggggagggg gtggagcacc tggggggaa    2760 aaaaaaggat tttgtgaaca aatggaaccg ggggaagaca gagctagtaa cttgttaaat    2820 aacttattt tctaatcctt ttttcccccca gcttatttct tatgaatgtc ggatagctgc    2880
accagcttgg tggggaaagg gtttgatgaa tagcacaaag acactggctg ttccctggag    2940 gctgtcccctt taaggagaa tcttagttta ttctgggggg aggggatgca cacattagag    3000
taggaaagag ggcttggaat aaaatgaaaa cactcccct tcatagtcat tgtactgaaa    3060
tgcaaagact gcttcctaag ctggagatgc taaccttggg tagctccttc tgttctcttc    3120 aagggaatt ttgtcaggct atggattcat ttacaactgt tagtcatgtg ggcatgtgtg    3180
aggaaacaga tgccagtttt aatgtattta gcccgaagtt ccaatttgat aggagccact    3240
gtcagtaagt ctcaggattt tcagctattt caaaatctcc ccttctcctc tgtctggaac    3300
agtgccaaga gtgcctccct ctctatctct tactcccaac cccacaacc accagcaccc    3360 ccgcccagcc cctccttctt ctctattaag atcaatattc ctgcaggtca ggggcaagca    3420
```

```
gcagatgggt cacaggcttt tttcaaccag ttcttttcac aagcagcaga ttgcagatct   3480
ggatctggct aatatttaaa atcccttctt ttttccttct ccttgtccct ttttgttttt   3540
gcctctcttc accccatcc ctttctccca cgctcaggtc tctgagggat ccaccggtcg    3600
ccaccatggc ctcctccgag aacgtcatca ccgagttcat gcgcttcaag gtgcgcatgg   3660
agggcaccgt gaacggccac gagttcgaga tcgagggcga gggcgagggc cgcccctacg   3720
agggccacaa caccgtgaag ctgaaggtga ccaagggcgg cccctgccc ttcgcctggg    3780 acatcctgtc cccccagttc cagtacggct ccaaggtgta cgtgaagcac cccgccgaca   3840
tccccgacta caagaagctg tccttccccg agggcttcaa gtgggagcgc gtgatgaact   3900
tcgaggacgg cggcgtggcg accgtgaccc aggactcctc cctgcaggac ggctgcttca   3960
tctacaaggt gaagttcatc ggcgtgaact tcccctccga cggccccgtg atgcagaaga   4020
agaccatggg ctgggaggcc tccaccgagc gcctgtaccc ccgcgacggc gtgctgaagg   4080
gcgagaccca caaggccctg aagctgaagg acggcggcca ctacctggtg gagttcaagt   4140
ccatctacat ggccaagaag cccgtgcagc tgcccggcta ctactacgtg gacgccaagc   4200
tggacatcac ctcccacaac gaggactaca ccatcgtgga gcagtacgag cgcaccgagg   4260
gccgccacca cctgttcctg tagcggccgc gactctagat cataatcagc cataccacat   4320
ttgtagaggt tttacttgct ttaaaaaacc tcccacacct cccctgaac ctgaaacata    4380 aaatgaatgc aattgttgtt gttaacttgt ttattgcagc ttataatggt tacaaataaa   4440
gcaatagcat cacaaatttc acaaataaag catttttttc actgcattct agttgtggtt   4500
tgtccaaact catcaatgta tcttaaggcg taaattgtaa cgttaatat tttgttaaaa    4560 ttcgcgttaa attttgtta aatcagctca ttttttaacc aataggccga aatcggcaaa    4620
atcccttata aatcaaaaga atagaccgag atagggttga gtgttgttcc agtttggaac   4680
aagagtccac tattaaagaa cgtggactcc aacgtcaaag gcgaaaaac cgtctatcag    4740 ggcgatggcc cactacgtga accatcaccc taatcaagtt ttttggggtc gaggtgccgt   4800
aaagcactaa atcggaaccc taaagggagc cccgattta gagcttgacg gggaaagccg    4860
gcgaacgtgg cgagaaagga agggaagaaa gcgaaaggag cggcgctag ggcgctggca    4920 agtgtagcgg tcacgctgcg cgtaaccacc cacccgccg cgcttaatgc cgctacag     4980 ggcgcgtcag gtggcacttt cgggggaaat gtgcgcggaa cccctatttg tttattttc   5040 taaatacatt caaatatgta tccgctcatg agacaataac cctgataaat gcttcaataa   5100
tattgaaaaa ggaagagtcc tgaggcgaaa gaaccagct gtggaatgtg tgtcagttag    5160
ggtgtggaaa gtccccaggc tccccagcag gcagaagtat gcaaagcatg catctcaatt   5220
agtcagcaac caggtgtgga agtcccag gctcccagc aggcagaagt atgcaaagca      5280
tgcatctcaa ttagtcagca accatagtcc cgcccctaac tccgcccatc cgcccctaa    5340 ctccgcccag ttccgcccat tctccgcccc atggctgact aatttttttt atttatgcag   5400
aggccgaggc cgcctcggcc tctgagctat tccagaagta gtgaggaggc ttttttggag   5460
gcctaggctt ttgcaaagat cgatcaagag acaggatgag gatcgtttcg catgattgaa   5520
caagatggat tgcacgcagg ttctccgccc gcttgggtgg agaggctatt cggctatgac   5580
tgggcacaac agacaatcgg ctgctctgat gccgccgtgt tccggctgtc agcgcagggg   5640
cgcccggttc tttttgtcaa gaccgacctg tccggtgccc tgaatgaact gcaagacgag   5700
gcagcgcggc tatcgtggct ggccacgacg ggcgttcctt gcgcagctgt gctcgacgtt   5760
```

```
gtcactgaag cgggaaggga ctggctgcta ttgggcgaag tgccggggca ggatctcctg    5820
tcatctcacc ttgctcctgc cgagaaagta tccatcatgg ctgatgcaat gcggcggctg    5880
catacgcttg atccggctac ctgcccattc gaccaccaag cgaaacatcg catcgagcga    5940
gcacgtactc ggatggaagc cggtcttgtc gatcaggatg atctggacga agagcatcag    6000
gggctcgcgc cagccgaact gttcgccagg ctcaaggcga gcatgcccga cggcgaggat    6060
ctcgtcgtga cccatggcga tgcctgcttg ccgaatatca tggtggaaaa tggccgcttt    6120
tctggattca tcgactgtgg ccggctgggt gtggcggacc gctatcagga catagcgttg    6180
gctacccgtg atattgctga agagcttggc ggcgaatggg ctgaccgctt cctcgtgctt    6240
tacggtatcg ccgctcccga ttcgcagcgc atcgccttct atcgccttct tgacgagttc    6300
ttctgagcgg gactctgggg ttcgaaatga ccgaccaagc gacgcccaac ctgccatcac    6360
gagatttcga ttccaccgcc gccttctatg aaaggttggg cttcggaatc gttttccggg    6420
acgccggctg gatgatcctc cagcgcgggg atctcatgct ggagttcttc gcccacccta    6480
gggggaggct aactgaaaca cggaaggaga caataccgga aggaacccgc gctatgacgg    6540
caataaaaag acagaataaa acgcacggtg ttgggtcgtt tgttcataaa cgcggggttc    6600
ggtcccaggg ctggcactct gtcgataccc caccgagacc ccattggggc caatacgccc    6660
gcgtttcttc cttttcccca ccccaccccc caagttcggg tgaaggccca gggctcgcag    6720
ccaacgtcgg gcggcaggc  cctgccatag cctcaggtta ctcatatata ctttagattg    6780
atttaaaact tcatttttaa tttaaaagga tctaggtgaa gatcctttt  gataatctca    6840 tgaccaaaat cccttaacgt gagttttcgt tccactgagc gtcagacccc gtagaaaaga    6900
tcaaaggatc ttcttgagat cctttttttc tgcgcgtaat ctgctgcttg caaacaaaaa    6960
aaccaccgct accagcggtg gtttgtttgc cggatcaaga gctaccaact cttttttccga   7020 aggtaactgg cttcagcaga gcgcagatac caaatactgt ccttctagtg tagccgtagt    7080
taggccacca cttcaagaac tctgtagcac cgcctacata cctcgctctg ctaatcctgt    7140
taccagtggc tgctgccagt ggcgataagt cgtgtcttac cgggttggac tcaagacgat    7200
agttaccgga taaggcgcag cggtcgggct gaacggggg  ttcgtgcaca cagcccagct    7260
tggagcgaac gacctacacc gaactgagat acctacagcg tgagctatga aaagcgcca     7320 cgcttcccga agggagaaag gcggacaggt atccggtaag cggcagggtc ggaacaggag    7380
agcgcacgag ggagcttcca gggggaaacg cctggtatct ttatagtcct gtcgggtttc    7440
gccacctctg acttgagcgt cgatttttgt gatgctcgtc aggggggcgg agcctatgga    7500
aaaacgccag caacgcggcc ttttacggtt cctggccctt ttgctggcct tttgctcaca    7560
tgttctttcc tgcgttatcc cctgattctg tggataaccg tattaccgcc atgcat       7616
```

```
<210> SEQ ID NO 9
<211> LENGTH: 18
<212> TYPE: DNA
<213> ORGANISM: Homo sapiens

<400> SEQUENCE: 9
aacacctatt aatgccca                                                  18

<210> SEQ ID NO 10
<211> LENGTH: 23
<212> TYPE: DNA
<213> ORGANISM: homo sapiens

<400> SEQUENCE: 10
```

```
tcagagacct gagcgtggga gaa                                              23

<210> SEQ ID NO 11
<211> LENGTH: 21
<212> TYPE: DNA
<213> ORGANISM: aequorea victoria

<400> SEQUENCE: 11
aagttcatct gcaccaccgg c                                                21

<210> SEQ ID NO 12
<211> LENGTH: 21
<212> TYPE: DNA
<213> ORGANISM: artificial sequence
<220> FEATURE:
<223> OTHER INFORMATION: derived from EGFP

<400> SEQUENCE: 12
ctttacttgt acagctcgtc c                                                21

<210> SEQ ID NO 13
<211> LENGTH: 21
<212> TYPE: DNA
<213> ORGANISM: artificial sequence
<220> FEATURE:
<223> OTHER INFORMATION: derived from construct comprised in DSM 15111

<400> SEQUENCE: 13
atggtgagca agggcgagga g                                                21

<210> SEQ ID NO 14
<211> LENGTH: 21
<212> TYPE: DNA
<213> ORGANISM: artificial sequence
<220> FEATURE:
<223> OTHER INFORMATION: derived from construct comprised in DSM 15111

<400> SEQUENCE: 14
cttgtacagc tcgtccatgc c                                                21

<210> SEQ ID NO 15
<211> LENGTH: 1910
<212> TYPE: DNA
<213> ORGANISM: homo sapiens

<400> SEQUENCE: 15
taatcatagg aggttggggg gattcactaa gcctgagtta catgggagaa gctggacaag       60
gcactaggac ctagaaggca tctatccacc ctggcaggaa tttcttgctt ggagctcaga      120
caacaaaggc atagagagat tggttttctt tctctcagca tctccaccca accagcagaa      180
aaccggtgag tggggctttt aagtgatttt caagaagaat gtaacagatg tcaaacggga      240
aaagcacaag gcaaagcctg ctctctctgt ctctctgtct cctcttctcc ttttttgcct      300
tattctatcc gatttttcc ctaagcttct acctgggatt ttcctttgga aaagtgagtt      360
tgatgttcct ttgttttcac tgtgatgtta atttagaata atactacctc tgatcctaaa      420
gcaaagcaaa gccttactgg catgcctggg gaaatgtttg ctgcttgcct tgaggaggtg      480
gggtctctta ccactgcagg ttgtctgaca gagacaatgc tgagctcagc ataggtcatg      540
gtgacattgg aaaaaggcg gaattgagcc tggcagaccc attaggcacc agtctttctt      600
atctcctgtc ctcctggtcc cttgcaaata tattgatgtg gcagtgtgta gcagctgagc      660
```

-continued

| | | |
|---|---|---|
| cctgcttgct tgtgagtcc ttttatcccc atctgtgaga tgcatgttaa tagtttggct | 720 |
| cgtaggatgt cactacattt gctagcattt gtggcttcag ttgtattggg tttcatgttt | 780 |
| tgattgtttg gggttcttgg tgggggaggg ggttcaacag aagggagaaa agcaaagcct | 840 |
| gacaaatgac catcttttct cagctaatgc acctgggcaa tatacaagtt tggggtgaat | 900 |
| tgcctgctgt gagggtaaat gtcacttcaa ttaaggtaga aacccagaac aatgaaaggt | 960 |
| gtgcttcctt ctaaaggtcc cgtatgctgt tcggagagtc atttgtgaat ctttcaacaa | 1020 |
| ttaaattatt ccattaagag gtgttgctgc atcagtgggg aggggtggag gcacctgggg | 1080 |
| gggaaaaaaa aggattttgt gaacaaatgg aaccgggga agacagagct agtaacttgt | 1140 |
| taaataactt attttttctaa tcctttttcc ccccagctta tttcttatga atgtcggata | 1200 |
| gctgcaccag cttggtgggg aaagggtttg atgaatagca caaagacact ggctgttccc | 1260 |
| tggaggctgt ccctttaaag gagaatctta gtttattctg gggggagggg atgcacacat | 1320 |
| tagagtagga agagggcttt ggaataaaat gaaaacactc cccctttcata gtcattgtac | 1380 |
| tgaaatgcaa agactgcttc ctaagctgga gatgctaacc ttgggtagct ccttctgttc | 1440 |
| tcttcaaggg gaattttgtc aggctatgga ttcatttaca actgttagtc atgtgggcat | 1500 |
| gtgtgaggaa acagatgcca gttttaatgt atttagcccg aagttccaat ttgataggag | 1560 |
| ccactgtcag taagtctcag gatttttcagc tatttcaaaa tctcccctttc tcctctgtct | 1620 |
| ggaacagtgc caagagtgcc tccctctcta tctcttactc ccaaccccca caaccaccag | 1680 |
| cacccccgcc cagcccctcc ttcttctcta ttaagatcaa tattcctgca ggtcaggggc | 1740 |
| aagcagcaga tgggtcacag ctttttttca accagttctt ttcacaagca gcagattgca | 1800 |
| gatctggatc tggctaatat ttaaaatccc ttctttttttc cttctccttg tccctttttg | 1860 |
| ttttttgcctc tcttcacccc catccctttc tcccacgctc aggtctctga | 1910 |

<210> SEQ ID NO 16
<211> LENGTH: 3103
<212> TYPE: DNA
<213> ORGANISM: homo sapiens

<400> SEQUENCE: 16

| | | |
|---|---|---|
| aacacctatt aatgcccaca tatctcaaac aaggaaatat tgatcctgcc tatccctctg | 60 |
| ctctctatta tatataaagc aaacaaagtc atttatccta ggctgtctca taaaaacatt | 120 |
| ttgtagcttc cacagtagca ttgcaaagcc tatattatga ggaattttcc tctgaaatac | 180 |
| attccaaatg gttcgtgttt aagttttatt atcccatcca ttgttgtatc ttcaccagaa | 240 |
| ataaaatgat ttttagttct gatgcaaaat taattgctac atatttactg aatgcttatg | 300 |
| atgtgcaaga aagaagtttt aagacattag ctttgttgga atttccatat tttcctgccc | 360 |
| ttattccttg attttttcttt gcctctagcc tgaataatgt tgattttttca tgaggttgcc | 420 |
| acaaggtaag gcaacaacac atggaagaaa acagggcaga cacatgcatt cccctgaggt | 480 |
| acttgtatag taaccaagaa atcagcagca aggtgttggg gggacttaac taggtaggtt | 540 |
| gcacatttga ggctatccac tcaactaaca gacagttcca ggctttgctg agtcaacacc | 600 |
| tttcacagaa gaaagaccat catatatttt atcccacttg gtggcagctt acaataaaac | 660 |
| acatgcagag aaaatgctta aatataaaag ttcaacagca ctatataaaa ggaagggtta | 720 |
| attatactag gaatcagata taaaataatt actgagcatg ctcttagctc tgagcttcct | 780 |
| ggaagccaag caaaaataga accatgatag ttcaaggctg ctacatattg atgcatgtag | 840 |
| cttcaattgt gaagatggta gcatccccct accccattta acctctcacc tttctctttt | 900 |

-continued

```
gttttatagt tcggcctgat ctaattagtt caatttggat gcttccttga gtttttttg      960 taacatattt tatataaaga agtcagttag tgacaaataa gcagtttgag gagaaatctg    1020
ttaatattta ttttgtagcc atcagattta cttcacatag aaaggtcttt gggttgggtt    1080
tgaacttcca aactctcaaa ggtaaatgcc acattaacct ttcattaacc aaattcttac    1140
accaagctga tagatttggg atgtccttt tacttctatc ttccataata ttctaaaatt     1200
attttccctt gttttgttcc tatcctactt cctcttagtc tactttgttg acttcattaa    1260
aaaacaaaaa accagttgtt ggatacttga gctaaactgc cttaaagaat ctgcagattt    1320 tatttattt tttttctctc aagagggtaa aaggaagaga gctacaattt ctaagaagcc     1380
tggcttggct gtctgagtct ggcccccagg cagattaggc caaggttttg gccaagtgaa    1440
attgccaatt ttctaaaaga aagggctagc acattgctca ttagagcatt ctgattttgt    1500
ctgcgcaatc tttttgctac cccgcaattt cctgttggtt ataaatgaaa cctttctagc    1560
tgttaatgca gcctgtgaat ttttttaaaa gcatgtaatt aatcatagga ggttgggggg    1620
attcactaag cctgagttac atgggagaag ctggacaagg cactaggacc tagaaggcat    1680
ctatccaccc tggcaggaat tcttgcttg gagctagctc agcataggtc atggtgacat     1740
tggaaaaaag gcggaattga gcctggcaga cccattaggc accagtcttt cttatctcct    1800
gtcctcctgg tcccttgcaa atatattgat gtggcagtgt gtagcagctg agccctgctt    1860
gctttgtgag tcctttttatc cccatctgtg agatgcatgt taatagtttg gctcgtagga   1920
tgtcactaca tttgctagca tttgtggctt cagttgtatt gggtttcatg ttttgattgt    1980
ttggggttct tggtggggga ggggttcaa cagaagggag aaaagcaaag cctgacaaat     2040
gaccatcttt tctcagctaa tgcacctggg caatatacaa gtttgggtg aattgcctgc     2100 tgtgagggta aatgtcactt caattaaggt agaaacccag aacaatgaaa ggtgtgcttc    2160
cttctaaagg tcccgtatgc tgttcggaga gtcatttgtg aatctttcaa caattaaatt    2220
attccattaa gaggtgttgc tgcatcagtg gggaggggt ggagcacctg gggggaaaa      2280 aaaaggattt tgtgaacaaa tggaaccggg ggaagacaga gctagtaact tgttaaataa    2340
cttatttttc taatccttt tccccccagc ttatttctta tgaatgtcgg atagctgcac     2400
cagcttggtg gggaaagggt ttgatgaata gcacaaagac actggctgtt ccctggaggc    2460 tgtccctta aaggagaatc ttagtttatt ctggggggag gggatgcaca cattagagta    2520
ggaaagaggg cttggaataa aatgaaaaca ctccccttc atagtcattg tactgaaatg     2580
caaagactgc ttcctaagct ggagatgcta accttgggta gctccttctg ttctcttcaa    2640
ggggaatttt gtcaggctat ggattcattt acaactgtta gtcatgtggg catgtgtgag    2700
gaaacagatg ccagttttaa tgtatttagc ccgaagttcc aatttgatag gagccactgt    2760
cagtaagtct caggattttc agctatttca aaatctcccc ttctcctctg tctggaacag    2820
tgccaagagt gcctccctct ctatctctta ctcccaaccc ccacaaccac cagcaccccc    2880
gcccagcccc tccttcttct ctattaagat caatattcct gcaggtcagg ggcaagcagc    2940
agatgggtca caggcttttt tcaaccagtt cttttcacaa gcagcagatt gcagatctgg    3000
atctggctaa tatttaaaat cccttctttt ttccttctcc ttgtcccttt ttgttttgc     3060 ctctcttcac ccccatccct ttctcccacg ctcaggtctc tga                       3103
```

<210> SEQ ID NO 17
<211> LENGTH: 2906
<212> TYPE: DNA

<213> ORGANISM: homo sapiens

<400> SEQUENCE: 17

```
aacacctatt aatgcccaca tatctcaaac aaggaaatat tgatcctgcc tatccctctg      60
ctctctatta tatataaagc aaacaaagtc atttatccta ggctgtctca taaaaacatt     120
ttgtagcttc cacagtagca ttgcaaagcc tatattatga ggaattttcc tctgaaatac     180
attccaaatg gttcgtgttt aagttttatt atcccatcca ttgttgtatc ttcaccagaa     240
ataaaatgat ttttagttct gatgcaaaat taattgctac atatttactg aatgcttatg     300
atgtgcaaga aagaagtttt aagacattag ctttgttgga atttccatat tttcctgccc     360
ttattccttg attttctttt gcctctagcc tgaataatgt tgattttca tgaggttgcc      420
acaaggtaag gcaacaacac atggaagaaa acagggcaga cacatgcatt cccctgaggt     480
acttgtatag taaccaagaa atcagcagca aggtgttggg gggacttaac taggtaggtt     540
gcacatttga ggctatccac tcaactaaca gacagttcca ggctttgctg agtcaacacc     600
tttcacagaa gaaagaccat catatatttt atcccacttg gtggcagctt acaataaaac     660
acatgcagag aaaatgctta aatataaaag ttcaacagca ctatataaaa ggaagggtta     720
attatactag gaatcagata taaaataatt actgagcatg ctcttagctc tgagcttcct     780
ggaagccaag caaaaataga accatgatag ttcaaggctg ctacatattg atgcatgtag     840
cttcaattgt gaagatggta gcatcccct accccattta acctctcacc tttctctttt      900
gttttatagt tcggcctgat ctaattagtt caatttggat gcttccttga gttttttttg     960
taacatattt tatataaaga agtcagttag tgacaaataa gcagtttgag gagaaatctg    1020
ttaatattta ttttgtagcc atcagattta cttcacatag aaaggtcttt gggttgggtt    1080
tgaacttcca aactctcaaa ggtaaatgcc acattaacct ttcattaacc aaattcttac    1140
accaagctga tagatttggg atgtcctttt tacttctatc ttccataata ttctaaaatt    1200
attttccctt gttttgttcc tatcctactt cctcttagtc tactttgttg acttcattaa    1260
aaaacaaaaa accagttgtt ggatacttga gctaaactgc cttaaagaat ctgcagattt    1320
tattttattt tttttctctc aagagggtaa aaggaagaga gctacaattt ctaagaagcc    1380
tggcttggct gtctgagtct ggcccccagg cagattaggc caaggttttg gccaagtgaa    1440
attgccaatt ttctaaaaga aagggctagc acattgctca ttagagcatt ctgattttgt    1500
ctgcgcaatc ttttttgctac cccgcaattt cctgttggtt ataaatgaaa cctttctagc    1560
tgttaatgca gcctgtgaat tttttttaaaa gcatgtaatt aatcatagga ggttgggggg    1620
attcactaag cctgagttac atgggagaag ctggacaagg cactaggacc tagaaggcat    1680
ctatccaccc tggcaggaat ttcttgcttg gagctcagac aacaaaggca tagagagatt    1740
ggttttcttt ctctcagcat ctccacccaa ccagcagaaa accggtgagt ggggctttta    1800
agtgattttc aagaagaatg taacagatgt caaacgggaa aagcacaagg caaagcctgc    1860
tctctctgtc tctctgtctc ctcttctcct tttttgcctt attctatccg atttttccc     1920
taagcttcta cctgggattt tccttttggaa aagtgagttt gatgttcctt tgtttttcact    1980
gtgatgttaa tttagaataa tactacctct gatcctaaag caaagcaaag ccttactggc    2040
atgcctgggg aaatgtttgc tgcttgcctt gaggaggtgg ggtctcttac cactgcaggt    2100
tgtctgacag agacaatgct gaagctagta acttgttaaa taacttattt ttctaatcct    2160
ttttcccccc agcttattc ttatgaatgt cggatagctg caccagcttg gtggggaaag     2220
ggtttgatga atagcacaaa gacactggct gttccctgga ggctgtccct ttaaaggaga    2280
```

```
atcttagttt attctggggg gaggggatgc acacattaga gtaggaaaga gggcttggaa    2340
taaaatgaaa acactccccc ttcatagtca ttgtactgaa atgcaaagac tgcttcctaa    2400
gctggagatg ctaaccttgg gtagctcctt ctgttctctt caaggggaat tttgtcaggc    2460 tatgattca  tttacaactg ttagtcatgt gggcatgtgt gaggaaacag atgccagttt    2520
taatgtattt agcccgaagt tccaatttga taggagccac tgtcagtaag tctcaggatt    2580
ttcagctatt tcaaaatctc cccttctcct ctgtctggaa cagtgccaag agtgcctccc    2640
tctctatctc ttactcccaa ccccacaac  caccagcacc ccgcccagc  ccctccttct    2700 tctctattaa gatcaatatt cctgcaggtc aggggcaagc agcagatggg tcacaggctt    2760
ttttcaacca gttcttttca caagcagcag attgcagatc tggatctggc taatatttaa    2820
aatcccttct ttttccttc  tccttgtccc ttttgtttt  tgcctctctt cacccccatc    2880
cctttctccc acgctcaggt ctctga                                         2906

<210> SEQ ID NO 18
<211> LENGTH: 2127
<212> TYPE: DNA
<213> ORGANISM: homo sapiens

<400> SEQUENCE: 18
aacacctatt aatgcccaca tatctcaaac aaggaaatat tgatcctgcc tatccctctg      60
ctctctatta tatataaagc aaacaaagtc atttatccta ggctgtctca taaaaacatt     120
ttgtagcttc cacagtagca ttgcaaagcc tatattatga ggaattttcc tctgaaatac     180
attccaaatg gttcgtgttt aagttttatt atcccatcca ttgttgtatc ttcaccagaa     240
ataaaatgat ttttagttct gatgcaaaat taattgctac atatttactg aatgcttatg     300
atgtgcaaga aagaagtttt aagacattag ctttgttgga atttccatat tttcctgccc     360
ttattccttg attttctttt gcctctagcc tgaataatgt tgattttca  tgaggttgcc     420 acaaggtaag gcaacaacac atggaagaaa acagggcaga cacatgcatt cccctgaggt     480
acttgtatag taaccaagaa atcagcagca aggtgttggg gggacttaac taggtaggtt     540
gcacatttga ggctatccac tcaactaaca gacagttcca ggctttgctg agtcaacacc     600
tttcacagaa gaaagaccat catatatttt atcccacttg gtggcagctt acaataaaac     660
acatgcagag aaaatgctta aatataaaag ttcaacagca ctatataaaa ggaagggtta     720
attatactag gaatcagata taaaataatt actgagcatg ctcttagctc tgagcttcct     780
ggaagccaag caaaaataga accatgatag ttcaaggctg ctacatattg atgcatgtag     840
cttcaattgt gaagatggta gcatcccct  accccattta acctctcacc tttctctttt     900
gttttatagt tcggcctgat ctaattagtt caatttggat gcttccttga gtttttttg     960 taacatattt tatataaaga agtcagttag tgacaaataa gcagtttgag gagaaatctg    1020
ttaatattta ttttgtagcc atcagattta cttcacatag aaaggtcttt gggttgggtt    1080
tgaacttcca aactctcaaa ggtaaatgcc acattaacct ttcattaacc aaattcttac    1140
accaagctga tagatttggg atgtcctttt tacttctatc ttccataata ttctaaaatt    1200
attttccctt gttttgttcc tatcctactt cctcttagtc tactttgttg acttcattaa    1260
aaaacaaaaa accagttgtt ggatacttga gctaaactgc cttaaagaat ctgcagattt    1320 tatttttattt tttttctctc aagagggtaa aaggaagaga gctacaattt ctaagaagcc    1380
tggcttggct gtctgagtct ggcccccagg cagattaggc caaggttctt ggtggggaaa    1440
```

-continued

| | |
|---|---|
| gggtttgatg aatagcacaa agacactggc tgttccctgg aggctgtccc tttaaaggag | 1500 |
| aatcttagtt tattctgggg ggaggggatg cacacattag agtaggaaag agggcttgga | 1560 |
| ataaaatgaa aacactcccc cttcatagtc attgtactga aatgcaaaga ctgcttccta | 1620 |
| agctggagat gctaaccttg ggtagctcct tctgttctct tcaaggggaa ttttgtcagg | 1680 |
| ctatggattc atttacaact gttagtcatg tgggcatgtg tgaggaaaca gatgccagtt | 1740 |
| ttaatgtatt tagcccgaag ttccaatttg ataggagcca ctgtcagtaa gtctcaggat | 1800 |
| tttcagctat ttcaaaatct ccccttctcc tctgtctgga acagtgccaa gagtgcctcc | 1860 |
| ctctctatct cttactccca accccacaa ccaccagcac cccgcccag cccctccttc | 1920 |
| ttctctatta agatcaatat tcctgcaggt caggggcaag cagcagatgg gtcacaggct | 1980 |
| tttttcaacc agttcttttc acaagcagca gattgcagat ctggatctgg ctaatattta | 2040 |
| aaatcccttc ttttttcctt ctccttgtcc cttttttgttt ttgcctctct tcaccccat | 2100 |
| cccttttctcc cacgctcagg tctctga | 2127 |

<210> SEQ ID NO 19
<211> LENGTH: 1315
<212> TYPE: DNA
<213> ORGANISM: homo sapiens

<400> SEQUENCE: 19

| | |
|---|---|
| cttttttactt ctatcttcca taatattcta aaattatttt cccttgtttt gttcctatcc | 60 |
| tacttcctct tagtctactt tgttgacttc attaaaaaac aaaaaaccag ttgttggata | 120 |
| cttgagctaa actgccttaa agaatctgca gattttattt tatttttttt ctctcaagag | 180 |
| ggtaaaagga agagagctac aatttctaag aagcctggct tggctgtctg agtctggccc | 240 |
| ccaggcagat taggccaagg ttttggccaa gtgaaattgc caattttcta aaagaaaggg | 300 |
| ctagcacatt gctcattaga gcattctgat tttgtctgcg caatcttttt gctaccccgc | 360 |
| aatttcctgt tggttataaa tgaaaccttt ctagctgtta atgcagcctg tgaattttt | 420 |
| taaaagcatg taattaatca taggaggttg gggggattca ctaagcctga gttacatggg | 480 |
| agaagctgga caaggcacta ggacctagaa ggcatctatc cacccctggca ggaatttctt | 540 |
| gcttggagct cagacaacaa aggcatagag agattggttt tctttctctc agcatctcca | 600 |
| cccaaccagc agaaaaccgg tgagtggggc ttttaagtga ttttcaagaa gaatgtaaca | 660 |
| gatgtcaaac gggaaaagca caaggcaaag cctgctctct ctgtctctct gtctcctctt | 720 |
| ctccttttttt gccttattct atccgatttt tccctaagc ttctacctgg gattttcctt | 780 |
| tggaaaagtg agtttgatgt tcctttgttt tcactgtgat gttaatttag aataatacta | 840 |
| cctctgatcc taaagcaaag caaagcctta ctggcatgcc tgggaactgt tagtcatgtg | 900 |
| ggcatgtgtg aggaaacaga tgccagtttt aatgtattta gcccgaagtt ccaatttgat | 960 |
| aggagccact gtcagtaagt ctcaggattt tcagctattt caaaatctcc ccttctcctc | 1020 |
| tgtctggaac agtgccaaga gtgcctccct ctctatctct tactcccaac ccccacaacc | 1080 |
| accagcaccc ccgcccagcc cctccttctt ctctattaag atcaatattc ctgcaggtca | 1140 |
| ggggcaagca gcagatgggt cacaggcttt tttcaaccag ttcttttcac aagcagcaga | 1200 |
| ttgcagatct ggatctggct aatatttaaa atcccttctt ttttccttct ccttgtccct | 1260 |
| ttttgttttt gcctctcttc accccatcc ctttctccca cgctcaggtc tctga | 1315 |

<210> SEQ ID NO 20
<211> LENGTH: 6036

<212> TYPE: DNA
<213> ORGANISM: artificial sequence
<220> FEATURE:
<223> OTHER INFORMATION: fusion construct homo sapiens and EGFP

<400> SEQUENCE: 20

| | | | | | |
|---|---|---|---|---|---|
| tagttattac | tagcgctacc | ggactcagat | ctcgagctca | agcttcgaat | ttaatcatag | 60 |
| gaggttgggg | ggattcacta | agcctgagtt | acatgggaga | agctggacaa | ggcactagga | 120 |
| cctagaaggc | atctatccac | cctggcagga | atttcttgct | tggagctcag | acaacaaagg | 180 |
| catagagaga | ttggttttct | ttctctcagc | atctccaccc | aaccagcaga | aaaccggtga | 240 |
| gtggggcttt | taagtgattt | tcaagaagaa | tgtaacagat | gtcaaacggg | aaaagcacaa | 300 |
| ggcaaagcct | gctctctctg | tctctctgtc | tcctcttctc | cttttttgcc | ttattctatc | 360 |
| cgattttttc | cctaagcttc | tacctgggat | tttcctttgg | aaaagtgagt | ttgatgttcc | 420 |
| tttgttttca | ctgtgatgtt | aatttagaat | aatactacct | ctgatcctaa | agcaaagcaa | 480 |
| agccttactg | gcatgcctgg | ggaaatgttt | gctgcttgcc | ttgaggaggt | ggggtctctt | 540 |
| accactgcag | gttgtctgac | agagacaatg | ctgagctcag | cataggtcat | ggtgacattg | 600 |
| gaaaaaggc | ggaattgagc | ctggcagacc | cattaggcac | cagtctttct | tatctcctgt | 660 |
| cctcctggtc | ccttgcaaat | atattgatgt | ggcagtgtgt | agcagctgag | ccctgcttgc | 720 |
| tttgtgagtc | cttttatccc | catctgtgag | atgcatgtta | atagtttggc | tcgtaggatg | 780 |
| tcactacatt | tgctagcatt | tgtggcttca | gttgtattgg | gtttcatgtt | ttgattgttt | 840 |
| ggggttcttg | gtgggggagg | gggttcaaca | gaagggagaa | aagcaaagcc | tgacaaatga | 900 |
| ccatcttttc | tcagctaatg | cacctgggca | atatacaagt | ttggggtgaa | ttgcctgctg | 960 |
| tgagggtaaa | tgtcacttca | attaaggtag | aaacccagaa | caatgaaagg | tgtgcttcct | 1020 |
| tctaaaggtc | ccgtatgctg | ttcggagagt | catttgtgaa | tctttcaaca | attaaattat | 1080 |
| tccattaaga | ggtgttgctg | catcagtggg | gaggggggtgg | agcacctggg | ggggaaaaaa | 1140 |
| aaggattttg | tgaacaaatg | gaaccggggg | aagacagagc | tagtaacttg | ttaaataact | 1200 |
| tatttttcta | atccttttc | ccccccagctt | attctcttatg | aatgtcggat | agctgcacca | 1260 |
| gcttggtggg | gaaagggttt | gatgaatagc | acaaagacac | tggctgttcc | ctggaggctg | 1320 |
| tcccttaaa | ggagaatctt | agtttattct | ggggggaggg | gatgcacaca | ttagagtagg | 1380 |
| aaagagggct | tggaataaaa | tgaaaacact | cccccttcat | agtcattgta | ctgaaatgca | 1440 |
| aagactgctt | cctaagctgg | agatgctaac | cttgggtagc | tccttctgtt | ctcttcaagg | 1500 |
| ggaattttgt | caggctatgg | attcatttac | aactgttagt | catgtgggca | tgtgtgagga | 1560 |
| aacagatgcc | agttttaatg | tatttagccc | gaagttccaa | tttgatagga | gccactgtca | 1620 |
| gtaagtctca | ggattttcag | ctatttcaaa | atctcccctt | ctcctctgtc | tggaacagtg | 1680 |
| ccaagagtgc | ctccctctct | atctcttact | cccaacccc | acaaccacca | gcaccccgc | 1740 |
| ccagcccctc | cttcttctct | attaagatca | atattcctgc | aggtcagggg | caagcagcag | 1800 |
| atgggtcaca | ggcttttttc | aaccagttct | tttcacaagc | agcagattgc | agatctggat | 1860 |
| ctggctaata | tttaaaatcc | cttctttttt | ccttctcctt | gtccctttt | gttttgcct | 1920 |
| ctcttcaccc | ccatcccttt | ctcccacgct | caggtctctg | agggatccac | cggtcgccac | 1980 |
| catggtgagc | aagggcgagg | agctgttcac | cggggtggtg | cccatcctgg | tcgagctgga | 2040 |
| cggcgacgta | aacggccaca | agttcagcgt | gtccggcgag | ggcgagggcg | atgccaccta | 2100 |
| cggcaagctg | accctgaagt | tcatctgcac | caccggcaag | ctgcccgtgc | cctggcccac | 2160 |

```
cctcgtgacc accctgacct acggcgtgca gtgcttcagc cgctaccccg accacatgaa    2220
gcagcacgac ttcttcaagt ccgccatgcc cgaaggctac gtccaggagc gcaccatctt    2280
cttcaaggac gacggcaact acaagacccg cgccgaggtg aagttcgagg gcgacaccct    2340
ggtgaaccgc atcgagctga agggcatcga cttcaaggag gacggcaaca tcctggggca    2400
caagctggag tacaactaca acagccacaa cgtctatatc atggccgaca agcagaagaa    2460
cggcatcaag gtgaacttca agatccgcca caacatcgag gacggcagcg tgcagctcgc    2520
cgaccactac cagcagaaca cccccatcgg cgacggcccc gtgctgctgc ccgacaacca    2580
ctacctgagc acccagtccg ccctgagcaa agaccccaac gagaagcgcg atcacatggt    2640
cctgctggag ttcgtgaccg ccgccgggat cactctcggc atggacgagc tgtacaagta    2700
aagcggccgc gactctagat cataatcagc cataccacat ttgtagaggt tttacttgct    2760
ttaaaaaacc tcccacacct ccccctgaac ctgaaacata aaatgaatgc aattgttgtt    2820
gttaacttgt ttattgcagc ttataatggt tacaaataaa gcaatagcat cacaaatttc    2880
acaaataaag cattttttc actgcattct agttgtggtt tgtccaaact catcaatgta    2940
tcttaaggcg taaattgtaa gcgttaatat tttgttaaaa ttcgcgttaa attttgtta    3000
aatcagctca ttttttaacc aataggccga atcggcaaa atcccttata atcaaaga    3060
atagaccgag atagggttga gtgttgttcc agtttggaac aagagtccac tattaaagaa    3120
cgtggactcc aacgtcaaag ggcgaaaaac cgtctatcag ggcgatggcc cactacgtga    3180
accatcaccc taatcaagtt ttttggggtc gaggtgccgt aaagcactaa atcggaaccc    3240
taaagggagc ccccgattta gagcttgacg gggaaagccg cgaacgtgg cgagaaagga    3300
agggaagaaa gcgaaaggag cgggcgctag gcgctggca agtgtagcgg tcacgctgcg    3360
cgtaaccacc acacccgccg cgcttaatgc gccgctacag ggcgcgtcag gtggcacttt    3420
tcggggaaat gtgcgcggaa cccctatttg tttattttc taaatacatt caaatatgta    3480
tccgctcatg agacaataac cctgataaat gcttcaataa tattgaaaaa ggaagagtcc    3540
tgaggcggaa agaaccagct gtggaatgtg tgtcagttag ggtgtggaaa gtccccaggc    3600
tccccagcag gcagaagtat gcaaagcatg catctcaatt agtcagcaac caggtgtgga    3660
aagtccccag gctccccagc aggcagaagt atgcaaagca tgcatctcaa ttagtcagca    3720
accatagtcc cgcccctaac tccgcccatc ccgcccctaa ctccgcccag ttccgcccat    3780
tctccgcccc atggctgact aatttttttt atttatgcag aggccgaggc cgcctcggcc    3840
tctgagctat tccagaagta gtgaggaggc tttttggag gcctaggctt ttgcaaagat    3900
cgatcaagag acaggatgag gatcgtttcg catgattgaa caagatggat tgcacgcagg    3960
ttctccggcc gcttgggtgg agaggctatt cggctatgac tgggcacaac agacaatcgg    4020
ctgctctgat gccgccgtgt tccggctgtc agcgcagggg cgcccggttc ttttgtcaa    4080
gaccgacctg tccggtgccc tgaatgaact gcaagacgag gcagcgcggc tatcgtggct    4140
ggccacgacg ggcgttcctt gcgcagctgt gctcgacgtt gtcactgaag cgggaaggga    4200
ctggctgcta ttgggcgaag tgccggggca ggatctcctg tcatctcacc ttgctcctgc    4260
cgagaaagta tccatcatgg ctgatgcaat gcggcggctg catacgcttg atccggctac    4320
ctgcccattc gaccaccaag cgaaacatcg catcgagcga gcacgtactc ggatggaagc    4380
cggtcttgtc gatcaggatg atctggacga agagcatcag gggctcgcgc cagccgaact    4440
gttcgccagg ctcaaggcga gcatgcccga cggcgaggat ctcgtcgtga cccatggcga    4500
tgcctgcttg ccgaatatca tggtggaaaa tggccgcttt tctggattca tcgactgtgg    4560
```

-continued

```
ccggctgggt gtggcggacc gctatcagga catagcgttg gctacccgtg atattgctga    4620
agagcttggc ggcgaatggg ctgaccgctt cctcgtgctt tacggtatcg ccgctcccga    4680
ttcgcagcgc atcgccttct atcgccttct tgacgagttc ttctgagcgg gactctgggg    4740
ttcgaaatga ccgaccaagc gacgcccaac ctgccatcac gagatttcga ttccaccgcc    4800
gccttctatg aaaggttggg cttcggaatc gttttccggg acgccggctg gatgatcctc    4860
cagcgcgggg atctcatgct ggagttcttc gcccaccta gggggaggct aactgaaaca    4920
cggaaggaga caataccgga aggaacccgc gctatgacgg caataaaaag acagaataaa    4980
acgcacggtg ttgggtcgtt tgttcataaa cgcggggttc ggtcccaggg ctggcactct    5040
gtcgataccc caccgagacc ccattggggc caatacgccc gcgtttcttc cttttcccca    5100
ccccaccccc caagttcggg tgaaggccca gggctcgcag ccaacgtcgg ggcggcaggc    5160
cctgccatag cctcaggtta ctcatatata ctttagattg atttaaaact tcatttttaa    5220
tttaaaagga tctaggtgaa gatcctttt gataatctca tgaccaaaat cccttaacgt    5280
gagttttcgt tccactgagc gtcagacccc gtagaaaaga tcaaaggatc ttcttgagat    5340 ccttttttc tgcgcgtaat ctgctgcttg caaacaaaaa aaccaccgct accagcggtg    5400
gtttgtttgc cggatcaaga gctaccaact ctttttccga aggtaactgg cttcagcaga    5460
gcgcagatac caaatactgt ccttctagtg tagccgtagt taggccacca cttcaagaac    5520
tctgtagcac cgcctacata cctcgctctg ctaatcctgt taccagtggc tgctgccagt    5580
ggcgataagt cgtgtcttac cgggttggac tcaagacgat agttaccgga taaggcgcag    5640
cggtcgggct gaacggggg ttcgtgcaca cagcccagct tggagcgaac gacctacacc    5700
gaactgagat acctacagcg tgagctatga gaaagcgcca cgcttcccga agggagaaag    5760
gcggacaggt atccggtaag cggcagggtc ggaacaggag agcgcacgag ggagcttcca    5820
gggggaaacg cctggtatct ttatagtcct gtcgggtttc gccacctctg acttgagcgt    5880
cgatttttgt gatgctcgtc agggggcgg agcctatgga aaaacgccag caacgcggcc    5940
tttttacggt tcctggcctt ttgctggcct tttgctcaca tgttctttcc tgcgttatcc    6000
cctgattctg tggataaccg tattaccgcc atgcat    6036
```

<210> SEQ ID NO 21
<211> LENGTH: 7238
<212> TYPE: DNA
<213> ORGANISM: artificial sequence
<220> FEATURE:
<223> OTHER INFORMATION: fusion construct homo sapiens and EGFP

<400> SEQUENCE: 21

```
tagttattac tagcgctacc ggactcagat ctcgaaattc tgcagtcgac ggtaccgcgg      60
gcccaacacc tattaatgcc cacatatctc aaacaaggaa atattgatcc tgcctatccc     120
tctgctctct attatatata aagcaaacaa agtcatttat cctaggctgt tcataaaaa     180 cattttgtag cttccacagt agcattgcaa agcctatatt atgaggaatt ttcctctgaa     240
atacattcca aatggttcgt gtttaagttt tattatccca tccattgttg tatcttcacc     300
agaaataaaa tgattttag ttctgatgca aaattaattg ctacatattt actgaatgct     360
tatgatgtgc aagaaagaag ttttaagaca ttagctttgt tggaatttcc atattttcct     420
gcccttattc cttgattttt ctttgcctct agcctgaata atgttgattt ttcatgaggt     480
tgccacaagg taaggcaaca acacatggaa gaaaacaggg cagacacatg cattcccctg     540
```

-continued

```
aggtacttgt atagtaacca agaaatcagc agcaaggtgt tgggggggact taactaggta    600
ggttgcacat ttgaggctat ccactcaact aacagacagt tccaggcttt gctgagtcaa    660
cacctttcac agaagaaaga ccatcatata ttttatccca cttggtggca gcttacaata    720
aaacacatgc agagaaaatg cttaaatata aagttcaac agcactatat aaaaggaagg    780
gttaattata ctaggaatca gatataaaat aattactgag catgctctta gctctgagct    840
tcctggaagc caagcaaaaa tagaaccatg atagttcaag gctgctacat attgatgcat    900
gtagcttcaa ttgtgaagat ggtagcatcc ccctacccca tttaacctct cacctttctc    960
ttttgtttta tagttcggcc tgatctaatt agttcaattt ggatgcttcc ttgagttttt   1020
tttgtaacat attttatata aagaagtcag ttagtgacaa ataagcagtt tgaggagaaa   1080
tctgttaata tttattttgt agccatcaga tttacttcac atagaaaggt ctttgggttg   1140
ggtttgaact tccaaactct caaaggtaaa tgccacatta ccttttcatt aaccaaattc   1200
ttacaccaag ctgatagatt tgggatgtcc tttttacttc tatcttccat aatattctaa   1260
aattattttc ccttgttttg ttcctatcct acttcctctt agtctacttt gttgacttca   1320
ttaaaaaaca aaaaaccagt tgttggatac ttgagctaaa ctgccttaaa gaatctgcag   1380
attttatttt attttttttc tctcaagagg gtaaaaggaa gagagctaca atttctaaga   1440
agcctggctt ggctgtctga gtctggcccc caggcagatt aggccaaggt tttggccaag   1500
tgaaattgcc aattttctaa agaaagggc tagcacattg ctcattagag cattctgatt   1560
ttgtctgcgc aatcttttg ctaccccgca atttcctgtt ggttataaat gaaacctttc   1620
tagctgttaa tgcagcctgt gaattttttt aaaagcatgt aattaatcat aggaggttgg   1680
ggggattcac taagcctgag ttacatggga gaagctggac aaggcactag gacctagaag   1740
gcatctatcc accctggcag gaatttcttg cttggagctc agcataggtc atggtgacat   1800
tggaaaaaag gcggaattga gcctggcaga cccattaggc accagtcttt cttatctcct   1860
gtcctcctgg tcccttgcaa atatattgat gtggcagtgt gtagcagctg agccctgctt   1920
gctttgtgag tccttttatc cccatctgtg agatgcatgt taatagtttg gctcgtagga   1980
tgtcactaca tttgctagca tttgtggctt cagttgtatt gggtttcatg ttttgattgt   2040
ttggggttct tggtggggga gggggttcaa cagaagggag aaaagcaaag cctgacaaat   2100
gaccatcttt tctcagctaa tgcacctggg caatatacaa gtttgggtg aattgcctgc   2160
tgtgagggta aatgtcactt caattaaggt agaaacccag aacaatgaaa ggtgtgcttc   2220
cttctaaagg tcccgtatgc tgttcggaga gtcatttgtg aatcttttcaa caattaaatt   2280
attccattaa gaggtgttgc tgcatcagtg gggagggggt ggagcacctg ggggggaaaa   2340
aaaaggattt tgtgaacaaa tggaaccggg ggaagacaga gctagtaact tgttaaataa   2400
cttattttc taatccttttt tccccccagc ttatttctta tgaatgtcgg atagctgcac   2460
cagcttggtg gggaaagggt ttgatgaata gcacaaagac actggctgtt ccctggaggc   2520
tgtccctta aaggagaatc ttagtttatt ctgggggag gggatgcaca cattagagta   2580
ggaaagaggg cttggaataa aatgaaaaca ctccccttc atagtcattg tactgaaatg   2640
caaagactgc ttcctaagct ggagatgcta accttgggta gctccttctg ttctcttcaa   2700
ggggaatttt gtcaggctat ggattcattt acaactgtta gtcatgtggg catgtgtgag   2760
gaaacagatg ccagttttaa tgtatttagc ccgaagttcc aatttgatag gagccactgt   2820
cagtaagtct caggattttc agctatttca aaatctcccc ttctcctctg tctgaacagg   2880
tgccaagagt gcctccctct ctatctctta ctcccaaccc ccacaaccac cagcaccccc   2940
```

```
gcccagcccc tccttcttct ctattaagat caatattcct gcaggtcagg ggcaagcagc    3000
agatgggtca caggcttttt tcaaccagtt cttttcacaa gcagcagatt gcagatctgg    3060
atctggctaa tatttaaaat cccttctttt ttccttctcc ttgtcccttt ttgtttttgc    3120
ctctcttcac ccccatccct ttctcccacg ctcaggtctc tgagggatcc accggtcgcc    3180
accatggtga gcaagggcga ggagctgttc accggggtgg tgcccatcct ggtcgagctg    3240
gacggcgacg taaacggcca caagttcagc gtgtccggcg agggcgaggg cgatgccacc    3300
tacggcaagc tgaccctgaa gttcatctgc accaccggca agctgcccgt gccctggccc    3360
accctcgtga ccaccctgac ctacggcgtg cagtgcttca gccgctaccc cgaccacatg    3420
aagcagcacg acttcttcaa gtccgccatg cccgaaggct acgtccagga gcgcaccatc    3480
ttcttcaagg acgacggcaa ctacaagacc cgcgccgagg tgaagttcga gggcgacacc    3540
ctggtgaacc gcatcgagct gaagggcatc gacttcaagg aggacggcaa catcctgggg    3600
cacaagctgg agtacaacta caacagccac aacgtctata tcatggccga caagcagaag    3660
aacggcatca aggtgaactt caagatccgc cacaacatcg aggacggcag cgtgcagctc    3720
gccgaccact accagcagaa cacccccatc ggcgacggcc ccgtgctgct gcccgacaac    3780
cactacctga gcacccagtc cgccctgagc aaagacccca acgagaagcg cgatcacatg    3840
gtcctgctgg agttcgtgac cgccgccggg atcactctcg gcatggacga gctgtacaag    3900
taaagcggcc gcgactctag atcataatca gccataccac atttgtagag gttttacttg    3960
ctttaaaaaa cctcccacac ctccccctga acctgaaaca taaaatgaat gcaattgttg    4020
ttgttaactt gtttattgca gcttataatg gttacaaata aagcaatagc atcacaaatt    4080
tcacaaataa agcatttttt tcactgcatt ctagttgtgg tttgtccaaa ctcatcaatg    4140
tatcttaagg cgtaaattgt aagcgttaat attttgttaa aattcgcgtt aaattttttgt    4200 taaatcagct cattttttaa ccataggcc gaaatcggca aaatccctta taatcaaaa    4260 gaatagaccg agataggtt gagtgttgtt ccagtttgga acaagagtcc actattaaag    4320
aacgtggact ccaacgtcaa agggcgaaaa accgtctatc agggcgatgg cccactacgt    4380
gaaccatcac cctaatcaag ttttttgggg tcgaggtgcc gtaaagcact aaatcggaac    4440
cctaaaggga gcccccgatt tagagcttga cggggaaagc cggcgaacgt ggcgagaaag    4500
gaagggaaga aagcgaaagg agcgggcgct agggcgctgg caagtgtagc ggtcacgctg    4560
cgcgtaacca ccacacccgc cgcgcttaat gcgccgctac agggcgcgtc aggtggcact    4620
tttcggggaa atgtgcgcgg aacccctatt tgtttatttt tctaaataca ttcaaatatg    4680
tatccgctca tgagacaata accctgataa atgcttcaat aatattgaaa aaggaagagt    4740
cctgaggcgg aaagaaccag ctgtggaatg tgtgtcagtt agggtgtgga agtccccag    4800 gctccccagc aggcagaagt atgcaaagca tgcatctcaa ttagtcagca accaggtgtg    4860
gaaagtcccc aggctcccca gcaggcagaa gtatgcaaag catgcatctc aattagtcag    4920
caaccatagt cccgccccta actccgccca tcccgcccct aactccgccc agttccgccc    4980
attctccgcc ccatggctga ctaatttttt ttatttatgc agaggccgag gccgcctcgg    5040
cctctgagct attccagaag tagtgaggag gctttttttgg aggcctaggc ttttgcaaag    5100
atcgatcaag agacaggatg aggatcgttt cgcatgattg aacaagatgg attgcacgca    5160
ggttctccgg ccgcttgggt ggagaggcta ttcggctatg actgggcaca acagacaatc    5220
ggctgctctg atgccgccgt gttccggctg tcagcgcagg ggcgcccggt tctttttgtc    5280
```

| | | |
|---|---|---|
| aagaccgacc tgtccggtgc cctgaatgaa ctgcaagacg aggcagcgcg gctatcgtgg | 5340 | |
| ctggccacga cgggcgttcc ttgcgcagct gtgctcgacg ttgtcactga agcgggaagg | 5400 | |
| gactggctgc tattgggcga agtgccgggg caggatctcc tgtcatctca ccttgctcct | 5460 | |
| gccgagaaag tatccatcat ggctgatgca atgcggcggc tgcatacgct tgatccggct | 5520 | |
| acctgcccat tcgaccacca agcgaaacat cgcatcgagc gagcacgtac tcggatggaa | 5580 | |
| gccggtcttg tcgatcagga tgatctggac gaagagcatc aggggctcgc gccagccgaa | 5640 | |
| ctgttcgcca ggctcaaggc gagcatgccc gacggcgagg atctcgtcgt gacccatggc | 5700 | |
| gatgcctgct tgccgaatat catggtggaa aatggccgct tttctggatt catcgactgt | 5760 | |
| ggccggctgg gtgtggcgga ccgctatcag gacatagcgt tggctacccg tgatattgct | 5820 | |
| gaagagcttg gcggcgaatg ggctgaccgc ttcctcgtgc tttacggtat cgccgctccc | 5880 | |
| gattcgcagc gcatcgcctt ctatcgcctt cttgacgagt tcttctgagc gggactctgg | 5940 | |
| ggttcgaaat gaccgaccaa gcgacgccca acctgccatc acgagatttc gattccaccg | 6000 | |
| ccgccttcta tgaaaggttg ggcttcggaa tcgttttccg ggacgccggc tggatgatcc | 6060 | |
| tccagcgcgg ggatctcatg ctggagttct cgcccacccc taggggagg ctaactgaaa | 6120 | |
| cacgaagga gacaataccg gaaggaaccc gcgctatgac ggcaataaaa agacagaata | 6180 | |
| aaacgcacgg tgttgggtcg tttgttcata aacgcggggt tcggtcccag ggctggcact | 6240 | |
| ctgtcgatac cccaccgaga ccccattggg gccaatacgc ccgcgtttct tccttttccc | 6300 | |
| caccccaccc cccaagttcg ggtgaaggcc cagggctcgc agccaacgtc ggggcggcag | 6360 | |
| gccctgccat agcctcaggt tactcatata tactttagat tgatttaaaa cttcatttt | 6420 | |
| aatttaaaag gatctaggtg aagatccttt ttgataatct catgaccaaa atcccttaac | 6480 | |
| gtgagttttc gttccactga gcgtcagacc ccgtagaaaa gatcaaagga tcttcttgag | 6540 | |
| atcctttttt tctgcgcgta atctgctgct tgcaaacaaa aaaaccaccg ctaccagcgg | 6600 | |
| tggtttgttt gccggatcaa gagctaccaa ctctttttcc gaaggtaact ggcttcagca | 6660 | |
| gagcgcagat accaaatact gtccttctag tgtagccgta gttaggccac cacttcaaga | 6720 | |
| actctgtagc accgcctaca tacctcgctc tgctaatcct gttaccagtg gctgctgcca | 6780 | |
| gtggcgataa gtcgtgtctt accgggttgg actcaagacg atagttaccg gataaggcgc | 6840 | |
| agcggtcggg ctgaacgggg ggttcgtgca cacagcccag cttggagcga acgacctaca | 6900 | |
| ccgaactgag atacctacag cgtgagctat gagaaagcgc cacgcttccc gaagggagaa | 6960 | |
| aggcggacag gtatccggta agcggcaggg tcggaacagg agagcgcacg agggagcttc | 7020 | |
| caggggggaaa cgcctggtat ctttatagtc ctgtcgggtt tcgccacctc tgacttgagc | 7080 | |
| gtcgattttt gtgatgctcg tcagggggc ggagcctatg gaaaaacgcc agcaacgcgg | 7140 | |
| ccttttttacg gttcctggcc ttttgctggc cttttgctca catgttcttt cctgcgttat | 7200 | |
| cccctgattc tgtggataac cgtattaccg ccatgcat | 7238 | |

<210> SEQ ID NO 22
<211> LENGTH: 7057
<212> TYPE: DNA
<213> ORGANISM: artificial sequence
<220> FEATURE:
<223> OTHER INFORMATION: fusion construct homo sapiens and EGFP

<400> SEQUENCE: 22

| | | |
|---|---|---|
| tagttattac tagcgctacc ggactcagat ctcgagctca agcttcgaat tctgcagtcg | 60 | |
| acggtaccgc gggcccaaca cctattaatg cccacatatc tcaaacaagg aaatattgat | 120 | |

```
cctgcctatc cctctgctct ctattatata taaagcaaac aaagtcattt atcctaggct      180
gtctcataaa aacattttgt agcttccaca gtagcattgc aaagcctata ttatgaggaa      240
ttttcctctg aaatacattc caaatggttc gtgtttaagt tttattatcc catccattgt      300
tgtatcttca ccagaaataa aatgattttt agttctgatg caaaattaat tgctacatat      360
ttactgaatg cttatgatgt gcaagaaaga agttttaaga cattagcttt gttggaattt      420
ccatattttc ctgcccttat tccttgtttt tctttgcct  ctagcctgaa taatgttgat      480
ttttcatgag gttgccacaa ggtaaggcaa caacacatgg aagaaaacag gcagacaca      540 tgcattcccc tgaggtactt gtatagtaac caagaaatca gcagcaaggt gttgggggga     600
cttaactagg taggttgcac atttgaggct atccactcaa ctaacagaca gttccaggct     660
ttgctgagtc aacacctttc acagaagaaa gaccatcata tattttatcc cacttggtgg    720
cagcttacaa taaacacat gcagagaaaa tgcttaaata taaaagttca acagcactat     780
ataaaaggaa gggttaatta tactaggaat cagatataaa ataattactg agcatgctct    840
tagctctgag cttcctggaa gccaagcaaa aatagaacca tgatagttca aggctgctac    900
atattgatgc atgtagcttc aattgtgaag atggtagcat cccctaccc  catttaacct    960 ctcacctttc tcttttgttt tatagttcgg cctgatctaa ttagttcaat ttggatgctt    1020
ccttgagttt ttttttgtaac atattttata taagaagtc  agttagtgac aaataagcag   1080
tttgaggaga aatctgttaa tatttatttt gtagccatca gatttacttc acatagaaag   1140
gtctttgggt tgggtttgaa cttccaaact ctcaaaggta aatgccacat taacctttca   1200
ttaaccaaat tcttcacacca agctgataga tttgggatgt cctttttact tctatcttcc   1260
ataatattct aaaattattt tcccttgttt tgttcctatc ctacttcctc ttagtctact   1320
ttgttgactt cattaaaaaa caaaaaacca gttgttggat acttgagcta aactgcctta   1380
aagaatctgc agattttatt ttatttttt  tctctcaaga gggtaaaagg aagagagcta   1440
caatttctaa gaagcctggc ttggctgtct gagtctggcc cccaggcaga ttaggccaag   1500
gttttggcca agtgaaattg ccaatttct  aaaagaaagg gctagcacat tgctcattag   1560
agcattctga ttttgtctgc gcaatctttt tgctaccccg caatttcctg ttggttataa   1620
atgaaacctt tctagctgtt aatgcagcct gtgaatttt  ttaaaagcat gtaattaatc   1680
ataggaggtt gggggggattc actaagcctg agttacatgg gagaagctgg acaaggcact   1740
aggacctaga aggcatctat ccaccctggc aggaatttct tgcttggagc tcagacaaca   1800
aaggcataga gagattggtt ttcttctct  cagcatctcc acccaaccag cagaaaaccg   1860
gtgagtgggg cttttaagtg attttcaaga agaatgtaac agatgtcaaa cgggaaaagc   1920
acaaggcaaa gcctgctctc tctgtctctc tgtctcctct tctccttttt tgccttattc    1980
tatccgattt tttcccctaag cttctacctg ggattttcct ttggaaaagt gagtttgatg   2040
ttcctttgtt ttcactgtga tgttaattta gaataatact acctctgatc ctaaagcaaa    2100
gcaaagcctt actggcatgc ctggggaaat gtttgctgct tgccttgagg aggtggggtc    2160
tcttaccact gcaggttgtc tgacagagac aatgctgaag ctagtaactt gttaaataac    2220
ttatttttct aatccttttt ccccccagct tatttcttat gaatgtcgga tagctgcacc    2280
agcttggtgg ggaaagggtt tgatgaatag cacaaagaca ctggctgttc cctggaggct    2340 gtcccttaa aggagaatct tagtttattc tgggggagg  ggatgcacac attagagtag    2400
gaaagagggc ttggaataaa atgaaaacac tcccccttca tagtcattgt actgaaatgc    2460
```

```
aaagactgct tcctaagctg agatgctaaa ccttgggtag ctccttctgt tctcttcaag    2520
gggaattttg tcaggctatg gattcattta caactgttag tcatgtgggc atgtgtgagg    2580
aaacagatgc cagttttaat gtatttagcc cgaagttcca atttgatagg agccactgtc    2640
agtaagtctc aggattttca gctatttcaa aatctcccct tctcctctgt ctggaacagt    2700
gccaagagtg cctccctctc tatctcttac tcccaacccc cacaaccacc agcaccccg     2760 cccagcccct ccttcttctc tattaagatc aatattcctg caggtcaggg gcaagcagca    2820
gatgggtcac aggcttttt caaccagttc ttttcacaag cagcagattg cagatctgga     2880
tctggctaat atttaaaatc ccttcttttt tccttctcct tgtcccttt tgttttgcc     2940 tctcttcacc cccatccctt tctcccacgc tcaggtctct gagggatcca ccggtcgcca    3000
ccatggtgag caagggcgag gagctgttca ccggggtggt gcccatcctg gtcgagctgg    3060
acggcgacgt aaacggccac aagttcagcg tgtccggcga gggcgagggc gatgccacct    3120
acggcaagct gaccctgaag ttcatctgca ccaccggcaa gctgcccgtg ccctggccca    3180 cccctcgtgac caccctgacc tacggcgtgc agtgcttcag ccgctacccc gaccacatga    3240
agcagcacga cttcttcaag tccgccatgc ccgaaggcta cgtccaggag cgcaccatct    3300
tcttcaagga cgacggcaac tacaagaccc gcgccgaggt gaagttcgag ggcgacaccc    3360
tggtgaaccg catcgagctg aagggcatcg acttcaagga ggacggcaac atcctggggc    3420
acaagctgga gtacaactac aacagccaca acgtctatat catggccgac aagcagaaga    3480
acggcatcaa ggtgaacttc aagatccgcc acaacatcga ggacggcagc gtgcagctcg    3540
ccgaccacta ccagcagaac acccccatcg gcgacggccc cgtgctgctg cccgacaacc    3600
actacctgag cacccagtcc gccctgagca agacccccaa cgagaagcgc gatcacatgg    3660
tcctgctgga gttcgtgacc gccgccggga tcactctcgg catggacgag ctgtacaagt    3720
aaagcggccg cgactctaga tcataatcag ccataccaca tttgtagagg ttttacttgc    3780
tttaaaaaac ctcccacacc tccccctgaa cctgaaacat aaaatgaatg caattgttgt    3840
tgttaacttg tttattgcag cttataatgg ttacaaataa agcaatagca tcacaaattt    3900
cacaaataaa gcatttttt cactgcattc tagttgtggt ttgtccaaac tcatcaatgt     3960
atcttaaggc gtaaattgta agcgttaata ttttgttaaa attcgcgtta aattttgtt    4020 aaatcagctc attttttaac caataggccg aaatcggcaa aatcccttat aaatcaaaag    4080
aatagaccga gatagggttg agtgttgttc cagtttggaa caagagtcca ctattaaaga    4140
acgtggactc caacgtcaaa gggcgaaaaa ccgtctatca gggcgatggc ccactacgtg    4200
aaccatcacc ctaatcaagt ttttgggt cgaggtgccg taaagcacta aatcggaacc      4260
ctaaagggag ccccgattt agagcttgac ggggaaagcc ggcgaacgtg gcgagaaagg     4320
aagggaagaa agcgaaagga gcgggcgcta gggcgctggc aagtgtagcg tcacgctgc     4380 gcgtaaccac cacacccgcc gcgcttaatg cgccgctaca gggcgcgtca ggtggcactt    4440
ttcggggaaa tgtgcgcgga accctatt gtttatttt ctaaatacat tcaaatatgt       4500
atccgctcat gagacaataa ccctgataaa tgcttcaata atattgaaaa aggaagagtc    4560
ctgaggcgga agaaccagc tgtggaatgt gtgtcagtta gggtgtggaa agtccccagg     4620
ctccccagca ggcagaagta tgcaaagcat gcatctcaat tagtcagcaa ccaggtgtgg    4680
aaagtcccca ggctcccag caggcagaag tatgcaaagc atgcatctca attagtcagc     4740
aaccatagtc ccgcccctaa ctccgcccat cccgccccta ctccgcccca gttccgccca    4800
ttctccgccc catggctgac taattttttt tatttatgca gaggccgagg ccgcctcggc    4860
```

```
ctctgagcta ttccagaagt agtgaggagg cttttttgga ggcctaggct tttgcaaaga   4920
tcgatcaaga gacaggatga ggatcgtttc gcatgattga acaagatgga ttgcacgcag   4980
gttctccggc cgcttgggtg gagaggctat tcggctatga ctgggcacaa cagacaatcg   5040
gctgctctga tgccgccgtg ttccggctgt cagcgcaggg gcgcccggtt cttttttgtca  5100
agaccgacct gtccggtgcc ctgaatgaac tgcaagacga ggcagcgcgg ctatcgtggc   5160
tggccacgac gggcgttcct tgcgcagctg tgctcgacgt tgtcactgaa gcgggaaggg   5220
actggctgct attgggcgaa gtgccggggc aggatctcct gtcatctcac cttgctcctg   5280
ccgagaaagt atccatcatg gctgatgcaa tgcggcggct gcatacgctt gatccggcta   5340
cctgcccatt cgaccaccaa gcgaaacatc gcatcgagcg agcacgtact cggatggaag   5400
ccggtcttgt cgatcaggat gatctggacg aagagcatca ggggctcgcg ccagccgaac   5460
tgttcgccag gctcaaggcg agcatgcccg acggcgagga tctcgtcgtg acccatggcg   5520
atgcctgctt gccgaatatc atggtggaaa atggccgctt ttctggattc atcgactgtg   5580
gccggctggg tgtggcggac cgctatcagg acatagcgtt ggctacccgt gatattgctg   5640
aagagcttgg cggcgaatgg gctgaccgct tcctcgtgct ttacggtatc gccgctcccg   5700
attcgcagcg catcgccttc tatcgccttc ttgacgagtt cttctgagcg ggactctggg   5760
gttcgaaatg accgaccaag cgacgcccaa cctgccatca cgagatttcg attccaccgc   5820
cgccttctat gaaaggttgg gcttcggaat cgttttccgg gacgccggct ggatgatcct   5880
ccagcgcggg gatctcatgc tggagttctt cgcccaccct aggggaggc taactgaaac   5940
acggaaggag acaataccgg aaggaacccg cgctatgacg caataaaaa gacagaataa   6000
aacgcacggt gttgggtcgt tgttcataa acgcggggtt cggtcccagg gctggcactc   6060
tgtcgatacc ccaccgagac cccattgggg ccaatacgcc cgcgtttctt ccttttcccc   6120
accccacccc caagttcgg gtgaaggccc agggctcgca gccaacgtcg gggcggcagg   6180
ccctgccata gcctcaggtt actcatatat actttagatt gatttaaaac ttcatttta    6240
atttaaaagg atctaggtga agatcctttt tgataatctc atgaccaaaa tcccttaacg   6300
tgagttttcg ttccactgag cgtcagaccc cgtagaaaag atcaaggat cttcttgaga   6360
tcctttttt ctgcgcgtaa tctgctgctt gcaaacaaaa aaaccaccgc taccagcggt   6420
ggtttgtttg ccggatcaag agctaccaac tcttttccg aaggtaactg gcttcagcag   6480
agcgcagata ccaaatactg tccttctagt gtagccgtag ttaggccacc acttcaagaa   6540
ctctgtagca ccgcctacat acctcgctct gctaatcctg ttaccagtgg ctgctgccag   6600
tggcgataag tcgtgtctta ccgggttgga ctcaagacga tagttaccgg ataaggcgca   6660
gcggtcgggc tgaacggggg gttcgtgcac acagcccagc ttggagcgaa cgacctacac   6720
cgaactgaga tacctacagc gtgagctatg agaaagcgcc acgcttcccg aagggagaaa   6780
ggcggacagg tatccggtaa gcggcagggt cggaacagga gagcgcacga gggagcttcc   6840
agggggaaac gcctggtatc tttatagtcc tgtcgggttt cgccacctct gacttgagcg   6900
tcgatttttg tgatgctcgt caggggggcg gagcctatgg aaaaacgcca gcaacgcggc   6960
cttttttacgg ttcctggcct tttgctggcc ttttgctcac atgttctttc ctgcgttatc   7020
ccctgattct gtggataacc gtattaccgc catgcat                            7057
```

<210> SEQ ID NO 23
<211> LENGTH: 6278
<212> TYPE: DNA

<213> ORGANISM: artificial sequence
<220> FEATURE:
<223> OTHER INFORMATION: fusion construct homo sapiens and EGFP

<400> SEQUENCE: 23

| | | | | | |
|---|---|---|---|---|---|
| tagttattac | tagcgctacc | ggactcagat | ctcgagctca | agcttcgaat | tctgcagtcg | 60 |
| acggtaccgc | gggcccaaca | cctattaatg | cccacatatc | tcaaacaagg | aaatattgat | 120 |
| cctgcctatc | cctctgctct | ctattatata | taaagcaaac | aaagtcattt | atcctaggct | 180 |
| gtctcataaa | aacattttgt | agcttccaca | gtagcattgc | aaagcctata | ttatgaggaa | 240 |
| ttttcctctg | aaatacattc | caaatggttc | gtgtttaagt | tttattatcc | catccattgt | 300 |
| tgtatcttca | ccagaaataa | aatgattttt | agttctgatg | caaaattaat | tgctacatat | 360 |
| ttactgaatg | cttatgatgt | gcaagaaaga | agttttaaga | cattagcttt | gttggaattt | 420 |
| ccatattttc | ctgcccttat | tccttgattt | ttctttgcct | ctagcctgaa | taatgttgat | 480 |
| ttttcatgag | gttgccacaa | ggtaaggcaa | caacacatgg | aagaaaacag | ggcagacaca | 540 |
| tgcattcccc | tgaggtactt | gtatagtaac | caagaaatca | gcagcaaggt | gttgggggga | 600 |
| cttaactagg | taggttgcac | atttgaggct | atccactcaa | ctaacagaca | gttccaggct | 660 |
| tgctgagtc | aacacctttc | acagaagaaa | gaccatcata | tattttatcc | cacttggtgg | 720 |
| cagcttacaa | taaaacacat | gcagagaaaa | tgcttaaata | taaagttca | acagcactat | 780 |
| ataaaaggaa | gggttaatta | tactaggaat | cagatataaa | ataattactg | agcatgctct | 840 |
| tagctctgag | cttcctggaa | gccaagcaaa | aatagaacca | tgatagttca | aggctgctac | 900 |
| atattgatgc | atgtagcttc | aattgtgaag | atggtagcat | cccctaccc | catttaacct | 960 |
| ctcacctttc | tcttttgttt | tatagttcgg | cctgatctaa | ttagttcaat | ttggatgctt | 1020 |
| ccttgagttt | ttttgtaac | atattttata | taaagaagtc | agttagtgac | aaataagcag | 1080 |
| tttgaggaga | aatctgttaa | tatttatttt | gtagccatca | gatttacttc | acatagaaag | 1140 |
| gtctttgggt | tgggtttgaa | cttccaaact | ctcaaaggta | aatgccacat | taacctttca | 1200 |
| ttaaccaaat | tcttacacca | agctgataga | tttgggatgt | cctttttact | tctatcttcc | 1260 |
| ataatattct | aaaattattt | tcccttgttt | tgttcctatc | ctacttcctc | ttagtctact | 1320 |
| ttgttgactt | cattaaaaaa | caaaaaacca | gttgttggat | acttgagcta | aactgcctta | 1380 |
| aagaatctgc | agatttttatt | ttattttttt | tctctcaaga | gggtaaaagg | aagagagcta | 1440 |
| caatttctaa | gaagcctggc | ttggctgtct | gagtctggcc | cccaggcaga | ttaggccaag | 1500 |
| gttcttggtg | gggaaagggt | ttgatgaata | gcacaaagac | actggctgtt | ccctggaggc | 1560 |
| tgtccctta | aaggagaatc | ttagtttatt | ctgggggag | gggatgcaca | cattagagta | 1620 |
| ggaaagaggg | cttggaataa | aatgaaaaca | ctcccccttc | atagtcattg | tactgaaatg | 1680 |
| caaagactgc | ttcctaagct | ggagatgcta | accttgggta | gctccttctg | ttctcttcaa | 1740 |
| ggggaatttt | gtcaggctat | ggattcattt | acaactgtta | gtcatgtggg | catgtgtgag | 1800 |
| gaaacagatg | ccagttttaa | tgtatttagc | ccgaagttcc | aatttgatag | gagccactgt | 1860 |
| cagtaagtct | caggattttc | agctatttca | aaatctcccc | ttctcctctg | tctggaacag | 1920 |
| tgccaagagt | gcctccctct | ctatctctta | ctcccaaccc | ccacaaccac | cagcaccccc | 1980 |
| gcccagcccc | tccttcttct | ctattaagat | caatattcct | gcaggtcagg | ggcaagcagc | 2040 |
| agatgggtca | caggcttttt | tcaaccagtt | cttttcacaa | gcagcagatt | gcagatctgg | 2100 |
| atctggctaa | tatttaaaat | cccttctttt | ttccttctcc | ttgtcccttt | tgttttttgc | 2160 |
| ctctcttcac | ccccatccct | ttctcccacg | ctcaggtctc | tgagggatcc | accggtcgcc | 2220 |

```
accatggtga gcaagggcga ggagctgttc accggggtgg tgcccatcct ggtcgagctg   2280
gacggcgacg taaacggcca caagttcagc gtgtccggcg agggcgaggg cgatgccacc   2340
tacggcaagc tgaccctgaa gttcatctgc accaccggca agctgcccgt gccctggccc   2400
accctcgtga ccaccctgac ctacggcgtg cagtgcttca gccgctaccc cgaccacatg   2460
aagcagcacg acttcttcaa gtccgccatg cccgaaggct acgtccagga gcgcaccatc   2520
ttcttcaagg acgacggcaa ctacaagacc cgcgccgagg tgaagttcga gggcgacacc   2580
ctggtgaacc gcatcgagct gaagggcatc gacttcaagg aggacggcaa catcctgggg   2640
cacaagctgg agtacaacta caacagccac aacgtctata tcatggccga caagcagaag   2700
aacggcatca aggtgaactt caagatccgc cacaacatcg aggacggcag cgtgcagctc   2760
gccgaccact accagcagaa cacccccatc ggcgacggcc ccgtgctgct gcccgacaac   2820
cactacctga gcacccagtc cgccctgagc aaagaccccca acgagaagcg cgatcacatg   2880
gtcctgctgg agttcgtgac cgccgccggg atcactctcg gcatggacga gctgtacaag   2940
taaagcggcc gcgactctag atcataatca gccataccac atttgtagag gttttacttg   3000
ctttaaaaaa cctcccacac ctccccctga acctgaaaca taaaatgaat gcaattgttg   3060
ttgttaactt gtttattgca gcttataatg gttacaaata agcaatagc atcacaaatt   3120 tcacaaataa agcattttttt tcactgcatt ctagttgtgg tttgtccaaa ctcatcaatg   3180
tatcttaagg cgtaaattgt aagcgttaat attttgttaa aattcgcgtt aaattttttgt   3240 taaatcagct cattttttaa ccataggcc gaaatcggca aaatccctta taaatcaaaa   3300
gaatagaccg agatagggtt gagtgttgtt ccagtttgga acaagagtcc actattaaag   3360
aacgtggact ccaacgtcaa agggcgaaaa accgtctatc agggcgatgg cccactacgt   3420
gaaccatcac cctaatcaag ttttttgggg tcgaggtgcc gtaaagcact aaatcggaac   3480
cctaaaggga gcccccgatt tagagcttga cggggaaagc cggcgaacgt ggcgagaaag   3540
gaagggaaga agcgaaagg agcgggcgct agggcgctgg caagtgtagc ggtcacgctg   3600
cgcgtaacca ccacacccgc cgcgcttaat gcgccgctac agggcgcgtc aggtggcact   3660
tttcggggaa atgtgcgcgg aacccctatt tgtttatttt tctaaataca ttcaaatatg   3720
tatccgctca tgagacaata accctgataa atgcttcaat aatattgaaa aaggaagagt   3780
cctgaggcgg aaagaaccag ctgtggaatg tgtgtcagtt agggtgtgga aagtccccag   3840
gctccccagc aggcagaagt atgcaaagca tgcatctcaa ttagtcagca accaggtgtg   3900
gaaagtcccc aggctcccca gcaggcagaa gtatgcaaag catgcatctc aattagtcag   3960
caaccatagt cccgcccta actccgccca tcccgcccct aactccgccc agttccgccc   4020
attctccgcc ccatggctga ctaatttttt ttatttatgc agaggccgag gccgcctcgg   4080
cctctgagct attccagaag tagtgaggag gcttttttgg aggcctaggc ttttgcaaag   4140
atcgatcaag agacaggatg aggatcgttt cgcatgattg aacaagatgg attgcacgca   4200
ggttctccgg ccgcttgggt ggagaggcta ttcggctatg actgggcaca acagacaatc   4260
ggctgctctg atgccgccgt gttccggctg tcagcgcagg ggcgcccggt tctttttgtc   4320
aagaccgacc tgtccggtgc cctgaatgaa ctgcaagacg aggcagcgcg gctatcgtgg   4380
ctggccacga cgggcgttcc ttgcgcagct gtgctcgacg ttgtcactga agcgggaagg   4440
gactggctgc tattgggcga agtgccgggg caggatctcc tgtcatctca ccttgctcct   4500
gccgagaaag tatccatcat ggctgatgca atgcggcggc tgcatacgct tgatccggct   4560
```

```
acctgcccat tcgaccacca agcgaaacat cgcatcgagc gagcacgtac tcggatggaa    4620
gccggtcttg tcgatcagga tgatctggac gaagagcatc aggggctcgc gccagccgaa    4680
ctgttcgcca ggctcaaggc gagcatgccc gacggcgagg atctcgtcgt gacccatggc    4740
gatgcctgct tgccgaatat catggtggaa aatggccgct tttctggatt catcgactgt    4800
ggccggctgg gtgtggcgga ccgctatcag gacatagcgt tggctacccg tgatattgct    4860
gaagagcttg gcggcgaatg ggctgaccgc ttcctcgtgc tttacggtat cgccgctccc    4920
gattcgcagc gcatcgcctt ctatcgcctt cttgacgagt tcttctgagc gggactctgg    4980
ggttcgaaat gaccgaccaa gcgacgccca acctgccatc acgagatttc gattccaccg    5040
ccgccttcta tgaaaggttg ggcttcggaa tcgttttccg gacgccggc tggatgatcc     5100 tccagcgcgg ggatctcatg ctggagttct cgcccaccc taggggagg ctaactgaaa      5160 cacggaagga gacaataccg gaaggaaccc gcgctatgac ggcaataaaa agacagaata    5220
aaacgcacgg tgttgggtcg tttgttcata acgcggggt tcggtcccag ggctggcact     5280
ctgtcgatac cccaccgaga ccccattggg gccaatacgc ccgcgtttct tccttttccc    5340
caccccaccc cccaagttcg ggtgaaggcc cagggctcgc agccaacgtc ggggcggcag    5400
gccctgccat agcctcaggt tactcatata tactttagat tgatttaaaa cttcattttt    5460
aatttaaaag gatctaggtg aagatccttt ttgataatct catgaccaaa atcccttaac    5520
gtgagttttc gttccactga gcgtcagacc ccgtagaaaa gatcaaagga tcttcttgag    5580
atcctttttt tctgcgcgta atctgctgct tgcaaacaaa aaaaccaccg ctaccagcgg    5640
tggtttgttt gccggatcaa gagctaccaa ctcttttttcc gaaggtaact ggcttcagca    5700
gagcgcagat accaaatact gtccttctag tgtagccgta gttaggccac cacttcaaga    5760
actctgtagc accgcctaca tacctcgctc tgctaatcct gttaccagtg gctgctgcca    5820
gtggcgataa gtcgtgtctt accgggttgg actcaagacg atagttaccg gataaggcgc    5880
agcggtcggg ctgaacgggg ggttcgtgca cacagcccag cttggagcga acgacctaca    5940
ccgaactgag atacctacag cgtgagctat gagaaagcgc cacgcttccc gaagggagaa    6000
aggcggacag gtatccggta agcggcaggg tcggaacagg agagcgcacg agggagcttc    6060 caggggaaa cgcctggtat ctttatagtc ctgtcgggtt tcgccacctc tgacttgagc     6120
gtcgattttt gtgatgctcg tcagggggc ggagcctatg gaaaaacgcc agcaacgcgg     6180 ccttttacg gttcctggcc ttttgctggc cttttgctca catgttcttt cctgcgttat      6240
cccctgattc tgtggataac cgtattaccg ccatgcat                              6278
```

<210> SEQ ID NO 24
<211> LENGTH: 6495
<212> TYPE: DNA
<213> ORGANISM: artificial sequence
<220> FEATURE:
<223> OTHER INFORMATION: fusion construct homo sapiens and EGFP

<400> SEQUENCE: 24

```
tagttattac tagcgctacc ggactcagat ctcgagctca agcttcgaat tctgcagtcg     60
acggtaccgc gggcccctttt ttacttctat cttccataat attctaaaat tattttccct    120
tgttttgttc ctatcctact tcctcttagt ctactttgtt gacttcatta aaaaacaaaa    180
aaccagttgt tggatacttg agctaaactg ccttaaagaa tctgcagatt ttatttttatt    240 tttttctct caagagggta aaaggaagag agctacaatt tctaagaagc ctggcttggc      300
tgtctgagtc tggccccccag gcagattagg ccaaggtttt ggccaagtga aattgccaat    360
```

-continued

```
tttctaaaag aaagggctag cacattgctc attagagcat tctgattttg tctgcgcaat      420
cttttttgcta ccccgcaatt tcctgttggt tataaatgaa acctttctag ctgttaatgc     480
agcctgtgaa ttttttttaaa agcatgtaat taatcatagg aggttggggg gattcactaa    540
gcctgagtta catgggagaa gctggacaag gcactaggac ctagaaggca tctatccacc     600
ctggcaggaa tttcttgctt ggagctcaga caacaaaggc atagagagat tggttttctt    660
tctctcagca tctccaccca accagcagaa aaccggtgag tggggctttt aagtgatttt    720
caagaagaat gtaacagatg tcaaacggga aaagcacaag gcaaagcctg ctctctctgt    780
ctctctgtct cctcttctcc ttttttgcct tattctatcc gatttttcc ctaagcttct     840
acctgggatt ttcctttgga aaagtgagtt tgatgttcct ttgttttcac tgtgatgtta    900
atttagaata atactacctc tgatcctaaa gcaaagcaaa gccttactgg catgcctggg    960
gaaatgtttg ctgcttgcct tgaggaggtg gggtctctta ccactgcagg ttgtctgaca   1020
gagacaatgc tgagctcagc ataggtcatg gtgacattgg aaaaaaggcg gaattgagcc   1080
tggcagaccc attaggcacc agtctttctt atctcctgtc ctcctggtcc cttgcaaata   1140
tattgatgtg gcagtgtgta gcagctgagc cctgcttgct ttgtgagtcc ttttatcccc   1200
atctgtgaga tgcatgttaa tagtttggct cgtaggatgt cactacattt gctagcattt   1260
gtggcttcag ttgtattggg tttcatgttt tgattgtttg gggttcttgg tgggggaggg   1320
ggttcaacag aagggagaaa agcaaagcct gacaaatgac catcttttct cagctaatgc   1380
acctgggcaa tatacaagtt tggggtgaat tgcctgctgt gagggtaaat gtcacttcaa   1440
ttaaggtaga aacccagaac aatgaaaggt gtgcttcctt ctaaaggtcc cgtatgctgt   1500
tcggagagtc atttgtgaat ctttcaacaa ttaaattatt ccattaagag gtgttgctgc   1560
atcagtgggg aggggtgga gcacctgggg gggaaaaaaa aggattttgt gaacaaatgg    1620
aaccggggga agacagagct agtaacttgt taaataactt attttctaa tccttttttcc   1680
ccccagctta tttcttatga atgtcggata gctgcaccag cttggtgggg aaagggtttg   1740
atgaatagca caaagacact ggctgttccc tggaggctgt ccctttaaag gagaatctta   1800
gtttattctg gggggagggg atgcacacat tagagtagga aagagggctt ggaataaaat   1860
gaaaacactc ccccttcata gtcattgtac tgaaatgcaa agactgcttc ctaagctgga   1920
gatgctaacc ttgggtagct ccttctgttc tcttcaaggg gaattttgtc aggctatgga   1980
ttcatttaca actgttagtc atgtgggcat gtgtgaggaa acagatgcca gttttaatgt   2040
atttagcccg aagttccaat ttgataggag ccactgtcag taagtctcag gattttcagc   2100
tatttcaaaa tctccccttc tcctctgtct ggaacagtgc caagagtgcc tccctctcta   2160
tctcttactc ccaaccccca caaccaccag cacccccgcc cagcccctcc ttcttctcta   2220
ttaagatcaa tattcctgca ggtcaggggc aagcagcaga tgggtcacag gcttttttca   2280
accagttctt ttcacaagca gcagattgca gatctggatc tggctaatat ttaaaatccc   2340
ttctttttttc cttctccttg tccttttttg tttttgcctc tcttcacccc catcccttttc  2400
tcccacgctc aggtctctga gggatccacc ggtcgccacc atggtgagca agggcgagga   2460
gctgttcacc ggggtggtgc ccatcctggt cgagctggac ggcgacgtaa acggccacaa   2520
gttcagcgtg tccggcgagg gcgagggcga tgccacctac ggcaagctga ccctgaagtt   2580
catctgcacc accggcaagc tgcccgtgcc ctggcccacc ctcgtgacca ccctgaccta   2640
cggcgtgcag tgcttcagcc gctaccccga ccacatgaag cagcacgact tcttcaagtc   2700
```

```
cgccatgccc gaaggctacg tccaggagcg caccatcttc ttcaaggacg acggcaacta    2760
caagacccgc gccgaggtga agttcgaggg cgacaccctg gtgaaccgca tcgagctgaa    2820
gggcatcgac ttcaaggagg acggcaacat cctggggcac aagctggagt acaactacaa    2880
cagccacaac gtctatatca tggccgacaa gcagaagaac ggcatcaagg tgaacttcaa    2940
gatccgccac aacatcgagg acggcagcgt gcagctcgcc gaccactacc agcagaacac    3000
ccccatcggc gacggccccg tgctgctgcc cgacaaccac tacctgagca ccagtccgc    3060 cctgagcaaa gaccccaacg agaagcgcga tcacatggtc ctgctggagt tcgtgaccgc    3120
cgccgggatc actctcggca tggacgagct gtacaagtaa agcggccgcg actctagatc    3180
ataatcagcc ataccacatt tgtagaggtt ttacttgctt taaaaaacct cccacacctc    3240
cccctgaacc tgaaacataa aatgaatgca attgttgttg ttaacttgtt tattgcagct    3300
tataatggtt acaaataaag caatagcatc acaaatttca caaataaagc atttttttca    3360
ctgcattcta gttgtggttt gtccaaactc atcaatgtat cttaaggcgt aaattgtaag    3420
cgttaatatt ttgttaaaat tcgcgttaaa ttttttgttaa atcagctcat tttttaacca    3480
ataggccgaa atcggcaaaa tcccttataa atcaaaagaa tagaccgaga tagggttgag    3540
tgttgttcca gtttggaaca agagtccact attaaagaac gtggactcca acgtcaaagg    3600
gcgaaaaacc gtctatcagg gcgatggccc actacgtgaa ccatcaccct aatcaagttt    3660
tttggggtcg aggtgccgta aagcactaaa tcggaacccct aaaggagcc cccgatttag    3720 agcttgacgg ggaaagccgg cgaacgtggc gagaaaggaa gggaagaaag cgaaaggagc    3780
gggcgctagg gcgctggcaa gtgtagcggt cacgctgcgc gtaaccacca cccgccgc    3840 gcttaatgcg ccgctacagg gcgcgtcagg tggcactttt cggggaaatg tgcgcggaac    3900
ccctatttgt ttatttttct aaatacattc aaatatgtat ccgctcatga caataaacc    3960 ctgataaatg cttcaataat attgaaaaag gaagagtcct gaggcggaaa gaaccagctg    4020
tggaatgtgt gtcagttagg gtgtggaaag tccccaggct ccccagcagg cagaagtatg    4080
caaagcatgc atctcaatta gtcagcaacc aggtgtggaa agtccccagg ctccccagca    4140
ggcagaagta tgcaaagcat gcatctcaat tagtcagcaa ccatagtccc gcccctaact    4200
ccgcccatcc cgcccctaac tccgcccagt tccgcccatt ctccgcccca tggctgacta    4260 attttttta tttatgcaga ggccgaggcc gcctcggcct ctgagctatt ccagaagtag    4320
tgaggaggct ttttttggagg cctaggcttt tgcaaagatc gatcaagaga caggatgagg    4380
atcgtttcgc atgattgaac aagatggatt gcacgcaggt tctccggccg cttgggtgga    4440
gaggctattc ggctatgact gggcacaaca gacaatcggc tgctctgatg ccgccgtgtt    4500
ccggctgtca gcgcaggggc gcccggttct ttttgtcaag accgacctgt ccggtgccct    4560
gaatgaactg caagacgagg cagcgcggct atcgtggctg gccacgacgg cgttccttg    4620 cgcagctgtg ctcgacgttg tcactgaagc gggaagggac tggctgctat tgggcgaagt    4680
gccggggcag gatctcctgt catctcacct tgctcctgcc gagaaagtat ccatcatggc    4740
tgatgcaatg cggcggctgc atacgcttga tccggctacc tgcccattcg accaccaagc    4800
gaaacatcgc atcgagcgag cacgtactcg gatggaagcc ggtcttgtcg atcaggatga    4860
tctggacgaa gagcatcagg ggctcgcgcc agccgaactg ttcgccaggc tcaaggcgag    4920
catgcccgac ggcgaggatc tcgtcgtgac ccatggcgat gcctgcttgc cgaatatcat    4980
ggtggaaaat ggccgctttt ctggattcat cgactgtggc cggctgggtg tggcggaccg    5040
ctatcaggac atagcgttgg ctacccgtga tattgctgaa gagcttggcg gcgaatgggc    5100
```

```
tgaccgcttc ctcgtgcttt acggtatcgc cgctcccgat tcgcagcgca tcgccttcta      5160
tcgccttctt gacgagttct tctgagcggg actctggggt tcgaaatgac cgaccaagcg      5220
acgcccaacc tgccatcacg agatttcgat tccaccgccg ccttctatga aggttgggc      5280 ttcggaatcg ttttccggga cgccggctgg atgatcctcc agcgcgggga tctcatgctg      5340
gagttcttcg cccaccctag ggggaggcta actgaaacac ggaaggagac aataccggaa      5400
ggaacccgcg ctatgacggc aataaaaaga cagaataaaa cgcacggtgt tgggtcgttt      5460
gttcataaac gcggggttcg gtcccagggc tggcactctg tcgatacccc accgagaccc      5520
cattggggcc aatacgcccg cgtttcttcc ttttccccac cccaccccca aagttcgggt      5580
gaaggcccag ggctcgcagc caacgtcggg gcggcaggcc ctgccatagc ctcaggttac      5640
tcatatatac tttagattga tttaaaactt cattttaat ttaaaggat ctaggtgaag      5700 atccttttg ataatctcat gaccaaaatc ccttaacgtg agttttcgtt ccactgagcg      5760 tcagacccg tagaaaagat caaaggatct tcttgagatc cttttttct gcgcgtaatc      5820 tgctgcttgc aaacaaaaaa accaccgcta ccagcggtgg tttgtttgcc ggatcaagag      5880
ctaccaactc tttttccgaa ggtaactggc ttcagcagag cgcagatacc aaatactgtc      5940
cttctagtgt agccgtagtt aggccaccac ttcaagaact ctgtagcacc gcctacatac      6000
ctcgctctgc taatcctgtt accagtggct gctgccagtg gcgataagtc gtgtcttacc      6060
gggttggact caagacgata gttaccggat aaggcgcagc ggtcgggctg aacggggggt      6120
tcgtgcacac agcccagctt ggagcgaacg acctacaccg aactgagata cctacagcgt      6180
gagctatgag aaagcgccac gcttcccgaa gggagaaagg cggacaggta tccggtaagc      6240
ggcagggtcg gaacaggaga gcgcacgagg gagcttccag ggggaaacgc ctggtatctt      6300
tatagtcctg tcgggtttcg ccacctctga cttgagcgtc gatttttgtg atgctcgtca      6360
ggggggcgga gcctatggaa aaacgccagc aacgcggcct ttttacggtt cctggccttt      6420
tgctggcctt ttgctcacat gttctttcct gcgttatccc ctgattctgt ggataaccgt      6480
attaccgcca tgcat                                                      6495
```

<210> SEQ ID NO 25
<211> LENGTH: 5466
<212> TYPE: DNA
<213> ORGANISM: artificial sequence
<220> FEATURE:
<223> OTHER INFORMATION: fusion construct homo sapiens and EGFP

<400> SEQUENCE: 25

```
tagttattac tagcgctacc ggactcagat ctcgagctca agcttcgaat tctgcagtcg       60
acggtaccgc gggccccttt ttacttctat cttccataat attctaaaat tattttccct      120
tgttttgttc ctatcctact tcctcttagt ctactttgtt gacttcatta aaaacaaaa      180 aaccagttgt tggatacttg agctaaactg ccttaaagaa tctgcagatt ttattttatt      240 tttttctct caagagggta aaaggaagag agctacaatt tctaagaagc ctggcttggc      300
tgtctgagtc tggccccccag gcagattagg ccaaggtttt ggccaagtga aattgccaat      360
tttctaaaag aaagggctag cacattgctc attagagcat tctgattttg tctgcgcaat      420 cttttttgcta ccccgcaatt tcctgttggt tataaatgaa cctttctag ctgttaatgc      480 agcctgtgaa ttttttaaa agcatgtaat taatcatagg aggttggggg gattcactaa      540
gcctgagtta catgggagaa gctggacaag gcactaggac ctagaaggca tctatccacc      600
```

```
ctggcaggaa tttcttgctt ggagctcaga caacaaaggc atagagagat tggttttctt    660
tctctcagca tctccaccca accagcagaa aaccggtgag tggggctttt aagtgatttt    720
caagaagaat gtaacagatg tcaaacggga aaagcacaag gcaaagcctg ctctctctgt    780
ctctctgtct cctcttctcc tttttttgcct tattctatcc gattttttcc ctaagcttct   840
acctgggatt ttcctttgga aaagtgagtt tgatgttcct ttgttttcac tgtgatgtta    900
atttagaata atactacctc tgatcctaaa gcaaagcaaa gccttactgg catgcctggg    960
aactgttagt catgtgggca tgtgtgagga aacagatgcc agttttaatg tatttagccc   1020
gaagttccaa tttgatagga gccactgtca gtaagtctca ggattttcag ctatttcaaa   1080
atctcccctt ctcctctgtc tggaacagtg ccaagagtgc ctccctctct atctcttact   1140
cccaaccccc acaaccacca gcaccccgc ccagcccctc cttcttctct attaagatca    1200
atattcctgc aggtcagggg caagcagcag atgggtcaca ggctttttc aaccagttct    1260 tttcacaagc agcagattgc agatctggat ctggctaata tttaaaatcc cttctttttt    1320
ccttctcctt gtcccttttt gttttgcct ctcttcaccc ccatccctt ctcccacgct    1380 caggtctctg agggatccac cggtcgccac catggtgagc aagggcgagg agctgttcac   1440
cggggtggtg cccatcctgg tcgagctgga cggcgacgta aacggccaca agttcagcgt   1500
gtccggcgag ggcgagggcg atgccaccta cggcaagctg accctgaagt tcatctgcac   1560
caccggcaag ctgcccgtgc cctggcccac cctcgtgacc accctgacct acggcgtgca   1620
gtgcttcagc cgctaccccg accacatgaa gcagcacgac ttcttcaagt ccgccatgcc   1680
cgaaggctac gtccaggagc gcaccatctt cttcaaggac gacggcaact acaagacccg   1740
cgccgaggtg aagttcgagg gcgacaccct ggtgaaccgc atcgagctga agggcatcga   1800
cttcaaggag gacggcaaca tcctggggca agctggagta caactaca cagccacaa    1860 cgtctatatc atggccgaca gcagaagaa cggcatcaag gtgaacttca gatccgcca    1920 caacatcgag gacggcagcg tgcagctcgc cgaccactac cagcagaaca ccccatcgg   1980 cgacggcccc gtgctgctgc cgacaacca ctacctgagc acccagtccg ccctgagcaa   2040
agaccccaac gagaagcgcg atcacatggt cctgctggag ttcgtgaccg ccgcgggat    2100 cactctcggc atggacgagc tgtacaagta aagcggccgc gactctagat cataatcagc   2160
cataccacat ttgtagaggt tttacttgct ttaaaaaacc tcccacacct cccctgaac    2220 ctgaaacata aaatgaatgc aattgttgtt gttaacttgt ttattgcagc ttataatggt   2280
tacaaataaa gcaatagcat cacaaatttc acaaataaag cattttttc actgcattct    2340 agttgtggtt tgtccaaact catcaatgta tcttaaggcg taaattgtaa gcgttaatat   2400
tttgttaaaa ttcgcgttaa attttttgtta aatcagctca ttttttaacc aataggccga   2460
aatcggcaaa atcccttata atcaaaaga atagaccgag ataggggttga gtgttgttcc    2520 agtttggaac aagagtccac tattaaagaa cgtggactcc aacgtcaaag gcgaaaaac    2580 cgtctatcag ggcgatggcc cactacgtga accatcaccc taatcaagtt ttttggggtc   2640
gaggtgccgt aaagcactaa atcggaaccc taaagggagc ccccgattta gagcttgacg   2700
gggaaagccg cgaacgtgg cgagaaagga agggaagaaa gcgaaaggag cgggcgctag   2760
ggcgctggca agtgtagcgg tcacgctgcg cgtaaccacc acaccgccg cgcttaatgc   2820 gccgctacag ggcgcgtcag gtggcacttt tcggggaaat gtgcgcggaa ccctatttg    2880 tttatttttc taaatacatt caaatatgta tccgctcatg agacaataac cctgataaat   2940
gcttcaataa tattgaaaaa ggaagagtcc tgaggcggaa agaaccagct gtggaatgtg   3000
```

-continued

```
tgtcagttag ggtgtggaaa gtccccaggc tccccagcag gcagaagtat gcaaagcatg   3060
catctcaatt agtcagcaac caggtgtgga aagtccccag gctccccagc aggcagaagt   3120
atgcaaagca tgcatctcaa ttagtcagca accatagtcc cgcccctaac tccgcccatc   3180
ccgcccctaa ctccgcccag ttccgcccat tctccgcccc atggctgact aattttttt   3240 atttatgcag aggccgaggc cgcctcggcc tctgagctat tccagaagta gtgaggaggc   3300
ttttttggag gcctaggctt ttgcaaagat cgatcaagag acaggatgag gatcgtttcg   3360
catgattgaa caagatggat tgcacgcagg ttctccggcc gcttgggtgg agaggctatt   3420
cggctatgac tgggcacaac agacaatcgg ctgctctgat gccgccgtgt tccggctgtc   3480
agcgcagggg cgcccggttc tttttgtcaa gaccgacctg tccggtgccc tgaatgaact   3540
gcaagacgag gcagcgcggc tatcgtggct ggccacgacg ggcgttcctt gcgcagctgt   3600
gctcgacgtt gtcactgaag cgggaaggga ctggctgcta ttgggcgaag tgccggggca   3660
ggatctcctg tcatctcacc ttgctcctgc cgagaaagta tccatcatgg ctgatgcaat   3720
gcggcggctg catacgcttg atccggctac ctgcccattc gaccaccaag cgaaacatcg   3780
catcgagcga gcacgtactc ggatggaagc cggtcttgtc gatcaggatg atctggacga   3840
agagcatcag gggctcgcgc cagccgaact gttcgccagg ctcaaggcga gcatgcccga   3900
cggcgaggat ctcgtcgtga cccatggcga tgcctgcttg ccgaatatca tggtggaaaa   3960
tggccgcttt tctggattca tcgactgtgg ccggctgggt gtggcggacc gctatcagga   4020
catagcgttg gctacccgtg atattgctga agagcttggc ggcgaatggg ctgaccgctt   4080
cctcgtgctt tacggtatcg ccgctcccga ttcgcagcgc atcgccttct atcgccttct   4140
tgacgagttc ttctgagcgg gactctgggg ttcgaaatga ccgaccaagc gacgcccaac   4200
ctgccatcac gagatttcga ttccaccgcc gccttctatg aaaggttggg cttcggaatc   4260
gttttccggg acgccggctg gatgatcctc cagcgcgggg atctcatgct ggagttcttc   4320
gcccacccta gggggaggct aactgaaaca cggaaggaga caataccgga aggaacccgc   4380
gctatgacgg caataaaaag acagaataaa acgcacggtg ttgggtcgtt tgttcataaa   4440
cgcggggttc ggtcccaggg ctggcactct gtcgataccc caccgagacc ccattgggc   4500 caatacgccc gcgtttcttc cttttcccca ccccacccc caagttcggg tgaaggccca   4560
gggctcgcag ccaacgtcgg ggcggcaggc cctgccatag cctcaggtta tcatatata   4620 ctttagattg atttaaaact tcattttaa tttaaaagga tctaggtgaa gatccttttt   4680
gataatctca tgaccaaaat cccttaacgt gagttttcgt tccactgagc gtcagacccc   4740
gtagaaaaga tcaaaggatc ttcttgagat cctttttttc tgcgcgtaat ctgctgcttg   4800
caaacaaaaa aaccaccgct accagcggtg gtttgtttgc cggatcaaga gctaccaact   4860
ctttttccga aggtaactgg cttcagcaga gcgcagatac caaatactgt ccttctagtg   4920
tagccgtagt taggccacca cttcaagaac tctgtagcac cgcctacata cctcgctctg   4980
ctaatcctgt taccagtggc tgctgccagt ggcgataagt cgtgtcttac cgggttggac   5040
tcaagacgat agttaccgga taaggcgcag cggtcgggct gaacggggg ttcgtgcaca   5100 cagcccagct tggagcgaac gacctacacc gaactgagat acctacagcg tgagctatga   5160
gaaagcgcca cgcttcccga agggagaaag gcggacaggt atccggtaag cggcagggtc   5220
ggaacaggag agcgcacgag ggagcttcca gggggaaacg cctggtatct ttatagtcct   5280
gtcgggtttc gccacctctg acttgagcgt cgatttttgt gatgctcgtc agggggggcgg   5340
```

| | |
|---|---|
| agcctatgga aaaacgccag caacgcggcc tttttacggt tcctggcctt ttgctggcct | 5400 |
| tttgctcaca tgttctttcc tgcgttatcc cctgattctg tggataaccg tattaccgcc | 5460 |
| atgcat | 5466 |

<210> SEQ ID NO 26
<211> LENGTH: 5468
<212> TYPE: DNA
<213> ORGANISM: artificial sequence
<220> FEATURE:
<223> OTHER INFORMATION: fusion construct homo sapiens and luciferase

<400> SEQUENCE: 26

| | |
|---|---|
| aacacctatt aatgcccaca tatctcaaac aaggaaatat tgatcctgcc tatccctctg | 60 |
| ctctctatta tatataaagc aaacaaagtc atttatccta ggctgtctca taaaaacatt | 120 |
| ttgtagcttc cacagtagca ttgcaaagcc tatattatga ggaattttcc tctgaaatac | 180 |
| attccaaatg gttcgtgttt aagttttatt atcccatcca ttgttgtatc ttcaccagaa | 240 |
| ataaaatgat tttagttct gatgcaaaat taattgctac atatttactg aatgcttatg | 300 |
| atgtgcaaga aagaagtttt aagacattag ctttgttgga atttccatat tttcctgccc | 360 |
| ttattccttg atttttcttt gcctctagcc tgaataatgt tgattttca tgaggttgcc | 420 |
| acaaggtaag gcaacaacac atggaagaaa acagggcaga cacatgcatt cccctgaggt | 480 |
| acttgtatag taaccaagaa atcagcagca aggtgttggg gggacttaac taggtaggtt | 540 |
| gcacatttga ggctatccac tcaactaaca gacagttcca ggctttgctg agtcaacacc | 600 |
| tttcacagaa gaaagaccat catatatttt atcccacttg gtggcagctt acaataaaac | 660 |
| acatgcagag aaaatgctta aatataaaag ttcaacagca ctatataaaa ggaagggtta | 720 |
| attatactag gaatcagata taaaataatt actgagcatg ctcttagctc tgagcttcct | 780 |
| ggaagccaag caaaaataga accatgatag ttcaaggctg ctacatattg atgcatgtag | 840 |
| cttcaattgt gaagatggta gcatcccct accccattta acctctcacc tttctctttt | 900 |
| gttttatagt tcggcctgat ctaattagtt caatttggat gcttccttga gttttttttg | 960 |
| taacatattt tatataaaga agtcagttag tgacaaataa gcagtttgag gagaaatctg | 1020 |
| ttaatattta ttttgtagcc atcagattta cttcacatag aaaggtcttt gggttgggtt | 1080 |
| tgaacttcca aactctcaaa ggtaaatgcc acattaacct ttcattaacc aaattcttac | 1140 |
| accaagctga tagatttggg atgtccttt tacttctatc ttccataata ttctaaaatt | 1200 |
| atttccctt gttttgttcc tatcctactt cctcttagtc tactttgttg acttcattaa | 1260 |
| aaaacaaaaa accagttgtt ggatacttga gctaaactgc cttaaagaat ctgcagattt | 1320 |
| tattttattt tttttctctc aagagggtaa aaggaagaga gctacaattt ctaagaagcc | 1380 |
| tggcttggct gtctgagtct ggcccccagg cagattaggc caaggttttg gccaagtgaa | 1440 |
| attgccaatt ttctaaaaga aagggctagc acattgctca ttagagcatt ctgattttgt | 1500 |
| ctgcgcaatc tttttgctac cccgcaattt cctgttggtt ataaatgaaa cctttctagc | 1560 |
| tgttaatgca gcctgtgaat ttttttaaaa gcatgtaatt aatcatagga ggttgggggg | 1620 |
| attcactaag cctgagttac atgggagaag ctggacaagg cactaggacc tagaaggcat | 1680 |
| ctatccaccc tggcaggaat tcttgcttg gagctcagac aacaaaggca tagagagatt | 1740 |
| ggttttcttt ctctcagcat ctccacccaa ccagcagaaa accggtgagt ggggctttta | 1800 |
| agtgattttc aagaagaatg taacagatgt caaacgggaa aagcacaagg caaagcctgc | 1860 |
| tctctctgtc tctctgtctc tcttctcct tttttgcctt attctatccg attttttccc | 1920 |

| | |
|---|---|
| taagcttcta cctgggattt tcctttggaa aagtgagttt gatgttcctt tgttttcact | 1980 |
| gtgatgttaa tttagaataa tactacctct gatcctaaag caaagcaaag ccttactggc | 2040 |
| atgcctgggg aaatgtttgc tgcttgcctt gaggaggtgg ggtctcttac cactgcaggt | 2100 |
| tgtctgacag agacaatgct gagctcagca taggtcatgg tgacattgga aaaaaggcgg | 2160 |
| aattgagcct ggcagaccca ttaggcacca gtctttctta tctcctgtcc tcctggtccc | 2220 |
| ttgcaaatat attgatgtgg cagtgtgtag cagctgagcc ctgcttgctt tgtgagtcct | 2280 |
| tttatcccca tctgtgagat gcatgttaat agtttggctc gtaggatgtc actacatttg | 2340 |
| ctagcatttg tggcttcagt tgtattgggt ttcatgtttt gattgtttgg ggttcttggt | 2400 |
| gggggagggg gttcaacaga agggagaaaa gcaaagcctg acaaatgacc atcttttctc | 2460 |
| agctaatgca cctgggcaat atacaagttt ggggtgaatt gcctgctgtg agggtaaatg | 2520 |
| tcacttcaat taaggtagaa acccagaaca atgaaaggtg tgcttccttc taaaggtccc | 2580 |
| gtatgctgtt cggagagtca tttgtgaatc tttcaacaat taattattc cattaagagg | 2640 |
| tgttgctgca tcagtgggga gggggtggag cacctggggg ggaaaaaaaa ggattttgtg | 2700 |
| aacaaatgga accgggggaa gacagagcta gtaacttgtt aaataactta tttttctaat | 2760 |
| cctttttccc cccagcttat ttcttatgaa tgtcggatag ctgcaccagc ttggtgggga | 2820 |
| aagggtttga tgaatagcac aaagacactg gctgttccct ggaggctgtc cctttaaagg | 2880 |
| agaatcttag tttattctgg ggggagggga tgcacacatt agagtaggaa agagggcttg | 2940 |
| gaataaaatg aaaacactcc cccttcatag tcattgtact gaaatgcaaa gactgcttcc | 3000 |
| taagctggag atgctaacct tgggtagctc cttctgttct cttcaagggg aattttgtca | 3060 |
| ggctatggat tcatttacaa ctgttagtca tgtgggcatg tgtgaggaaa cagatgccag | 3120 |
| ttttaatgta tttagcccga agttccaatt tgataggagc cactgtcagt aagtctcagg | 3180 |
| attttcagct atttcaaaat ctccccttct cctctgtctg gaacagtgcc aagagtgcct | 3240 |
| ccctctctat ctcttactcc caaccccac aaccaccagc acccccgccc agcccctcct | 3300 |
| tcttctctat taagatcaat attcctgcag gtcaggggca agcagcagat gggtcacagg | 3360 |
| cttttttcaa ccagttcttt tcacaagcag cagattgcag atctggatct ggctaatatt | 3420 |
| taaaatccct tctttttttcc ttctccttgt cccttttgt ttttgcctct cttcacccc | 3480 |
| atcccttct cccacgctca ggtctctgag ggatctgcga tctaagtaag cttggcattc | 3540 |
| cggtactgtt ggtaaagcca ccatggaaga cgccaaaaac ataagaaag gcccggcgcc | 3600 |
| attctatccg ctggaagatg gaaccgctgg agagcaactg cataaggcta tgaagagata | 3660 |
| cgccctggtt cctggaacaa ttgcttttac agatgcacat atcgaggtgg acatcactta | 3720 |
| cgctgagtac ttcgaaatgt ccgttcggtt ggcagaagct atgaaacgat atgggctgaa | 3780 |
| tacaaatcac agaatcgtcg tatgcagtga aaactctctt caattcttta tgccggtgtt | 3840 |
| gggcgcgtta tttatcggag ttgcagttgc cccgcgaac gacatttata tgaacgtga | 3900 |
| attgctcaac agtatgggca tttcgcagcc taccgtggtg ttcgtttcca aaagggtt | 3960 |
| gcaaaaaatt ttgaacgtgc aaaaaaagct cccaatcatc caaaaaatta ttatcatgga | 4020 |
| ttctaaaacg gattaccagg gatttcagtc gatgtacacg ttcgtcacat ctcatctacc | 4080 |
| tcccggtttt aatgaatacg attttgtgcc agagtccttc gatagggaca agacaattgc | 4140 |
| actgatcatg aactcctctg gatctactgg tctgcctaaa ggtgtcgctc tgcctcatag | 4200 |
| aactgcctgc gtgagattct cgcatgccag agatcctatt tttggcaatc aaatcattcc | 4260 |

| | |
|---|---|
| ggatactgcg attttaagtg ttgttccatt ccatcacggt tttggaatgt ttactacact | 4320 |
| cggatatttg atatgtggat ttcgagtcgt cttaatgtat agatttgaag aagagctgtt | 4380 |
| tctgaggagc cttcaggatt acaagattca aagtgcgctg ctggtgccaa ccctattctc | 4440 |
| cttcttcgcc aaaagcactc tgattgacaa atacgattta tctaatttac acgaaattgc | 4500 |
| ttctggtggc gctcccctct ctaaggaagt cggggaagcg gttgccaaga ggttccatct | 4560 |
| gccaggtatc aggcaaggat atgggctcac tgagactaca tcagctattc tgattacacc | 4620 |
| cgaggggat gataaaccgg gcgcggtcgg taaagttgtt ccattttttg aagcgaaggt | 4680 |
| tgtggatctg ataccggga aaacgctggg cgttaatcaa agaggcgaac tgtgtgtgag | 4740 |
| aggtcctatg attatgtccg gttatgtaaa caatccggaa gcgaccaacg ccttgattga | 4800 |
| caaggatgga tggctacatt ctggagacat agcttactgg gacgaagacg aacacttctt | 4860 |
| catcgttgac cgcctgaagt ctctgattaa gtacaaaggc tatcaggtgg ctcccgctga | 4920 |
| attggaatcc atcttgctcc aacacccaa catcttcgac gcaggtgtcg caggtcttcc | 4980 |
| cgacgatgac gccggtgaac ttcccgccgc cgttgttgtt ttggagcacg aaagacgat | 5040 |
| gacggaaaaa gagatcgtgg attacgtcgc cagtcaagta acaaccgcga aaaagttgcg | 5100 |
| cggaggagtt gtgtttgtgg acgaagtacc gaaaggtctt accggaaaac tcgacgcaag | 5160 |
| aaaaatcaga gagatcctca taaaggccaa gaagggcgga agatcgccg tgtaattcta | 5220 |
| gagtcggggc ggccggccgc ttcgagcaga catgataaga tacattgatg agtttggaca | 5280 |
| aaccacaact agaatgcagt gaaaaaaatg ctttatttgt gaatttgtg atgctattgc | 5340 |
| tttatttgta accattataa gctgcaataa acaagttaac aacaacaatt gcattcattt | 5400 |
| tatgtttcag gttcagggg aggtgtggga ggttttttaa agcaagtaaa acctctacaa | 5460 |
| atgtggta | 5468 |

<210> SEQ ID NO 27
<211> LENGTH: 8307
<212> TYPE: DNA
<213> ORGANISM: artificial sequence
<220> FEATURE:
<223> OTHER INFORMATION: fusion construct homo sapiens and luciferase

<400> SEQUENCE: 27

| | |
|---|---|
| ggtaccgcgg gcccaacacc tattaatgcc cacatatctc aaacaaggaa atattgatcc | 60 |
| tgcctatccc tctgctctct attatatata aagcaaacaa agtcatttat cctaggctgt | 120 |
| ctcataaaaa cattttgtag cttccacagt agcattgcaa agcctatatt atgaggaatt | 180 |
| ttcctctgaa atacattcca aatggttcgt gtttaagttt tattatccca tccattgttg | 240 |
| tatcttcacc agaaataaaa tgattttag ttctgatgca aaattaattg ctacatattt | 300 |
| actgaatgct tatgatgtgc aagaaagaag ttttaagaca ttagctttgt tggaatttcc | 360 |
| atatttcct gcccttattc cttgattttt ctttgcctct agcctgaata atgttgattt | 420 |
| ttcatgaggt tgccacaagg taaggcaaca acacatggaa gaaacaggg cagacacatg | 480 |
| cattcccctg aggtacttgt atagtaacca agaaatcagc agcaaggtgt tgggggact | 540 |
| taactaggta ggttgcacat ttgaggctat ccactcaact aacagacagt tccaggctt | 600 |
| gctgagtcaa caccttcac agaagaaaga ccatcatata ttttatccca cttggtggca | 660 |
| gcttacaata aaacacatgc agagaaaatg cttaaatata aagttcaac agcactatat | 720 |
| aaaaggaagg gttaattata ctaggaatca gatataaaat aattactgag catgctctta | 780 |
| gctctgagct tcctggaagc caagcaaaaa tagaaccatg atagttcaag gctgctacat | 840 |

```
attgatgcat gtagcttcaa ttgtgaagat ggtagcatcc ccctacccca tttaacctct      900
cacctttctc ttttgtttta tagttcggcc tgatctaatt agttcaattt ggatgcttcc      960
ttgagttttt tttgtaacat attttatata aagaagtcag ttagtgacaa ataagcagtt     1020
tgaggagaaa tctgttaata tttattttgt agccatcaga tttacttcac atagaaaggt     1080
ctttgggttg ggtttgaact tccaaactct caaaggtaaa tgccacatta acctttcatt     1140
aaccaaattc ttacaccaag ctgatagatt tgggatgtcc tttttacttc tatcttccat     1200
aatattctaa aattatttc ccttgtttg ttcctatcct acttcctctt agtctacttt       1260
gttgacttca ttaaaaaaca aaaaccagt tgttggatac ttgagctaaa ctgccttaaa      1320
gaatctgcag atttttatttt atttttttc tctcaagagg gtaaaaggaa gagagctaca     1380
atttctaaga agcctggctt ggctgtctga gtctggcccc caggcagatt aggccaaggt     1440
tttggccaag tgaaattgcc aattttctaa aagaaagggc tagcacattg ctcattagag     1500
cattctgatt ttgtctgcgc aatcttttg ctacccgca atttcctgtt ggttataaat       1560
gaaacctttc tagctgttaa tgcagcctgt gaattttttt aaaagcatgt aattaatcat     1620
aggaggttgg ggggattcac taagcctgag ttacatggga gaagctggac aaggcactag    1680
gacctagaag gcatctatcc accctggcag gaatttcttg cttggagctc agacaacaaa    1740
ggcatagaga gattggtttt ctttctctca gcatctccac ccaaccagca gaaaaccggt    1800
gagtggggct tttaagtgat tttcaagaag aatgtaacag atgtcaaacg ggaaaagcac    1860
aaggcaaagc ctgctctctc tgtctctctg tctcctcttc tccttttttg ccttattcta    1920
tccgattttt tccctaagct tctacctggg attttccttt ggaaaagtga gtttgatgtt    1980
cctttgtttt cactgtgatg ttaatttaga ataatactac ctctgatcct aaagcaaagc    2040
aaagccttac tggcatgcct ggggaaatgt ttgctgcttg ccttgaggag gtggggtctc    2100
ttaccactgc aggttgtctg acagagacaa tgctgagctc agcataggtc atggtgacat    2160
tggaaaaaag gcggaattga gcctggcaga cccattaggc accagtcttt cttatctcct    2220
gtcctcctgg tcccttgcaa atatattgat gtggcagtgt gtagcagctg agccctgctt    2280
gctttgtgag tccttttatc cccatctgtg agatgcatgt taatagtttg gctcgtagga    2340
tgtcactaca tttgctagca tttgtggctt cagttgtatt gggtttcatg ttttgattgt    2400
ttggggttct tggtggggga gggggttcaa cagaaggag aaaagcaaag cctgacaaat    2460
gaccatcttt tctcagctaa tgcacctggg caatatacaa gtttggggtg aattgcctgc    2520
tgtgagggta aatgtcactt caattaaggt agaaacccag aacaatgaaa ggtgtgcttc    2580
cttctaaagg tcccgtatgc tgttcggaga gtcatttgtg aatctttcaa caattaaatt    2640
attccattaa gaggtgttgc tgcatcagtg gggaggggt ggagcacctg ggggggaaaa    2700
aaaaggattt tgtgaacaaa tggaaccggg ggaagacaga gctagtaact tgttaaataa    2760
cttatttttc taatcctttt tcccccagc ttatttctta tgaatgtcgg atagctgcac     2820
cagcttggtg gggaaagggt ttgatgaata gcacaaagac actggctgtt ccctggaggc    2880
tgtccctta aaggagaatc ttagtttatt ctgggggag gggatgcaca cattagagta     2940
ggaaagaggg cttggaataa aatgaaaaca ctcccccttc atagtcattg tactgaaatg    3000
caaagactgc ttcctaagct ggagatgcta accttgggta gctccttctg ttctcttcaa    3060
ggggaatttt gtcaggctat ggattcattt acaactgtta gtcatgtggg catgtgtgag    3120
gaaacagatg ccagttttaa tgtatttagc ccgaagttcc aatttgatag gagccactgt    3180
```

```
cagtaagtct caggatttc agctatttca aaatctcccc ttctcctctg tctggaacag    3240
tgccaagagt gcctccctct ctatctctta ctcccaaccc ccacaaccac cagcaccccc    3300
gcccagcccc tccttcttct ctattaagat caatattcct gcaggtcagg ggcaagcagc    3360
agatgggtca caggcttttt tcaaccagtt cttttcacaa gcagcagatt gcagatctgg    3420
atctggctaa tatttaaaat cccttctttt ttccttctcc ttgtcccttt ttgttttttgc   3480
ctctcttcac ccccatccct ttctcccacg ctcaggtctc tgagggatct gcgatctaag    3540
taagcttggc attccggtac tgttggtaaa gccaccatgg aagacgccaa aaacataaag    3600
aaaggcccgg cgccattcta tccgctggaa gatggaaccg ctggagagca actgcataag    3660
gctatgaaga gatacgccct ggttcctgga acaattgctt ttacagatgc acatatcgag    3720
gtggacatca cttacgctga gtacttcgaa atgtccgttc ggttggcaga agctatgaaa    3780
cgatatgggc tgaatacaaa tcacagaatc gtcgtatgca gtgaaaactc tcttcaattc    3840
tttatgccgg tgttgggcgc gttatttatc ggagttgcag ttgcgcccgc gaacgacatt    3900
tataatgaac gtgaattgct caacagtatg ggcatttcgc agcctaccgt ggtgttcgtt    3960
tccaaaaagg ggttgcaaaa aattttgaac gtgcaaaaaa agctcccaat catccaaaaa    4020
attattatca tggattctaa aacggattac cagggatttc agtcgatgta cacgttcgtc    4080
acatctcatc tacctcccgg ttttaatgaa tacgattttg tgccagagtc cttcgataggg   4140
gacaagacaa ttgcactgat catgaactcc tctggatcta ctggtctgcc taaaggtgtc    4200
gctctgcctc atagaactgc ctgcgtgaga ttctcgcatg ccagagatcc tattttttggc   4260
aatcaaatca ttccggatac tgcgatttta agtgttgttc cattccatca cggttttgga    4320
atgtttacta cactcggata tttgatatgt ggatttcgag tcgtcttaat gtatagattt    4380
gaagaagagc tgtttctgag gagccttcag gattacaaga ttcaaagtgc gctgctggtg    4440
ccaaccctat tctccttctt cgccaaaagc actctgattg acaaatacga tttatctaat    4500
ttacacgaaa ttgcttctgg tggcgctccc ctctctaagg aagtcgggga agcggttgcc    4560
aagaggttcc atctgccagg tatcaggcaa ggatatgggc tcactgagac tacatcagct    4620
attctgatta cacccgaggg ggatgataaa ccgggcgcgg tcggtaaagt tgttccattt    4680
tttgaagcga aggttgtgga tctggatacc gggaaaacgc tgggcgttaa tcaaagaggc    4740
gaactgtgtg tgagaggtcc tatgattatg tccggttatg taaacaatcc ggaagcgacc    4800
aacgccttga ttgacaagga tggatggcta cattctggag acatagctta ctgggacgaa    4860
gacgaacact tcttcatcgt tgaccgcctg aagtctctga ttaagtacaa aggctatcag    4920
gtggctcccg ctgaattgga atccatcttg ctccaacacc ccaacatctt cgacgcaggt    4980
gtcgcaggtc ttcccgacga tgacgccggt gaacttcccg ccgccgttgt tgttttggag    5040
cacggaaaga cgatgacgga aaagagatc gtggattacg tcgccagtca agtaacaacc    5100
gcgaaaagt tgcgcggagg agttgtgttt gtggacgaag taccgaaagg tcttaccgga    5160
aaactcgacg caagaaaaat cagagagatc ctcataaagg ccaagaaggg cggaaagatc    5220
gccgtgtaat tctagagtcg gggcggccgg ccgcttcgag cagacatgat aagatacatt    5280
gatgagtttg gacaaaccac aactagaatg cagtgaaaaa aatgctttat ttgtgaaatt    5340
tgtgatgcta ttgcttttatt tgtaaccatt ataagctgca ataaacaagt taacaacaac    5400
aattgcattc attttatgtt tcaggttcag ggggaggtgt gggaggtttt ttaaagcaag    5460
taaaacctct acaaatgtgg taaaatcgat aaggatccgt cgaccgatgc ccttgagagc    5520
cttcaaccca gtcagctcct tccggtgggc gcggggcatg actatcgtcg ccgcacttat    5580
```

```
gactgtcttc tttatcatgc aactcgtagg acaggtgccg gcagcgctct tccgcttcct    5640
cgctcactga ctcgctgcgc tcggtcgttc ggctgcggcg agcggtatca gctcactcaa    5700
aggcggtaat acggttatcc acagaatcag gggataacgc aggaaagaac atgtgagcaa    5760
aaggccagca aaaggccagg aaccgtaaaa aggccgcgtt gctggcgttt ttccataggc    5820
tccgcccccc tgacgagcat cacaaaaatc gacgctcaag tcagaggtgg cgaaacccga    5880
caggactata aagataccag gcgtttcccc ctggaagctc cctcgtgcgc tctcctgttc    5940
cgaccctgcc gcttaccgga tacctgtccg cctttctccc ttcgggaagc gtggcgcttt    6000
ctcatagctc acgctgtagg tatctcagtt cggtgtaggt cgttcgctcc aagctgggct    6060
gtgtgcacga accccccgtt cagcccgacc gctgcgcctt atccggtaac tatcgtcttg    6120
agtccaaccc ggtaagacac gacttatcgc cactggcagc agccactggt aacaggatta    6180
gcagagcgag gtatgtaggc ggtgctacag agttcttgaa gtggtggcct aactacggct    6240
acactagaag aacagtattt ggtatctgcg ctctgctgaa gccagttacc ttcggaaaaa    6300
gagttggtag ctcttgatcc ggcaaacaaa ccaccgctgg tagcggtggt ttttttgttt    6360
gcaagcagca gattacgcgc agaaaaaaag gatctcaaga agatcctttg atcttttcta    6420
cggggtctga cgctcagtgg aacgaaaact cacgttaagg gattttggtc atgagattat    6480
caaaaaggat cttcacctag atccttttaa attaaaaatg aagttttaaa tcaatctaaa    6540
gtatatatga gtaaacttgg tctgacagtt accaatgctt aatcagtgag gcacctatct    6600
cagcgatctg tctatttcgt tcatccatag ttgcctgact ccccgtcgtg tagataacta    6660
cgatacggga gggcttacca tctggcccca gtgctgcaat gataccgcga gacccacgct    6720
caccggctcc agatttatca gcaataaacc agccagccgg aagggccgag cgcagaagtg    6780
gtcctgcaac tttatccgcc tccatccagt ctattaattg ttgccgggaa gctagagtaa    6840
gtagttcgcc agttaatagt ttgcgcaacg ttgttgccat tgctacaggc atcgtggtgt    6900
cacgctcgtc gtttggtatg gcttcattca gctccggttc ccaacgatca aggcgagtta    6960
catgatcccc catgttgtgc aaaaaagcgg ttagctcctt cggtcctccg atcgttgtca    7020
gaagtaagtt ggccgcagtg ttatcactca tggttatggc agcactgcat aattctctta    7080
ctgtcatgcc atccgtaaga tgcttttctg tgactggtga gtactcaacc aagtcattct    7140
gagaatagtg tatgcggcga ccgagttgct cttgcccggc gtcaatacgg gataataccg    7200
cgccacatag cagaacttta aaagtgctca tcattggaaa acgttcttcg ggcgaaaac    7260 tctcaaggat cttaccgctg ttgagatcca gttcgatgta acccactcgt gcacccaact    7320
gatcttcagc atcttttact ttcaccagcg tttctgggtg agcaaaaaca ggaaggcaaa    7380
atgccgcaaa aaagggaata agggcgacac ggaaatgttg aatactcata ctcttccttt    7440
ttcaatatta ttgaagcatt tatcagggtt attgtctcat gagcggatac atatttgaat    7500
gtatttagaa aaataaacaa ataggggttc cgcgcacatt tccccgaaaa gtgccacctg    7560
acgcgccctg tagcggcgca ttaagcgcgg cgggtgtggt ggttacgcgc agcgtgaccg    7620
ctacacttgc cagcgcccta gcgcccgctc ctttcgcttt cttcccttcc tttctcgcca    7680
cgttcgccgg ctttccccgt caagctctaa atcggggggc tcctttaggg ttccgattta    7740
gtgctttacg gcacctcgac cccaaaaaac ttgattaggg tgatggttca cgtagtgggc    7800
catcgccctg atagacggtt tttcgccctt tgacgttgga gtccacgttc tttaatagtg    7860
gactcttgtt ccaaactgga acaacactca accctatctc ggtctattct tttgatttat    7920
```

```
aagggattttt gccgatttcg gcctattggt taaaaaatga gctgatttaa caaaaattta    7980 acgcgaatttt taacaaaata ttaacgctta caatttgcca ttcgccattc aggctgcgca    8040
actgttggga agggcgatcg gtgcgggcct cttcgctatt acgccagccc aagctaccat    8100
gataagtaag taatattaag gtacgggagg tacttggagc ggccgcaata aaatatcttt    8160
attttcatta catctgtgtg ttggttttt gtgtgaatcg atagtactaa catacgctct    8220
ccatcaaaac aaaacgaaac aaaacaaact agcaaaatag gctgtcccca gtgcaagtgc    8280
aggtgccaga acatttctct atcgata                                        8307

<210> SEQ ID NO 28
<211> LENGTH: 2344
<212> TYPE: DNA
<213> ORGANISM: homo sapiens

<400> SEQUENCE: 28 cttttactt ctatcttcca taatattcta aaattatttt cccttgtttt gttcctatcc      60
tacttcctct tagtctactt tgttgacttc attaaaaaac aaaaaaccag ttgttggata    120
cttgagctaa actgccttaa agaatctgca gatttttattt tattttttt ctctcaagag    180 ggtaaaagga agagagctac aatttctaag aagcctggct tggctgtctg agtctggccc    240
ccaggcagat taggccaagg ttttggccaa gtgaaattgc caattttcta aaagaaaggg    300
ctagcacatt gctcattaga gcattctgat tttgtctgcg caatcttttt gctaccccgc    360
aatttcctgt tggttataaa tgaaaccttt ctagctgtta atgcagcctg tgaattttttt    420 taaaagcatg taattaatca taggaggttg ggggattca ctaagcctga gttacatggg    480
agaagctgga caaggcacta ggacctagaa ggcatctatc caccctggca ggaatttctt    540
gcttggagct cagacaacaa aggcatagag agattggttt tctttctctc agcatctcca    600
cccaaccagc agaaaaccgg tgagtggggc ttttaagtga ttttcaagaa gaatgtaaca    660
gatgtcaaac gggaaaagca caaggcaaag cctgctctct ctgtctctct gtctcctctt    720
ctcctttttt gccttattct atccgatttt ttccctaagc ttctacctgg gattttcctt    780
tggaaaagtg agtttgatgt tccttttgttt tcactgtgat gttaatttag aataatacta    840
cctctgatcc taaagcaaag caaagcctta ctggcatgcc tggggaaatg tttgctgctt    900
gccttgagga ggtggggtct cttaccactg caggttgtct gacagagaca atgctgagct    960
cagcataggt catggtgaca ttggaaaaaa ggcggaattg agcctggcag acccattagg    1020
caccagtctt tcttatctcc tgtcctcctg gtcccttgca aatatattga tgtggcagtg    1080
tgtagcagct gagccctgct tgctttgtga gtccttttat ccccatctgt gagatgcatg    1140
ttaatagttt ggctcgtagg atgtcactac atttgctagc attttgtggct tcagttgtat    1200 tgggtttcat gttttgattg tttggggttc ttggtggggg aggggttca acagaaggga    1260 gaaaagcaaa gcctgacaaa tgaccatctt ttctcagcta atgcacctgg gcaatataca    1320
agtttggggt gaattgcctg ctgtgagggt aaatgtcact tcaattaagg tagaaaccca    1380
gaacaatgaa aggtgtgctt ccttctaaag gtcccgtatg ctgttcggag agtcatttgt    1440
gaatctttca acaattaaat tattccatta agaggtgttg ctgcatcagt ggggaggggg    1500
tggagcacct gggggggaaa aaaaggatt ttgtgaacaa atggaaccgg gggaagacag    1560
agctagtaac ttgttaaata acttatttt ctaatccttt ttcccccag cttatttctt    1620 atgaatgtcg gatagctgca ccagcttggt ggggaagggg tttgatgaat agcacaaaga    1680
cactggctgt tccctggagg ctgtcccttt aaaggagaat cttagtttat tctgggggga    1740
```

```
gggatgcac acattagagt aggaaagagg gcttggaata aaatgaaaac actcccctt    1800 catagtcatt gtactgaaat gcaaagactg cttcctaagc tggagatgct aaccttgggt  1860
agctccttct gttctcttca aggggaattt tgtcaggcta tggattcatt tacaactgtt  1920
agtcatgtgg gcatgtgtga ggaaacagat gccagttta atgtatttag cccgaagttc   1980
caatttgata ggagccactg tcagtaagtc tcaggatttt cagctatttc aaaatctccc  2040
cttctcctct gtctggaaca gtgccaagag tgcctccctc tctatctctt actcccaacc  2100
cccacaacca ccagcacccc cgcccagccc ctccttcttc tctattaaga tcaatattcc  2160
tgcaggtcag gggcaagcag cagatgggtc acaggctttt ttcaaccagt tcttttcaca  2220
agcagcagat tgcagatctg gatctggcta atatttaaaa tcccttcttt tttccttctc  2280
cttgtccctt tttgtttttg cctctcttca cccccatccc tttctcccac gctcaggtct  2340
ctga                                                              2344
```